United States Patent
Kumar et al.

(10) Patent No.: US 11,866,427 B2
(45) Date of Patent: Jan. 9, 2024

(54) KINASE INHIBITOR COMPOUNDS AND COMPOSITIONS AND METHODS OF USE

(71) Applicant: Icahn School of Medicine at Mount Sinai, New York, NY (US)

(72) Inventors: Kunal Kumar, New York, NY (US); Peng Wang, New York, NY (US); Roberto Sanchez, New York, NY (US); Adolfo Garcia Ocaña, New York, NY (US); Andrew Stewart, New York, NY (US); Robert Devita, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 688 days.

(21) Appl. No.: 16/981,742

(22) PCT Filed: Mar. 20, 2019

(86) PCT No.: PCT/US2019/023206
§ 371 (c)(1),
(2) Date: Sep. 17, 2020

(87) PCT Pub. No.: WO2019/183245
PCT Pub. Date: Sep. 26, 2019

(65) Prior Publication Data
US 2021/0094950 A1  Apr. 1, 2021

Related U.S. Application Data

(60) Provisional application No. 62/645,560, filed on Mar. 20, 2018.

(51) Int. Cl.
*A61K 31/437* (2006.01)
*C07D 471/04* (2006.01)
*A61K 45/06* (2006.01)

(52) U.S. Cl.
CPC .......... *C07D 471/04* (2013.01); *A61K 31/437* (2013.01); *A61K 45/06* (2013.01)

(58) Field of Classification Search
CPC .................................................... A61K 31/437
USPC ........................................................ 514/292
See application file for complete search history.

(56) References Cited

U.S. PATENT DOCUMENTS

| | | |
|---|---|---|
| 9,951,050 B2 | 4/2018 | Aberger et al. |
| 11,266,647 B2 | 3/2022 | Stewart et al. |
| 11,547,712 B2 | 1/2023 | Devita et al. |
| 2004/0116474 A1 | 6/2004 | Munchhof et al. |
| 2004/0192583 A1 | 9/2004 | Medicherla et al. |
| 2005/0032869 A1 | 2/2005 | Berta et al. |
| 2007/0060619 A1 | 3/2007 | Burns et al. |
| 2007/0208053 A1 | 9/2007 | Arnold et al. |
| 2008/0221171 A1 | 9/2008 | Eberle et al. |
| 2009/0196912 A1 | 8/2009 | Eickhoff et al. |
| 2009/0312322 A1 | 12/2009 | Berg et al. |
| 2010/0173931 A1 | 7/2010 | Ellies et al. |
| 2010/0184758 A1 | 7/2010 | Dobbelaar et al. |
| 2010/0197562 A1 | 8/2010 | De Lera Ruiz et al. |
| 2011/0053930 A1 | 3/2011 | Yu et al. |
| 2011/0123651 A1 | 5/2011 | Mower et al. |
| 2012/0071512 A1 | 3/2012 | Hu et al. |
| 2013/0023491 A1 | 1/2013 | Annes et al. |
| 2013/0102627 A1 | 4/2013 | Higgins et al. |
| 2013/0210060 A1 | 8/2013 | Hosoya et al. |
| 2014/0275064 A1 | 9/2014 | Leblond et al. |
| 2014/0288068 A1 | 9/2014 | Ellies et al. |
| 2015/0174034 A1 | 6/2015 | Hu et al. |
| 2015/0266878 A1 | 9/2015 | Yang et al. |
| 2015/0297573 A1 | 10/2015 | Dalle et al. |
| 2016/0038500 A1 | 2/2016 | Klein et al. |
| 2016/0039845 A1 | 2/2016 | Wang et al. |
| 2016/0122361 A1 | 5/2016 | Reddy et al. |

(Continued)

FOREIGN PATENT DOCUMENTS

| | | |
|---|---|---|
| CN | 102977096 A | 3/2013 |
| CN | 105884767 A | 8/2016 |

(Continued)

OTHER PUBLICATIONS

US 11,746,330 B2, 09/2023, Devita et al. (withdrawn)

(Continued)

*Primary Examiner* — Raymond J Henley, III
(74) *Attorney, Agent, or Firm* — Troutman Pepper Hamilton Sanders LLP (Rochester)

(57) ABSTRACT

Described herein are compounds having the following structure: formula (I) or a stereoisomer, pharmaceutically acceptable salt, oxide, or solvate thereof. Also disclosed are compositions containing the compounds, methods of inhibiting activity of DYRK1 A in a cell, methods of increasing cell proliferation in a population of pancreatic beta cells, methods of treating a subject for a condition associated with insufficient insulin secretion, and methods of treating a subject for a neurological disorder.

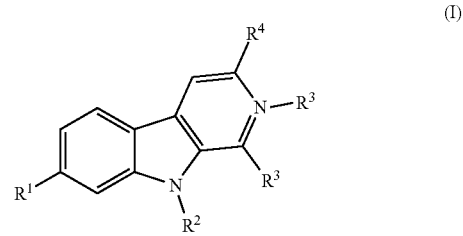

(I)

20 Claims, 15 Drawing Sheets

(56) References Cited

U.S. PATENT DOCUMENTS

| | | |
|---|---|---|
| 2016/0186143 A1 | 6/2016 | Melton et al. |
| 2016/0289315 A1 | 10/2016 | Mirza et al. |
| 2017/0056379 A1 | 3/2017 | Chen et al. |
| 2017/0280720 A1 | 10/2017 | Chesworth et al. |
| 2017/0281607 A1 | 10/2017 | Davies |
| 2018/0216076 A1 | 8/2018 | Hebrok et al. |
| 2019/0328738 A1 | 10/2019 | Stewart et al. |
| 2020/0306257 A1 | 10/2020 | Devita et al. |
| 2021/0032601 A1 | 2/2021 | Stewart et al. |
| 2022/0064146 A1 | 3/2022 | Devita et al. |
| 2022/0162182 A1 | 5/2022 | Devita et al. |
| 2023/0234935 A1 | 7/2023 | Devita et al. |

FOREIGN PATENT DOCUMENTS

| | | |
|---|---|---|
| GB | 2447791 A | 9/2008 |
| WO | 2010/123583 A2 | 10/2010 |
| WO | 2010/137350 A1 | 12/2010 |
| WO | 2011/075665 A2 | 6/2011 |
| WO | 2011/133795 A2 | 10/2011 |
| WO | 2011/133882 A1 | 10/2011 |
| WO | 2011/133888 A1 | 10/2011 |
| WO | 2011/138421 A1 | 11/2011 |
| WO | 2011/161256 A1 | 12/2011 |
| WO | 2012/024433 A2 | 2/2012 |
| WO | 2013/119518 A1 | 8/2013 |
| WO | 2014/004857 A1 | 1/2014 |
| WO | 2014/058080 A1 | 4/2014 |
| WO | 2014/063477 A1 | 5/2014 |
| WO | 2014/153203 A2 | 9/2014 |
| WO | 2014/202638 A1 | 12/2014 |
| WO | 2014/203217 A1 | 12/2014 |
| WO | 2015/011331 A1 | 1/2015 |
| WO | 2015/058031 A1 | 4/2015 |
| WO | 2015/157093 A1 | 10/2015 |
| WO | 2016/064676 A1 | 4/2016 |
| WO | 2016/161410 A2 | 10/2016 |
| WO | 2017/040993 A1 | 3/2017 |
| WO | 2017/085198 A1 | 5/2017 |
| WO | 2017/106630 A1 | 6/2017 |
| WO | 2017/117556 A1 | 7/2017 |
| WO | 2017/168245 A1 | 10/2017 |
| WO | 2017/197151 A1 | 11/2017 |
| WO | 2018/081401 A1 | 5/2018 |
| WO | 2018/083157 A1 | 5/2018 |
| WO | 2018/098561 A1 | 6/2018 |
| WO | 2018/210994 A1 | 11/2018 |
| WO | 2019/100062 A1 | 5/2019 |
| WO | 2019/136320 A1 | 7/2019 |
| WO | 2020/142485 A1 | 7/2020 |
| WO | 2020/142486 A1 | 7/2020 |

OTHER PUBLICATIONS

European Search Report and Opinion in EP Application No. 19907897.3, dated Sep. 12, 2022.
Gupta et al., "Synthesis of 4-Aryl and Unsymmetrical 4,6-Diarylpyrimidines by the Suzuki-Miyaura Cross-Coupling Reaction," Heterocycles 96(9):1549-1569 (2018).
Coombs et al., "Small-Molecule Pyrimidine Inhibitors of the CDC2-Like (Clk) and Dual Specificity Tyrosine Phosphorylation-Regulated (Dyrk) Kinases: Development of Chemical Probe ML315," Bioorganic & Medicinal Chemistry Letters 23(12):3654-3661 (2013) [Author Manuscript].
Kumar et al., "Novel Selective Thiadiazine DYRK1A Inhibitor Lead Scaffold with Human Pancreatic Beta-Cell Proliferation Activity," European Journal of Medicinal Chemistry 157:1005-1016 (2018) [Author Manuscript].
European Search Report and Opinion in EP Application No. 19907044.2, dated Aug. 5, 2022.
Pu et al., "Design, Synthesis and Biological Evaluation of Indole Derivatives as Vif Inhibitors," Bioorganic & Medicinal Chemistry Letters 27(17):4150-4155 (2017).
Office Action in U.S. Appl. No. 16/959,390 (dated Sep. 15, 2022).
Wang et al., "Induction of Human Pancreatic Beta Cell Replication by Inhibitors of Dual Specificity Tyrosine Regulated Kinase," Nat. Med. 21(4):383-388 (2015).
Annes et al., "Adenosine Kinase Inhibition Selectively Promotes Rodent and Porcine Islet β-cell Replication," PNAS 109:3915-3920 (2012).
Abdolazimi et al., "CC-401 Promotes β-Cell Replication via Pleiotropic Consequences of DYRK1A/B Inhibition," Endocrinology 159(9):3143-3157 (2018).
Screenshot of the MedChem Express webpage identifying CC-401 by structure and as CAS No. 395104-30-0.
Parnaud et al., "Proliferation of Sorted Human and Rat Beta Cells," 51(1):91-100 (2008).
Dai et al., "Age-Dependent Human Beta Cell Proliferation Induced by Glucagon-Like Peptide-1 and Calcineurin Signaling," J. Clin. Invest. 127(10):3835-3844 (2017).
Examination Report in EP Application No. 17863636.1, dated Aug. 11, 2022.
Coskun et al., "LY3298176, A Novel Dual GIP and GLP-1 Receptor Agonist for the Treatment of Type 2 Diabetes Mellitus: From Discovery to Clinical Proof of Concept," Mol. Metab. 18:3-14 (2018).
Willard et al., "Tirzepatide is an Imbalanced and Biased Dual GIP and GLP-1 Receptor Agonist," JCI Insight 5(17): e140532 (2020).
Tahtouh et al., "Selectivity, Cocrystal Structures, and Neuroprotective Properties of Leucettines, a Family of Protein Kinase Inhibitors Derived from the Marine Sponge Alkaloid Leucettamine B," J. Med. Chem. 55:9312-9330 (2012).
Office Action in U.S. Appl. No. 16/765,542 (dated Apr. 8, 2022).
Supplementary Partial European Search Report and Opinion in EP Application No. 19771612.9, dated Dec. 20, 2021.
Balint et al., "Structure-Based Design and Synthesis of Harmine Derivatives with Different Selectivity Profiles in Kinase versus Monoamine Oxidase Inhibition," ChemMedChem. 12(12):932-939 (2017).
Drung et al., "Computational & Experimental Evaluation of the Structure/Activity Relationship of β-Carbolines as DYRK1A Inhibitors," Bioorg. Med. Chem. Lett. 24(20):4854-4860 (2014).
Yadav and Nandi, "QSAR and Anticancer Drug Design of β-Carboline Compounds Utilizing Computed Molecular Descriptors," Journal of Computational Methods in Molecular Design 4(3):92-105 (2014).
Frederick et al., "Novel Trisubstituted Harmine Derivatives with Original in Vitro Anticancer Activity," J. Med. Chem. 55(14):6489-6501 (2012).
Cuny et al., "Structure-Activity Relationship Study of Beta-Carboline Derivatives as Haspin Kinase Inhibitors," Bioorg. Med. Chem. Lett. 22(5):2015-2019 (2012) [Author Manuscript].
Filali et al., "Synthesis of New Harmine Isoxazoles and Evaluation of their Potential Anti-Alzheimer, Anti-Inflammatory, and Anticancer Activities," Med. Chem. 12(2):184-190 (2016).
Filali et al., "Synthesis of New Isoxazoline Derivatives from Harmine and Evaluation of their Anti-Alzheimer, Anti-Cancer and Antiinflammatory Activities," 30(3):371-376 (2015).
European Search Report and Opinion in EP Application No. 19771612.9, dated Mar. 22, 2022.
International Search Report and Written Opinion International Application No. PCT/US21/39132 (dated Dec. 7, 2021).
Gupta et al., "Models for the Prediction of Receptor Tyrosine Kinase Activity of Substituted 3-Aminoindazole Analogues," Sci. Pharm. 79:239-257 (2011).
Pubchem SID 194152017, pp. 1-7 (2014).
Pubchem SID 245038163, pp. 1-7 (2015).
Bresson et al., "Anti-CD3 and Nasal Proinsulin Combination Therapy Enhances Remission from Recent-Onset Autoimmune Diabetes by Inducing Tregs," J. Clin. Invest. 116(5):1371-1381 (2006).
Herold et al., "An Anti-CD3 Antibody, Teplizumab, in Relatives at Risk for Type 1 Diabetes," N. Engl. J. Med. 381:603-613 (2019).
Sims et al., "Teplizumab Improves and Stabilizes Beta Cell Function in Antibody Positive High-Risk Individuals," Sci. Transl. Med. 13(583):eabc8980 (2021) [Author Manuscript].

(56) References Cited

OTHER PUBLICATIONS

Heagopian et al., "Teplizumab Preserves C-Peptide in Recent-Onset Type 1 Diabetes: Two-Year Results from the Randomized, Placebo-Controlled Protégé Trial," Diabetes 62(11):3901-3908 (2013).
Herold et al., "Teplizumab (Anti-CD3 mAb) Treatment Preserves C-Peptide Responses in Patients With New-Onset Type 1 Diabetes in a Randomized Control Trial: Metabolic and Immunologic Features at Baseline Identify a Subgroup of Responders," Diabetes 62(11):3766-3774 (2013).
Sherry et al., "Teplizumab for Treatment of Type 1 Diabetes (Protégé Study): 1 Year Results from a Randomised, Placebo-Controlled Trial," Lancet 378:487-497 (2011).
Bluestone et al., "Immunotherapy: Building a Bridge to a Cure for Type 1 Diabetes," Science 373:510-516 (2021).
Von Herrath et al., "Anti-Interleukin-21 Antibody and Liraglutide for the Preservation of β-Cell Function in Adults with Recent-Onset Type 1 Diabetes: A Randomised, Double-Blind, Placebo-Controlled, Phase 2 Trial," Lancet Diabetes Endocrinol. 9:212-224 (2021).
Office Action in U.S. Appl. No. 16/959,390 (dated Mar. 30, 2022).
Rosselot et al., "Human Beta Cell Mass Expansion in Vivo with a Harmine and Extendin-4 Combination: Quantification and Visualization by iDISCO+ 3D Imaging," bioRxiv preprint (2021).
Examination Report in EP Application No. 19771612.9, dated May 12, 2023.
First Office Action for CN201980032475.X, dated Mar. 19, 2023.
Examination Report for EP19907044.2, dated May 10, 2023.
First Office Action for CN201980093305.2, dated Mar. 22, 2023.
STN Search Results, cited in CN Office Action for 201980093305.2 (dated Mar. 22, 2023).
Office Action in Europe Application No. 17863636.1, dated Jan. 12, 2021.
Wang et al., "Diabetes Mellitus—Advances and Challenges in Human β-Cell Proliferation," Nat. Rev. Endocrinol. 11 (4):201-212 (2015).
EP Search Report and Opinion for EP Application No. 178636361. 1, dated May 6, 2020.
Shen et al., "Inhibition of DYRK1A and GSK3B induces human β-cell proliferation," Nature Comm. 6:8372 (2015).
Madhu et al., "Dual Inhibition of Activin/Nodal/TGF-β and BMP Signaling Pathways by SB431542 and Dorsomorphin Induces Neuronal Differentiation of Human Adipose Derived Stem Cells," Stem Cells Int. 1-13 (2016).
Vogt et al., "The Specificities of Small Molecule Inhibitors of the TGFβ and BMP Pathways," Cell. Signal. 23 (11):1831-1842 (2011).
Wang et al., "Combined Inhibition of DYRK1A, SMAD, and Trithorax Pathways Synergizes to Induce Robust Replication in Adult Human Beta Cells," Cell Metab. 29(3):638-652 (2019).
Nassar et al. "A TGF-Beta Receptor 1 Inhibitor for Prevention of Proliferative Vitreoretinopathy," Experimental Eye Research, 2014, vol. 123, pp. 72-86. (Year: 2014).
Wang et al., "A High-Throughput Chemical Screen Reveals That Harmine-Mediated Inhibition of DYRK1A Increases Human Pancreatic Bela Cell Replication," Nature Medicine 21(4):383-388 (2015).
Huynh et al., "Screening and Identification of a Novel Class of TGF-[beta] Type 1 Receptor Kinase Inhibitor," Journal of Biomolecular Screening 16(7):724-733 (2011).
Dhawan et al., "Inhibition of TGF-beta Signaling Promotes Human Pancreatic Bela Cell Replication," Diabetes 65 (5):1208-1218 (2016).
Pagliuca et al., "Generation of Functional Human Pancreatic [beta] Cells In Vitro," Cell 159(2):428-439 (2014).
PCT International Search Report and Opinion for International Application No. PCT/US2017/058498, dated Jan. 9, 2018.
Xiao et al., "Resveratrol Attenuates Renal Injury and Fibrosis by Inhibiting Transforming Growth Factor β Pathway on Matrix Metalloproteinase 7," Experimental Biology and Medicine, Jan. 2016, vol. 241, pp. 140-146. (Year: 2016).
Office Action in Europe Application No. 17863636.1, dated Oct. 22, 2021.

Restriction Requirement in U.S. Appl. No. 16/344,230 (dated Feb. 6, 2020).
Office Action in U.S. Appl. No. 16/344,230 (dated May 4, 2020).
Office Action in U.S. Appl. No. 16/344,230 (dated Nov. 2, 2020).
Office Action in U.S. Appl. No. 16/344,230 (dated Apr. 13, 2021).
International Search Report and Written Opinion for International Application No. PCT/US2018/062023 (dated Feb. 4, 2019).
Chunduru et al., "One-Pot Synthesis of 1,3.4-Tliiadiazin-5-yl-chromen-2-one Derivatives via Three-Component Reaction," Synthetic Communications 42:1454-1460 (2012).
Kumar et al, "Novel Selective Thiadiazine DYRK1A inhibitor Lead Scaffold with Human Pancreatic B-Cell Proliferation Activity," European Journal of Medicinal Chemistry 157:1005-1016 (2018).
PubmedCompound Summary for CID 17565749, "PNJQHHXWPZEHTA-UHFFFAOYSAN-N," U.S. National Library of Medicine, pp. 1-10 (2007).
Extended European Search Report in EPO Application No. 18878625.5 (dated Feb. 23, 2021).
Restriction Requirement in U.S. Appl. No. 16/765,542 (dated Nov. 27, 2020).
Office Action in U.S. Appl. No. 16/765,542 (dated Feb. 18, 2021).
Office Action in U.S. Appl. No. 16/765,542 (dated May 24, 2021).
Office Action in U.S. Appl. No. 16/765,542 (dated Nov. 8, 2021).
International Search Report and Written Opinion for International Application No. PCT/US2019/012442 (dated Apr. 24, 2019).
Shah et al., "The DPP-4 Inhibitor Linagliptin Restores Beta-Cell Function and Survival in Human Isolated Islets through GLP-1 Stabilization," J. Clin. Endocrinol. Metabol. 98(7):1163-1172 (2013).
Navarro et al., "Genetic Disruption of Adenosine Kinase in Mouse Pancreatic Beta-Cells Protects Against High-Fat Diet-Induced Glucose Intolerance," Diabetes 66(7):1928-1938 (2017).
Supplementary European Search Report and Written Opinion in EP 19735846.8 (dated Aug. 18, 2021).
Kumar et al., "Development of Kinase-Selective, Harmine-Based DYRK1A Inhibitors that Induce Pancreatic Human β-Cell Proliferation," J. Med. Chem. 61(17):7687-7699 (2018).
Amisten et al., "An Atlas and Functional Analysis of G-Protein Coupled Receptors in Human Islets of Langerhans," Pharmacology & Therapeutics 139:359-391 (2013).
Zhao et al., "Repurposing cAMP-Modulating Medications to Promoate β-Cell Replication," Mol. Endocrinol. 28 (10):1682-1697 (2014).
Reimann & Gribble, "G Protein-Coupled Receptors as New Therapeutic Targets for Type 2 Diabetes," Diabetologica 59:229-233 (2016).
Bachem, "Peptides for Diabetes Research," Peptides and Diabetes, published by Global Marketing Bachem Group (2017).
Nance et al., "Discovery of a Novel Series of Orally Bioavailable and CNS Penetrant Glucagon-Like Peptide-1 Receptor (GLP-1R) Noncompetitive Antagonists Based on a 1,3-Disubstituted-7-Aryl-5,5-Bis(Trifluoromethyl)-5,8-Dihydropyrimido[4,5-d]Pyrimidine-2,4(1H,3H)-Dione Core," J. Med. Chem. 60:1611-1616 (2017).
Restriction Requirement in U.S. Appl. No. 16/959,390 (dated Nov. 1, 2021).
International Search Report and Written Opinion for International Application No. PCT/US2019/069057 (dated Mar. 9, 2020).
Multhoff et al., "Chronic Inflammation in Cancer Development," Front. Immunol. 2(98):1-17 (2012).
International Search Report and Written Opinion for PCT/US2019/069059, dated Mar. 9, 2020.
Dirice, E., et al., "Inhibition of DYRK1A Stimulates Human beta-Cell Proliferation," Diabetes, 65:1660-1671 (2016).
Pubchem CID 53496098, pp. 1-9 (2011).
Pubchem CID 116977135, pp. 1-7 (2016).
Pubchem CID 84152473, pp. 1-7 (2104).
Pubchem CID 66793828, pp. 1-9 (2012).
Pubchem CID 20199687, pp. 1-9 (2007).
Pubchem CID 68046670, pp. 1-8 (2012).
Pubchem CID 76281619, pp. 1-10 (2014).
International Search Report and Written Opinion for PCT/US2019/023206, dated Jul. 29, 2019.
Ishida, et al., "Antitumor Agents 201. Cytotoxicity of Harmine and B-Carboline Analogs," Bioorg. Med. Chem. Lett. 9:3319-3324 (1999).

(56) References Cited

OTHER PUBLICATIONS

Office Action and Search Report in JP 2020-527899 (dated Oct. 18, 2022).
"5-(2-Benzylimino-3,6-dihydro-1,3,4-thiadiazin-5-yl)-1,3-dihydrobenzimidazol-2-one," Web page <https://pubchem.ncbi.hlm.nih.gov/compound/135783279>, 11 pages, Jan. 17, 2019, retrieved from <https://pubchem.ncbi.nlm.nih.gov/compound/135783279> on Oct. 24, 2022.
Office Action and Search Report in CN 201980017277.6 (dated Oct. 25, 2022).
Office Action and Search Report in JP 2020-537237 (dated Dec. 26, 2022).
Office Action and Search Report in JP 2020-550798 (dated Feb. 9, 2023).
Decision of Rejection in Japan Application No. JP 2020-537237 (dated Jul. 27, 2023).
Decision of Rejection in Japan Application No. JP 2020-550798 (dated Oct. 6, 2023).

KINASE INHIBITOR COMPOUNDS AND COMPOSITIONS AND METHODS OF USE

This application is a national stage application under 35 U.S.C. § 371 of PCT Application Serial No. PCT/US2019/023206, filed Mar. 20, 2019, which claims the priority benefit of U.S. Provisional Patent Application Ser. No. 62/645,560, filed Mar. 20, 2018, both of which are hereby incorporated by reference in their entirety.

This invention was made with government support under grant number R01 DK105015 awarded by the National Institutes of Health. The government has certain rights in the invention.

FIELD

The present disclosure relates to kinase inhibitor compounds and compositions and methods of their use.

BACKGROUND

The Dual-Specificity Tyrosine-Regulated kinases ("DYRKs") belong to the CMCG family of eukaryotic protein kinases which include the CDK-like kinases (CLKs), Glycogen Synthase Kinase 3 (GSK3), Cyclin Dependent Kinases (CDKs), and Mitogen-Activated Protein Kinases (MAPKs). DYRK family proteins self-activate by autophosphorylation of the conserved tyrosine residue in the activation loop, then subsequently phosphorylate substrates only on serine and threonine residues (Lochhead et al., "Activation-Loop Autophosphorylation is Mediated by a Novel Transitional Intermediate Form of DYRKs," *Cell* 121(6): 925-936 (2005); Walte et al., "Mechanism of Dual Specificity Kinase Activity of DYRK1A," *FEBS J.* 280(18):4495-4511 (2013); and Becker et al., "Activation, Regulation, and Inhibition of DYRK1A," *FEBS J.* 278(2):246-256 (2011)). The DYRK family has five subtypes, including 1A, 1B, 2, 3, and 4. Among them, DYRK1A is the most extensively studied subtype. It is ubiquitously expressed and has been shown to play an important role in brain development and function (Becker et al., "DYRK1A: A Potential Drug Target for Multiple Down Syndrome Neuropathologies," *CNS Neurol. Disord.: Drug Targets* 13(1):26-33 (2014)), neurodegenerative diseases (Wegiel et al., "The Role of DYRK1A in Neurodegenerative Diseases," *FEBS J.* 278(2):236-245 (2011) and Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012)), tumorigenesis, apoptosis (Ionescu et al., "DYRK1A Kinase Inhibitors With Emphasis on Cancer," *Mini-Rev. Med. Chem.* 12(13):1315-1329 (2012) and Fernandez-Martinez et al., "DYRK1A: The Double-Edged Kinase as a Protagonist in Cell Growth and Tumorigenesis," *Mol. Cell. Oncol.* 2(1):e970048 (2015)), and human pancreatic β-cell proliferation (Wang et al., "A High-Throughput Chemical Screen Reveals That Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human β-cell Proliferation," *Nat. Commun.* 6:8372 (2015); Rachdi et al., "Dyrk1A Induces Pancreatic β Cell Mass Expansion and Improves Glucose Tolerance," *Cell Cycle* 13(14):2221-2229 (2014); and Dirice et al., "Inhibition of DYRK1A Stimulates Human Beta-Cell Proliferation," *Diabetes* 65:(6):1660-1671 (2016)).

Regulated expression of DYRK1A during fetal, postnatal life, as well as in adults, is essential for normal neuronal development and brain function. DYRK1A is located in the Down Syndrome Critical region (DSCR) on human chromosome 21, a genomic region that has an important role in pathogenesis of Down Syndrome (DS), one of the most common and frequent human genetic disorders (Becker et al., "Activation, Regulation, and Inhibition of DYRK1A," *FEBS J.* 278(2):246-256 (2011) and Becker et al., "Structural and Functional Characteristics of Dyrk, a Novel Subfamily of Protein Kinases With Dual Specificity," *Prog. Nucleic Acid Res. Mol. Biol.* 62:1-17 (1999)). Overexpression of DYRK1A in mouse and *drosophila* models mimics the neurodevelopmental abnormalities associated with DS (Becker et al., "DYRK1A: A Potential Drug Target for Multiple Down Syndrome Neuropathologies," *CNS Neurol. Disord.: Drug Targets* 13(1):26-33 (2014); Wegiel et al., "The Role of DYRK1A in Neurodegenerative Diseases," *FEBS J.* 278(2):236-245 (2011); Park et al., "Function and Regulation of Dyrk1A: Towards Understanding Down Syndrome," *Cell. Mol. Life Sci.* 66(20):3235-3240 (2009); and Ogawa et al., "Development of a Novel Selective Inhibitor of the Down Syndrome-Related Kinase Dyrk1A," *Nat. Commun.* 1: Article Number 86 (2010)). Recent evidence also implicated DYRK1A in the tau dysfunction and tau pathology of Alzheimer's disease (AD), dementia with Lewy bodies, and Parkinson's disease (Wegiel et al., "The Role of DYRK1A in Neurodegenerative Diseases," *FEBS J.* 278(2):236-245 (2011); Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012); and Stotani et al., "DYRK1A Inhibition as Potential Treatment for Alzheimer's Disease," *Future Med. Chem.* 8(6):681-696 (2016)).

It has been reported that DYRK1A is overexpressed in various tumors such as ovarian cancer, colon cancer, lung cancer, and pancreatic cancer, signifying its role in tumorigenesis and uncontrolled cell proliferation (Ionescu et al., "DYRK1A Kinase Inhibitors With Emphasis on Cancer," *Mini-Rev. Med. Chem.* 12(13):1315-1329 (2012) and Fernandez-Martinez et al., "DYRK1A: The Double-Edged Kinase as a Protagonist in Cell Growth and Tumorigenesis," *Mol. Cell. Oncol.* 2(1):e970048 (2015)). Inhibition of DYRK1A leads to destabilized EGFR and reduced EGFR-dependent tumor growth in glioblastoma (Pozo et al., "Inhibition of DYRK1A Destabilizes EGFR and Reduces EGFR-Dependent Glioblastoma Growth," *J. Clin. Invest.* 123(6): 2475-2487 (2013)). Also, DYRK1A inhibition induces activation of caspase-9, which leads to massive apoptosis in specific cancer cell types (Seifert et al., "DYRK1A Phosphorylates Caspase 9 at an Inhibitory Site and is Potently Inhibited in Human Cells by Harmine," *FEBS J.* 275(24): 6268-6280 (2008)).

In contrast to its role in cancer cells, inhibition of DYRK1A has been shown to drive human β-cell proliferation, making it a potential therapeutic target for β-cell regeneration in Type 1 and Type 2 diabetes (Wang et al., "A High-Throughput Chemical Screen Reveals That Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human β-cell Proliferation," *Nat. Commun.* 6:8372 (2015); Rachdi et al., "Dyrk1A Induces Pancreatic β Cell Mass Expansion and Improves Glucose Tolerance," *Cell Cycle* 13(14):2221-2229 (2014); and Dirice et al., "Inhibition of DYRK1A Stimulates Human Beta-cell Proliferation," *Diabetes* 65:(6):1660-1671 (2016)). DYRK1A inhibition has been proposed to drive β-cell proliferation by inducing translocation of the nuclear factor of activated T cells (NFAT) family of transcription factors to the nucleus, allowing access to the promoters of genes which subsequently activate human β-cell proliferation (Wang et al., "A High-Throughput Chemical Screen Reveals That Harmine-Mediated Inhibition of DYRK1A Increases Human Pancreatic Beta Cell Replication," *Nat. Med.* 21(4):383-388 (2015) and Rachdi et al., "Dyrk1A Induces Pancreatic β Cell Mass Expansion and Improves Glucose Tolerance," *Cell Cycle* 13(14):2221-2229 (2014)).

Because of its involvement in neurodegenerative disease, cancer, and diabetes, DYRK1A has attracted increasing interest as a potential therapeutic target. A significant amount of work has been carried out to not only understand its underlying role in diseases, but also in identifying novel DYRK1A inhibitors (Becker et al., "Activation, Regulation, and Inhibition of DYRK1A," *FEBS J.* 278(2):246-256 (2011); Becker et al., "DYRK1A: A Potential Drug Target for Multiple Down Syndrome Neuropathologies," *CNS Neurol. Disord.: Drug Targets* 13(1):26-33 (2014); Wegiel et al., "The Role of DYRK1A in Neurodegenerative Diseases," *FEBS J.* 278(2):236-245 (2011); Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012); Ionescu et al., "DYRK1A Kinase Inhibitors with Emphasis on Cancer," *Mini Rev. Med. Chem.* 12(13):1315-1329 (2012); Fernandez-Martinez et al., "DYRK1A: The Double-Edged Kinase as a Protagonist in Cell Growth and Tumorigenesis," *Mol. Cell. Oncol.* 2(1): e970048 (2015); Wang et al., "A High-Throughput Chemical Screen Reveals That Harmine-Mediated Inhibition of DYRK1A Increases Human Pancreatic Beta Cell Replication," *Nat. Med.* 21(4):383-388 (2015); Shen et al., "Inhibition of DYRK1A and GSK3B Induces Human β-cell Proliferation," *Nat. Commun.* 6:8372 (2015); and Dirice et al., "Inhibition of DYRK1A Stimulates Human Beta-cell Proliferation," *Diabetes* 65:(6):1660-1671 (2016)).

Several DYRK1A inhibitors have been identified, synthesized, and characterized. Apart from harmine, other natural products that have been shown to inhibit DYRK1A and other kinases are EGCg and other flavan-3-ols (Guedj et al., "Green Tea Polyphenols Rescue of Brain Defects Induced by Overexpression of DYRK1A," *PLoS One* 4(2):e4606 (2009) and Bain et al., "The Specificities of Protein Kinase Inhibitors: An Update," *Biochem. J.* 371(1):199-204 (2003)), leucettines (Tahtouh et al., "Selectivity, Cocrystal Structures, and Neuroprotective Properties of Leucettines, a Family of Protein Kinase Inhibitors Derived from the Marine Sponge Alkaloid Leucettamine B," *J. Med. Chem.* 55(21):9312-9330 (2012) and Naert et al., "Leucettine L41, a DYRK1A-preferential DYRKs/CLKs Inhibitor, Prevents Memory Impairments and Neurotoxicity Induced by Oligomeric Aβ25-35 Peptide Administration in Mice," *Eur. Neuropsychopharmacol.* 25(11):2170-2182 (2015)), quinalizarine (Cozza et al., "Quinalizarin as a Potent, Selective and Cell-permeable Inhibitor of Protein Kinase CK2," *Biochem. J.* 421(3):387-395 (2009)), peltogynoids Acanilol A and B (Ahmadu et al, "Two New Peltogynoids from Acacia nilotica Delile with Kinase Inhibitory Activity," *Planta Med.* 76(5):458-460 (2010)), benzocoumarins (dNBC) (Sarno et al., "Structural Features Underlying the Selectivity of the Kinase Inhibitors NBC and dNBC: Role of a Nitro Group that Discriminates Between CK2 and DYRK1A," *Cell. Mol. Life Sci.* 69(3):449-460 (2012)), and indolocarbazoles (Staurosporine, rebeccamycin, and their analogues) (Sanchez et al., "Generation of Potent and Selective Kinase Inhibitors by Combinatorial Biosynthesis of Glycosylated Indolocarbazoles," *Chem. Commun.* 27:4118-4120 (2009)). Among the other scaffolds identified from small molecule drug discovery attempts, INDY (Ogawa et al., "Development of a Novel Selective Inhibitor of the Down Syndrome-Related Kinase Dyrk1A," *Nat. Commun.* 1: Article Number 86 (2010)), DANDY (Gourdain et al., "Development of DANDYs, New 3,5-Diaryl-7-Azaindoles Demonstrating Potent DYRK1A Kinase Inhibitory Activity," *J. Med. Chem.* 56(23):9569-9585 (2013)), FINDY (Kii et al., "Selective Inhibition of the Kinase DYRK1A by Targeting its Folding Process," *Nat. Commun.* 7:11391 (2016)), pyrazolidine-diones (Koo et al., "QSAR Analysis of Pyrazolidine-3,5-Diones Derivatives as Dyrk1A Inhibitors," *Bioorg. Med. Chem. Lett.* 19(8):2324-2328 (2009); Kim et al., "Putative Therapeutic Agents for the Learning and Memory Deficits of People with Down Syndrome," *Bioorg. Med. Chem. Lett.* 16(14):3772-3776 (2006)), amino-quinazolines (Rosenthal et al., "Potent and Selective Small Molecule Inhibitors of Specific Isoforms of Cdc2-Like Kinases (Clk) and Dual Specificity Tyrosine-Phosphorylation-Regulated Kinases (Dyrk)," *Bioorg. Med. Chem. Lett.* 21(10):3152-3158 (2011)), meriolins (Giraud et al., "Synthesis, Protein Kinase Inhibitory Potencies, and In Vitro Antiproliferative Activities of Meridianin Derivatives," *J. Med. Chem.* 54(13):4474-4489 (2011); Echalier et al., "Meriolins (3-(Pyrimidin-4-yl)-7-Azaindoles): Synthesis, Kinase Inhibitory Activity, Cellular Effects, and Structure of a CDK2/Cyclin A/Meriolin Complex," *J. Med. Chem.* 51(4):737-751 (2008); and Akue-Gedu et al., "Synthesis and Biological Activities of Aminopyrimidyl-Indoles Structurally Related to Meridianins," *Bioorg. Med. Chem.* 17(13):4420-4424 (2009)), pyridine and pyrazines (Kassis et al., "Synthesis and Biological Evaluation of New 3-(6-hydroxyindol-2-yl)-5-(Phenyl) Pyridine or Pyrazine V-Shaped Molecules as Kinase Inhibitors and Cytotoxic Agents," *Eur. J. Med. Chem.* 46(11):5416-5434 (2011)), chromenoidoles (Neagoie et al., "Synthesis of Chromeno[3, 4-b]indoles as Lamellarin D Analogues: A Novel DYRK1A Inhibitor Class," *Eur. J. Med. Chem.* 49:379-396 (2012)), 11H-indolo[3,2-c]quinoline-6-carboxylic acids (Falke et al., "10-Iodo-11H-Indolo[3,2-c]Quinoline-6-Carboxylic Acids are Selective Inhibitors of DYRK1A," *J. Med. Chem.* 58(7): 3131-3143 (2015)), thiazolo[5,4-f]quinazolines (EHT 5372) (Foucourt et al., "Design and Synthesis of Thiazolo[5,4-f] Quinazolines as DYRK1A Inhibitors, Part I.," *Molecules* 19(10):15546-15571 (2014) and Coutadeur et al., "A Novel DYRK1A (Dual Specificity Tyrosine Phosphorylation-Regulated Kinase 1A) Inhibitor for the Treatment of Alzheimer's Disease: Effect on Tau and Amyloid Pathologies In Vitro," *J. Neurochem.* 133(3):440-451 (2015)), and 5-iodotubercidin (Dirice et al., "Inhibition of DYRK1A Stimulates Human Beta-cell Proliferation," *Diabetes* 65:(6): 1660-1671 (2016) and Annes et al., "Adenosine Kinase Inhibition Selectively Promotes Rodent and Porcine Islet β-cell Replication," *Proc. Natl. Acad. Sci.* 109(10):3915-3920 (2012)) showed potent DYRK1A activity with varying degrees of kinase selectivity. Most of these compounds are non-selective inhibitors of DYRK1A and exhibit pharmacological side effects, such as CNS activity or apoptosis. In particular, harmine is known to exhibit hallucinogenic properties acting as CNS stimulant, due to its affinity for the serotonin, tryptamine and other receptors (Brierley et al., "Developments in Harmine Pharmacology-Implications for Ayahuasca Use and Drug-Dependence Treatment," *Prog. Neuro-Psychopharmacol. Biol. Psychiatry* 39(2):263-272

(2012) and Airaksinen et al., "Tremorigenic Effect and Inhibition of Tryptamine and Serotonin Receptor Binding by β-Carbolines," *Pharmacol. Toxicol.* (Copenhagen) 60(1), 5-8 (1987)). Studies have revealed multiple psychoactive effects of harmine, including excitation, tremors, convulsion, and anxiety (Fuentes et al., "Central Effects of Harmine, Harmaline, and Related β-Carbolines," *Neuropharmacology* 10(1):15-23 (1971)).

Among all the DYRK1A inhibitors, harmine and its analogues (β-carbolines) are the most commonly studied and remain the most potent and orally bioavailable class of inhibitors covered to date (Becker et al., "Activation, Regulation, and Inhibition of DYRK1A," *FEBS J.* 278(2):246-256 (2011) and Smith et al., "Recent Advances in the Design, Synthesis, and Biological Evaluation of Selective DYRK1A Inhibitors: A New Avenue for a Disease Modifying Treatment of Alzheimer's?," *ACS Chem. Neurosci.* 3(11):857-872 (2012)). Harmine and several related analogues have been found to inhibit DYRK1A mediated phosphorylation of tau protein, which is thought to be relevant to AD and DS (Frost et al., "β-Carboline Compounds, Including Harmine, Inhibit DYRK1A and Tau Phosphorylation at Multiple Alzheimer's Disease-Related Sites," *PLoS One* 6:5 e19264 (2011).

Harmine has also attracted serious interest for cancer therapy (Chen et al., "Antitumor and Neurotoxic Effects of Novel Harmine Derivatives and Structure-Activity Relationship Analysis," *Int. J. Cancer* 114(5): 675-682 (2005); Ishida et al., "*Antitumor Agents* 201.1 Cytotoxicity of Harmine and β-carboline Analogs," *Bioorg. Med. Chem. Lett.* 9(23):3319-3324 (1999); Cao et al., "Synthesis, Acute Toxicities, and Antitumor Effects of Novel 9 Substituted β-Carboline Derivatives," *Bioorg. Med. Chem.* 12(17):4613-4623 (2004); Cao et al., "Synthesis and Structure-Activity Relationships of Harmine Derivatives as Potential Antitumor Agents," *Eur. J. Med. Chem.* 60:135-143 (2013); and Zhang et al., "Synthesis and Mechanisms of Action of Novel Harmine Derivatives as Potential Antitumor Agents," *Sci. Rep.* 6:33204 (2016)). Using systematic structure modifications, several harmine analogues have been identified to show potent antitumor activity, in vitro and in vivo through multiple mechanism of action including inhibition of topoisomerase I (Cao et al., "DNA Binding Properties of 9-Substituted Harmine Derivatives," *Biochem. Biophys. Res. Commun.* 338(3):1557-1563 (2005) and Sobhani et al., "An In Vitro Evaluation of Human DNA Topoisomerase I Inhibition by *Peganum harmala* L. Seeds Extract and its β-Carboline Alkaloids," *J. Pharm. Pharm. Sci.* 5(1):18-22 (2002)), inhibition of CDKs (Song et al., "Specific Inhibition of Cyclin-Dependent Kinases and Cell Proliferation by Harmine," *Biochem. Biophys. Res. Commun.* 317(1):128-132 (2004)), induction of cell apoptosis (Cao et al., "Harmine Induces Apoptosis in HepG2 Cells via Mitochondrial Signaling Pathway," *Hepatobiliary Pancreatic Dis. Int.* 10(6):599-604 (2011)), and DNA intercalation (Taira et al., "Intercalation of Six β-Carboline Derivatives into DNA," *Jpn. J Toxicol. Environ. Health* 43(2):83-91 (1997)).

Harmine was also identified as a new class of compounds that cause approximately 10 to 15-fold induction in human β-cell proliferation, which is in the relevant range for therapeutic human β-cell expansion (Wang et al., "A High-Throughput Chemical Screen Reveals That Harmine-Mediated Inhibition of DYRK1A Increases Human Pancreatic Beta Cell Replication," *Nat. Med.* 21(4):383-388 (2015)). DYRK1A was defined as the likely target of harmine through genetic silencing and other studies, likely working through the NFAT family of transcription factors as mediators of human β-cell proliferation and differentiation (Wang et al., "A High-Throughput Chemical Screen Reveals That Harmine-Mediated Inhibition of DYRK1A Increases Human Pancreatic Beta Cell Replication," *Nat. Med.* 21(4): 383-388 (2015)). Using three different mouse, rat, and human islet-implant models, it was also shown that harmine is able to induce β-cell proliferation, increase islet mass, and improve glycemic control in mice and rats in vivo (Wang et al., "A High-Throughput Chemical Screen Reveals That Harmine-Mediated Inhibition of DYRK1A Increases Human Pancreatic Beta Cell Replication," *Nat. Med.* 21(4): 383-388 (2015)).

Since DYRK1A and NFATs are widely expressed outside β-cells, harmine analogs are known to have off-target effects, leading to pharmacological side effects, including CNS and antitumor activity, thereby limiting its therapeutic utility and potential for pharmaceutical development for a chronic disease like diabetes. Thus, there is an urgent need to develop strategies to identify selective harmine analogs with limited off-target activities at both kinases and other receptors. Optimized selective harmine analogs are needed for specific targeted delivery to the β-cell.

The present disclosure is directed to overcoming deficiencies in the art.

SUMMARY

One aspect of the disclosure relates to a compound of formula (I) having the following structure:

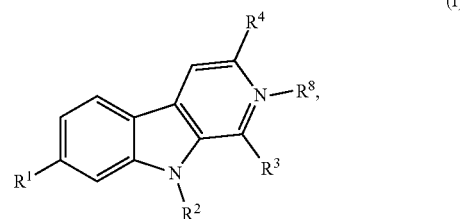

or a stereoisomer, pharmaceutically acceptable salt, oxide, or solvate thereof, wherein
$R^1$ is a branched or unbranched $C_{1-6}$ alkoxy optionally substituted with Y, $NHR^5$, —C(O)NHCH(CH$_3$)$_2$, or —O(CH$_2$)$_2$OR$^6$, where the alkoxy is optionally halogenated or deuterated;
$R^2$ is H, or branched or unbranched $C_{1-6}$ alkyl, $C_{2-6}$ alkenyl, or $C_{2-6}$ alkynyl, where the branched or unbranched $C_{1-6}$ alkyl, $C_{2-6}$ alkenyl, or $C_{2-6}$ alkynyl is optionally substituted with Z;
$R^3$ is $C_{1-6}$ alkyl, halogen, branched or unbranched $C_{1-6}$ hydroxyalkyl, —C(O)CH$_3$, —OH, or heterocyclyl optionally substituted with $R^7$;
$R^4$ is H, —OH, branched or unbranched $C_{1-6}$ hydroxyalkyl, or —C(O)CH$_3$;
$R^5$ is H, —C(O)CH$_3$, or —C(O)Ar;
$R^6$ is branched or unbranched $C_{1-6}$ alkyl, —(CH$_2$)$_2$NHBoc, —(CH$_2$)$_2$NH(O)CH$_3$, or —(CH$_2$)$_2$NH$_3$Cl;
$R^7$ is —ArX or —CH$_2$ArX;
$R^8$ is optional, and when present is O;
X is H or halogen;
Y is —CO$_2$CH$_3$, —NHBoc, —C(O)NH$_2$, —CO$_2$H, —NH$_3$Cl, —NHC(O)CH$_3$; and
Z is —CO$_2$CH$_3$, —CO$_2$H, —C(O)NH$_2$, or an amino-substituted heteroaryl selected from the group consisting of furan, thiophene, pyrrole, oxazole, thiazole, imidazole, pyrazole, isoxazole, isothiazole, 1,2,3-oxadiazole, 1,2,4-oxadiazole, 1,2,3-thiadiazole, 1,2,3-triazole, 1,2,4-triazole, tetrazole, and 1,2,3,4-oxatriazole; with the following provisos:

when $R^1$ is —$OCH_3$, $R^3$ is —$CH_3$, and $R^4$ is H, $R^2$ cannot be —$(CH_2)_2CO_2CH_3$, $(CH_2)_2CO_2H$, or —$(CH_2)_2C(O)NH_2$;

when $R^1$ is —$OCH_3$, $R^2$ is H, and $R^4$ is H, $R^3$ cannot be —$CH_2OH$ or Cl; and when $R^1$ is —$OCH_3$, $R^2$ is H, $R^3$ is —$CH_3$, $R^4$ cannot be H.

Another aspect of the disclosure relates to a method of inhibiting activity of dual-specificity tyrosine phosphorylation-regulated kinase 1A (DYRK1A) in a cell. This method involves contacting the cell with a compound of formula (I) under conditions effective to inhibit activity of DYRK1A in the cell.

A further aspect relates to a method of increasing cell proliferation in a population of pancreatic beta cells. This method involves contacting a population of pancreatic beta cells with a compound of formula (I) under conditions effective to increase cell proliferation in the population of pancreatic beta cells.

Another aspect relates to a composition comprising a compound of formula (I) and a carrier.

An additional aspect relates to a method of treating a subject for a condition associated with insufficient insulin secretion. This method involves administering to a subject in need of treatment for a condition associated with an insufficient level of insulin secretion a compound or composition described herein under conditions effective to treat the subject for the condition.

A further aspect relates to a method of treating a subject for a neurological disorder. This method involves administering to a subject in need of treatment for a neurological disorder a compound of formula (I) under conditions effective to treat the subject for the condition.

Although efforts have been made toward the discovery of potent and selective DYRK1A inhibitors, most of them are still in early stages of lead identification.

Described herein infra is the identification and evaluation of a highly potent and novel class of harmine-based DYRK1A inhibitors.

BRIEF DESCRIPTION OF THE DRAWINGS

FIG. 4A is a graph showing the results of initial screening of harmine analogs on human beta cell proliferation at 10 µM. DMSO was used as negative control and harmine was used as positive control (n=4). FIG. 4B are images showing a representative example from FIG. 4A of a Ki-67 and insulin double positive cells induced by analog 2-8. FIGS. 4C-4D are graphs showing the results of dose-response curves for compound 2-2 and compound 2-8 in human β cells (n=4 for each dose). FIG. 4E is a graph showing the quantification of nuclear frequency of Ad.N-FATC1-GFP in R7T1 rodent beta cell lines treated with harmine, compound 2-2, and compound 2-8 (10 µM, 24 hours; n=3 for each compound). FIG. 4F are a pair of images showing a representative example of compound 2-8 (10 µM, 24 hr) increasing the nuclear frequency of adenoviral NFATC1-GFP in R7T1 rodent beta cell lines. In all relevant panels, error bars indicate sem *p<0.05. A minimum of 1,000 beta cells was counted for each graph.

DETAILED DESCRIPTION

Figure 1:
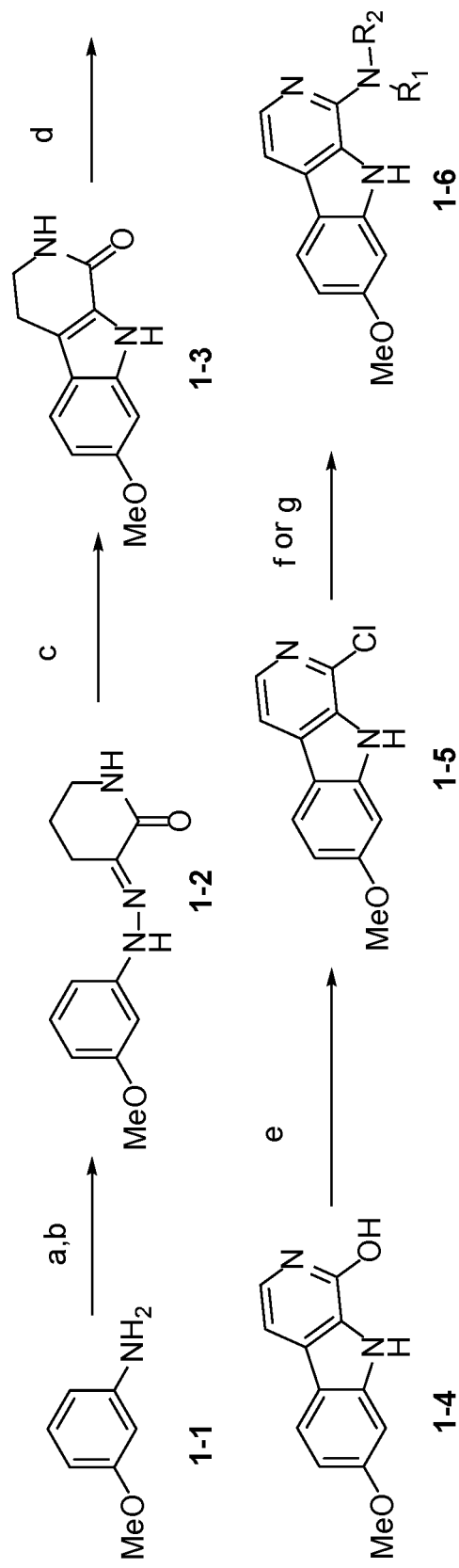
FIG. 1 is a schematic illustration showing the synthesis of a 1-amino harmine analog compound. Reagents and conditions: (a) $NaNO_2$ (1.03 eq.), HCl, 10° C., 1 hour, (b) Ethyl 2-oxopiperidine-3-carboxylate (1.05 eq.), KOH (1.2 eq.), water, 150° C., 5 hours; (c) formic acid, reflux, 1 hour; (d) DDQ (1.2 eq.), 1,4-dioxane, 0° C.-room temperature, 1 hour, 23% (4 step); (e) $POCl_3$, 150° C., 24 hours, 79%; (f) $R_1R_2NH$ (10 eq.), 170° C., 24 hours, 43-87% (for 1-6b-1-6j); (g) Ruphos (1 mol %), RuPhos Precat (1 mol %), Azetidine (1.2 eq.), LiHMDS (1 M in THF, 2.4 eq.), 90° C., 96 hours, 12% (for 1-6a).

Disclosed herein are kinase inhibitor compounds and compositions and methods of their use.

One aspect relates to a compound of formula (I) having the following structure:

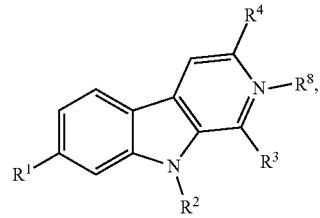

(I)

or a stereoisomer, pharmaceutically acceptable salt, oxide, or solvate thereof, wherein
R$^1$ is a branched or unbranched C$_{1-6}$ alkoxy optionally substituted with Y, NHR$^5$, —C(O)NHCH(CH$_3$)$_2$, or —O(CH$_2$)$_2$OR$^6$, where the alkoxy is optionally halogenated or deuterated;
R$^2$ is H, or branched or unbranched C$_{1-6}$ alkyl, C$_{2-6}$ alkenyl, or C$_{2-6}$ alkynyl, where the branched or unbranched C$_{1-6}$ alkyl, C$_{2-6}$ alkenyl, or C$_{2-6}$ alkynyl is optionally substituted with Z;
R$^3$ is C$_{1-6}$ alkyl, halogen, branched or unbranched C$_{1-6}$ hydroxyalkyl, —C(O)CH$_3$, —OH, or heterocyclyl optionally substituted with R$^7$;
R$^4$ is H, —OH, branched or unbranched C$_{1-6}$ hydroxyalkyl, or —C(O)CH$_3$;
R$^5$ is H, —C(O)CH$_3$, or —C(O)Ar;
R$^6$ is branched or unbranched C$_{1-6}$ alkyl, —(CH$_2$)$_2$NHBoc, —(CH$_2$)$_2$NH(O)CH$_3$, or —(CH$_2$)$_2$NH$_3$Cl;
R$^7$ is —ArX or —CH$_2$ArX;
R$^8$ is optional, and when present is O;
X is H or halogen;
Y is —CO$_2$CH$_3$, —NHBoc, —C(O)NH$_2$, —CO$_2$H, —NH$_3$Cl, —NHC(O)CH$_3$; and
Z is —CO$_2$CH$_3$, —CO$_2$H, —C(O)NH$_2$, or an amino-substituted heteroaryl selected from the group consisting of furan, thiophene, pyrrole, oxazole, thiazole, imidazole, pyrazole, isoxazole, isothiazole, 1,2,3-oxadiazole, 1,2,4-oxadiazole, 1,2,3-thiadiazole, 1,2,3-triazole, 1,2,4-triazole, tetrazole, and 1,2,3,4-oxatriazole;
with the following provisos:
when R$^1$ is —OCH$_3$, R$^3$ is —CH$_3$, and R$^4$ is H, R$^2$ cannot be —(CH$_2$)$_2$CO$_2$CH$_3$, (CH$_2$)$_2$CO$_2$H, or —(CH$_2$)$_2$C(O)NH$_2$;
when R$^1$ is —OCH$_3$, R$^2$ is H, and R$^4$ is H, R$^3$ cannot be —CH$_2$OH or Cl; and when R$^1$ is —OCH$_3$, R$^2$ is H, R$^3$ is —CH$_3$, R$^4$ cannot be H.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs.

The term "alkoxy" means groups of from 1 to 6 carbon atoms of a straight, branched, or cyclic configuration and combinations thereof attached to the parent structure through an oxygen. Examples include methoxy, ethoxy, propoxy, isopropoxy, butoxy, cyclopropyloxy, cyclohexyloxy, and the like. Alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

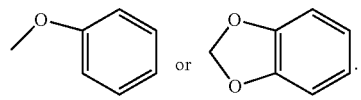

The term "halogen" means fluoro, chloro, bromo, or iodo. The term "halogenated" means containing a halogen substituent. Thus, for example, a halogenated alkoxy is an alkoxy substituted with a halogen.

The term "deuterated" means one or more of the hydrogen atoms contained in the compound have been replaced by its heavier stable isotope deuterium.

The term "ArX" means Aryl-X, or an aryl group substituted with H or a halogen. The term "aryl" means an aromatic monocyclic or multicyclic (polycyclic) ring system (including fused, bridged, or spiro ring systems) of 6 to about 19 carbon atoms, preferably of 6 to about 10 carbon atoms, and includes arylalkyl groups. In the case of a multicyclic ring system, only one of the rings needs to be aromatic for the ring system to be defined as "aryl." The ring system of the aryl group may be optionally substituted with halogen. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "alkyl" means an aliphatic hydrocarbon group which may be straight or branched having about 1 to about 6 carbon atoms in the chain (or the number of carbons designated by "C$_n$-C$_n$", where n is the numerical range of carbon atoms). Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkenyl chain. Exemplary alkenyl groups include, without limitation, ethenyl, propenyl, n-butenyl, and i butenyl.

The term "alkynyl" means an aliphatic hydrocarbon group containing a carbon-carbon triple bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "heterocyclyl" refers to a stable 3- to 18-membered ring (radical) of carbon atoms and from one to five heteroatoms selected from nitrogen, oxygen, and sulfur. The heterocyclyl may be a monocyclic or a polycyclic ring system, which may include fused, bridged, or spiro ring systems; and the nitrogen, carbon, or sulfur atoms in the heterocyclyl may be optionally oxidized; the nitrogen atom may be optionally quaternized; and the ring may be partially or fully saturated. Examples of such heterocyclyls include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" means an aromatic monocyclic or multi-cyclic ring system of about 5 to about 14 ring atoms, or about 5 to about 10 ring atoms, in which one or more of the atoms in the ring system is/are element(s) other than carbon, for example, nitrogen, oxygen, or sulfur. In the case of multi-cyclic ring systems, only one of the rings needs to be aromatic for the ring system to be defined as "heteroaryl." The heteroaryl may contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydrobenzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-c]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

Further heterocyclyls and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The phrases "substituted or unsubstituted" and "optionally substituted" mean a group may (but does not necessarily) have a substituent at each substitutable atom of the group (including more than one substituent on a single atom), and the identity of each substituent is independent of the others.

The term "substituted" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. However, exceptions to these rules exist in the compound of formula (I), specifically with respect to N-oxides (i.e., when $R^8$ is present as 0). Combinations of substituents and/or variables are permissible only if such combinations result in stable compounds. By "stable compound" it is meant a compound that is sufficiently robust to survive isolation to a useful degree of purity from a reaction mixture and formulation into an efficacious therapeutic agent.

The term "compound(s)" and equivalent expressions means compounds herein described, which expression includes the prodrugs, the pharmaceutically acceptable salts, the oxides, and the solvates, e.g. hydrates, where the context so permits.

Compounds described herein may contain one or more asymmetric centers and may thus give rise to enantiomers, diastereomers, and other stereoisomeric forms. Each chiral center may be defined in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. All tautomeric forms are also intended to be included.

The recitation of "a compound" is intended to include salts, solvates, oxides, and inclusion complexes of that compound as well as any stereoisomeric form, or a mixture of any such forms of that compound in any ratio. Thus, in accordance with some embodiments, a compound as described herein, including in the contexts of pharmaceutical compositions, methods of treatment, and compounds per se, is provided as the salt form.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed by the present invention.

The term "pharmaceutically acceptable salt" refers to salts prepared from pharmaceutically acceptable non-toxic acids or bases including inorganic acids and bases and organic acids and bases.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

In one embodiment of the compound of formula (I), $R^1$ is a branched or unbranched $C_{1-6}$ alkoxy. For example, and without limitation, $R^1$ may be methoxy, ethoxy, propoxy, isopropoxy, butoxy, cyclopropyloxy, cyclohexyloxy. In one embodiment, the $C_{1-6}$ alkoxy is unbranched. In another embodiment, the $C_{1-6}$ alkoxy is branched. In one embodiment, the branched or unbranched $C_{1-6}$ alkoxy is substituted with Y, as defined herein (i.e., —$CO_2CH_3$, —NHBoc, —C(O)$NH_2$, —$CO_2H$, —$NH_3Cl$, —NHC(O)$CH_3$). In another embodiment, the branched or unbranched $C_{1-6}$ alkoxy is substituted with —$NHR^5$, —C(O)NHCH($CH_3$)$_2$, or O($CH_2$)$_2$O$R^6$. In one embodiment, the alkoxy is halogenated. In another embodiment, the alkoxy is deuterated.

In one embodiment of the compound of formula (I), $R^2$ is H. In another embodiment, $R^2$ is branched or unbranched $C_{1-6}$ alkyl, branched or unbranched $C_{2-6}$ alkenyl, or branched or unbranched $C_{2-6}$ alkynyl. The branched or unbranched $C_{1-6}$ alkyl, branched or unbranched $C_{2-6}$ alkenyl, or branched or unbranched $C_{2-6}$ alkynyl is, in one embodiment, optionally substituted with Z, as defined herein.

In one embodiment of the compound of formula (I), $R^3$ is selected from $C_{1-6}$ alkyl, halogen, branched or unbranched $C_{1-6}$ hydroxyalkyl, —C(O)$CH_3$, —OH, or heterocyclyl optionally substituted with $R^7$, as defined herein (i.e., —ArX or —$CH_2$ArX).

In one embodiment of the compound of formula (I), $R^4$ is selected from H, —OH, branched or unbranched $C_{1-6}$ hydroxyalkyl, or —C(O)$CH_3$.

In one embodiment of the compound of formula (I), $R^5$ is H, —C(O)$CH_3$, or C(O)Ar. In one embodiment of the compound of formula (I), $R^6$ is branched or unbranched $C_{1-6}$ alkyl, —($CH_2$)$_2$NHBoc, —($CH_2$)$_2$NH(O)$CH_3$, or —($CH_2$)$_2$$NH_3Cl$.

In one embodiment of the compound of formula (I), $R^7$ is —ArX or —$CH_2$ArX, where "Ar" means "aryl" as defined herein. "Aryl-X" means an aryl group substituted with H or a halogen.

In one embodiment of the compound of formula (I), $R^8$ is optional, and when present is O. Thus, when $R^8$ is present, the compound of formula (I) is an N-oxide.

In one embodiment of the compound of formula (I), X is H or halogen.

In one embodiment of the compound of formula (I), Y is selected from the following substituents: —$CO_2CH_3$, —NHBoc, —C(O)$NH_2$, —$CO_2H$, —$NH_3Cl$, —NHC(O)$CH_3$.

In one embodiment of the compound of formula (I), Z is —$CO_2CH_3$, —$CO_2H$, C(O)$NH_2$, or an amino-substituted heteroaryl. When Z is an amino-substituted heteroaryl, suitable heteroaryl substituents include furan, thiophene, pyrrole, oxazole, thiazole, imidazole, pyrazole, isoxazole, isothiazole, 1,2,3-oxadiazole, 1,2,4-oxadiazole, 1,2,3-thiadiazole, 1,2,3-triazole, 1,2,4-triazole, tetrazole, and 1,2,3,4-oxatriazole.

Compounds of formula (I) have the following provisos:
when $R^1$ is —$OCH_3$, $R^3$ is —$CH_3$, and $R^4$ is H, $R^2$ cannot be —($CH_2$)$_2$$CO_2CH_3$, ($CH_2$)$_2$$CO_2H$, or —($CH_2$)$_2$C(O)$NH_2$;
when $R^1$ is —$OCH_3$, $R^2$ is H, and $R^4$ is H, $R^3$ cannot be —$CH_2OH$ or Cl; and
when $R^1$ is —$OCH_3$, $R^2$ is H, $R^3$ is —$CH_3$, $R^4$ cannot be H.

In one embodiment of the compound of formula (I), $R^1$ is —$OCH_3$;
$R^2$ is branched or unbranched $C_{1-6}$ alkyl substituted with —$CO_2CH_3$;
$R^3$ is methyl; and
$R^4$ is H.

In accordance with this embodiment, $R^2$ is selected from the group consisting of

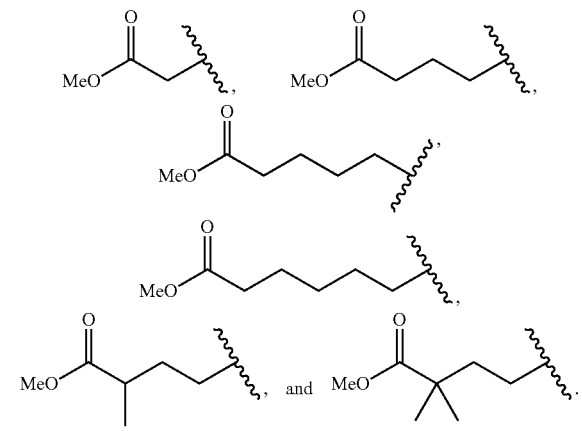

In another embodiment of the compound of formula (I), $R^1$ is —$OCH_3$;
$R^2$ is branched or unbranched $C_{1-6}$ alkyl substituted with —$CO_2H$;
$R^3$ is methyl; and
$R^4$ is H.

In accordance with this embodiment, $R^2$ is selected from the group consisting of

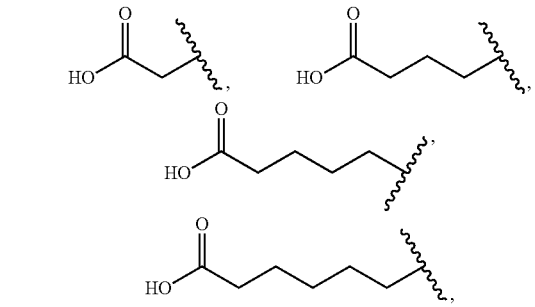

-continued

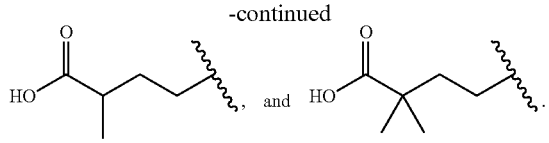

In yet another embodiment of the compound of formula (I),
$R^1$ is —OCH$_3$;
$R^2$ is branched or unbranched $C_{1-6}$ alkyl substituted with —C(O)NH$_2$;
$R^3$ is methyl; and
$R^4$ is H.

In accordance with this embodiment, $R^2$ is selected from the group consisting of

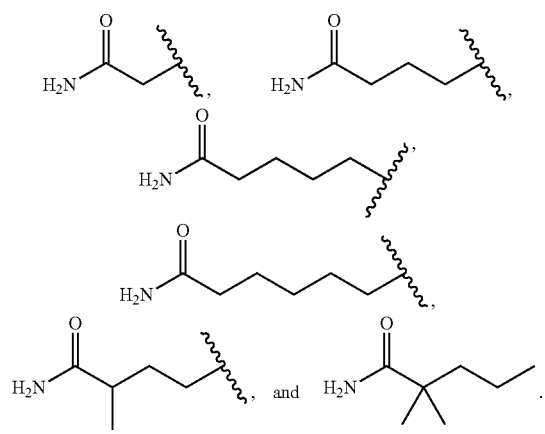

In a further embodiment of the compound of formula (I),
$R^1$ is —OCH$_3$;
$R^2$ is branched or unbranched $C_{1-6}$ alkyl substituted with an amino-substituted heteroaryl;
$R^3$ is methyl; and
$R^4$ is H.

In one specific embodiment, the amino-substituted heteroaryl is 1,2,4-oxadiazole. In accordance with this embodiment, $R^2$ is selected from the group consisting of

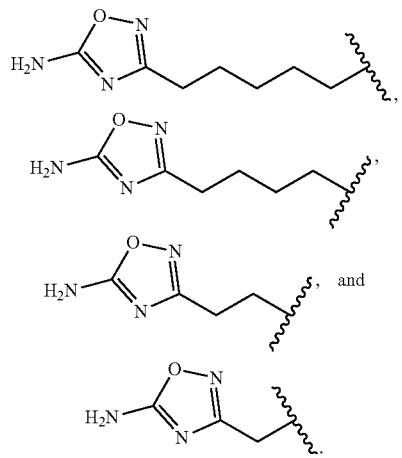

In a further embodiment of the compound of formula (I),
$R^2$ is H;
$R^3$ is methyl; and
$R^4$ is H.

In accordance with this embodiment, $R^1$ is $C_{1-6}$ alkoxy substituted with CO$_2$CH$_3$. In specific embodiments, $R^1$ is selected from the group consisting of

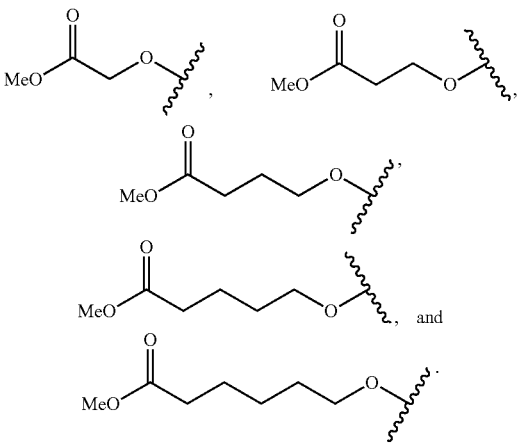

In another embodiment, $R^1$ is $C_{1-6}$ alkoxy substituted with —NHBoc. In specific embodiments, $R^1$ is selected from the group consisting of

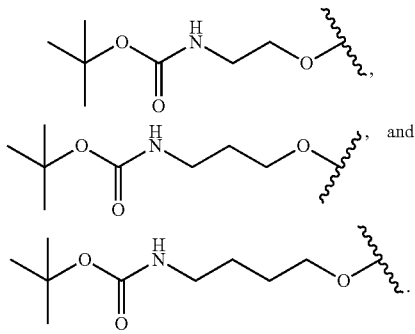

In a further embodiment, $R^1$ is $C_{1-6}$ alkoxy substituted with —C(O)NH$_2$. In specific embodiments, $R^1$ is selected from the group consisting of

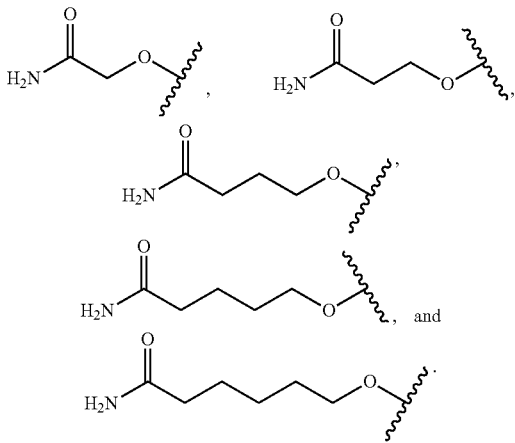

In yet another embodiment, $R^1$ is $C_{1-6}$ alkoxy substituted with —$CO_2H$. In specific embodiments, $R^1$ is selected from the group consisting of

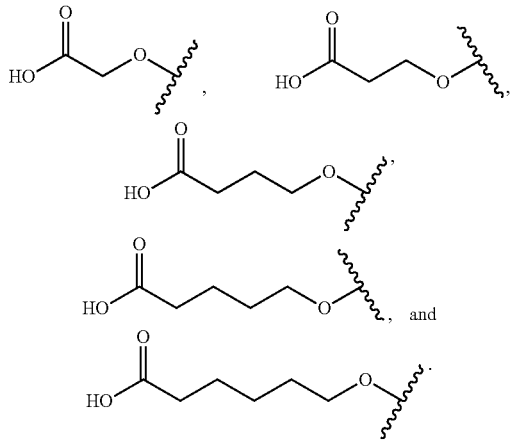

In another embodiment, $R^1$ is $C_{1-6}$ alkoxy substituted with —$NH_3Cl$. In accordance with this embodiment, $R^1$ may be selected from the group consisting of

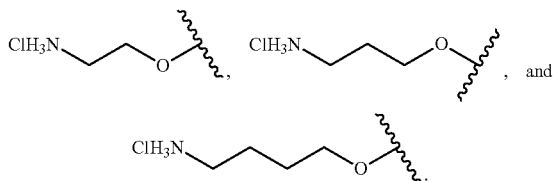

In one embodiment, $R^1$ is $C_{1-6}$ alkoxy substituted with —$NHC(O)CH_3$. In specific embodiments, $R^1$ is selected from the group consisting of

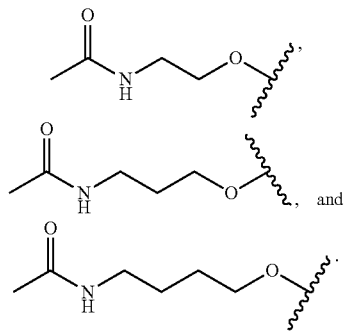

In another embodiment, $R^1$ is —$NH_2$.
In a further embodiment, $R^1$ is selected from the group consisting of

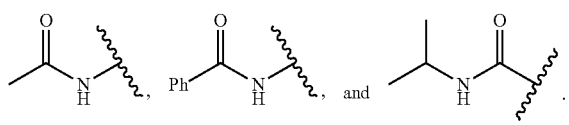

In yet another embodiment, $R^1$ is —$O(CH_2)_2OR^6$. In specific embodiments, $R^1$ is selected from the group consisting of

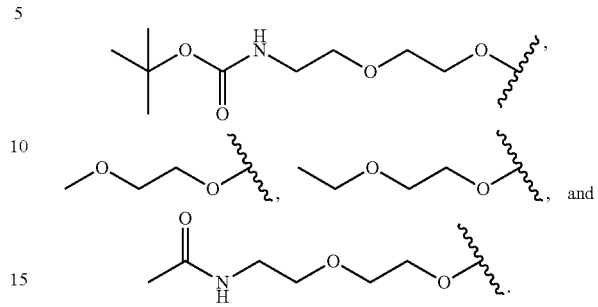

In yet another embodiment, $R^1$ is selected from —$OCD_3$ or —$OCF_3$.

In another embodiment of the compound of formula (I),
$R^1$ is —$OCH_3$;
$R^2$ is H; and
$R^4$ is H.

According to this embodiment, $R^3$ may be halogen. In one particular embodiment, $R^3$ is Cl.

In another embodiment, $R^3$ is selected from the group consisting of

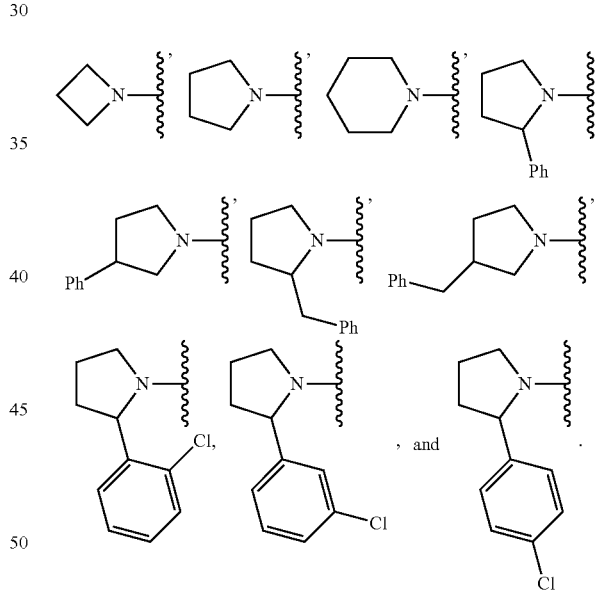

In another embodiment of the compound of formula (I),
$R^1$ is —$OCH_3$;
$R^3$ is methyl; and
$R^4$ is H.

According to this embodiment, $R^2$ is selected from the group consisting of

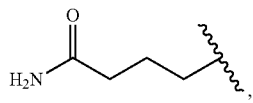

-continued
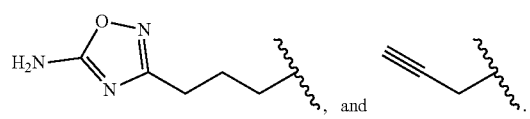, and
In another embodiment, the compound of formula (I) is selected from the group consisting of:
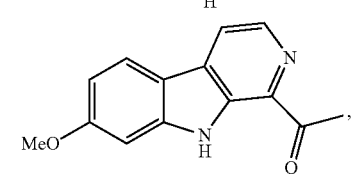
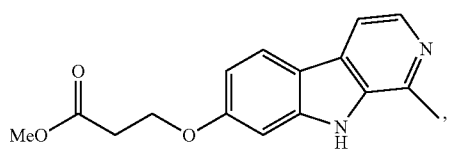
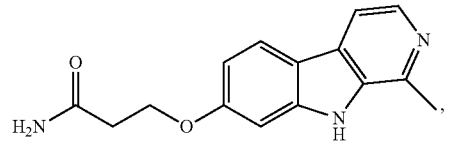
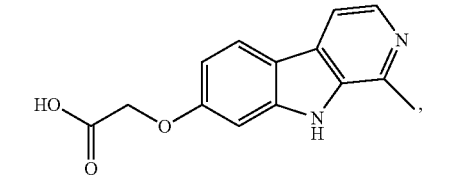
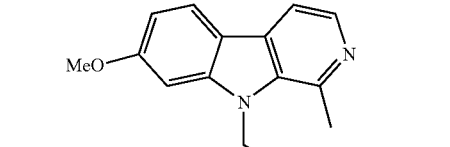
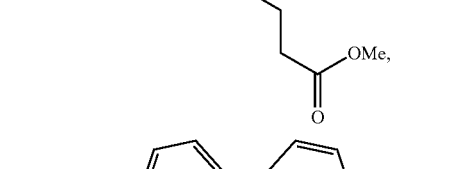
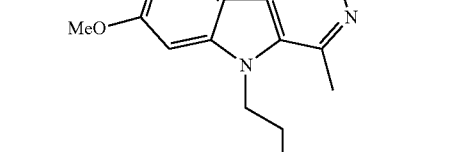
-continued
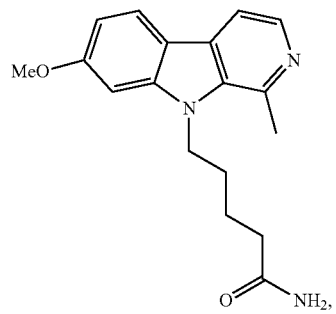
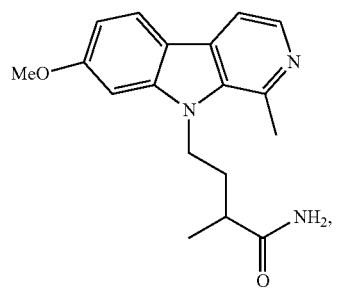
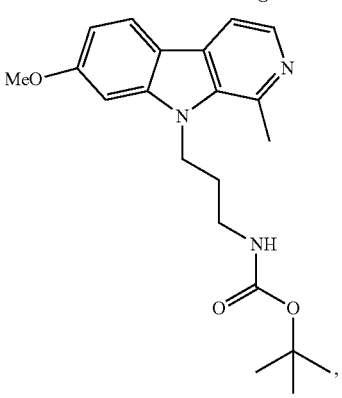
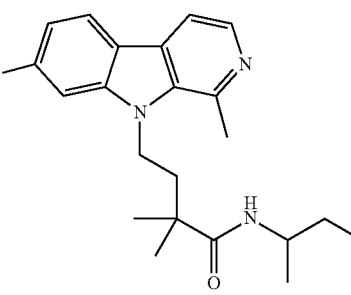
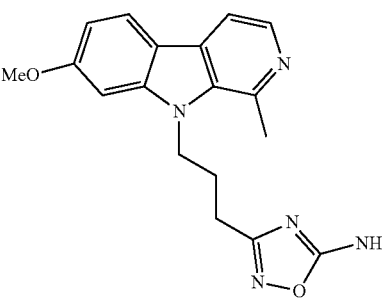

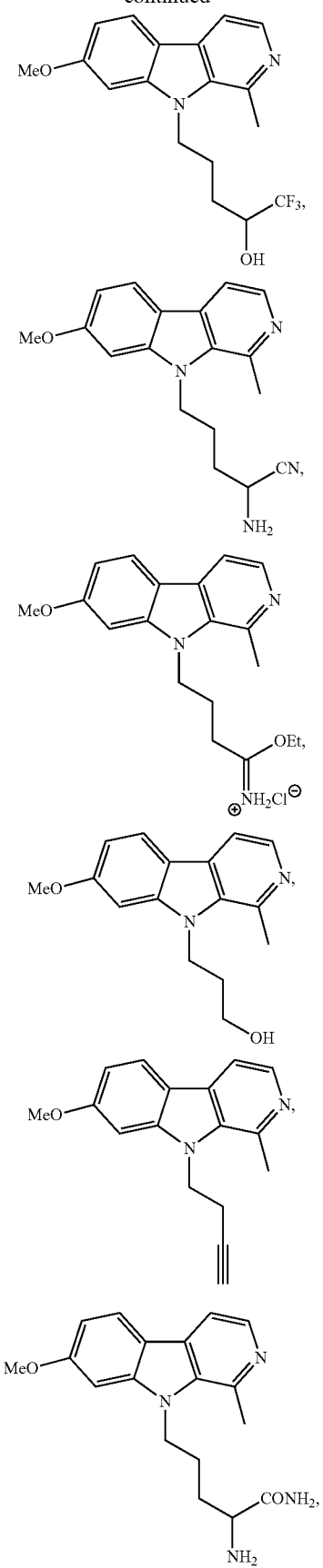

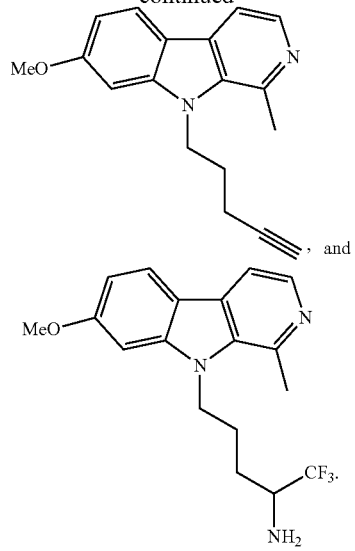

Another aspect relates to a method of inhibiting activity of dual-specificity tyrosine phosphorylation-regulated kinase 1A (DYRK1A) in a cell. This method involves contacting the cell with a compound of formula (I) to inhibit activity of DYRK1A in the cell.

According to this aspect, in one embodiment the cell is a mammalian cell. Mammalian cells may include cells from, for example, mice, hamsters, rats, cows, sheep, pigs, goats, horses, monkeys, dogs (e.g., *Canis familiaris*), cats, rabbits, guinea pigs, and primates, including humans. For example, the cell may be a human cell.

In one embodiment, the cell is a pancreatic beta cell. If needed, methods for determining whether a cell has a pancreatic beta cell phenotype are known in the art and include, without limitation, incubating the cell with glucose and testing whether insulin expression in the cell is increased or induced. Other methods include testing whether beta cell specific transcription factors are expressed, the detection of beta cell specific gene products with the help of RNA quantitative PCR, the transplantation of a candidate cell in diabetic mice, and subsequent testing of the physiologic response following said transplantation as well analyzing the cells with electron microscopy.

In another embodiment, the cell is a cancer cell.

In yet another embodiment, the cell is a neural cell.

Methods descried herein may be carried out ex vivo or in vivo. When carried out ex vivo, a population of cells may be, according to one embodiment, provided by obtaining cells from a pancreas and culturing the cells in a liquid medium suitable for the in vitro or ex vivo culture of mammalian cells, in particular human cells. For example, and without limitation, a suitable and non-limiting culture medium may be based on a commercially available medium such as RPMI1640 from Invitrogen.

A further aspect relates to a method of increasing cell proliferation in a population of pancreatic beta cells. This method involves contacting a population of pancreatic beta cells with a compound of formula (I) to increase cell proliferation in the population of pancreatic beta cells.

In one embodiment, contacting is carried out with a composition (i.e., a single composition) comprising the compound.

The method may further involve contacting the population of pancreatic beta cells with a transforming growth factor beta (TGFβ) superfamily signaling pathway inhibitor. In accordance with this embodiment, the method may be carried out with a composition comprising a compound of formula (I) and the TGFβ superfamily signaling pathway inhibitor. In another embodiment, the compound of formula (I) and the TGFβ superfamily signaling pathway inhibitor separately contact a population of pancreatic beta cells simultaneously or in sequence.

TGFβ superfamily signaling pathway inhibitors include small molecules and other (e.g., neutralizing monoclonal antibodies, synthetic/recombinant peptide inhibitors, and siRNA) inhibitors of the BMP family of receptors, activin and inhibin receptors, and GDF11 receptors and related receptors.

TGFβ superfamily signaling pathway inhibitors are known in the art and include, without limitation, SB431542, SB505124, A-83-01, Decorin, soluble TGF-β receptor, Ierdelimumab, metelimumab, AP-12009, Follistatin, FLRG, GAST-1, GDF8 propeptide, MYO-029, Noggin, chordin, Cer/Dan, ectodin, and Sclerostin (see Tsuchida et al., "Inhibitors of the TGF-beta Superfamily and their Clinical Applications," *Mini Rev. Med Chem.* 6(11):1255-61 (2006), which is hereby incorporated by reference in its entirety).

Other inhibitors of TGF-β signaling include, without limitation, 2-(3-(6-Methylpyridin-2-yl)-1H-pyrazol-4-yl)-1,5 napththyridine; [3-(Pyridin-2-yl)-4-(4-quinoyl)]-1H-pyrazole; 3-(6-Methylpyridin-2-yl)-4-(4-quinolyl)-1-phenylthiocarbamoyl-1H-pyrazole; SB-431542; SM16; SB-505124; and 2-(3-(6-Methylpyridin-2-yl)-1H-pyrazol-4-yl)-1,5 napththyridine (ALK5 Inhibitor II) (see U.S. Pat. No. 8,298,825, which is hereby incorporated by reference in its entirety).

Inhibitors of TGF-β signaling are described in Callahan et al., "Identification of Novel Inhibitors of the Transforming Growth Factor β1 (TGF-β1) Type 1 Receptor (ALK5)," *J. Med Chem.* 45:999-1001 (2002); Sawyer et al., "Synthesis and Activity of New Aryl- and Heteroaryl-substituted Pyrazole Inhibitors of the Transforming Growth Factor-beta Type I Receptor Kinase Domain," *J. Med Chem.* 46:3953-3956 (2003); Gellibert et al., "Identification of 1,5-naphthyridine Derivatives as a Novel Series of Potent and Selective TGF-beta Type I Receptor Inhibitors," *J. Med. Chem.* 47:4494-4506 (2004); Tojo et al., *Cancer Sci.* 96:791-800 (2005); Valdimarsdottir et al., "Functions of the TGFbeta Superfamily in Human Embryonic Stem Cells," *APMIS* 113:773-389 (2005); Petersen et al., "Oral Administration of GW788388, an Inhibitor of TGF-beta Type I and II Receptor Kinases, Decreases Renal Fibrosis," *Kidney International* 73:705-715 (2008); Yingling et al., "Development of TGF-beta Signalling Inhibitors for Cancer Therapy," *Nature Rev. Drug Disc.* 3:1011-1022 (2004); Byfield et al., "SB-505124 Is a Selective Inhibitor of Transforming Growth Factor-β Type Receptors ALK4, ALK5, and ALK7," *Mol. Pharmacol.* 65:744-752 (2004); Dumont et al., "Targeting the TGF Beta Signaling Network in Human Neoplasia," *Cancer Cell* 3:531-536 (2003); PCT Publication No. WO 2002/094833; PCT Publication No. WO 2004/026865; PCT Publication No. WO 2004/067530; PCT Publication No. WO 2009/032667; PCT Publication No. WO 2004/013135; PCT Publication No. WO 2003/097639; PCT Publication No. WO 2007/048857; PCT Publication No. WO 2007/018818; PCT Publication No. WO 2006/018967; PCT Publication No. WO 2005/039570; PCT Publication No. WO 2000/031135; PCT Publication No. WO 1999/058128; U.S. Pat. Nos. 6,509,318; 6,090,383; 6,419,928; 9,927,738; 7,223,766; 6,476,031; 6,419,928; 7,030,125; 6,943,191; U.S. Patent Application Publication No. 2005/0245520; U.S. Patent Application Publication No. 2004/0147574; U.S. Patent Application Publication No. 2007/0066632; U.S. Patent Application Publication No. 2003/0028905; U.S. Patent Application Publication No. 2005/0032835; U.S. Patent Application Publication No. 2008/0108656; U.S. Patent Application Publication No. 2004/015781; U.S. Patent Application Publication No. 2004/0204431; U.S. Patent Application Publication No. 2006/0003929; U.S. Patent Application Publication No. 2007/0155722; U.S. Patent Application Publication No. 2004/0138188 and U.S. Patent Application Publication No. 2009/0036382, which are hereby incorporated by reference in their entirety.

Exemplary inhibitors of TGF-β signaling include, but are not limited to, AP-12009 (TGF-β Receptor type II antisense oligonucleotide), Lerdelimumab (CAT 152, antibody against TGF-β Receptor type II) GC-1008 (antibody to all isoforms of human TGF-β), ID11 (antibody to all isoforms of murine TGF-β), soluble TGF-β, soluble TGF-β Receptor type II, dihydropyrroloimidazole analogs (e.g., SKF-104365), tri-arylimidazole analogs (e.g., SB-202620 (4-(4-(4-fluorophenyl)-5-(pyridin-4-yl)-1H-imidazol-2-yl)benzoic acid) and SB-203580 (4-(4-Fluorophenyl)-2-(4-methylsulfinyl phenyl)-5-(4-pyridyl)-1H-imidazole)), RL-0061425, 1,5-naphthyridine aminothiazole and pyrazole derivatives (e.g., 4-(6-methyl-pyridin-2-yl)-5-(1,5-naphthyridin-2-yl)-1,3-thiazole-2-amine and 2-[3-(6-methyl-pyridin-2-yl)-1H-pyrazole-4-yl]-1,5-naphthyridine), SB-431542 (4-(5-Benzol[1,3]dioxol-5-yl-4-pyridin-2-yl-1H-imidazol-2-yl)-benzamide), GW788388 (4-(4-(3-(pyridin-2-yl)-1H-pyrazol-4-yl)pyridin-2-yl)-N-(tetrahydro-2H-pyran-4-yl) benzamide), A-83-01 (3-(6-Methyl-2-pyridinyl)-N-phenyl-4-(4-quinolinyl)-1H-pyrazole-β-carbothioamide), Decorin, Lefty 1, Lefty 2, Follistatin, Noggin, Chordin, Cerberus, Gremlin, Inhibin, BIO (6-bromo-indirubin-3'-oxime), Smad proteins (e.g., Smad6, Smad7), and Cystatin C.

Inhibitors of TGF-β signaling also include molecules which inhibit TGF-β Receptor type I. Inhibitors of TGF-β Receptor type I include, but are not limited to, soluble TGF-β Receptor type I; AP-11014 (TGF-β Receptor type I antisense oligonucleotide); Metelimumab (CAT 152, TGF-β Receptor type I antibody); LY550410; LY580276 (3-(4-fluorophenyl)-5,6-dihydro-2-(6-methylpyridin-2-yl)-4H-pyrrolo[1,2-b]pyrazole); LY364947 (4-[3-(2-Pyridinyl)-1H-pyrazol-4-yl]-quinoline); LY2109761; LY573636 (N-((5-bromo-2-thienyl)sulfonyl)-2,4-dichlorobenzamide); SB-505124 (2-(5-Benzo[1,3]dioxol-5-yl-2-tert-butyl-3H-imidazol-4-yl)-6-methylpyridine); SD-208 (2-(5-Chloro-2-fluorophenyl)-4-[(4-pyridyl)amino]pteridine); SD-093; KI2689; SM16; FKBP12 protein; and 3-(4-(2-(6-methylpyridin-2-yl)H-imidazo[1,2-a]pyridin-3-yl)quinolin-7-yloxy)-N,N-dimethylpropan-1-amine.

Inhibitors of TGF-β Receptor type I are described in Byfield and Roberts, "Lateral Signaling Enhances TGF-beta Response Complexity," *Trends Cell Biol.* 14:107-111 (2004); Sawyer et al., "Synthesis and Activity of New Aryl- and Heteroaryl-substituted 5,6-dihydro-4H-pyrrolo[1,2-b] pyrazole Inhibitors of the Transforming Growth Factor-beta Type I Receptor Kinase Domain," *Bioorg. Med Chem. Lett.* 14:3581-3584 (2004); Sawyer et al., "Synthesis and Activity of New Aryl- and Heteroaryl-substituted Pyrazole Inhibitors of the Transforming Growth Factor-beta Type I Receptor Kinase Domain," *J. Med. Chem.* 46:3953-3956 (2003); Byfield et al., "SB-505124 Is a Selective Inhibitor of Transforming Growth Factor-beta Type I Receptors ALK4, ALK5, and ALK7," *Mol. Pharmacol.* 65:744-752 (2004);

Gellibert et al., "Identification of 1,5-naphthyridine Derivatives as a Novel Series of Potent and Selective TGF-beta Type I Receptor Inhibitors," *J. Med. Chem.* 47:4494-4506 (2004); Yingling et al., "Development of TGF-beta Signalling Inhibitors for Cancer Therapy," *Nature Rev. Drug Disc.* 3:1011-1022 (2004); Dumont et al., "Targeting the TGF Signaling Network in Human Neoplasia," *Cancer Cell* 3:531-536 (2003); Tojo et al., "The ALK-5 Inhibitor A-83-01 Inhibits Smad Signaling and Epithelial-to-mesenchymal Transition by Transforming Growth Factor-β," *Cancer Sci.* 96:791-800 (2005); PCT Publication No. WO 2004/026871; PCT Publication No. WO 2004/021989; PCT Publication No. WO 2004/026307; PCT Publication No. WO 2000/012497; U.S. Pat. Nos. 5,731,424; 5,731,144; 7,151,169; U.S. Patent Application Publication No. 2004/00038856 and U.S. Patent Application Publication No. 2005/0245508, all of which are herein incorporated in their entirety.

In one embodiment, the TGFβ superfamily signaling pathway inhibitor includes compounds that interfere with TGFβ superfamily ligands, receptors, and/or downstream signaling molecules (e.g., SMADs) or nuclear targets (e.g., chromatin modifying complexes and transcription factors).

In one embodiment, the TGFβ superfamily signaling pathway inhibitor may be antisera that neutralize, e.g., TGFβ ligand.

In another embodiment, the TGFβ superfamily signaling pathway inhibitor is selected from the group consisting of an inhibitor of TGFβ/TGFβ receptor binding, activin or inhibin/activin receptor binding, and bone morphogenetic protein (BMP)/BMP receptor binding.

In a specific embodiment, the TGFβ superfamily signaling pathway inhibitor is an inhibitor of TGFβ/TGFβ receptor binding selected from the group consisting of LY364947 and GW788388.

In another specific embodiment, the TGFβ superfamily signaling pathway inhibitor is an inhibitor of activin or inhibin/activin receptor binding selected from the group consisting of SB431542 and Alk5 inhibitor II. Additional exemplary inhibitors of activin or inhibin/activin receptor binding may be selected from the group consisting of SB-505124, BYM388, follistatin, follistatin-related protein (FSRP), follistatin domains (i.e., Fs2, Fs12, Fs123), A-83-01, Cripto, GW788388, BAMBI, and Sotatercept (see Byfield et al., "SB-505124 is a Selective Inhibitor of Transforming Growth Factor-Beta Type I Receptors ALK4, ALK5, and ALK7," *Mol. Pharmacol.* 65(3):744-52 (2004); Lach-Trifilieffa et al., "An Antibody Blocking Activin Type II Receptors Induces Strong Skeletal Muscle Hypertrophy and Protects from Atrophy," *Mol. Cell. Biol.* 34(4):606-18 (2014); Zhang et al., "Inhibition of Activin Signaling Induces Pancreatic Epithelial Cell Expansion and Diminishes Terminal Differentiation of Pancreatic O-Cells," *Diabetes* 53(8):2024-33 (2004); Harrington et al., "Structural Basis for the Inhibition of Activin Signalling by Follistatin," *EMBO J.* 25(5):1035-45 (2006); Tojo et al., "The ALK-5 Inhibitor A-83-01 Inhibits Smad Signaling and Epithelial-to-Mesenchymal Transition by Transforming Growth Factor-Beta," *Cancer Sci.* 96(11):790-800 (2005); Yan et al., "Human BAMBI Cooperates with Smad7 to Inhibit Transforming Growth Factor-Beta Signaling," *J. Biol. Chem.* 284(44):30097-104 (2009); Tan et al., "Targeted Inhibition of Activin Receptor-Like Kinase 5 Signaling Attenuates Cardiac Dysfunction Following Myocardial Infarction," *Am. J. Physiol. Heart Circ. Physiol.* 298(5):H1415-25 (2010); and Gokoffski et al., "Activin and GDF11 Collaborate in Feedback Control of Neuroepithelial Stem Cell Proliferation and Fate," *Develop.* 138(19):4131-42 (2011), which are hereby incorporated by reference in their entirety).

In another specific embodiment, the TGFβ superfamily signaling pathway inhibitor is an inhibitor of BMP/BMP receptor binding. An exemplary inhibitor of BMP/BMP receptor binding is LDN193189. Additional exemplary BMP inhibitors may be selected from the group consisting of noggin, sclerostin, chordin, CTGF, follistatin, gremlin, inhibin, DMH1, DMH2, Dorsomorphin, K02288, LDN212854, DM 3189, BMP-3, and BAMBI (see PCT Publication No. WO 2014/018691 and Mohedas et al., "Development of an ALK2-Biased BMP Type I Receptor Kinase Inhibitor," *ACS Chem. Biol.* 8(6):1291-302 (2013); Yan et al., "Human BAMBI Cooperates with Smad7 to Inhibit Transforming Growth Factor-Beta Signaling," *J. Biol. Chem.* 284(44):30097-104 (2009), which are hereby incorporated by reference in their entirety).

According to another embodiment, the TGFβ superfamily signaling pathway inhibitor is a SMAD signaling pathway inhibitor. Exemplary SMAD signaling pathway inhibitors may be selected from the group including, without limitation, SMAD3 siRNA, SMAD 2/3 siRNA, PD169316, SB203580, SB202474, specific inhibitor of Smad3 (SIS3), HSc025, and SB525334 (see Qureshi et al., "Smad Signaling Pathway is a Pivotal Component of Tissue Inhibitor of Metalloproteinases-3 Regulation by Transforming Growth Factor Beta in Human Chondrocytes," *BBA Mol. Cell Res.* 1783(9):1605-12 (2008); Hasegawa et al., "A Novel Inhibitor of Smad-Dependent Transcriptional Activation Suppresses Tissue Fibrosis in Mouse Models of Systemic Sclerosis," *Arthritis Rheum.* 60(11):3465-75 (2009); and Ramdas et al., "Canonical Transforming Growth Factor-β Signaling Regulates Disintegrin Metalloprotease Expression in Experimental Renal Fibrosis via miR-29," *Am. J. Pathol.* 183(6):1885-96 (2013), which are hereby incorporated by reference in their entirety).

Additional exemplary SMAD signaling pathway inhibitors include, without limitation, miR-100, LDN 193189, SMAD-binding peptide aptamers (e.g., Trx-FoxH1, Trx-Le1, Trx-CBP, Trx-SARA), pirfenidone, and LDN193189 (see Fu et al., "MicroRNA-100 Inhibits Bone Morphogenetic Protein-Induced Osteoblast Differentiation by Targeting Smad," *Eur. Rev. Med. Pharmacol. Sci.* 20(18):3911-19 (2016); Boergermann et al., "Dorsomorphin and LDN-193189 Inhibit BMP-Mediated Smad, p38 and Akt signalling in C2C12 Cells," *Int. J. Biochem. Cell Biol.* 42(11):1802-7 (2010); Cui et al., "Selective Inhibition of TGF-Responsive Genes by Smad-Interacting Peptide Aptamers from FoxH1, Lef1 and CBP," *Oncogene* 24:3864-74 (2005); Zhao et al., "Inhibition of Transforming Growth Factor-Beta1-Induced Signaling and Epithelial-to-Mesenchymal Transition by the Smad-Binding Peptide Aptamer Trx-SARA," *Mol. Biol. Cell* 17:3819-31 (2006); Li et al., "Oral Pirfenidone Protects Against Fibrosis by Inhibiting Fibroblast Proliferation and TGF-β Signaling in a Murine Colitis Model," *Biochem. Pharmacol.* 117:57-67 (2016); and Cook et al., "BMP Signaling Balances Murine Myeloid Potential Through SMAD-Independent p38MAPK and NOTCH Pathways," *Blood* 124(3):393-402 (2014), which are hereby incorporated by reference in their entirety).

In another specific embodiment, the TGFβ superfamily signaling pathway inhibitor is an inhibitor of the trithorax complex. Exemplary trithorax complex inhibitors include, without limitation, WDR5-0103, MI-1, MI-2, MI-2-2, MLS001171971-01, ML227, MCP-1, RBB5 siRNA, and MLL1 siRNA (see Senisterra et al., "Small-Molecule Inhibition of MLL Activity by Disruption of its Interaction with WDR5," *Biochem. J.* 449(1):151-9 (2013); Cierpicki et al., "Challenges and Opportunities in Targeting the Menin-MLL Interaction," *Future Med. Chem.* 6(4):447-62 (2014); Lee et al., "Roles of DPY30 in the Proliferation and Motility of Gastric Cancer Cells," *PLOS One* 10(7):e0131863 (2015); and Zhou et al., "Combined Modulation of Polycomb and Trithorax Genes Rejuvenates β Cell Replication," *J. Clin. Invest.* 123(11):4849-4858 (2013), which are hereby incorporated by reference in their entirety).

In another embodiment, the TGFβ superfamily signaling pathway inhibitor is an inhibitor of the polycomb repressive complex 2 ("PRC2"). Exemplary PRC2 inhibitors include GSK926, EPZ005687, GSK126, GSK343, Eli, UNC1999, EPZ6438, Constellation Compound 3, EZH2 siRNA, and 3-deazaneplanocin A (see Verma et al., "Identification of Potent, Selective, Cell-Active Inhibitors of the Histone Lysine Methyltransferase EZH2," *ACS Med Chem. Lett.* 3:1091-6 (2012); Xu et al., "Targeting EZH2 and PRC2 Dependence as Novel Anticancer Therapy," *Exp. Hematol.* 43:698-712 (2015); Knutson et al., "A Selective Inhibitor of EZH2 Blocks H3K27 Methylation and Kills Mutant Lymphoma Cells," *Nat. Chem. Biol.* 8:890-6 (2012); Qi et al., "Selective Inhibition of Ezh2 by a Small Molecule Inhibitor Blocks Tumor Cells Proliferation," *Proc. Natl Acad Sci. USA* 109:21360-65 (2012); McCabe et al., "EZH2 Inhibition as a Therapeutic Strategy for Lymphoma with EZH2-Activating Mutations," *Nature* 492:108-12 (2012); Nasveschuk et al., "Discovery and Optimization of Tetramethylpiperidinyl Benzamides as Inhibitors of EZH2," *ACS Med. Chem. Lett.* 5:378-83 (2014); Broonn et al., "Polycomb Repressive Complex 2 Structure with Inhibitor Reveals a Mechanism of Activation and Drug Resistance," *Nature Comm.* 7:11384 (2016); Fiskus et al., "Histone Deacetylase Inhibitors Deplete Enhancer of Zeste 2 and Associated Polycomb Repressive Complex 2 Proteins in Human Acute Leukemia Cells," *Mol. Cancer Ther.* 5(12):3096-104 (2006); and Fiskus et al., "Combined Epigenetic Therapy with the Histone Methyltransferase EZH2 Inhibitor 3-Deazaneplanocin A and the Histone Deacetylase Inhibitor Panobinostat Against Human AML Cells," *Blood* 114(13):2733-43 (2009), which are hereby incorporated by reference in their entirety.) The method may further involve contacting the population of pancreatic beta cells with a glucagon-like peptide-1 receptor (GLP1R) agonist or a Dipeptidyl Peptidase IV ("DPP4") inhibitor. In accordance with this embodiment, the method may be carried out with a composition comprising a compound according to formula (I) of the present invention and the glucagon-like peptide-1 receptor (GLP1R) agonist or the DPP4 inhibitor, and, optionally, the TGFβ superfamily signaling pathway inhibitor. In another embodiment, the compound of formula (I), the GLP1R agonist or the DPP4 inhibitor, and, optionally, the TGFβ superfamily signaling pathway inhibitor each contact the population of pancreatic beta cells simultaneously or in sequence.

Glucagon-like peptide-1 receptor agonists mimic the effects of the incretin hormone GLP-1, which is released from the intestine in response to food intake. Their effects include increasing insulin secretion, decreasing glucagon release, increasing satiety, and slowing gastric emptying. An alternate approach to enhancing GLP1 concentrations in blood is prevention of its degradation by the enzyme Dipeptidyl Peptidase IV ("DPP4"). The GLP1 receptor agonists and the DPP4 inhibitors are among the most widely used drugs for the treatment of Type 2 diabetes (Campbell et al., "Pharmacology, Physiology and Mechanisms of Incretin Hormone Action," *Cell Metab.* 17:819-37 (2013); Guo X-H., "The Value of Short- and Long-Acting Glucagon-Like Peptide Agonists in the Management of Type 2 Diabetes Mellitus: Experience with Exenatide," *Curr. Med. Res. Opinion* 32(1):61-76 (2016); Deacon et al., "Dipeptidyl Peptidase-4 Inhibitors for the Treatment of Type 2 Diabetes: Comparison, Efficacy and Safety," *Expert Opinion on Pharmacotherapy* 14:2047-58 (2013); Lovshin, "Glucagon-Like Peptide-1 Receptor Agonists: A Class Update for Treating Type 2 Diabetes," *Can. J. Diabetes* 41:524-35 (2017); and Yang et al., "Lixisenatide Accelerates Restoration of Normoglycemia and Improves Human Beta Cell Function and Survival in Diabetic Immunodeficient NOD-scid IL2rg(null) RIP-DTR Mice Engrafted With Human Islets," *Diabetes Metab. Syndr. Obes.* 8:387-98 (2015), which are hereby incorporated by reference in their entirety).

Suitable GLP1R agonists include, e.g. and without limitation, exenatide, liraglutide, exenatide LAR, taspoglutide, lixisenatide, albiglutide, dulaglutide, and semaglutide. Exenatide and Exenatide LAR are synthetic exendin-4 analogues obtained from the saliva of the Heloderma suspectum (lizard). Liraglutide is an acylated analogue of GLP-1 that self-associates into a heptameric structure that delays absorption from the subcutaneous injection site. Taspoglutide shares 93% homology with the native GLP-1 and is fully resistant to DPP-4 degradation. Lixisenatide is a human GLP1R agonist. Albiglutide is a long-acting GLP-1 mimetic, resistant to DPP-4 degradation. Dulaglutide is a long-acting GLP1 analogue. Semaglutide is a GLP1R agonist approved for the use of T2D. Clinically available GLP1R agonists include, e.g., exenatide, liraglutide, albiglutide, dulaglutide, lixisenatide, semaglutide.

In some embodiments of the methods and compositions disclosed herein, the GLP1R agonist is selected from the group consisting of GLP1(7-36), GLP1 analogs, extendin-4, liraglutide, lixisenatide, semaglutide, and combinations thereof.

Additional suitable GLP1 agonists include, without limitation, disubstituted-7-aryl-5,5-bis(trifluoromethyl)-5,8-dihydropyrimido[4,5-d]pyrimidine-2,4(1H,3H)-dione compounds and derivatives thereof, e.g., 7-(4-Chlorophenyl)-1,3-dimethyl-5,5-bis(trifluoromethyl)-5,8-dihydropyrimido[4,5-d]pyrimidine-2,4(1H,3H)-dione (see, e.g., Nance et al., "Discovery of a Novel Series of Orally Bioavailable and CNS Penetrant Glucagon-like Peptide-1 Receptor (GLP-1R) Noncompetitive Antagonists Based on a 1,3-Disubstituted-7-aryl-5,5-bis(trifluoromethyl)-5,8-dihydropyrimido[4,5-d] pyrimidine-2,4(1H,3H)-dione Core," *J. Med. Chem.* 60:1611-1616 (2017), which is hereby incorporated by reference in its entirety).

Further suitable GLP1 agonists include positive allosteric modulators ("PAMS") of GLP1R, e.g., (S)-2-cyclopentyl-N-((1-isopropylpyrrolidin-2-yl)methyl)-10-methyl-1-oxo-1,2-dihydropyrazino[1,2-a]indole-4-carboxamide; (R)-2-cyclopentyl-N-((1-isopropylpyrrolidin-2-yl)methyl)-10-methyl-1-oxo-1,2-dihydropyrazino[1,2-a]indole-4-carboxamide; 2-cyclopentyl-N—(((S)-1-isopropylpyrrolidin-2-yl)methyl)-10-methyl-1-oxo-1,2,3,4-tetrahydropyrazino[1,2-a]indole-4-carboxamide; N—(((S)-1-isopropylpyrrolidin-2-yl)methyl)-10-methyl-1-oxo-2-((S)-tetrahydrofuran-3-yl)-1,2-dihydropyrazino[1,2-a] indole-4-carboxamide; N—(((R)-1-isopropylpyrrolidin-2-yl)methyl)-10-methyl-1-oxo-2-((S)-tetrahydrofuran-3-yl)-1,2-dihydropyrazino[1,2-a]indole-4-carboxamide; (S)-2-cyclopentyl-8-fluoro-N-((1-isopropylpyrrolidin-2-yl) methyl)-10-methyl-1-oxo-1,2-dihydropyrazino[1,2-a] indole-4-carboxamide; (R)-2-cyclopentyl-8-fluoro-N-((1-isopropylpyrrolidin-2-yl)methyl)-10-methyl-1-oxo-1,2- dihydropyrazino[1,2-a]indole-4-carboxamide; (R)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide; (S)-2-cyclopentyl-N—(((S)-1-isopropylpyrrolidin-2-yl)methyl)-10-methyl-1-oxo-1,2,3,4-tetrahydropyrazino[1,2-a]indole-4-carboxamide; (S)-10-chloro-2-cyclopentyl-N-((1-isopropylpyrrolidin-2-yl)methyl)-1-oxo-1,2-dihydropyrazino[1,2-a]indole-4-carboxamide; (R)-10-chloro-2-cyclopentyl-N-((1-isopropylpyrrolidin-2-yl)methyl)-1-oxo-1,2-dihydropyrazino[1,2-a]indole-4-carboxamide; (S)-10-bromo-2-cyclopentyl-N-((1-isopropylpyrrolidin-2-yl)methyl)-1-oxo-1,2-dihydropyrazino[1,2-a]indole-4-carboxamide; (R)-10-bromo-2-cyclopentyl-N-((1-isopropylpyrrolidin-2-yl)methyl)-1-oxo-1,2-dihydropyrazino[1,2-a]indole-4-carboxamide; (R)—N-((1-isopropylpyrrolidin-2-yl)methyl)-10-methyl-1-oxo-2-phenyl-1,2-dihydropyrazino[1,2-a]indole-4-carboxamide; (S)-10-cyano-2-cyclopentyl-N-((1-isopropylpyrrolidin-2-yl)methyl)-1-oxo-1,2-dihydropyrazino[1,2-a]indole-4-carboxamide; (S)-2-cyclopentyl-N-((1-isopropylpyrrolidin-2-yl)methyl)-1-oxo-10-vinyl-1,2-dihydropyrazino[1,2-a]indole-4-carboxamide; (S)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide; (R)—N-((1-isopropylpyrrolidin-2-yl)methyl)-10-methyl-2-(1-methyl-1H-pyrazol-4-yl)-1-oxo-1,2-dihydropyrazino[1,2-a]indole-4-carboxamide; (S)—N-((1-isopropylpyrrolidin-2-yl)methyl)-10-methyl-1-oxo-2-(pyridin-3-yl)-1,2-dihydropyrazino[1,2-a]indole-4-carboxamide; (R)—N-((1-isopropylpyrrolidin-2-yl)methyl)-10-methyl-1-oxo-2-(pyridin-3-yl)-1,2-dihydropyrazino[1,2-a]indole-4-carboxamide; N-(azetidin-2-ylmethyl)-2-cyclopentyl-10-methyl-1-oxo-1,2-dihydropyrazino[1,2-a]indole-4-carboxamide; and 2-cyclopentyl-N-((1-isopropylazetidin-2-yl)methyl)-10-methyl-1-oxo-1,2-dihydropyrazino[1,2-a]indole-4-carboxamide; or pharmaceutically acceptable salts thereof (see PCT Publication No. WO 2017/117556, which is hereby incorporated by reference in its entirety).

Suitable DPP4 inhibitors include, without limitation, sitagliptin, vildagliptin, saxagliptin, alogliptin, teneligliptin, and anagliptin.

According to one embodiment, "pancreatic beta cells" are primary human pancreatic beta cells.

In one embodiment of carrying out this and other methods described herein, contacting does not induce beta cell death or DNA damage. Moreover, contacting may induce beta cell differentiation and increase glucose-stimulated insulin secretion.

In another embodiment, the method is carried out to enhance cell survival. For example, the method may be carried out to enhance cell survival of a treated population of cells relative to an untreated population of cells. Alternatively, the method may be carried out to decrease cell death or apoptosis of a treated population of cells relative to an untreated population of cells.

A further aspect relates to a composition comprising a compound of formula (I) and a carrier.

In one embodiment, the composition may further comprise a transforming growth factor beta (TGFβ) superfamily signaling pathway inhibitor.

In another embodiment, the composition may further comprise a glucagon-like peptide-1 receptor (GLP1R) agonist or a Dipeptidyl Peptidase IV (DPP4) inhibitor.

The carrier may be a pharmaceutically-acceptable carrier.

While it may be possible for the compounds of formula (I) to be administered as the raw chemical, it may be preferable to present them as a pharmaceutical composition. In accordance with one embodiment, there is provided a pharmaceutical composition comprising a compound of formula (I) or a pharmaceutically acceptable salt or solvate thereof, together with one or more pharmaceutical carriers thereof and optionally one or more other therapeutic ingredients.

The carrier(s) must be "acceptable" in the sense of being compatible with the other ingredients of the formulation and not deleterious to the recipient thereof. Furthermore, notwithstanding the statements herein regarding the term "compound" including salts thereof as well, so that independent claims reciting "a compound" will be understood as referring to salts thereof as well, if in an independent claim reference is made to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

Formulations include those suitable for oral, parenteral (including subcutaneous, intradermal, intramuscular, intravenous, and intraarticular), rectal, and topical (including dermal, buccal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula (I) or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier," and this expression is intended to include one or more inert excipients, which include, for example and without limitation, starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula (I) to insure the stability of the formulation. The composition may contain other additives as needed including, for example, lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to, binders, fillers, disintegrants, lubricants, anti-microbial agents, and coating agents.

Dose ranges for adult humans vary, but may generally be from about 0.005 mg to 10 g/day orally. Tablets or other forms of presentation provided in discrete units may conveniently contain an amount of compound of formula (I) which is effective at such dosage or as a multiple of the same, for instance, units containing 5 mg to 500 mg, or around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

Additional information about pharmaceutical compositions and their formulation is described in *Remington: The Science and Practice of Pharmacy,* 20$^{th}$ Edition, 2000, which is hereby incorporated by reference in its entirety.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g., PCT Publication No. WO 97/11682, which is hereby incorporated by reference in its entirety) via a liposomal formulation (see, e.g., EP Patent No. 736299, PCT Publication No. WO 99/59550, and PCT Publication No. WO 97/13500, which is hereby incorporated by reference in its entirety), via formulations described in PCT Publication No. WO 03/094886 (which is hereby incorporated by reference in its entirety) or in some other form. The agents can also be administered transdermally (i.e., via reservoir-type or matrix-type patches, microneedles, thermal poration, hypodermic needles, iontophoresis, electroporation, ultrasound, or other forms of sonophoresis, jet injection, or a combination of any of the preceding methods (Prausnitz et al., "Current Status and Future Potential of Transdermal Drug Delivery," *Nature Reviews Drug Discovery* 3:115 (2004), which is hereby incorporated by reference in its entirety). The agents can be administered locally.

The agents can be administered in the form a suppository or by other vaginal or rectal means. The agents can be administered in a transmembrane formulation as described in PCT Publication No. WO 90/07923, which is hereby incorporated by reference in its entirety. The agents can be administered non-invasively via the dehydrated particles described in U.S. Pat. No. 6,485,706, which is hereby incorporated by reference in its entirety. The agents can be administered in an enteric-coated drug formulation as described in PCT Publication No. WO 02/49621, which is hereby incorporated by reference in its entirety. The agents can be administered intranasaly using the formulation described in U.S. Pat. No. 5,179,079, which is hereby incorporated by reference in its entirety. Formulations suitable for parenteral injection are described in PCT Publication No. WO 00/62759, which is hereby incorporated by reference in its entirety. The agents can be administered using the casein formulation described in U.S. Patent Application Publication No. 2003/0206939 and PCT Publication No. WO 00/06108, which are hereby incorporated by reference in their entirety. The agents can be administered using the particulate formulations described in U.S. Patent Application Publication No. 20020034536, which is hereby incorporated by reference in its entirety.

The agents, alone or in combination with other suitable components, can be administered by pulmonary route utilizing several techniques including, but not limited to, intratracheal instillation (delivery of solution into the lungs by syringe), intratracheal delivery of liposomes, insufflation (administration of powder formulation by syringe or any other similar device into the lungs), and aerosol inhalation. Aerosols (e.g., jet or ultrasonic nebulizers, metered-dose inhalers ("MDIs"), and dry-Powder inhalers ("DPIs")) can also be used in intranasal applications. Aerosol formulations are stable dispersions or suspensions of solid material and liquid droplets in a gaseous medium and can be placed into pressurized acceptable propellants, such as hydrofluoroalkanes (IFAs, i.e., HIFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion.

Pulmonary formulations may also include surfactants which include, but are not limited to, bile salts and those described in U.S. Pat. No. 6,524,557 and references therein, which are hereby incorporated by reference in their entirety. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation.

Also suitable are dry powder formulations comprising a therapeutically effective amount of active compound blended with an appropriate carrier and adapted for use in connection with a dry-powder inhaler. Absorption enhancers that can be added to dry powder formulations include those described in U.S. Pat. No. 6,632,456, which is hereby incorporated by reference in its entirety. PCT Publication No. WO 02/080884, which is hereby incorporated by reference in its entirety, describes new methods for the surface modification of powders. Aerosol formulations may include those described in U.S. Pat. Nos. 5,230,884 and 5,292,499; PCT Publication Nos. WO 017/8694 and 01/78696; and U.S. Patent Application Publication No. 2003/019437, 2003/0165436; and PCT Publication No. WO 96/40089 (which includes vegetable oil), which are hereby incorporated by reference in their entirety. Sustained release formulations suitable for inhalation are described in U.S. Patent Application Publication Nos. 2001/0036481, 2003/0232019, and 2004/0018243 as well as in PCT Publication Nos. WO 01/13891, 02/067902, 03/072080, and 03/079885, which are hereby incorporated by reference in their entirety.

Pulmonary formulations containing microparticles are described in PCT Publication No. WO 03/015750, U.S. Patent Application Publication No. 2003/0008013, and PCT Publication No. WO 00/00176, which are hereby incorporated by reference in their entirety. Pulmonary formulations containing stable glassy state powder are described in U.S. Patent Application Publication No. 2002/0141945 and U.S. Pat. No. 6,309,671, which are hereby incorporated by reference in their entirety. Other aerosol formulations are described in EP Patent No. 1338272, PCT Publication No. WO 90/09781, U.S. Pat. Nos. 5,348,730 and 6,436,367, PCT Publication No. WO 91/04011, and U.S. Pat. Nos. 6,294,153 and 6,290,987, which are hereby incorporated by reference in their entirety, which describe a liposomal based formulation that can be administered via aerosol or other means.

Powder formulations for inhalation are described in U.S. Patent Application Publication No. 2003/0053960 and PCT Publication No. WO 01/60341, which are hereby incorporated by reference in their entirety. The agents can be administered intranasally as described in U.S. Patent Application Publication No. 2001/0038824, which is hereby incorporated by reference in its entirety.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Joseph Barnett Sprowls, *Sprowls' American Pharmacy* (7th ed., Lippincott 1974) and *Remington: The Science and Practice of Pharmacy* (21st ed., Lippincott 2005), which are hereby incorporated by reference in their entirety.

Other devices for generating aerosols employ compressed gases, usually hydrofluorocarbons and chlorofluorocarbons, which are mixed with the medicament and any necessary excipients in a pressurized container. These devices are likewise described in standard textbooks such as Joseph Barnett Sprowls, *Sprowls' American Pharmacy* (7th ed., Lippincott 1974) and *Remington: The Science and Practice of Pharmacy* (21st ed., Lippincott 2005), which are hereby incorporated by reference in their entirety.

The agent can be incorporated into a liposome to improve half-life. The agent can also be conjugated to polyethylene glycol ("PEG") chains. Methods for pegylation and additional formulations containing PEG-conjugates (i.e., PEG-based hydrogels, PEG modified liposomes) can be found in Harris and Chess, "Effect of Pegylation on Pharmaceuticals," *Nature Reviews Drug Discovery* 2:214-221, which is hereby incorporated by reference in its entirety, and the references therein. The agent can be administered via a nanocochleate or cochleate delivery vehicle (BioDelivery Sciences International). The agents can be delivered transmucosally (i.e., across a mucosal surface such as the vagina, eye or nose) using formulations such as that described in U.S. Pat. No. 5,204,108, which is hereby incorporated by reference in its entirety. The agents can be formulated in microcapsules as described in PCT Publication No. WO 88/01165, which is hereby incorporated by reference in its entirety. The agent can be administered intra-orally using the formulations described in U.S. Patent Application Publication No. 2002/0055496, PCT Publication No. WO 00/47203, and U.S. Pat. No. 6,495,120, which are hereby incorporated by reference in their entirety. The agent can be delivered using nanoemulsion formulations described in PCT Publication No. WO 01/91728, which is hereby incorporated by reference in its entirety.

Another aspect relates to a method of treating a subject for a condition associated with an insufficient level of insulin secretion. This method involves administering to a subject in need of treatment for a condition associated with an insufficient level of insulin secretion a compound or composition described herein under conditions effective to treat the subject for the condition.

In one embodiment, the treatment methods described herein are carried out under conditions effective to increase pancreatic beta cell mass in the subject to treat the subject for an insufficient level of insulin secretion.

In one embodiment, the compound or composition may be administered with or coincident with a TGFβ superfamily signaling pathway inhibitor. Suitable transforming growth factor beta (TGFβ) superfamily signaling pathway inhibitors are described in detail above.

In another embodiment, the compound or composition may be administered with or coincident with a glucagon-like peptide-1 receptor (GLP1R) agonist or a Dipeptidyl Peptidase IV (DPP4) inhibitor. Suitable glucagon-like peptide-1 receptor (GLP1R) agonists or a Dipeptidyl Peptidase IV (DPP4) inhibitors are described in detail above. In accordance with this embodiment, the administering is carried out under conditions effective to cause a synergistic increase in pancreatic beta cell mass in the subject to treat the subject for an insufficient level of insulin secretion.

As used herein, a condition associated with an insufficient level of insulin secretion means a condition where a subject produces a lower plasma level of insulin than is required to maintain normal glucose levels in the blood such that the subject with the condition associated with insufficient insulin secretion becomes hyperglycemic. In such a condition, the pancreatic beta cells of the afflicted subject secrete an insufficient level of insulin to maintain the presence of a normal concentration of glucose in the blood (i.e., normoglycemica).

According to one embodiment, one of the conditions associated with an insufficient level of insulin secretion is insulin resistance. Insulin resistance is a condition in which a subject's cells become less sensitive to the glucose-lowering effects of insulin. Insulin resistance in muscle and fat cells reduces glucose uptake (and, therefore, local storage of glucose as glycogen and triglycerides), whereas insulin resistance in liver cells results in reduced glycogen synthesis and storage and a failure to suppress glucose production and release into the blood. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations, reduced muscle glucose uptake, and increased liver glucose production all contribute to elevated blood glucose levels. If insulin resistance exists, more insulin needs to be secreted by the pancreas. If this compensatory increase does not occur, blood glucose concentrations increase and type II diabetes occurs.

According to another embodiment, one of the conditions associated with an insufficient level of insulin secretion is diabetes. Diabetes can be divided into two broad types of diseases: type I (T1D) and type II (T2D). The term "diabetes" also refers herein to a group of metabolic diseases in which patients have high blood glucose levels, including type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes (e.g., steroid diabetes), and several forms of monogenic diabetes.

Thus, in one embodiment, the subject has been diagnosed as having one or more of type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes, or monogenic diabetes. For example, the subject has been diagnosed with Type 1 diabetes. Or, the subject has been diagnosed with Type II diabetes.

According to another embodiment, a condition associated with an insufficient level of insulin secretion is metabolic syndrome. Metabolic syndrome is generally used to define a constellation of abnormalities that is associated with increased risk for the development of type II diabetes and atherosclerotic vascular disease. Related conditions and symptoms include, but are not limited to, fasting hyperglycemia (diabetes mellitus type II or impaired fasting glucose, impaired glucose tolerance, or insulin resistance), high blood pressure; central obesity (also known as visceral, male-pattern or apple-shaped adiposity), meaning overweight with fat deposits mainly around the waist; decreased HDL cholesterol; and elevated triglycerides.

In one embodiment, the subject has been diagnosed as having metabolic syndrome or insulin resistance.

Other conditions that may be associated with an insufficient level of insulin secretion include, without limitation, hyperuricemia, fatty liver (especially in concurrent obesity) progressing to non-alcoholic fatty liver disease, polycystic ovarian syndrome (in women), and acanthosis *nigricans*.

Related disorders may also be treated including, without limitation, any disease associated with a blood or plasma glucose level outside the normal range, preferably hyperglycemia. Consequently, the term "related disorders" includes impaired glucose tolerance (IGT), impaired fasting glucose (IFG), insulin resistance, metabolic syndrome, postprandial hyperglycemia, and overweight/obesity. Such related disorders can also be characterized by an abnormal blood and/or plasma insulin level.

According to another embodiment, the methods described herein are carried out to treat a subject with conditions associated with beta cell failure or deficiency. Such conditions include, without limitation, type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes, or monogenic diabetes. Drug-induced diabetes relates to a condition that is caused through the use of drugs that are toxic to beta cells (e.g., steroids, antidepressants, second generation antipsychotics, and immunosuppressive. Exemplary immunosuppressive drugs include, but are not limited to, members of the cortisone family (e.g., prednisone and dexamethasome), rapamycin/sirolimus, everolimus, and calciuneurin inhibitors (e.g., FK-506/tacrolimus).

Additional conditions associated with beta cell deficiency include, without limitation, hypoglycemia unawareness, labile insulin dependent diabetes, pancreatectomy, partial pancreatectomy, pancreas transplantation, pancreatic islet allotransplantation, pancreatic islet autotransplantation, and pancreatic islet xenotransplantation. Thus, the methods described herein may be carried out to treat a subject with pancreatectomy-induced diabetes. In some embodiments, the methods described herein are carried out to treat a subject that has undergone islet allotransplantation (e.g., for T1D) or islet autotransplantation (e.g., for a subject undergoing pancreatectomy for chronic pancreatitis).

As used herein, hypoglycemia unawareness is a complication of diabetes in which the patient is unaware of a deep drop in blood sugar because it fails to trigger the secretion of epinephrine which generates the characteristic symptoms of hyperglycemia (e.g., palpitations, sweating, anxiety) that serve to warn the patient of the dropping blood glucose.

Pancreas transplantation may occur alone, after, or in combination with kidney transplantation. For example, pancreas transplantation alone may be considered medically necessary in patients with severely disabling and potentially life-threatening complications due to hypoglycemia unawareness and labile insulin dependent diabetes that persists in spite of optimal medical management. Pancreas transplantation following prior kidney transplantation may occur in a patient with insulin dependent diabetes. Pancreas transplantation may occur in combination with kidney transplantation in an insulin dependent diabetic patient with uremia. Pancreas retransplantation may be considered after a failed primary pancreas transplant.

As used herein, pancreatic islet transplantation is a procedure in which only the islets of Langerhans, which contain the endocrine cells of the pancreas, including the insulin producing beta cells and glucagon producing alpha cells, are isolated and transplanted into a patient. Pancreatic islet allotransplantation occurs when islets of Langerhans are isolated from one or more human donors pancreas. Pancreatic islets may also be derived from human embryonic stem cells or induced pluripotent stem cells. Pancreatic islet xenotransplantation occurs when islets of Langerhans are isolated from one or more non-human pancreas (e.g., a porcine pancreas or primate pancreas). Pancreatic islet autotransplantation occurs when islets of Langerhans are isolated from the pancreas of a patient undergoing pancreatectomy (e.g., for chronic pancreatitis from gall stone, drugs, and/or familial genetic causes) and returned to the same patient, e.g., via infusion into the portal vein, via laparoscopy to the omentum, via endoscopy to the gastric wall, or subcutaneously via minor incision. As with pancreas transplantation, pancreatic islet transplantation can be performed alone, after, or in combination with kidney transplantation. For example, pancreatic islet transplantation may occur alone to restore hypoglycemia awareness, provide glycemic control, and/or protect a patient from severe hypoglycemic events (Hering et al., "Phase 3 Trial of Transplantation of Human Islets in Type 1 Diabetes Complicated by Severe Hypoglycemia," *Diabetes Care* 39(7):1230-1240 (2016), which is hereby incorporated by reference in its entirety).

Pancreatic islet transplantation may occur in combination with total pancreatectomy. For example, pancreatic islet transplantation may be performed after total pancreatectomy to prevent or ameliorate surgically induced diabetes by preserving β cell function (Johnston et al., "Factors Associated with Islet Yield and Insulin Independence after Total Pancreatectomy and Islet Cell Autotransplantation in Patients with Chronic Pancreatitis Utilizing Off-Site Islet Isolation: Cleveland Clinic Experience," *J. Chem. Endocrinol. Metab.* 100(5):1765-1770 (2015), which is hereby incorporated by reference in its entirety). Thus, pancreatic islet transplantation may provide sustained long-term insulin-independence.

In some embodiments, pancreatic islet transplantation occurs in the context of an encapsulation device to protect the transplanted pancreatic islet cells from the host autoimmune response, while allowing glucose and nutrients to reach the transplanted pancreatic islet cells.

The methods described herein may be carried out to enhance pancreas, pancreatic islet allotransplantation, pancreatic islet autotransplantation, and/or pancreatic islet xenotransplantation by regenerating pancreatic β cells in a patient. For example, the methods may be used to prevent or ameliorate surgically induced diabetes by preserving β cell function, restore hypoglycemia awareness, provide glycemic control, and/or protect a patient from severe hypoglycemic events. Thus, another aspect of the disclosure relates to a method of regenerating pancreatic beta cells in a transplant patient. This method involves administering to a transplant patient a compound of formula (I) and, optionally, a TGFβ superfamily signaling pathway inhibitor, a glucagon-like peptide-1 receptor (GLP1R) agonist, and/or a Dipeptidyl Peptidase IV (DPP4) inhibitor, where said administering is carried out under conditions effective to regenerate pancreatic beta cells in the patient.

In another embodiment, the methods described herein are carried out to treat a subject at risk of developing Type II Diabetes. In one embodiment, a patient at risk of developing Type II Diabetes has pre-diabetes/metabolic syndrome. In another embodiment, the patient at risk of developing Type II Diabetes has been has been treated with a psychoactive drug, including but not limited to a selective serotonin reuptake inhibitors ("SSRI") for depression, obsessive compulsive disorder ("OCD"), etc.

In carrying out the treatment methods, a compound or composition of the present invention and, optionally, a TGFβ superfamily signaling pathway inhibitor, a glucagon-like peptide-1 receptor (GLP1R) agonist, and/or a DPP4 inhibitor, are administered under conditions effective to increase pancreatic beta cell mass in the subject to treat the subject for a condition associated with an insufficient level of insulin secretion.

According to one embodiment, a compound of formula (I) or a composition containing a compound of formula (I) and/or a TGFβ superfamily signaling pathway inhibitor are administered to increase pancreatic beta cell mass in the subject, which will result in an increased level of insulin secretion in the subject.

The compound and/or composition and a TGFβ superfamily signaling pathway inhibitor are, according to one embodiment, formulated as separate pharmaceutical compositions or a single pharmaceutical composition comprising both the compound of formula (I) and TGFβ superfamily signaling pathway inhibitor. According to one embodiment, such pharmaceutical composition(s) comprises a therapeutically effective amount of the compound of formula (I) and/or TGFβ superfamily signaling pathway inhibitor.

Thus, according to one embodiment, a combination or combinatorial therapy or treatment of a compound of the present invention and TGFβ superfamily signaling pathway inhibitor are administered. The terms "combination" or "combinatorial therapy" or "combinatory treatment" mean a treatment where at least two compounds are co-administered to a subject to cause a biological effect, in this case a synergistic effect. In a combinatorial therapy, the at least two drugs may be administered together or separately, at the same time or sequentially. Simultaneous administration is not required, as long as the drugs produce a synergistic effect in the subject to improve the subject's conditions. Also, the at least two drugs may be administered through different routes and protocols. As a result, although they may be formulated together, the drugs of a combination may also be formulated separately.

A further aspect relates to a method of treating a subject for a neurological disorder. This method involves administering to a subject in need of treatment for a neurological disorder a compound of the present invention under conditions effective to treat the subject for the condition.

In one embodiment, the subject has diabetes and/or has been diagnosed as having one or more of Down's Syndrome and a neurodegenerative disease.

In carrying out the treatment methods, administering of compounds to a subject may involve administering pharmaceutical compositions containing the compound(s) (i.e., a compound of formula (I) and TGFβ superfamily signaling pathway inhibitor) in therapeutically effective amounts, which means an amount of compound effective in treating the stated conditions and/or disorders in the subject. Such amounts generally vary according to a number of factors well within the purview of ordinarily skilled artisans. These include, without limitation, the particular subject, as well as its age, weight, height, general physical condition, and medical history, the particular compound used, as well as the carrier in which it is formulated and the route of administration selected for it; the length or duration of treatment; and the nature and severity of the condition being treated.

Administering typically involves administering pharmaceutically acceptable dosage forms, which means dosage forms of compounds described herein and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in *Remington's Pharmaceutical Sciences*, Mack Publishing Co., Easton, Pa., latest edition, which is hereby incorporated by reference in its entirety.

In carrying out treatment methods, the drug (i.e., a compound of formula (I) and, optionally, a TGFβ superfamily signaling pathway inhibitor, a glucagon-like peptide-1 receptor (GLP1R) agonist, and/or a Dipeptidyl Peptidase IV (DPP4) inhibitor) may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

Pharmaceutical compositions according to the present invention may be formulated to release the active drug substantially immediately upon administration or at any predetermined time or time period after administration.

Controlled release formulations include (i) formulations that create a substantially constant concentration of the drug(s) within the body over an extended period of time; (ii) formulations that after a predetermined lag time create a substantially constant concentration of the drug(s) within the body over an extended period of time; (iii) formulations that sustain drug(s) action during a predetermined time period by maintaining a relatively, constant, effective drug level in the body with concomitant minimization of undesirable side effects associated with fluctuations in the plasma level of the active drug substance; (iv) formulations that localize drug(s) action by, e.g., spatial placement of a controlled release composition adjacent to or in the diseased tissue or organ; and (v) formulations that target drug(s) action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index ("TI") is defined as the ratio of median lethal dose ($LD_{50}$) to median effective dose (EDS)); (ii) a narrow absorption window in the gastro-intestinal tract; or (iii) a very short biological half-life so that frequent dosing during a day is required in order to sustain the plasma level at a therapeutic level.

Any of a number of strategies can be pursued to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Thus, administering may be carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. In one embodiment, the administrating is carried out orally, transdermally, parenterally, subcutaneously, intravenously, intramuscularly, or intraperitoneally. Compounds may be administered alone or with suitable pharmaceutical carriers, and can be in solid or liquid form, such as tablets, capsules, powders, solutions, suspensions, or emulsions.

The subject may be a mammalian subject. In one embodiment, the subject is a human subject. Suitable human subjects include, without limitation, children, adults, and elderly subjects having a beta-cell and/or insulin deficiency.

In other embodiments, the subject may be bovine, ovine, porcine, feline, equine, murine, canine, lapine, etc.

In one embodiment, the administering step may increase the number of proliferating pancreatic beta cells in the subject by at least about 5%, 6%, 7%, or more.

In some embodiments, the administering increases glucose-stimulated insulin secretion in pancreatic beta cells of the subject.

In one embodiment of this and other aspects, the designation of a compound is meant to designate the compound per se, as well as any pharmaceutically acceptable salt, hydrate, isomer, racemate, ester, or ether thereof. The designation of a compound is meant to designate the compound as specifically designated per se, as well as any pharmaceutically acceptable salt thereof.

Within the context of the present invention, by "treating" it is meant preventive or curative treatment.

In one embodiment, the term treatment designates in particular the correction, decrease in the rate of change, or reduction of an impaired glucose homeostasis. The level of glucose in blood fluctuates throughout the day. Glucose levels are usually lower in the morning, before the first meal of the day and rise after meals for some hours. Consequently, the term treatment includes the control of blood glucose level by increasing or decreasing blood glucose level depending on the condition of the subject and the daytime in order to reach normal glucose levels. The term treatment more particularly includes a temporary or persistent reduction of blood glucose level in a subject having diabetes or a related disorder. The term "treatment" or "treating" also designates an improvement in insulin release (e.g., by pancreatic beta cells).

As used herein, the phrase "control of blood glucose level" refers to the normalization or the regulation of the blood or plasma glucose level in a subject having abnormal levels (i.e., levels that are below or above a known reference, median, or average value for a corresponding subject with a normal glucose homeostasis).

EXAMPLES

Example 1—Materials and Methods for Examples 2-5

$^1$H and $^{13}$C NMR Spectra. $^1$H and $^{13}$C NMR spectra were acquired on a Bruker DRX-600 spectrometer at 600 MHz for $^1$H and 150 MHz for $^{13}$C. TLC was performed on silica coated aluminum sheets (thickness 200 μm) or alumina coated (thickness 200 μm) aluminum sheets supplied by Sorbent Technologies and column chromatography was carried out on Teledyne ISCO combiflash equipped with a variable wavelength detector and a fraction collector using a RediSep Rf high performance silica flash columns by Teledyne ISCO. LCMS analysis was conducted on an Agilent Technologies G1969A high-resolution API-TOF mass spectrometer attached to an Agilent Technologies 1200 HPLC system. Samples were ionized by electrospray ionization (ESI) in positive mode. Chromatography was performed on a 2.1×150 mm Zorbax 300SB-C18 5-μm column with water containing 0.1% formic acid as solvent A and acetonitrile containing 0.1% formic acid as solvent B at a flow rate of 0.4 mL/min. The gradient program was as follows: 1% B (0-1 minutes), 1-99% B (1-4 minutes), and 99% B (4-8 minutes). The temperature of the column was held at 50° C. for the entire analysis. The chemicals and reagents were purchased from Aldrich Co., Alfa Aesar, Enamine, TCI USA. All solvents were purchased in anhydrous from Acros Organics and used without further purification.

DYRKA Binding Assays. Compounds were tested for DYRK1A binding activity at a commercial kinase profiling services, Life Technologies, which uses the FRET-based LanthaScreen® Eu Kinase Binding Assay. Compounds were screened for DYRK1A activity at concentrations of 1000 nM and 300 nM in duplicates. The $IC_{50}$ was determined by 10 point LanthaScreen® Eu Kinase Binding Assay in duplicates.

B-Cell Proliferation Assay. Human pancreatic islets were obtained from the NIH/NIDDK-supported Integrated Islet Distribution Program (IIDP). Islets were first dispersed with Accutase (Sigma, St. Louis, MO) onto coverslips as described earlier (Wang et al., 2015, which is hereby incorporated by reference in its entirety). After 2 hours, dispersed human islet cells were treated with compound in in RPMI1640 complete medium for 96 hours. Then the cells were fixed and stained for insulin and Ki67 staining (Wang et al., 2015, which is hereby incorporated by reference in its entirety). Total insulin positive cells and double Ki67 and insulin positive cells were imaged and counted. At least 1000 cells were counted.

NFAT2T Translocation Assay. R7T1 rodent beta cells were infected with adenovirus expressing NFAT2-GFP for 48 hours, then the cells were treated with different compounds at 10 μM for another 24 hours. The cells were imaged and counted for the NFAT2-GFP nuclear translocation. At least 1000 cells were counted.

Kinome Scan Profile. Compounds were screened against 468 kinases at single concentration of 10 μM in duplicates at DiscoverX using their proprietary KINOMEscan® Assay (Fabian et al., "A Small Molecule-Kinase Interaction Map for Clinical Kinase Inhibitors," *Nat. Biotechnol.* 23(3):329-336 (2005), which is hereby incorporated by reference in its entirety). The results for primary screen binding interactions are reported as '% DMSO Ctrl', where lower values indicate stronger affinity.

Synthesis of 7-Methoxy-2,9-Dihydro-β-Carbolin-1-One (1-4). m-Anisidine (1.096 mL, 38.56 mmol) was dissolved in 15 mL of concentrated hydrochloric acid and, after cooling 15 mL of water was added to the solution. Sodium nitrite (2.74 g, 39.71 mmol) in 15 mL of water was added dropwise to the cold suspension and stirred for 1 hour while maintaining the temperature below 10° C. This solution was added to a cold solution of ethyl 3-carboxy-2-piperidone (7.0 g, 40.88 mmol) and potassium hydroxide (2.63 g, 47.01 mmol) in 20 mL of water which had been kept overnight at room temperature. The pH of the reaction mixture was adjusted to 4-5 by saturated aqueous solution of sodium acetate. The resultant mixture was stirred at room temperature for 5 hours. The yellow solid was filtered and washed with small amount of water and ethanol to give 6-methoxy-phenylhydrazone 1-2 which was immediately taken to the next step. The phenylhydrazone 1-2 was refluxed in 25 mL of formic acid for 1 hour. The solution was neutralized with saturated aqueous solution of sodium carbonate and extracted with 100 mL of ethyl acetate three times. The organic layer was collected, dried over magnesium sulfate, filtered, and solvent was rotary evaporated to give the desired tetrahydro-oxo-β-carboline 2-3. To a solution of Compound 2-3 in 60 mL of 1,4-dioxane was added DDQ (2.65 g, 11.7 mmol) in 40 mL 1,4-dioxane dropwise at 0° C. and stirred for 1 hour at room temperature. Upon completion of the reaction, 100 mL of water was added to the reaction. The product mixture was transferred to a separatory funnel and extracted with ethyl acetate (100 mL×3) three times. The organic layer was washed with 0.1 N sodium hydroxide solution (50 mL×3). The combined organic layer was then dried over magnesium sulfate, filtered and concentrated to provide the desired 7-methoxy-2,9-dihydro-β-carbolin-1-one 1-4 (1.91 g, 23% in 4 steps) as yellow solid. $^1$H-NMR (600 MHz, $CD_3OD$): δ 7.85 (d, 1H, J=9 Hz), 7.12 (d, 1H, J=4.8 Hz), 7.06-7.08 (m, 2H), 6.86 (d, 1H, J=6.6 Hz), 3.89 (s, 3H); $^{13}$C-NMR (150 MHz, $d_6$-DMSO): δ159.40, 155.72, 140.74, 127.75, 125.12, 122.58, 116.40, 110.78, 99.85, 94.69, 55.61; HRMS (ESI): m/z [M+H]+ calcd for C12H11N2O2+: 215.0815, found: 215.0806.

Synthesis of 1-Chloro-7-Methoxy-9H-β-Carboline (1-5). A solution of 7-methoxy-2,9-dihydro-β-carbolin-β-one (1.80 g, 8.49 mmol) in $POCl_3$ (20 mL) was stirred at 150° C. for 24 hours. The mixture was neutralized with the saturated aqueous solution of sodium carbonate. The solution was transferred to separatory funnel and extracted with ethyl acetate (50 mL×3). The organic layer was collected, dried over magnesium sulfate, filtered and concentrated to provide the desired 1-Chloro-7-methoxy-9H-β-carboline 1-5 (1.56 g, 79%) as yellow solid. $^1$H-NMR (600 MHz, $CDCl_3$): δ 8.31 (s, 1H), 8.19 (d, 1H, J=5.4 Hz), 7.96 (d, 1H, J=8.4 Hz), 7.78 (s, 1H, J=5.4 Hz), 7.0 (s, 1H), 6.95 (m, 1H), 3.93 (s, 3H); $^{13}$C-NMR (150 MHz, $d_6$-DMSO): δ161.14, 142.87, 138.10, 132.93, 132.83, 130.73, 123.44, 115.06, 114.39, 110.60, 95.28, 55.78; HRMS (ESI): m/z [M+H]+ calculated for C12H10CN2O+: 233.0476, found: 233.0471.

General Procedure for the Synthesis of 1-Amino-7-Methoxy-9H-β-Carboline (1-6). A solution of 1-chloro-7-methoxy-9H-β-carboline (1 mmol) and amine (10 mmol) in a sealed pressure vessel was heated to 170° C. for 24 hours. Upon the completion of the reaction monitored by LCMS, the reaction mixture was concentrated and purified by flash column chromatography using DCM/MeOH as eluent to afford the desired 1-amino-7-methoxy-9H-β-carboline 1-6 as white solid.

Synthesis of 1-(Azetidin-1-yl)-7-Methoxy-9H-β-Carboline (1-6a). A screw-cap pressure vessel, equipped with a magnetic stir bar, was charged with 1-5 (50 mg, 0.21 mmol) RuPhos (1 mg, 1 mol %) and RuPhos precatalyst (P1) (1.75 mg, 1 mol %). The vial was evacuated and backfilled with argon, and sealed with a Teflon screw cap. LiHMDS (1M in THF, 2.4 eq.) was added via syringe, followed by azetidine (0.25 mmol, 1.2 equiv.). The reaction mixture was heated at 90° C. for 96 hours. The solution was allowed to cool to room temperature, then quenched by the addition of 1M HCl (1 mL), diluted with EtOAc and poured into sat. $NaHCO_3$. After extracting with EtOAc, the combined organic layers were washed with brine, dried over MgSO4, then concentrated and purified by flash column chromatography using MeOH/DCM (10/90) as eluent to afford compound 1-6a (6.5 mg, 12%) as white solid. Yield 64%. $^1$H-NMR (600 MHz, $CDCl_3$): δ 7.98 (m, 1H), 7.90 (d, 1H, J=9 Hz), 7.30 (m, 1H), 6.94 (m, 1H), 6.89 (d, 1H, J=8.4 Hz), 4.38 (t, 4H, J=7.2 Hz), 3.90 (s, H), 2.52 (m, 2H); $^{13}$C-NMR (150 MHz, $d_6$-DMSO): 159.83, 149.05, 141.87, 136.84, 128.30, 123.52, 122.33, 115.48, 109.56, 106.39, 95.22, 55.61, 51.82, 17.42; HRMS (ESI): m/z [M+H]+ calculated for $C^{15}H_{16}N3O$+: 254.1288, found: 254.1284; Purity>95%

1-(Pyrrolidin-1-yl)-7-Methoxy-9H-β-Carboline (1-6b). White solid. Yield 64%. $^1$H-NMR (600 MHz, $d_6$-DMSO): δ 8.32 (s, 1H), 7.94 (d, 1H, J=5.4 Hz), 7.89 (d, 1H, J=8.4 Hz), 7.22 (d, 1H, J=5.4 Hz), 6.93 (s, H), 6.88 (d, 1H, J=8.4 Hz), 3.90 (m, 7H), 2.07 (s, 4H); $^{13}$C-NMR (150 MHz, $d_6$-DMSO): δ 159.64, 146.72, 141.52, 136.88, 128.60, 123.63, 122.09, 115.48, 109.43, 104.82, 95.28, 55.58, 48.39, 25.35; HRMS (ESI): m/z [M+H]+ calculated for C16H18N3O+: 268.1444, found: 268.1460; Purity>95%.

1-(Piperidin-1-yl)-7-Methoxy-9H-β-Carboline (1-6c). White solid. Yield 87%. $^1$H-NMR (600 MHz, $d_6$-DMSO): δ 8.05 (d, 1H, J=5.4 Hz), 7.90 (d, 1H, J=8.4 Hz), 7.48 (d, 1H, J=4.8 Hz), 7.04 (s, 1H), 6.90 (m, 1H), 3.90 (s, 3H), 3.48 (broad s, 4H), 1.84 (broad s, 4H), 1.70 (m, 2H); $^{13}$C-NMR (150 MHz, $d_6$-DMSO): δ159.98, 149.23, 141.74, 136.57, 129.05, 126.62, 122.33, 115.66, 109.43, 108.75, 95.20, 55.60, 49.92, 26.09, 24.82; HRMS (ESI): m/z [M+H]+ calculated for C17H20N3O+: 282.1601, found: 282.1590; Purity>95%.

1-(2-Phenylpyrrolidin-1-yl)-7-Methoxy-9H-β-Carboline (1-6d). Brown solid. Yield 80%. $^1$H-NMR (600 MHz, CDCl$_3$): δ 7.98 (d, 1H, J=5.4 Hz), 7.82 (d, 1H, J=8.4 Hz), 7.61 (s, 1H), 7.51 (d, 2H, J=7.2 Hz), 7.44 (t, 2H, J=7.8 Hz), 7.34 (t, 2H, J=7.2 Hz), 7.24 (d, 1H, J=5.4 Hz), 6.79 (m, 1H), 6.49 (d, 1H, J=1.8 Hz), 5.48 (d, 1H, J=8.4 Hz), 4.06 (m, 1H), 4.01 (m, 1H), 3.82 (s, 3H), 2.46 (m, 1H), 2.04 (m, 3H); $^{13}$C-NMR (150 MHz, $d_6$-DMSO): δ 159.75, 146.24, 145.92, 141.60, 136.78, 128.85, 128.39, 126.45, 126.28, 124.43, 122.15, 115.49, 109.43, 105.63, 95.25, 61.35, 55.62, 50.48, 24.53; HRMS (ESI): m/z [M+H]+ calculated for C22H22N3O+: 344.1757, found: 344.1761; Purity>95%.

1-(3-Phenylpyrrolidin-1-yl)-7-Methoxy-9H-β-Carboline (1-6e). Brown solid. Yield 59%. $^1$H-NMR (600 MHz, $d_6$-DMSO): δ 8.17 (s, 1H), 7.98 (d, 1H, J=6 Hz), 7.91 (d, 1H, J=9 Hz), 7.37 (m, 4H), 7.27 (m, 2H), 6.91 (s, 1H), 6.88 (d, 2H, J=9 Hz), 4.33 (t, (d, 1H, J=8.4 Hz), 4.09 (m, 1H), 4.01 (m, 1H), 3.94 (t, 1H, J=8.4 Hz), 3.81 (s, 3H), 3.60 (m, 1H), 2.49 (m, 1H), 2.24 (m, 1H); $^{13}$C-NMR (150 MHz, CDCl$_3$): δ161.19, 143.50, 141.54, 139.47, 130.03, 128.60, 126.97, 121.83, 114.64, 112.61, 104.69, 95.30, 55.53, 50.12, 43.47, 32.24; HRMS (ESI): m/z [M+H]+ calculated for C22H22N3O+: 344.1757, found: 344.1750; Purity>95%.

1-(2-Benzylpyrrolidin-1-yl)-7-Methoxy-9H-β-Carboline (1-6f). Brown solid. Yield 65%. $^1$H-NMR (600 MHz, CDCl$_3$): δ 8.05 (d, 1H, J=5.4 Hz), 7.91 (d, 2H, J=9 Hz), 7.28 (m, 5H), 6.88 (m, 2H), 4.68 (s, 1H), 3.90 (m, 5H), 3.22 (m, 1H), 2.79 (m, 1H), 1.97 (m, 3H), 1.84 (m, 1H); $^1$C-NMR (150 MHz, CDCl$_3$): δ160.66, 142.04, 138.44, 129.63, 128.26, 126.31, 121.94, 115.48, 110.80, 105.33, 94.95, 60.45, 55.54, 50.04, 39.36, 29.77, 23.65; HRMS (ESI): m/z [M+H]+ calcd for C23H24N3O+: 358.1914, found: 358.1900; Purity>95%.

1-(3-Benzylpyrrolidin-1-yl)-7-Methoxy-9H-β-Carboline (1-6g). Brown solid. Yield 71%. $^1$H-NMR (600 MHz, CDCl$_3$): δ 8.14 (s, 1H), 7.96 (d, 1H, J=5.4 Hz), 7.90 (d, 2H, J=9 Hz), 7.32 (m, 2H), 7.25 (m, 4H), 6.93 (s, 1H), 6.87 (d, 1H, J=5.4 Hz), 4.01 (m, 2H), 3.90 (m, 4H), 1.08 (t, 1H, J=9 Hz), 2.87 (m, 1H), 2.81 (m, 1H), 2.69 (m, 1H), 2.17 (m, 1H), 1.83 (m, 1H); $^1$C-NMR (150 MHz, $d_6$-DMSO): δ159.62, 146.71, 141.52, 141.15, 137.03, 129.15, 128.76, 126.38, 123.56, 122.08, 115.49, 109.41, 104.81, 95.29, 55.58, 53.80, 47.95, 31.18; HRMS (ESI): m/z [M+H]+ calculated for C23H24N3O+: 358.1914, found: 358.1901; Purity>95%.

1-(2-(2-Chlorophenyl)Pyrrolidin-1-yl)-7-Methoxy-9H-β-Carboline (1-6h). Yellow solid. Yield 77%. $^1$H-NMR (600 MHz, CDCl$_3$): δ 7.98 (d, 1H, J=5.4 Hz), 7.83 (d, 1H, J=8.4 Hz), 7.52 (m, 3H), 7.25 (m, 3H), 6.80 (m, 1H), 6.59 (d, 1H, J=2.4 Hz), 5.80 (d, 1H, J=8.4 Hz), 4.10 (m, 2H), 3.84 (s, 3H), 2.54 (m, 1H), 2.04 (m, 3H); $^{13}$C-NMR (150 MHz, $d_6$-DMSO): δ159.82, 145.77, 142.92, 141.72, 136.88, 131.91, 129.73, 129.08, 128.20, 127.30, 124.39, 122.17, 115.53, 109.47, 105.73, 95.33, 59.41, 55.62, 50.31, 32.65, 24.60; HRMS (ESI): m/z [M+H]+ calculated for C22H21CN3O+: 378.1368, found: 378.1366; Purity>95%.

1-(2-(3-Chlorophenyl) Pyrrolidin-1-yl)-7-Methoxy-9H-β-Carboline (1-6i). Yellow solid. Yield 68%. $^1$H-NMR (600 MHz, CDCl$_3$): δ 7.96 (d, 1H, J=5.4 Hz), 7.86 (d, 1H, J=8.4 Hz), 7.69 (s, 1H), 7.39 (m, 1H), 7.37 (d, 1H, J=7.8 Hz), 7.33 (t, 1H, J=7.2 Hz), 7.28 (m, 2H), 6.83 (m, 1H), 6.65 (m, 1H), 5.51 (d, 1H, J=8.4 Hz), 4.07 (m, 2H), 3.84 (s, 3H), 2.46 (m, 1H), 2.04 (m, 3H); $^1$C-NMR (150 MHz, $d_6$-DMSO): δ159.84, 148.77, 146.08, 141.72, 136.73, 133.18, 130.33, 129.03, 126.48, 125.14, 122.20, 115.53, 109.51, 105.94, 95.30, 61.51, 55.62, 50.60, 35.23, 24.75; HRMS (ESI): m/z [M+H]+ calculated for C22H21CN3O+: 378.1368, found: 378.1377; Purity>95%.

1-(2-(4-Chlorophenyl)pyrrolidin-1-yl)-7-Methoxy-9H-β-Carboline (1-6j). Yellow solid. Yield 43%. $^1$H-NMR (600 MHz, CDCl$_3$): δ 7.97 (d, 1H, J=5.4 Hz), 7.84 (d, 1H, J=8.4 Hz), 7.66 (s, 1H), 7.44 (d, 2H, J=8.4 Hz), 7.38 (d, 2H, J=8.4 Hz), 7.27 (m, 1H), 6.83 (m, 1H), 6.64 (m, 1H), 5.50 (d, 1H, J=8.4 Hz), 4.06 (m, 2H), 3.84 (s, 3H), 2.47 (m, 1H), 2.04 (m, 3H); $^{13}$C-NMR (150 MHz, $d_6$-DMSO): δ159.80, 146.08, 144.98, 141.66, 136.78, 130.85, 128.95, 128.33, 124.47, 122.16, 115.51, 109.46, 105.81, 95.28, 60.99, 55.61, 50.49, 35.26, 24.63; HRMS (ESI): m/z [M+H]+ calculated for C22H21CN3O+: 378.1368, found: 378.1365; Purity>95%.

Synthesis of β-Carboline-N-Oxide (2-1). To a solution of harmine (500 mg, 2.35 mmol) in 8 mL of chloroform was added 3-chloroperoxybenzoic acid (1.22 g, 7.05 mmol) and refluxed for 24 hours. The reaction mixture was concentrated and purified by flash chromatography using DCM/MeOH as eluent to give the desired product β-carboline-N-oxide 2-1 (255 mg, 47%) as white solid. $^1$H-NMR (600 MHz, $d_6$-DMSO): δ 11.60 (s, 1H), 8.04 (d, 1H, J=6.6 Hz), 8.00 (d, 1H, J=8.4 Hz), 7.86 (d, 1H, J=6.6 Hz), 6.97 (s, 1H), 6.85 (m, 1H), 3.85 (s, 3H), 2.61 (s, 3H); $^{13}$C-NMR (150 MHz, $d_6$-DMSO): δ159.82, 143.39, 136.55, 132.79, 131.31, 122.35, 119.13, 115.62, 113.67, 109.57, 95.18, 55.78, 13.00; HRMS (ESI): m/z [M+H]+ calculated for C13H13N2O2+: 229.0972, found: 229.0962; Purity>95%.

Synthesis of 1-Hydroxymethyl-7-Methoxy-9H-β-Carboline (2-2). Trifluoroacetic anhydride (2.20 mL, 15.87 mmol) was added to a stirred mixture of β-carboline-N-oxide (2-1) (724 mg, 3.17 mmol) and CH$_2$Cl$_2$ (20 mL) at 0° C. After being stirred for 30 min, the mixture was refluxed 12 hours. Upon completion of the reaction monitored by TLC, the mixture was concentrated and purified by flash column chromatography using DCM/MeOH as eluent to afford the 1-hydroxymethyl-7-methoxy-9H-β-carboline 2-2 (358 mg, 49%) as white solid. $^1$H-NMR (600 MHz, CD$_3$OD): δ 8.39 (d, 1H, J=6 Hz), 8.27 (d, 1H, J=6 Hz), 8.22 (d, 1H, J=9 Hz), 7.15 (s, 1H), 7.06 (m, 1H), 5.31 (s, 2H), 3.96 (s, 3H); $^{13}$C-NMR (150 MHz, $d_6$-DMSO): δ163.11, 145.98, 140.04, 133.09, 131.95, 129.49, 124.80, 115.17, 113.83, 112.77, 94.96, 58.27, 56.10; HRMS (ESI): m/z [M+H]+ calculated for C13H13N2O2+: 229.0972, found: 229.0967; Purity>95%.

Synthesis of 3-Bromo-2-Hydroxyimino-Propionic Acid Ethyl Ester (2-3). Hydroxylamine hydrochloride (1.81 g, 25.63 mmol) was added to a stirred solution of ethyl bromopyruvate (5.01 g, 25.63 mmol) in chloroform (50 mL) and methanol (70 mL) at room temperature. The reaction mixture was stirred for 18 hours and concentrated under reduced pressure. The crude was dissolved in dichloromethane (300 mL) and washed with 0.1 N of hydrochloric acid and brine. The organic layer was collected, dried over magnesium sulfate, filtered, and concentrated to give 3-bromo-2-hydroxyimino-propionic acid ethyl ester 2-3 (4.36 g, 81%) as white solid. $^1$H-NMR (600 MHz, CDCl$_3$): δ 10.08 (bs, 1H), 4.38 (q, J=7.2 Hz, 2H), 4.27 (s, 2H), 1.39 (t, 3=7.2 Hz, 3H); ESI: m/z [M+H]+ 209.97.

Synthesis of 3-(6-Methoxy-1H-Indol-3-yl)-Propionic Acid Ethyl Ester (2-4). A solution of 3-bromo-2-hydroxyimino-propionic acid ethyl ester 2-2 (1.75 g, 8.35 mmol) in CH$_2$Cl$_2$ (20 mL) was slowly added dropwise to a stirring mixture of 6-methoxyindole (1.23 g, 8.35 mmol) and Na$_2$CO$_3$ (4.86 g, 45.92 mmol) in CH$_2$Cl$_2$ (20 mL) at room temperature. The mixture was stirred for 48 h, filtered through Celite, concentrated, and purified by flash column chromatography using ethyl acetate\Hexanes as eluent to give 3-(6-methoxy-1H-indol-3-yl)-propionic acid ethyl ester 2-4 (800 mg, 34%) as white solid. $^1$H-NMR (600 MHz, d$_6$-DMSO): δ 7.91 (s, 1H), 7.65 (d, 1H, J=12 Hz), 7.00 (s, 1H), 6.81 (m, 1H), 4.05 (s, 2H), 4.26 (m, 2H), 1.31 (t, 3H, J=6 Hz); $^{13}$C-NMR (150 MHz, d$_6$-DMSO): δ164.20, 155.94, 150.66, 137.05, 122.75, 121.74, 119.65, 109.07, 94.78, 61.15, 55.53, 20.47, 14.36; HRMS (ESI): m/z [M+H]+ calculated for C14H17N2O4+: 227.1183, found: 227.1192; Purity>95%.

Synthesis of 2-Amino-3-(6-Methoxy-1H-Indol-3-yl)-Propionic Acid Ethyl Ester (2-5). Zn dust (3.11 g, 47.62 mmol) was added portion wise to a stirred solution of 2-4 (1.64 g, 5.95 mmol) in acetic acid (20 mL) over 30 min. After addition, the mixture was stirred overnight at room temperature. After completion of the reaction monitored by LCMS, the mixture was filtered through Celite, washed with acetic acid (20 mL) and concentrated. The residue was neutralized with saturated aqueous solution of sodium bicarbonate and extracted with ethyl acetate (30 mL×3). Organic layers were collected, dried over magnesium sulfate, filtered, concentrated to get 2-amino-3-(6-methoxy-1H-indol-3-yl)-propionic acid ethyl ester 2-5 (1.5 g, 96%) as white solid $^1$H-NMR (600 MHz, d$_6$-DMSO): δ 10.64 (s, 1H), 7.35 (d, 1H, J=8.4 Hz), 6.96 (s, 1H), 6.82 (s, 1H), 6.63 (m, 1H), 3.99 (m, 2H), 3.74 (s, 3H), 3.56 (m, 1H), 2.86-2.97 (m, 2H), 1.90 (s, 1H), 1.10 (t, 3H, J=7.2 Hz); $^1$C-NMR (150 MHz, d$_6$-DMSO): δ155.85, 137.21, 122.60, 119.31, 110.32, 108.92, 94.81, 60.28, 55.60, 31.29, 14.42; HRMS (ESI): m/z [M+H]+ calculated for C14H19N2O3+: 263.1390, found: 263.1399; Purity>95%.

Synthesis of Ethyl 1-methyl-7-methoxy-9H-pyrido[3,4-b]indole-3-carboxylate (2-7). To the mixture of 2-4 (1 g, 3.81 mmol) and acetaldehyde (40% in water, 0.46 mL, 4.19 mmol) in 15 mL of dichloromethane, 0.4 mL of trifluoroacetic acid was added drops wise at 0° C. Then, reaction mixture was stirred at room temperature for 18 hours. After completion of reaction as monitored by TLC, the reaction mixture was transferred to separatory funnel and washed with 50 mL of saturated sodium bicarbonate solution and brine. Organic layer was dried over anhydrous magnesium sulfate, filtered and concentrated under vacuum to get 2-6 as a white solid which was taken to next step without purification. A mixture of 2-6 (1.04 g, 3.81 mmol) and sulfur (248 mg, 7.63 mmol) in xylene (150 mL) was heated at reflux for 12 hours. Then the mixture was concentrated under reduced pressure and purified by flash column chromatography using DCM\MeOH as eluent to afford Ethyl 1-Methyl-7-methoxy-9H-pyrido[3,4-b]indole-3-carboxylate 2-7 (755 mg, 75%) as brown solid. $^1$H-NMR (600 MHz, d$_6$-DMSO): δ 11.49 (s, 1H), 9.10 (s, 1H), 8.62 (d, 1H, J=8.4 Hz), 7.54 (s, 1H), 7.38 (m, 1H), 4.84 (q, 2H, J=7.2 Hz), 4.33 (s, 3H), 3.22 (s, 3H), 1.82 (t, 1H, J=6.6 Hz); $^{13}$C-NMR (150 MHz, d$_6$-Acetone): δ166.31, 161.50, 143.09, 141.66, 137.98, 136.84, 128.25, 123.03, 116.01, 115.32, 110.61, 95.33, 60.72, 55.36, 19.94, 14.30; HRMS (ESI): m/z [M+H]+ calcd for C16H17N2O3+: 185.1234, found: 285.1237; Purity>95%.

Synthesis of (1-Methyl-7-methoxy-9H-pyrido[3,4-b]indol-3-yl)methanol (2-8). To a solution of ester 2-7 (160 mg, 0.56 mmol) in THF (15 mL) was added LiAH$_4$ (44 mg, 1.17 mmol) in portions at 0° C., and then the mixture was stirred overnight at room temperature. Then the reaction was quenched by water and stirred at room temperature for 2 hours, the slurry was filtered, the cake was washed with dichloromethane, the filtrate was concentrated to afford 2-8 (135 mg, 91%) as white solid. $^1$H-NMR (600 MHz, d$_6$-DMSO): δ 11.31 (s, 1H), 8.05 (d, 1H, J=8.4 Hz), 7.83 (s, 1H), 6.98 (s, 1H), 6.82 (d, 1H, J=8.4 Hz), 5.25 (s, 1H), 4.64 (d, 2H, J=5.4 Hz) 3.86 (s, 3H), 2.68 (s, 3H); $^{13}$C-NMR (150 MHz, d$_6$-DMSO): δ160.43, 150.39, 142.71, 140.30, 133.87, 128.53, 122.95, 115.41, 109.31, 108.51, 94.99, 65.02, 55.71, 20.56; HRMS (ESI): m/z [M+H]+ calcd for C14H15N2O2+: 243.1128, found: 243.1131; Purity>95%.

Synthesis of 1-methyl-3-methyl-7-methoxy-9H-β-carboline (2-9). To a solution of 2-8 (20 mg, 0.082 mmol) and PdCl$_2$ (4 mg, 0.016 mmol) in EtOH (1 mL) was added Et$_3$SiH (0.201 mL, 1.28 mmol) and the mixture was stirred at 90° C. for 5 hours. Upon completion of reaction monitored by TLC, catalyst was filtered over celite and the filtrate was evaporated. The crude reaction mixture was purified by column chromatography using ethyl acetate as eluent to afford 2-9 (5 mg, 27%) as white solid. $^1$H-NMR (600 MHz, d$_6$-DMSO): δ 8.01 (d, 1H, J=7.8 Hz), 7.66 (s, 1H), 6.96 (s, 1H), 6.81 (d, 1H, J=7.8 Hz), 3.86 (s, 3H), 2.68 (s, 3H), 2.53 (s, 3H).

Synthesis of 1-acetyl-7-methoxy-9H-β-carboline (3-2). To the mixture of 6-methoxytryptamine (300 mg, 1.57 mmol) and pyruvicaldehyde (45% in water, 0.34 mL, 1.89 mmol) in 6 mL of dichloromethane, 0.157 mL of trifluoroacetic acid was added drops wise at 0° C. Then, reaction mixture was stirred at room temperature for 18 hours. After completion of reaction as monitored by TLC, the reaction mixture was transferred to separatory funnel and washed with 50 mL of saturated sodium bicarbonate solution and brine. Organic layer was dried over anhydrous magnesium sulfate, filtered and concentrated under vacuum to get 3-1 as yellow solid which was taken to next step without purification. A mixture of 3-1 (1.57 mmol) and KMnO$_4$ (744 mg, 4.71 mmol) in THF (5 mL) was stirred at room temperature for 12 hours. Then the mixture was concentrated under reduced pressure and purified by flash column chromatography using ethyl acetate as eluent to afford 1-acetyl-7-methoxy-9H-β-carboline 3-2 (60 mg, 16%) as brown solid. $^1$H-NMR (600 MHz, d$_6$-DMSO): δ 11.75 (s, 1H), 8.45 (d, 1H, J=5.4 Hz), 8.30 (d, 1H, J=4.8 Hz), 8.16 (d, 1H, J=8.4 Hz), 7.31 (m, 1H), 6.92 (m, 1H), 3.86 (s, 3H), 2.77 (s, 3H); $^{13}$C-NMR (150 MHz, d$_6$-DMSO): δ 201.88, 161.20, 144.06, 138.14, 135.78, 134.69, 131.58, 123.18, 118.88, 113.89, 110.24, 96.40, 55.76, 26.32; HRMS (ESI): m/z [M+H]+ calculated for C14H13N2O2+: 241.0972, found: 241.0966; Purity>95%.

Synthesis of 1-(1-hydroxyethyl)-7-methoxy-9H-β-carboline (3-3). To a solution of 3-2 (12 mg, 0.05 mmol) in MeOH (2 mL) was added NaBH$_4$ (4 mg, 0.1 mmol) and the mixture was stirred overnight at room temperature. Then the reaction was quenched by water, transferred to separatory funnel and extracted with ethyl acetate. Organic layer was collected, dried over magnesium sulfate, filtered and rotary evaporated to get the desired compound 3-3 (6 mg, 49%) as yellow solid. $^1$H-NMR (600 MHz, d$_6$-DMSO): δ 11.09 (s, 1H), 8.17 (d, 1H, J=4.8 Hz), 8.05 (d, 1H, J=8.4 Hz), 7.86 (d, 1H, J=4.8 Hz), 7.17 (m, 1H), 6.82 (m, 1H), 5.67 (d, 1H, J=4.8 Hz), 5.16 (m, 1H), 3.85 (s, 3H), 1.53 (d, 3H, J=6 Hz); C-NMR (150 MHz, d$_6$-DMSO): δ 160.46, 148.37, 142.56, 137.25, 132.78, 128.93, 122.66, 114.66, 113.15, 109.32, 95.46, 69.59, 55.67, 23.36; HRMS (ESI): m/z [M+H]+ calculated for C14H15N2O2+: 243.1128, found: 243.1131; Purity>95%.

Example 2—Chemical Synthesis of Selected Harmine Analogs 1-position harmine amine analogs were synthesized by following the reaction sequence outlined in FIG. 1. m-Anisidine underwent classical diazotization to form corresponding aryldiazonium salt which was coupled with 3-carboxy-2-piperidone to give arylhydrazone 1-2 (Luis et al., "The Fischer Indole Synthesis of 8-Methyl-5-Substituted-1-Oxo-O-Carbolines: A Remarkable High Yield of a [1,2]-Methyl Migration," Tetrahedron 47(9):1737-44 (1991), which is hereby incorporated by reference in its entirety). Fisher indole cyclization of the resulting arylhydrazone in the presence of formic acid afforded 1,2,3,4-tetrahydro-1-oxo-β-carboline 1-3 (Luis et al., "The Fischer Indole Synthesis of 8-Methyl-5-Substituted-1-Oxo-β-Carbolines: A Remarkable High Yield of a [1,2]-Methyl Migration," Tetrahedron 4(9): 1737-44 (1991), which is hereby incorporated by reference in its entirety). Oxidation of 1-3 using DDQ followed by chlorination with phosphorous oxychloride generated 1-chloro-β-carboline 1-5 in 79% yield (Roggero et al., "Efficient Synthesis of Eudistomin U and Evaluation of its Cytotoxicity," Bioorg. Med. Chem. Lett. 24(15):3549-3551 (2014) and Thompson et al., "Synthesis and Evaluation of 1-Amino-6-Halo-β-Carbolines as Antimalarial and Antiprion Agents," ChemMedChem 7(4):578-586 (2012), which are hereby incorporated by reference in their entirety). Finally, 1-amino-β-carbolines 1-6 (10 analogs) were prepared via amination of 1-chloro-precursors 1-5 by heating with an excess of neat amine at 170° C. in 43-87% yield (Thompson et al., "Synthesis and Evaluation of 1-Amino-6-Halo-β-Carbolines as Antimalarial and Antiprion Agents," ChemMedChem 7(4):578-586 (2012), which is hereby incorporated by reference in its entirety). Analog 1-6a was synthesized by Pd catalyzed amination of 1-5 (Henderson et al., "Palladium-Catalyzed Amination of Unprotected Halo-7-Azaindoles," Org. Lett. 12(20):4438-4441 (2010), which is hereby incorporated by reference in its entirety).

Figure 2:
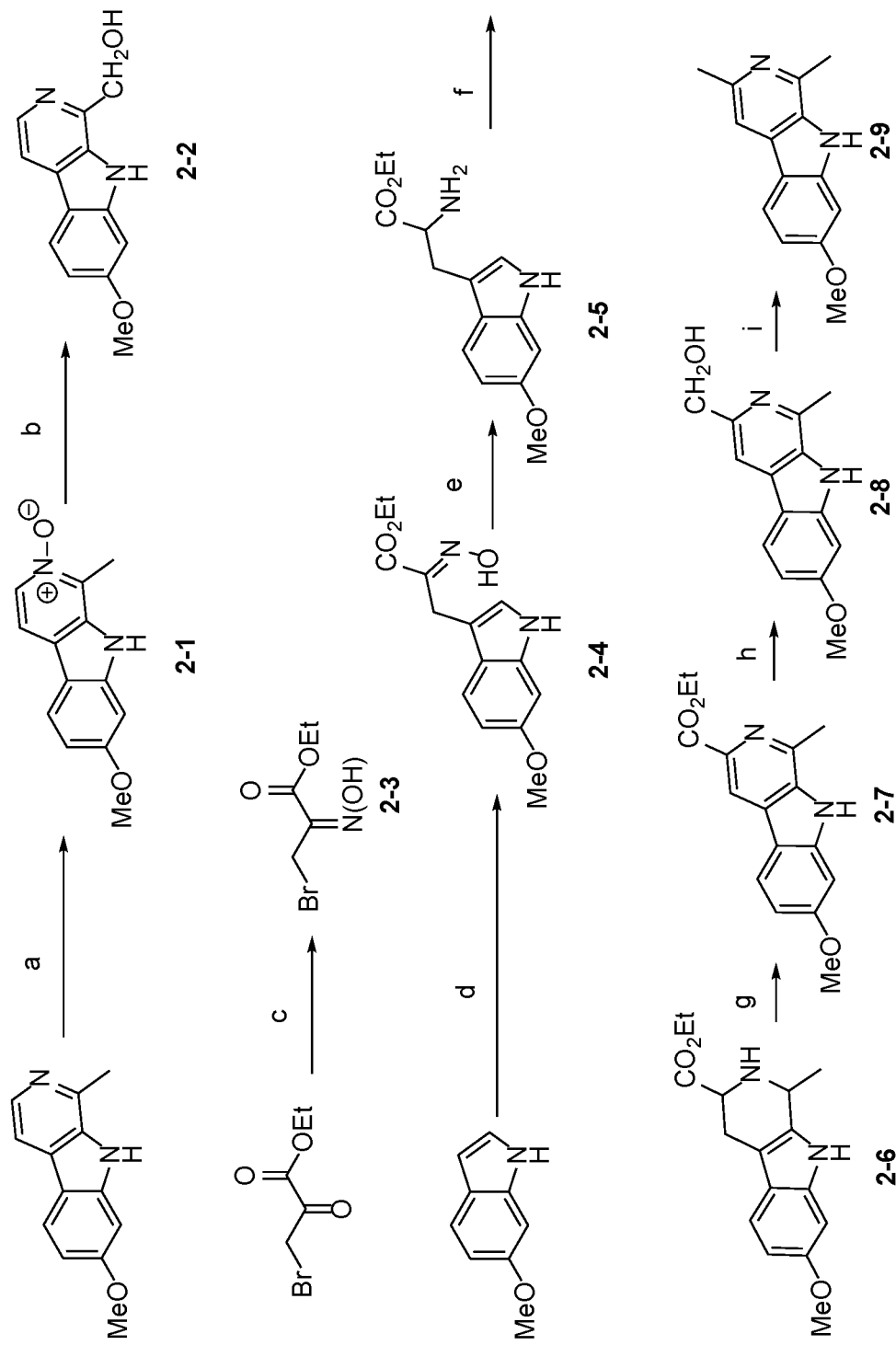
FIG. 2 is a schematic illustration showing the synthesis of 1-hydroxymethyl and 3-hydroxymethyl harmine analog compounds. Reagents and conditions: (a) m-CPBA (3 eq.), $CHCl_3$, 70° C., 12 hours, 47%; (b) TFA anhydride (2.5 eq.), $CH_2Cl_2$, reflux, overnight, 49%; (c) $N_2H_4OH.HCl$ (1 eq.), MeOH, $CHCl_3$, room temperature, 24 hours, 81%; (d) 2-3 (1 eq.), $K_2CO_3$ (5.5 eq.), DCM, room temperature, 24 hours, 34%; (e) Zn dust, AcOH, room temperature, overnight, 96%; (f) Acetaldehyde (1 eq.), TFA (5%), DCM, room temperature, overnight; (g) S (2 eq.), Xylene, reflux, overnight, 75%; (h) $LiAlH_4$ (2 eq.), THF, room temperature, 12 hours, 91%; (i) $Et_3SiH$ (16 eq.), $PdCl_2$ (0.2 eq.), EtOH, 90° C., 5 h, 27%.

1-Hydroxymethyl and 3-Hydroxymethyl substituted-β-carbolines were synthesized using the sequence shown in FIG. 2. Oxidation of harmine with m-CPBA generated the corresponding N-oxide 2-1, which subsequently underwent Boekelheide rearrangement in the presence of trifluoroacetic anhydride to give the desired 1-hydroxymethyl O-carboline 2-2 as white solid in 49% yield (Lin et al., "A Facile Synthesis of 3-Substituted 9H-Pyrido[3,4-b]Indol-1(2H)-One Derivatives from 3-Substituted O-Carbolines," Molecules 15:5680-5691 (2010) and Fontenas et al., "The Boekelheide Reaction: Trifluoroacetic Anhydride as a Convenient Acylating Agent," Synth. Commun. 25(5):629-33 (1995), which are hereby incorporated by reference in its entirety). Alternatively, 6-methoxyindole was reacted with oxime 2-3, prepared from ethyl 3-bromo-2-oxopropanoate, in the presence of sodium carbonate at room temperature to give indole-oxime 2-4 (Park et al., "Synthesis and Activity of Tryptophan Sulfonamide Derivatives as Novel Non-Hydroxamate TNF-α Converting Enzyme (TACE) Inhibitors," Bioorg. Med. Chem. 17(11):3857-3865 (2009), which is hereby incorporated by reference in its entirety). Oxime reduction of 2-4 with zinc powder in acetic acid then provided tryptophanyl ester 2-5 which was underwent Pictet-Spengler cyclization with acetaldehyde to provide 1-methyl-3-hydroxymethyl tetrahydro-β-carboline 2-6 (Park et al., "Synthesis and Activity of Tryptophan Sulfo-namide Derivatives as Novel Non-Hydroxamate TNF-α Converting Enzyme (TACE) Inhibitors," Bioorg. Med. Chem. 17(11):3857-3865 (2009) and Song et al., Synthesis and Antiviral and Fungicidal Activity Evaluation of β-Carboline, Dihydro-β-carboline, Tetrahydro-β-carboline Alkaloids, and Their Derivatives," J. Agric. Food Chem. 62(5): 1010-1018 (2014), which are hereby incorporated by reference in its entirety). Aromatization of compound 2-6 followed by reduction of the ester afforded the final compound 2-8 as white solid (Song et al., Synthesis and Antiviral and Fungicidal Activity Evaluation of β-Carboline, Dihydro-β-carboline, Tetrahydro-β-carboline Alkaloids, and Their Derivatives," J. Agric. Food Chem. 62(5):1010-1018 (2014), which is hereby incorporated by reference in its entirety).

Figure 3:
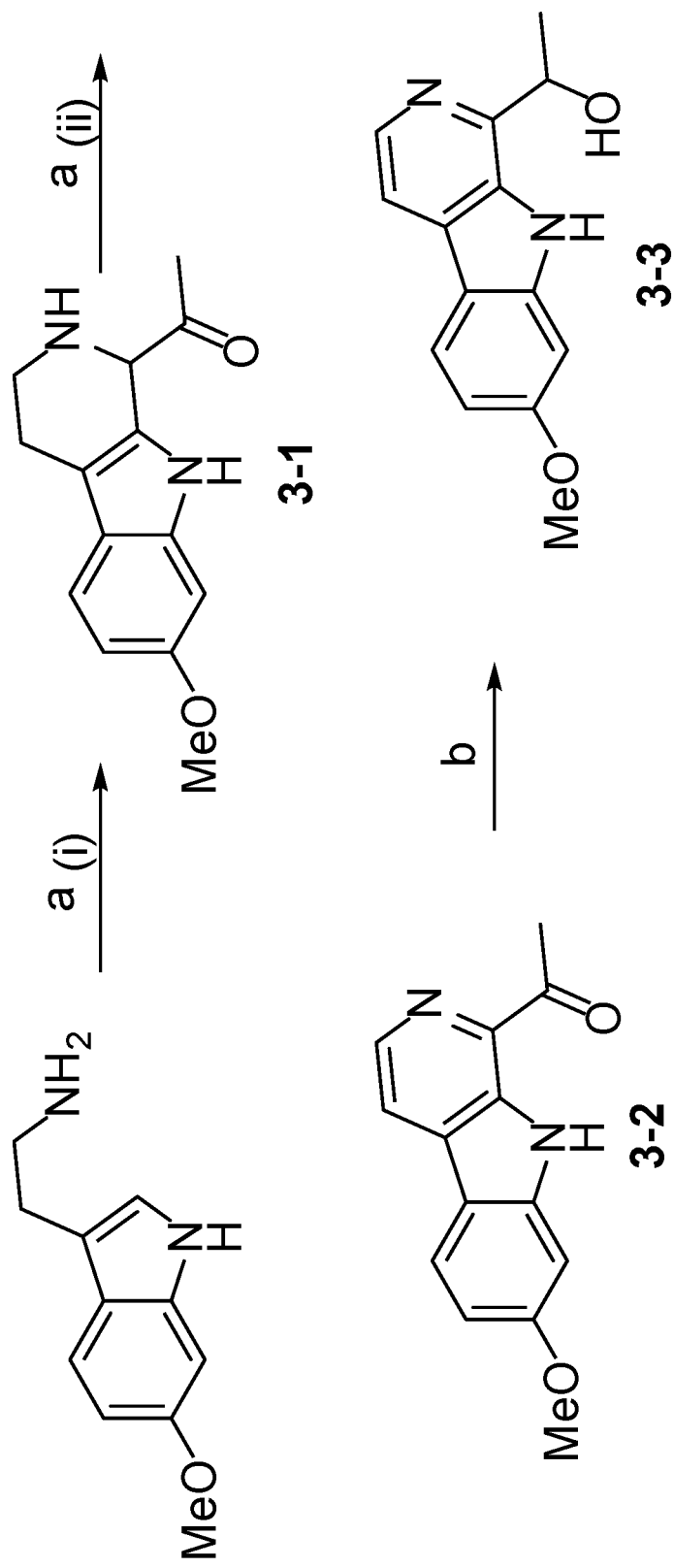
FIG. 3 is a schematic illustration showing the synthesis of 1-(1-hydroxy)ethyl and 1-acetyl harmine analog compounds. Reagents and conditions: (a(i)) pyruvic aldehyde (1.2 eq.), TFA (5%), DCM, room temperature, 12 hours; (a(ii)) $KMnO_4$ (4 eq.), THF, room temperature, 12 hours, 16% (2 steps); (b) $NaBH_4$ (2 eq.), MeOH, room temperature, 12 hours, 49%.

Synthesis of 1-(1-hydroxy)ethyl and 1-acetyl harmine analogs are outlined in FIG. 3. 6-methoxy tryptamine underwent Pictet-spengler cyclization with pyruvic aldehyde in presence of 5% TFA to provide 1-acetyl-7-methoxy-tetrahydro-β-carboline 3-1. Aromatization of compound 3-1 followed by reduction of the acetyl group afforded the 1-(1-hydroxyethyl) harmine analog 3-3 as white solid in 49% yield.

Example 3—Structure-Activity Relationship Studies (SAR) of Selected Harmine Analogs Structural modifications were introduced to the 1-position of harmine to identify new harmine-based DYRK1A inhibitors which can be linked to GLP-1 agonists for β-cell targeted delivery. A total of 15 harmine analogs were synthesized following the routes described in FIGS. 1-2. DYRK1A binding activity of these analogs was screened using FRET-based LanthaScreen binding assay (Life Technologies), initially at 1000 nM and 300 nM. Those compounds showing ≥50% inhibition at 300 nM were titrated using ten serial three fold dilutions (in duplicate) for $IC_{50}$ determination.

The effect of cycloalkylamines at the 1-position of harmine on DYRK1A binding was investigated. First, three analogs with azetidine (1-6a), pyrrolidine (1-6b) and piperidine (1-6c) substituents at the 1-position were synthesized. Compound 1-6a showed the best activity with $IC_{50}$ of 159 nM. However, this compound was 5-fold less active than harmine. Increasing the ring size to 5-membered (pyrrolidine, 1-6b) and 6-membered (piperidine, 1-6c) reduced the DYRK1A inhibitory activity, with DYRK1A $IC_{50}$ of 264 nM and 1500 nM, respectively. 7 harmine analogues were synthesized from commercially available building blocks bearing substituents on the pyrrolidine at harmine 1-position. As predicted, the substitution pattern on the pyrrolidine ring was very sensitive to the DYRK1A inhibition activity. Among these analogues, 1-6d and 1-6f showed potent DYRK1A inhibition activity (Table 1). 2-Substituted pyrrolidine analogs were more potent inhibitors as compared to their 3-substituted analogs. Compound 1-6d with 2-phenyl pyrrolidine substituent showed a DYRK1A $IC_{50}$ of 123 nM comparable to 1-6a (azetidine), and a 2-fold improvement over the corresponding analog 1-6b (Table 1). Introduction of a 3-chloro group on 2-phenyl of the pyrrolidine 1-harmine analog was detrimental for the activity (compound 1-6i, 22% inhibition at 300 nM.) (Table 1).

TABLE 1
DYRK1A Inhibition of Examples
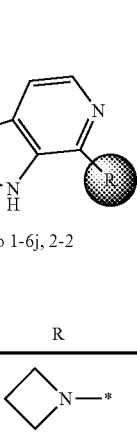
1-4, 1-5, 1-6a to 1-6j, 2-2
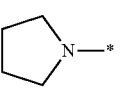
2-8
| Compound | R | DYRK1A inhibition | | |
|---|---|---|---|---|
| | | 1000 nM | 300 nM | IC$_{50}$ (nM)$^a$ |
| 1-6a | 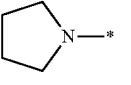 | 89 | 72 | 159 |
| 1-6b | 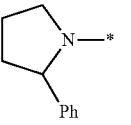 | 97 | 90 | 264 |
| 1-6c | 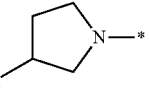 | 81 | 57 | 1500 |
| 1-6d | 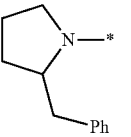 | 91 | 71 | 123 |
| 1-6e | 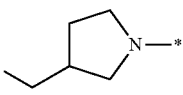 | 61 | 34 | nd |
| 1-6f | 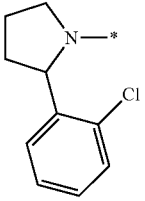 [SMILES: *N1CCCC1c1ccccc1Cl] | 84 | 57 | 221 |
| 1-6g | 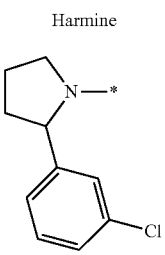 | 38 | 15 | nd |
| 1-6h | | 49 | 12 | nd |
| Harmine | | nd | nd | 28 |
| 1-6i | | 22 | 1 | nd |

TABLE 1-continued

DYRK1A Inhibition of Examples

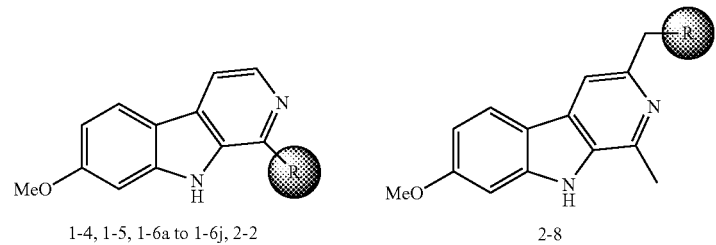

1-4, 1-5, 1-6a to 1-6j, 2-2          2-8

Figures 4A, 4B, 4C, 4D, 4E, 4F:
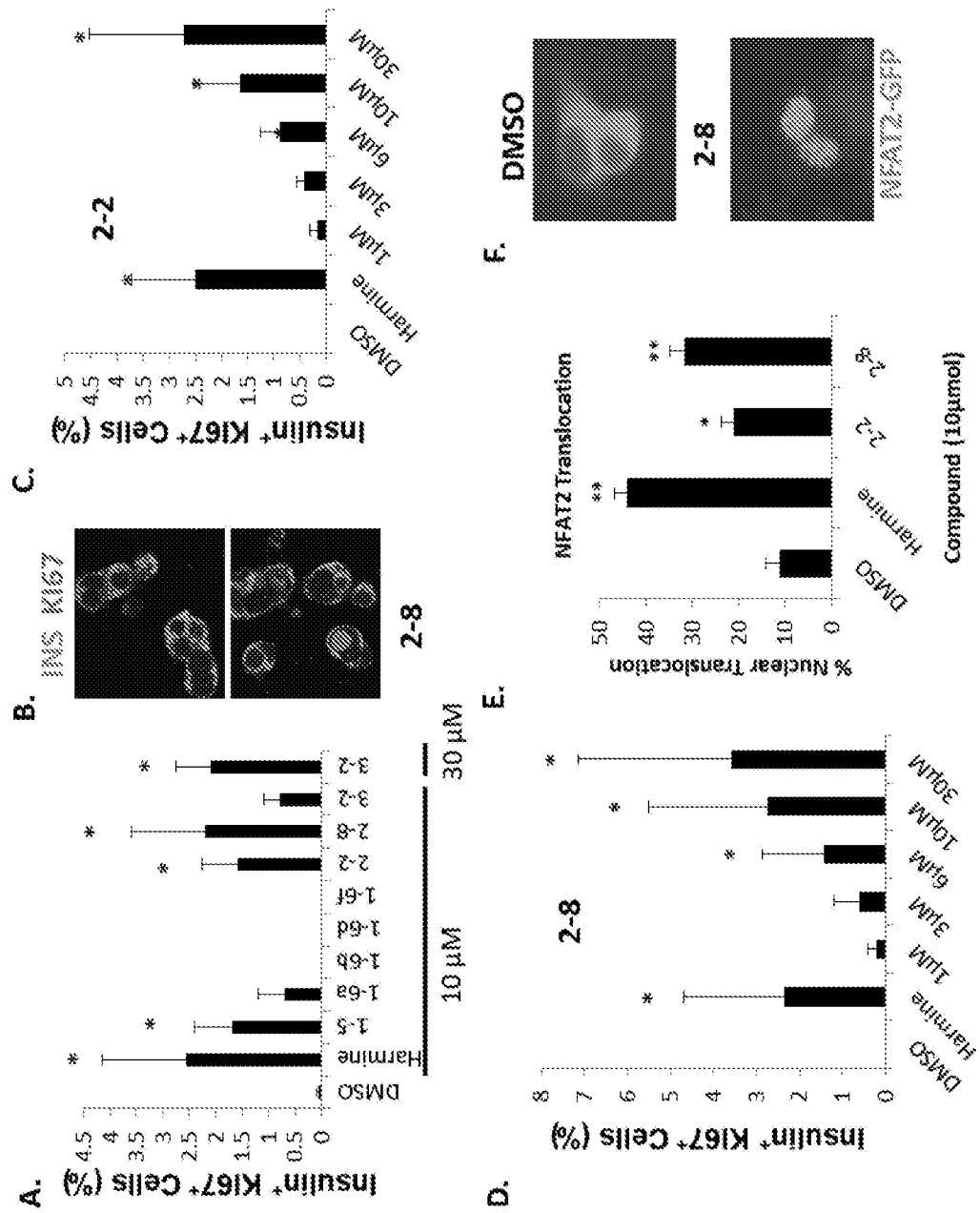
FIGS. 4A-4F demonstrate the effects of harmine analog compounds of the disclosure on human beta cell proliferation.

| Compound | R | DYRK1A inhibition | | |
|---|---|---|---|---|
| | | 1000 nM | 300 nM | IC$_{50}$ (nM)$^a$ |
| 1-6j | (2-(4-chlorophenyl)pyrrolidin-1-yl) | 60 | 27 | nd |
| 1-5 | Cl—* | 100 | 98 | 8.8 |
| 1-4 | HO—* | 38 | 17 | nd |
| 2-2 | HOCH$_2$—* | 75 | 49 | 54.8 |
| 2-8 | HO—* | 98 | 90 | 49.5 |
| 2-9 | —* | — | — | 971 |
| 3-2 | CH$_3$C(O)—* | 92 | 85 | 66.7 |
| 3-3 | CH$_3$CH(OH)—* | 67 | 38 | 858 | a = IC$_{50}$ values are determined using ten serial three fold dilutions (in duplicate)
nd = not determined As shown in Table 1, simple substitution of the harmine 1-methyl group with a chlorine atom (1-5) significantly improved the DYRK1A inhibition by 3-fold compared to harmine with IC$_{50}$ of 8.81 nM. The effect of introducing polar groups like hydroxyl, hydroxyl methyl, and acetyl at the 1-position of harmine was also investigated. Replacing 1-methyl by hydroxyl substituent dramatically reduced the DYRK1A inhibition, rendering the compound inactive. In contrast, introduction of 1-hydroxymethyl group (2-2) showed potent DYRK1A inhibition with IC$_{50}$ of 55 nM, comparable but slightly less potent than harmine and a 2-fold improvement over 1-(2-phenylpyrrolidin-1-yl) harmine analog 1-6d (Table 1). A version of compound 2-2 with a hydroxymethyl group at the 3-carboline position of harmine was synthesized as shown in FIG. 4B. 3-hydroxymethyl substituted analog 2-8 showed IC$_{50}$ comparable to compound 2-2 (Table 1). Removal of the hydroxyl group (3-methyl carboline analog) had an IC$_{50}$=971 nM which indicates the importance of the hydroxyl group in 2-8.

Introduction of an alpha methyl group to the 1-hydroxymethyl substituent of harmine 3-3 led to a complete loss of DYRK1A binding activity at the screening concentration while the planar 1-Acetyl substituted analog (3-2) had an IC$_{50}$ (66.7 nM) similar to compounds 2-2 and 2-8. This indicates that the 1-hydroxymethyl group of 2-2 occupies constrained space that does not accommodate further steric bulk, most likely in either binding mode.

Example 4—Human β-Cell Proliferation Assay

Eight compounds, 1-5, 1-6a, 1-6b, 1-6d, 1-6f, 2-2, 2-8, and 3-2 which showed DYRK1A inhibition IC$_{50}$<250 nM (Table 1) were assessed for their ability to induce human β-cell proliferation in vitro. Among harmine analogs, compounds 2-2, 2-8, and 1-5 exhibited very good human β-cell proliferation at 10 μM comparable to harmine, as measured by Kl67 labeling of insulin cells (FIGS. 4A-4B) (Wang et al., 2015, which is hereby incorporated by reference in its entirety). Compound 3-2 with acetyl substituent at the harmine 1-position, despite having IC$_{50}$ comparable to 2-2 and 2-8 (Table 1) showed reduced β-cell proliferation at 10 μM (Table 2). However, when the compound was tested at higher concentration of 30 µM, proliferation in the range comparable to harmine was observed. Both the compounds 2-2 and 2-8 caused proliferation in a dose dependent manner (FIGS. 4C-4D) with compound 2-8 showing superior human β-cell proliferation at lower dose as compared to 2-2. Unlike harmine, which causes beta cell toxicity at doses higher than 10 µM, compound 2-2 and 2-8 did not cause toxicity even at 30 µM. This suggests that these compounds might be administered at higher concentrations (>10 µM) in vivo/in vitro for β-cell proliferation with reduced potential for cytotoxicity. Compounds 2-2 and 2-8 also drove NFAT2 translocation to nucleus as observed for harmine. These data indicate that these compounds drive β-cell proliferation like harmine, by inducing translocation of the NFATs to the nucleus, likely allowing access to promoter of genes that subsequently drive human β-cell proliferation (FIGS. 4E-4F).

Unfortunately, the 1-amino substituted harmine analogs 1-6a, 1-6b, 1-6d and 1-6f did not show any β-cell proliferation despite showing DYRK1A inhibition <200 nM, which may indicate a DYRK1A potency threshold for β-cell proliferation. One alternate explanation is that some of the compounds with reduced β-cell proliferation may be targeting other anti-proliferative kinases in addition to DYRK1A.

TABLE 2

β-Cell Proliferation of Exemplary Harmine Analogs

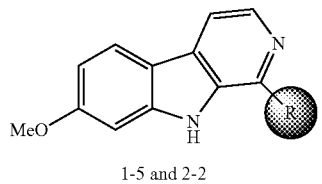

1-5 and 2-2

TABLE 2-continued

| Compound | R | Human β-Cell proliferation (Concentration µM) | DYRK1A IC$_{50}$ (nM)$^a$ |
|---|---|---|---|
| 1-5 | Cl—* | 1.7 (10) | — |
| 2-2 | ![HO-CH2-*] | 1.5 (10) | 54.8 |
| 2-8 | HO—* | 1.7 (10) | 49.5 |
|  | Harmine | 1.5 (10) | 27 |

Example 5—Kinome Scan Profile

To understand kinase selectivity on a subset of compounds, kinome profiling of compound 2-2 and harmine was carried out on 468 kinases at 10 µM concentration (Table 3, activities <20% indicated below). Harmine inhibited 16 kinases (<20% activity remaining) in addition to DYRK1A at a screening concentration of 10 µM. Compound 2-2 exhibited a cleaner kinome profile as compared to harmine with no inhibition against DYRK1B, CSNKG2, CSNK2A1, HIPK2, HIPK3, IRAK1, and VPS3 at 10 µM (Table 3). Additionally, in comparison to harmine, it only showed affinity greater than harmine to PIK4CB at the screening concentration. More selective kinome profile indicates that the improvements in the selectivity have been achieved for compound 2-2 as compared to harmine.

TABLE 3

Kinome Scan of Compound 2-2 and Harmine$^a$

| Target | 2-2 | Harmine |
|---|---|---|
| CDK7 | 27 | 21 |
| CLK1 | 3.5$^b$ | 0.35$^b$ |
| CLK2 | 5.5$^b$ | 2.4$^b$ |
| CLK4 | 17$^c$ | 13$^c$ |
| CSNK1A1 | 10$^b$ | 5$^b$ |
| CSNK1D | 17$^c$ | 13$^c$ |
| CSNK1E | 6.5$^b$ | 1.7$^b$ |
| CSNK1G2 | 30 | 19$^c$ |
| CSNK2A1 | 34 | 11$^c$ |
| DYRK1A | 0$^b$ | 0$^b$ |
| DYRK1B | 66 | 6.1$^b$ |
| DYRK2 | 6.5$^b$ | 3.2$^b$ |
| FLT3(D835V) | 37 | 25 |
| HASPIN | 4.8$^b$ | 2$^b$ |
| HIPK2 | 30 | 8.6$^b$ |
| HIPK3 | 21 | 9.4$^b$ |
| IRAK1 | 32 | 17$^c$ |
| IRAK3 | 39 | 35 |
| JAK3(JH1DOMAIN-CATALYTIC) | 99 | 61 |

TABLE 3-continued

Kinome Scan of Compound 2-2 and Harmine[a]

| Target | 2-2 | Harmine |
|---|---|---|
| PIK3CG | 44 | 49 |
| PIK4CB | 3.7[b] | 12[c] |
| PIM1 | 65 | 45 |
| PIM2 | 58 | 39 |
| PIM3 | 77 | 43 |
| ROCK1 | 53 | 26 |
| VPS34 | 53 | 13[c] |

[a]Compounds were screened 10 μM against 468 kinases, and results for primary screen binding interactions are reported as '% DMSO Ctrl,' where lower values indicate stronger affinity.
[b]≤10.
[c]11 ≤ 20.

Example 6—Discussion of Examples 1-5

Examples 1-4 describe the structure-activity relationships of DYRK1A inhibition and j-cell proliferation for new harmine analogs. Several 1-amino harmine analogs (1-6a to 1-6j) were synthesized to investigate their effect on DYRK1A kinase binding and human β-cell proliferation. Most of the compounds showed reduced DYRK1A inhibition activity at the screening concentration of 10 uM with the exceptions of harmine analogs 1-6a, 1-6b, 1-6d. These analogs showed 5- to 9-fold reduced DYRK1A inhibitory activity as compared to harmine.

In contrast, harmine analogs 2-2, 2-8, and 3-2 (each bearing small polar groups, e.g., hydroxymethyl or acetyl) exhibited potent DYRK1A inhibition with $IC_{50}$ in the range of 49-67 nM, 2-fold more active than 1-azetidine harmine analog 1-6b. However, introduction of directly attached 1-hydroxy substituent was detrimental for DYRK1A inhibition. 1-chloro substituted harmine analog significantly improved DYRK1A inhibition and was the most potent compound with $IC_{50}$ of 8.8 nM. Among the 8 compounds with $IC_{50}$<250 nM against DYRK1A, (1-5, 1-6a, 1-6b, 1-6d, 1-6f, 2-2, 2-8, 3-2) 1-5, 2-2, 2-8, and 3-2 exhibited human β-cell proliferation comparable to that of harmine at similar or reduced concentrations. Harmine analogs 2-2 and 2-8 were most effective for inducing human β-cell proliferation, indicating that introduction of polar groups like hydroxymethyl at 1- and 3-positions of harmine improves the 0-cell proliferation possibly by improving kinase selectivity. None of the 1-amino harmine analogs caused any proliferation. Kinome scan of compound 2-2 for 468 kinases showed that it exhibits a cleaner kinome profile as compared to harmine. These data indicate the potential for improvement of the harmine scaffold for kinase selectivity, resulting in β-cell proliferation at lower concentration in vitro, possibly leading to a safer, off-target profile. These results show the successful modification of harmine to identify a novel kinase selective DYRK1A inhibitor 2-8 with improved β-cell proliferation ability.

Example 7—Materials and Methods for Example 8

Synthesis of 1-Methyl-9H-pyrido[3,4-b]indol-7-ol (10-1). A solution of harmine (1.0 g, 4.02 mmol) in glacial acetic acid (16 mL) and 48% hydrobromic acid solution (20 mL) was heated at reflux for 10 hours. After cooling to room temperature, the mixture was adjusted to pH 8 with a saturated aqueous solution of $NaHCO_3$. The yellow slurry was filtered, and the cake was washed with water to afford harmol 10-1 as a white solid (0.91 g, 99%). $^1$H-NMR (600 MHz, $d_6$-DMSO): δ 11.24 (s, 1H), 9.72 (s, 1H), 8.11 (d, J=5.2 Hz, 1H), 7.94 (d, J=8.0 Hz, 1H), 7.75 (d, J=5.2 Hz, 1H), 6.90 (d, J=1.2 Hz, 1H), 6.69 (dd, J=8.4 Hz, 1H,), 2.69 (s, 3H); MS (ESI) m/z 199.08 (M+H)+.

General procedure for the synthesis of 10-2. A solution of harmalol 10-1 (2.02 mmol) and cesium carbonate (1.5 eq.) in DMF (7 mL) was stirred at 60° C. for 1 hour. To this solution was added alkyl bromide (1.5 eq.) and stirred at 50° C. for 12 hours. After completion of the reaction confirmed by TLC, the reaction mixture was diluted with water, transferred to separatory funnel and extracted with ethyl acetate (50 mL×2). The organic layer was washed with water, dried over magnesium sulfate, filtered, evaporated and purified by flash column chromatography to yield the desired product 10-2 as white solid.

2-(7-oxy-1-methyl-9-H-b-carbolin)acetic acid methyl ester (10-2a). White solid. Yield 59%. $^1$H-NMR (600 MHz, $CD_3OD$): δ 8.07 (d, J=5.4 Hz, 1H), 7.96 (d, J=9 Hz, 1H), 7.75 (d, J=5.4 Hz, 1H), 6.96 (d, J=2.4 Hz, 1H), 6.87 (m, 1H), 4.79 (s, 2H), 3.80 (s, 3H), 2.73 (s, 3H); MS (ESI) m/z 271.18 (M+H)+.

3-(7-oxy-1-methyl-9-H-b-carbolin)propionic acid methyl ester (10-2b). White solid. Yield 44%. $^1$H-NMR (600 MHz, $CD_3OD$): S 8.08 (d, J=5.4 Hz, 1H), 7.96 (d, J=8.4 Hz, 1H), 7.80 (d, J=5.4 Hz, 1H), 6.92 (s, 1H), 6.79 (m, 1H), 4.84 (t, J=7.2 Hz, 2H), 3.57 (s, 3H), 2.98 (s, 3H), 2.80 (t, J=7.2 Hz, 2H); MS (ESI) m/z 285.6 (M+H)+.

4-(7-oxy-1-methyl-9-H-b-carbolin)butnoic acid methyl ester (10-2c). White solid. Yield 68%. $^1$H-NMR (600 MHz, $CD_3OD$): δ 8.08 (d, J=5.4 Hz, 1H), 7.98 (d, J=8.4 Hz, 1H), 7.79 (d, J=5.4 Hz, 1H), 7.02 (s, 1H), 6.84 (d, J=9 Hz, 1H), 4.11 (t, J=6 Hz, 2H), 3.68 (s, 3H), 2.75 (s, 3H), 2.56 (t, J=7.2 Hz, 2H), 2.13 (t, J=6.6 Hz, 2H); MS (ESI) m/z 299.8 (M+H)+.

5-(7-oxy-1-methyl-9-H-b-carbolin)pentanoic acid methyl ester (10-2d). White solid. Yield 50%. $^1$H-NMR (600 MHz, $CD_3OD$): S 8.08 (d, J=5.4 Hz, 1H), 7.98 (d, J=8.4 Hz, 1H), 7.79 (d, J=6 Hz, 1H), 7.02 (d, J=1.8 Hz, 1H), 6.85 (m, 1H), 4.10 (t, J=6 Hz, 2H), 3.65 (s, 3H), 2.75 (s, 3H), 2.45 (t, J=7.2 Hz, 2H), 1.85 (m, 2H); MS (ESI) m/z 313.6 (M+H)+.

6-(7-oxy-1-methyl-9-H-b-carbolin)hexanoic acid methyl ester (10-2e). White solid. Yield 50%. $^1$H-NMR (600 MHz, CD$_3$OD): S 8.08 (d, J=5.4 Hz, 1H), 7.98 (d, J=9 Hz, 1H), 7.78 (d, J=5.4 Hz, 1H), 7.01 (d, J=2.4 Hz, 1H), 6.83 (m, 1H), 4.06 (t, J=6 Hz, 2H), 3.65 (s, 3H), 2.75 (s, 3H), 2.38 (t, J=7.8 Hz, 2H), 1.84 (m, 2H), 1.70 (m, 2H), 1.54 (m, 2H); MS (ESI) m/z 327.5 (M+H)+.

2-(7-oxy-1-methyl-9-H-b-carbolin)acetic acid tert-butyl ester (10-2f). White solid. Yield 42%. $^1$H-NMR (600 MHz, d$_6$-DMSO): δ 11.49 (s, 1H), 8.15 (d, J=5.4 Hz, 1H), 8.07 (d, J=8.4 Hz, 1H), 7.84 (d, J=5.4 Hz, 1H), 6.93 (d, J=2.4 Hz, 1H), 6.83 (m, 1H), 4.77 (s, 2H), 2.73 (s, 3H), 1.45 (s, 9H); MS (ESI) m/z 313.1 (M+H)+.

3-(7-oxy-1-methyl-9-H-b-carbolin)propionic acid tert-butyl ester (10-2g). White solid. Yield 32%. $^1$H-NMR (600 MHz, d$_6$-DMSO): δ 9.82 (s, 1H), 8.12 (d, J=4.8 Hz, 1H), 7.98 (d, J=8.4 Hz, 1H), 7.80 (d, J=4.8 Hz, 1H), 6.93 (d, J=1.2 Hz, 1H), 6.74 (m, 1H), 4.72 (t, J=7.2 Hz, 2H), 2.92 (s, 3H), 2.62 (t, J=7.2 Hz, 2H), 1.24 (s, 9H); MS (ESI) m/z 327.1 (M+H)+.

4-(7-oxy-1-methyl-9-H-b-carbolin)butnoic acid tert-butyl ester (10-2h). White solid. Yield 55%. H-NMR (600 MHz, d$_6$-DMSO): δ 11.37 (s, 1H), 8.13 (d, J=5.4 Hz, 1H), 8.03 (d, J=9 Hz, 1H), 7.80 (d, J=5.4 Hz, 1H), 6.98 (d, J=1.8 Hz, 1H), 6.83 (m, 1H), 4.08 (t, J=6.6 Hz, 2H), 2.71 (s, 3H), 2.41 (t, J=7.2 Hz, 2H), 1.99 (m, 2H), 1.41 (s, 9H); MS (ESI) m/z 341.1 (M+H)+.

5-(7-oxy-1-methyl-9-H-b-carbolin)pentanoic acid tert-butyl ester (10-2i). White solid. Yield 40%. H-NMR (600 MHz, CDCl$_3$): δ 9.40 (s, 1H), 8.31 (d, J=4.8 Hz, 1H), 7.85 (d, J=8.4 Hz, 1H), 7.72 (d, J=5.4 Hz, 1H), 6.89 (d, J=1.8 Hz, 1H), 6.86 (m, 1H), 4.00 (t, J=6 Hz, 2H), 2.79 (s, 3H), 2.31 (t, J=6.6 Hz, 2H), 1.81 (m, 4H), 1.45 (s, 9H); MS (ESI) m/z 355.2 (M+H)+.

6-(7-oxy-1-methyl-9-H-b-carbolin)hexanoic acid tert-butyl ester (10-2j). White solid. Yield 39%. $^1$H-NMR (600 MHz, CDCl$_3$): δ 9.83 (s, 1H), 8.31 (d, J=5.4 Hz, 1H), 7.94 (d, J=8.4 Hz, 1H), 7.72 (d, J=5.4 Hz, 1H), 6.88 (s, 1H), 6.84 (d, J=8.4 Hz, 1H), 3.96 (t, J=6.6 Hz, 2H), 2.79 (s, 3H), 2.25 (t, J=7.8 Hz, 2H), 1.81 (m, 2H), 1.65 (m, 2H), 1.50 (m, 2H), 1.44 (s, 9H); MS (ESI) m/z 369.2 (M+H)+.

2-(7-oxy-1-methyl-9-H-b-carbolin)ethyltert-butyl carbamate (10-2k). White solid. Yield 67%. $^1$H-NMR (600 MHz, CD$_3$OD): δ 8.08 (d, J=5.4 Hz, 1H), 7.98 (d, J=9 Hz, 1H), 7.78 (d, J=5.4 Hz, 1H), 7.05 (d, J=1.8 Hz, 1H), 6.88 (m, 1H), 4.10 (t, J=5.4 Hz, 2H), 3.48 (t, J=6 Hz, 2H), 2.75 (s, 3H), 1.44 (s, 9H); MS (ESI) m/z 342.21 (M+H)+.

3-(7-oxy-1-methyl-9-H-b-carbolin)propyl tert-butyl carbamate (10-2l). White solid. Yield 57%. $^1$H-NMR (600 MHz, d$_6$-DMSO): δ 11.38 (s, 1H), 8.13 (d, J=4.8 Hz, 1H), 8.04 (d, J=8.4 Hz, 1H), 7.79 (d, J=4.8 Hz, 1H), 6.97 (d, J=1.8 Hz, 1H), 6.94 (t, J=5.4 Hz, 1H), 6.82 (m, 1H), 4.07 (t, J=6.6 Hz, 2H), 3.12 (t, J=6.6 Hz, 2H), 2.71 (s, 3H), 1.89 (m, 2H), 1.38 (s, 9H); MS (ESI) m/z 356.21 (M+H)+.

4-(7-oxy-1-methyl-9-H-b-carbolin)butyl tert-butyl carbamate (10-2m). White solid. Yield 67%. $^1$H-NMR (600 MHz, d$_6$-DMSO): δ 11.39 (s, 1H), 8.13 (d, J=4.8 Hz, 1H), 8.04 (d, J=9 Hz, 1H), 7.81 (d, J=5.4 Hz, 1H), 6.97 (d, J=2.4 Hz, 1H), 6.87 (t, J=5.4 Hz, 1H), 6.82 (m, 1H), 4.06 (t, J=6 Hz, 2H), 2.99 (m, 2H), 2.71 (s, 3H), 1.75 (m, 2H), 1.56 (m, 2H), 1.37 (s, 9H); MS (ESI) m/z 370.22 (M+H)+.

2-((7-oxy-1-methyl-9-H-b-carbolin)ethoxy)ethyl tert-butyl carbamate (10-2n). White solid. Yield 46%. $^1$H-NMR (600 MHz, d$_6$-DMSO): δ 11.40 (s, 1H), 8.13 (d, J=4.8 Hz, 1H), 8.04 (d, J=8.4 Hz, 1H), 7.80 (d, J=5.4 Hz, 1H), 7.0 (d, J=1.8 Hz, 1H), 6.84 (m, 1H), 6.81 (t, J=5.4 Hz, 1H), 4.19 (t, J=4.8 Hz, 2H), 3.78 (t, J=4.2 Hz, 2H), 3.48 (t, J=6 Hz, 2H), 3.12 (m, 2H), 2.71 (s, 3H), 1.37 (s, 9H); MS (ESI) m/z 386.22 (M+H)+.

2-(7-oxy-1-methyl-9-H-b-carbolin)methoxyethyl (10-2o). White solid. Yield 38%. $^1$H-NMR (600 MHz, CD$_3$OD): δ 8.10 (d, J=6 Hz, 1H), 8.01 (d, J=8.4 Hz, 1H), 7.83 (d, J=5.4 Hz, 1H), 7.05 (d, J=2.4 Hz, 1H), 6.89 (m, 1H), 4.22 (t, J=4.8 Hz, 2H), 3.80 (t, J=4.2 Hz, 2H), 3.45 (s, 3H), 2.77 (s, 3H); MS (ESI) m/z 257.34 (M+H)+.

3-(7-oxy-1-methyl-9-H-b-carbolin)ethoxyethyl (10-2p). White solid. Yield 48%. $^1$H-NMR (600 MHz, CD$_3$OD): δ 8.10 (d, J=5.4 Hz, 1H), 8.0 (d, J=8.4 Hz, 1H), 7.80 (d, J=5.4 Hz, 1H), 7.06 (d, J=1.2 Hz, 1H), 6.90 (m, 1H), 4.22 (t, J=4.8 Hz, 2H), 3.84 (t, J=4.2 Hz, 2H), 3.63 (m, 2H), 3.45 (s, 3H), 2.76 (s, 3H), 1.23 (t, J=6.6 Hz, 2H); MS (ESI) m/z 271.76 (M+H)+.

General procedure for the synthesis of 10-3. A solution of 10-2a to 10-2e (0.175 mmol) and 7 N ammonia in methanol (4 mL) in a sealed pressure vessel was stirred at 90° C. for 12 hours. After the completion of the reaction, the mixture was evaporated and purified by flash column chromatography using DCM/MeOH/Ammonia (90/9/1) as eluent to give the desired final compound 10-3 as white solid.

2-(7-oxy-1-methyl-9-H-b-carbolin)acetamide (10-3a) White solid. Yield 91%. $^1$H-NMR (600 MHz, d$_6$-DMSO): δ 11.45 (s, 1H), 8.14 (d, J=5.4 Hz, 1H), 8.07 (d, J=8.4 Hz, 1H), 7.80 (d, J=5.4 Hz, 1H), 7.63 (s, 1H), 7.46 (s, 1H), 7.0 (d, J=1.8 Hz, 1H), 6.90 (m, 1H), 4.53 (s, 2H), 2.71 (s, 3H); MS (ESI) m/z 256.1 (M+H)+.

3-(7-oxy-1-methyl-9-H-b-carbolin)propionamide (10-3b). White solid. Yield 97%. MS (ESI) m/z 270.1 (M+H)+. H-NMR (600 MHz, d$_6$-DMSO): δ 9.84 (s, 1H), 8.13 (d, J=5.4 Hz, 1H), 8.98 (d, J=8.4 Hz, 1H), 7.81 (d, J=5.4 Hz, 1H), 7.44 (s, 1H), 6.96 (s, 2H), 6.73 (m, 1H), 4.67 (t, J=7.8 Hz, 2H), 2.95 (s, 3H), 2.54 (t, J=7.8 Hz, 2H), 4.53 (s, 2H), 2.71 (s, 3H); MS (ESI) m/z 270.1 (M+H)+.

4-(7-oxy-1-methyl-9-H-b-carbolin)butanamide (10-3c). White solid. Yield 84%. MS (ESI) m/z 284.16 (M+H)+. H-NMR (600 MHz, d$_6$-DMSO): δ 11.39 (s, 1H), 8.13 (d, J=5.4 Hz, 1H), 8.03 (d, J=8.4 Hz, 1H), 7.80 (d, J=5.4 Hz, 1H), 7.35 (s, 1H), 6.98 (s, 1H), 6.82 (m, 2H), 4.06 (t, J=6 Hz, 2H), 2.71 (s, 3H), 2.27 (t, J=7.8 Hz, 2H), 1.98 (m, 2H); MS (ESI) m/z 284.16 (M+H)+.

5-(7-oxy-1-methyl-9-H-b-carbolin)pentanamide (10-3d). White solid. Yield 85%. $^1$H-NMR (600 MHz, d$_6$-DMSO): δ 11.38 (s, 1H), 8.13 (d, J=5.4 Hz, 1H), 8.03 (d, J=8.4 Hz, 1H), 7.80 (d, J=5.4 Hz, 1H), 7.29 (s, 1H), 6.98 (d, J=2.4 Hz, 1H), 6.82 (m, 1H), 6.75 (s, 1H), 4.07 (t, J=6.6 Hz, 2H), 2.71 (s, 3H), 2.13 (t, J=7.2 Hz, 2H), 1.76 (m, 2H), 1.69 (m, 2H); MS (ESI) m/z 298.1 (M+H)+.

6-(7-oxy-1-methyl-9-H-b-carbolin)hexanamide (10-3e). White solid. Yield 94%. MS (ESI) m/z 312.1 (M+H)+. H-NMR (600 MHz, d$_6$-DMSO): δ 11.38 (s, 1H), 8.13 (d, J=5.4 Hz, 1H), 8.03 (d, J=8.4 Hz, 1H), 7.80 (d, J=4.8 Hz, 1H), 7.26 (s, 1H), 6.98 (d, J=2.4 Hz, 1H), 6.82 (m, 1H), 6.72 (s, 1H), 4.07 (t, J=6.6 Hz, 2H), 2.71 (s, 3H), 2.09 (t, J=7.2 Hz, 2H), 1.77 (m, 2H), 1.57 (m, 2H), 1.45 (m, 2H); MS (ESI) m/z 312.1 (M+H)+.

General procedure for the synthesis of 10-4. A solution of 10-2f to 10-2j (0.18 mmol) and TFA/DCM (1:1, 4 mL) was stirred at room temperature for 24 hours. The reaction mixture was evaporated and triturated with diethyl ether to get the desired acid 10-4 as white solid.

2-(7-oxy-1-methyl-9-H-b-carbolin)acetic acid (10-4a). White solid. Yield 89%. $^1$H-NMR (600 MHz, d$_6$-DMSO): δ 12.73 (s, 1H), 8.48 (d, J=6 Hz, 1H), 8.43 (d, J=6 Hz, 1H), 8.38 (d, J=9 Hz, 1H), 7.09 (m, 2H), 4.90 (s, 2H), 2.97 (s, 3H); MS (ESI) m/z 257.1 (M+H)+.

3-(7-oxy-1-methyl-9-H-b-carbolin)propionic acid (10-4b). White solid. Yield 98%. $^1$H-NMR (600 MHz, $d_6$-DMSO): δ 12.59 (s, 1H), 10.64 (s, 1H), 8.45 (d, J=6 Hz, 1H), 8.40 (d, J=6.6 Hz, 1H), 8.30 (d, J=9 Hz, 1H), 7.14 (s, 1H), 6.97 (d, J=9 Hz, 1H), 4.81 (t, J=7.8 Hz, 2H), 3.16 (s, 3H), 2.82 (t, J=7.2 Hz, 2H), 2.97 (s, 3H); MS (ESI) m/z 271.4 (M+H)+.

4-(7-oxy-1-methyl-9-H-b-carbolin)butnoic acid (10-4c). White solid. Yield 82%. $^1$H-NMR (600 MHz, $d_6$-DMSO): δ 12.71 (s, 1H), 12.23 (s, 1H), 8.45 (d, J=6 Hz, 1H), 8.40 (d, J=6 Hz, 1H), 8.35 (d, J=9 Hz, 1H), 7.12 (s, 1H), 7.05 (d, J=9 Hz, 1H), 4.17 (t, J=6 Hz, 2H), 2.97 (s, 3H), 2.45 (t, J=7.2 Hz, 2H), 2.03 (m, 2H); MS (ESI) m/z 285.4 (M+H)+.

5-(7-oxy-1-methyl-9-H-b-carbolin)pentanoic acid (10-4d). White solid. Yield 85%. $^1$H-NMR (600 MHz, $d_6$-DMSO): δ 12.68 (s, 1H), 12.10 (s, 1H), 8.45 (d, J=6.6 Hz, 1H), 8.40 (d, J=6 Hz, 1H), 8.35 (d, J=9 Hz, 1H), 7.11 (s, 1H), 7.05 (d, J=9 Hz, 1H), 4.16 (t, J=6.6 Hz, 2H), 2.97 (s, 3H), 2.32 (t, J=7.2 Hz, 2H), 1.83 (m, 2H), 1.83 (m, 2H); MS (ESI) m/z 299.8 (M+H)+.

6-(7-oxy-1-methyl-9-H-b-carbolin)hexanoic acid (10-4e). White solid. Yield 91%. $^1$H-NMR (600 MHz, $d_6$-DMSO): δ 12.71 (s, 1H), 8.45 (d, J=6.6 Hz, 1H), 8.40 (d, J=6 Hz, 1H), 8.35 (d, J=9 Hz, 1H), 7.11 (s, 1H), 7.05 (d, J=9 Hz, 1H), 4.16 (t, J=6.6 Hz, 2H), 2.97 (s, 3H), 2.26 (t, J=7.8 Hz, 2H), 1.80 (m, 2H), 1.59 (m, 2H), 1.47 (m, 2H); MS (ESI) m/z 313.5 (M+H)+.

General procedure for the synthesis of 10-5. To a solution of 10-2k to 10-2n (1.93 mmol) in 1,4-dioxane (4 mL) was added 4 N HCl in dioxane (4 eq.) and stirred at room temperature for 24 hours. After the completion of the reaction as monitored by LCMS, the mixture was evaporated to give the desired product 10-5 as white solid.

2-(7-oxy-1-methyl-9-H-b-carbolin)ethylamine hydrochloric acid (10-5a). White solid. Yield 90%. $^1$H-NMR (600 MHz, $d_6$-DMSO): δ 13.08 (s, 1H), 8.47 (d, J=6.6 Hz, 1H), 8.38 (m, 2H), 8.33 (bs, 2H), 7.19 (d, J=1.8 Hz, 1H), 7.10 (m, 1H), 4.37 (t, J=5.4 Hz, 2H), 3.30 (t, J=4.8 Hz, 2H), 3.03 (s, 3H); MS (ESI) m/z 242.22 (M+H)+.

3-(7-oxy-1-methyl-9-H-b-carbolin)propylamine hydrochloric acid (10-5b). White solid. Yield 98%. $^1$H-NMR (600 MHz, $d_6$-DMSO): δ 13.03 (s, 1H), 8.45 (d, J=6 Hz, 1H), 8.38 (d, J=6.6 Hz, 1H), 8.35 (s, 1H), 8.09 (bs, 2H), 7.15 (d, J=2.4 Hz, 1H), 7.06 (m, 1H), 4.25 (t, J=6 Hz, 2H), 3.03 (m, 5H), 2.12 (m, 2H); MS (ESI) m/z 256.11 (M+H)+.

4-(7-oxy-1-methyl-9-H-b-carbolin)butylamine hydrochloric acid (10-5c). White solid. Yield 99%. $^1$H-NMR (600 MHz, $d_6$-DMSO): δ 12.98 (s, 1H), 8.45 (d, J=6 Hz, 1H), 8.38 (d, J=6 Hz, 1H), 8.35 (d, J=8.4 Hz, 1H), 7.97 (bs, 2H), 7.14 (d, J=1.8 Hz, 1H), 7.05 (d, J=9 Hz, 1H), 4.17 (t, J=6 Hz, 2H), 3.02 (s, 3H), 2.87 (t, J=6.6 Hz, 2H), 1.87 (m, 2H), 1.77 (m, 2H); MS (ESI) m/z 270.45 (M+H)+.

2-((7-oxy-1-methyl-9-H-b-carbolin)ethoxy)ethylamine hydrochloric acid (1-5d). White solid. Yield 97%. $^1$H-NMR (600 MHz, $d_6$-DMSO): δ 13.14 (s, 1H), 8.45 (d, J=6 Hz, 1H), 8.36 (m, 2H), 8.10 (bs, 2H), 7.18 (d, J=1.8 Hz, 1H), 7.06 (d, J=9 Hz, 1H), 4.31 (t, J=4.8 Hz, 2H), 3.88 (t, J=4.2 Hz, 2H), 3.73 (t, J=5.4 Hz, 2H), 3.03 (s, 3H), 3.0 (t, J=5.4 Hz, 2H), 1.87 (m, 2H), 1.77 (m, 2H); MS (ESI) m/z 286.27 (M+H)+.

General procedure for the synthesis of 10-6. To a solution of 10-5 (0.36 mmol) and triethylamine (2.2 eq.) in DCM was added acetic anhydride dropwise and the reaction mixture was stirred at room temperature for 1 hour. Upon completion of the reaction, the mixture was diluted with DCM, transferred to separatory funnel and washed with water. The organic layer was collected, dried over magnesium sulfate, filtered and evaporated to get the desired product 10-6 as white solid.

2-(7-oxy-1-methyl-9-H-b-carbolin)-2-acetyl-ethylamine (10-6a). White solid. Yield 74%. $^1$H-NMR (600 MHz, $d_6$-DMSO): δ 11.39 (s, 1H), 8.14 (d, J=5.4 Hz, 1H), 8.36 (d, J=8.4 Hz, 1H), 7.95 (t, J=5.4 Hz, 1H), 7.90 (t, J=5.4 Hz, 1H), 6.99 (d, J=2.4 Hz, 1H), 6.82 (m, 1H), 4.08 (t, J=6 Hz, 2H), 3.21 (t, J=6.6 Hz, 2H), 2.71 (s, 3H), 1.81 (s, 3H); MS (ESI) m/z 284.62 (M+H)+.

3-(7-oxy-1-methyl-9-H-b-carbolin)-2-acetyl-propylamine (10-6b). White solid. Yield 79%. $^1$H-NMR (600 MHz, $d_6$-DMSO): δ 11.39 (s, 1H), 8.14 (d, J=5.4 Hz, 1H), 8.36 (d, J=8.4 Hz, 1H), 7.95 (t, J=5.4 Hz, 1H), 7.90 (t, J=5.4 Hz, 1H), 6.99 (d, J=2.4 Hz, 1H), 6.82 (m, 1H), 4.08 (t, J=6 Hz, 2H), 3.22 (m, 2H), 2.71 (s, 3H), 1.90 (m, 2H), 1.81 (s, 3H); MS (ESI) m/z 298.71 (M+H)+.

4-(7-oxy-1-methyl-9-H-b-carbolin)-2-acetyl-butylamine (10-6c). White solid. Yield 70%. M$^1$H-NMR (600 MHz, $d_6$-DMSO): δ 11.47 (s, 1H), 8.14 (d, J=5.4 Hz, 1H), 8.05 (d, J=8.4 Hz, 1H), 7.93 (m, 1H), 7.80 (d, J=4.8 Hz, 1H), 7.01 (d, J=2.4 Hz, 1H), 6.84 (m, 1H), 4.08 (t, J=5.4 Hz, 2H), 3.10 (m, 2H), 2.73 (s, 3H), 1.80 (m, 5H), 1.59 (m, 2H); MS (ESI) m/z 312.18 (M+H)+.

2-((7-oxy-1-methyl-9-H-b-carbolin)ethoxy)-2-acetyl-ethylamine (10-6d). White solid. Yield 49%. $^1$H-NMR (600 MHz, $d_6$-DMSO): δ 11.40 (s, 1H), 8.14 (d, J=5.4 Hz, 1H), 8.06 (d, J=8.4 Hz, 1H), 7.87 (m, 1H), 7.84 (t, J=5.4 Hz, 1H), 6.99 (d, J=1.8 Hz, 1H), 6.84 (m, 1H), 4.20 (t, J=4.8 Hz, 2H), 3.79 (m, 2H), 3.50 (t, J=6 Hz, 2H), 3.55 (m, 2H), 2.71 (s, 3H), 1.79 s, 3H); MS (ESI) m/z 328.44 (M+H)+.

O-Trifluoromethanesulfonyl-1-methyl-9H-b-carbolin-7-ol (10-7). To a solution of 10-1 (500 mg, 2.52 mmol) and pyridine (25.2 mmol) in DCM (4 mL) was added trifluoromethanesulfonic anhydride (1.2 eq.) at 0° C. dropwise. The reaction mixture was allowed to warm to room temperature and stirred for 12 hours. Upon completion of the reaction, the mixture was evaporated and purified by flash column chromatography using DCM/MeOH (95/5) as eluent to get the desired product 10-7 as white solid (875 mg, 92%). $^1$H-NMR (600 MHz, $d_6$-DMSO): δ 13.01 (s, 1H), 8.67 (d, J=9 Hz, 1H), 8.61 (d, J=6 Hz, 1H), 8.51 (d, J=6 Hz, 1H), 7.87 (m, 1H), 7.51 (d, J=9 Hz, 1H), 2.99 (s, 3H); MS (ESI) m/z 331.5 (M+H)+.

7-nitro-1-methyl-9H-b-carboline (10-8). A pressure vessel was charged with 1-7 (100 mg, 0.30 mmol), Pd2(dba)3 (5 mol %), BrettPhos (6 mol %) and sodium nitrite (42 mg, 0.6 mmol) and evacuated and back filled with argon three times. To the mixture was added tert-butanol (0.6 ml) and TDA (5 mol %) under argon. The pressure was sealed and heated to 150° C. for 24 hours. Upon completion of the reaction, the mixture was evaporated and purified by column chromatography to get 10-8 as yellow solid (80 mg, 77%). $^1$H-NMR (600 MHz, CD$_3$OD): δ 8.41 (m, 1H), 8.30 (d, J=8.4 Hz, 1H), 8.23 (d, J=5.4 Hz, 1H), 8.08 (m, 1H), 8.01 (d, J=5.4 Hz, 1H), 2.82 (s, 3H); MS (ESI) m/z 228.31 (M+H)+.

7-amino-1-methyl-9H-b-carboline (10-9). To a solution of 10-8 (80 mg, 0.35 mmol) and palladium on carbon (10% by wt, 100 mg) in methanol (4 mL) was added hydrazine monohydrate (0.34 mL, 7 mmol) and heated to 85° C. for 1 hour. Upon completion of the reaction, catalyst was filtered over celite and filterate was evaporated and purified by column chromatography using DCM/MeOH (90/10) as eluent to get the desired amino compound 10-9 as brown solid (65 mg, 98%). $^1$H-NMR (600 MHz, CD$_3$OD): δ 8.02 (d, J=5.4 Hz, 1H), 7.82 (d, J=8.4 Hz, 1H), 7.69 (d, J=4.8 Hz, 1H), 6.80 (s, 1H), 6.68 (d, J=8.4 Hz, 1H), 2.71 (s, 3H); MS (ESI) m/z 198.16 (M+H)+.

7-benzamide-1-methyl-9H-b-carboline (10-10). To a solution of 10-9 (20 mg, 0.10 mmol) and triethylamine (0.028 mL, 0.20 mmol) in THF (1 mL) was added benzoyl chloride at 0° C. and stirred at room temperature for 2 hours. Upon completion of the reaction monitored by LCMS, the mixture was evaporated and purified by column chromatography using DCM/MeOH (95/5) as eluent to get the desired product 10-10 as white solid (23 mg, 77%). $^1$H-NMR (600 MHz, $d_6$-DMSO): δ 11.53 (s, 1H), 10.47 (s, 2H), 8.32 (s, 1H), 8.17 (d, J=4.8 Hz, 1H), 8.13 (d, J=8.4 Hz, 1H), 8.0 (d, J=7.2 Hz, 2H), 7.85 (d, J=5.4 Hz, 1H), 7.61 (t, J=7.8 Hz, 1H), 2.55 (m, 3H), 2.74 (s, 3H); MS (ESI) m/z 302.29 (M+H)+.

7-acetamide-1-methyl-9H-b-carboline (10-11). To a solution of 10-9 (20 mg, 0.10 mmol) and triethylamine (0.028 mL, 0.20 mmol) in THF (2 mL) was added acetic anhydride dropwise at 0° C. and the reaction mixture was stirred at room temperature for 12 hours. Upon completion of the reaction, the mixture was diluted with DCM, transferred to separatory funnel and washed with water. The organic layer was collected, dried over magnesium sulfate, filtered and evaporated to get the desired product 10-6 as white solid (18 mg, 75%). $^1$H-NMR (600 MHz, $d_6$-DMSO): δ 11.44 (s, 1H), 10.16 (s, 1H), 8.19 (s, 1H), 8.15 (d, J=5.4 Hz, 1H), 8.06 (d, J=8.4 Hz, 1H), 7.81 (m, 1H), 7.23 (d, J=8.4 Hz, 1H), 2.71 (s, 3H), 2.10 (s, 3H); MS (ESI) m/z 240.52 (M+H)+.

1-Methyl-9H-pyrido[3,4-b]indol-7-yl isopropylcarbamate (10-12). To a solution of harmalol 10-1 (50 mg, 0.25 mmol) in DMF (2 mL) was added isopropyl isocyanate (0.030 mL, 0.3 mmol) and stirred at room temperature for 2 hours. The reaction mixture was evaporated and purified by column chromatography using DCM/MeOH (95/5) as eluent to get the desired product 10-12 as white solid (23 mg, 32%). $^1$H-NMR (600 MHz, $CD_3OD$): δ 8.09 (d, J=5.4 Hz, 1H), 8.12 (d, J=8.4 Hz, 1H), 7.90 (d, J=5.4 Hz, 1H), 7.31 (m, 1H), 7.09 (m, 1H), 3.80 (m, 1H), 2.79 (s, 3H), 1.23 (d, J=6.6 Hz, 6H); MS (ESI) m/z 298.77 (M+H)+.

DYRK1A Binding Assays. Compounds were tested for DYRK1A binding activity at a commercial kinase profiling services, Life Technologies which uses the FRET-based LanthaScreen Eu Kinase Binding Assay. Compounds were screened for DYRK1A activity at concentrations of 1000 nM and 300 nM in duplicates. The $IC_{50}$ was determined by 10 point LanthaScreen® Eu Kinase Binding Assay in duplicates.

B-Cell Proliferation Assay. Human pancreatic islets were obtained from the NIH/NIDDK-supported Integrated Islet Distribution Program (IIDP). Islets were first dispersed with Accutase (Sigma, St. Louis, MO) and seeded onto coverslips as described earlier (Wang et al., 2015, which is hereby incorporated by reference in its entirety). After 2 hours, dispersed human islet cells were treated with compound in RPMI1640 complete medium for 96 hours. Then the cells were fixed and stained for insulin and Ki67 (Wang et al., 2015, which is hereby incorporated by reference in its entirety). Total insulin positive cells and double Ki67 and insulin positive cells were imaged and counted. At least 1000 cells were counted.

Figure 5:
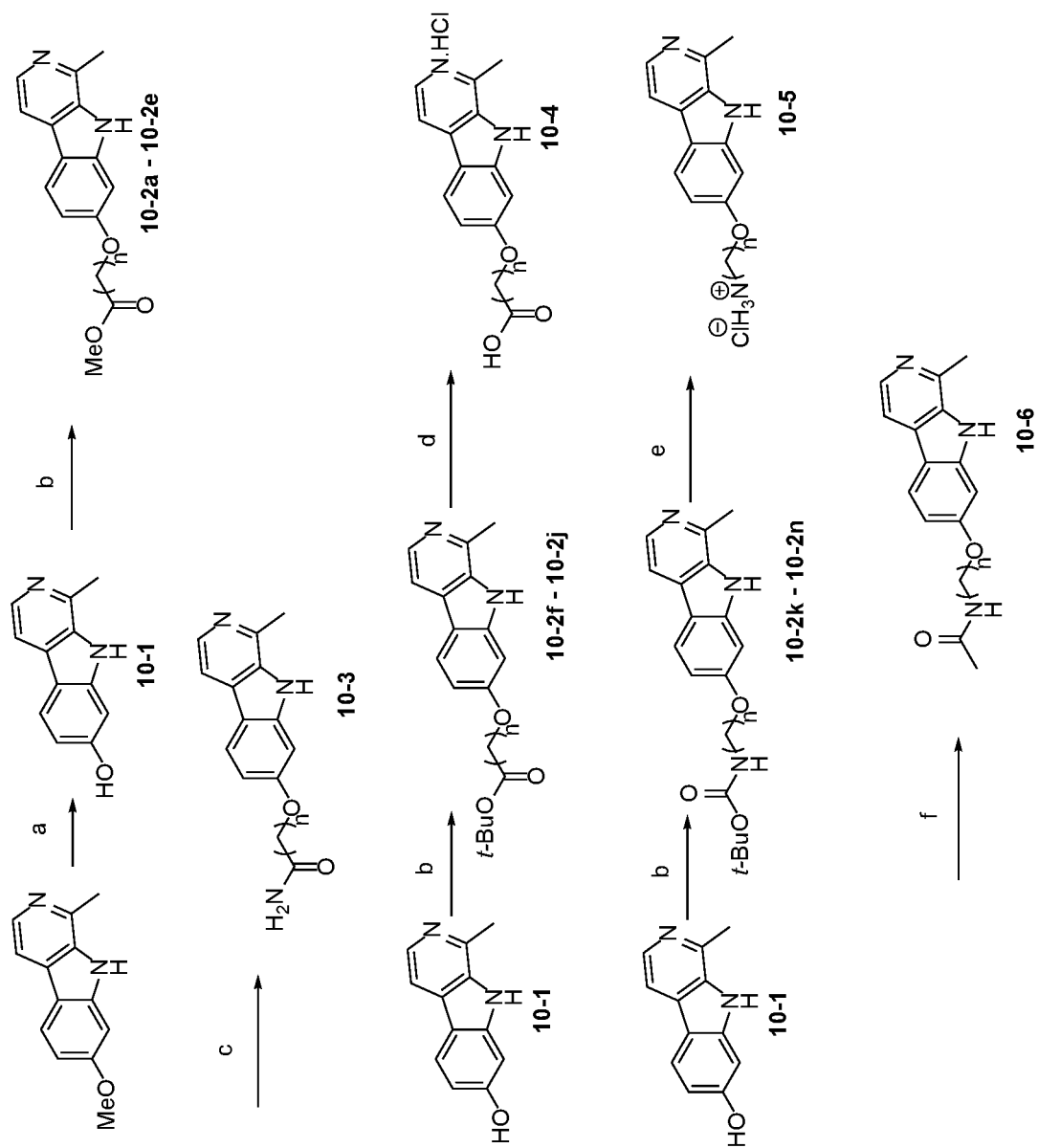
FIG. 5 is a schematic illustration showing the synthesis of 7-substituted harmine analog compounds. Reagents and conditions: (a) AcOH, 48% HBr, reflux, 12 hours; (b) $Cs_2CO_3$ (1.5 eq.), RBr (1.5 eq.), DMF, 50° C., 12 hours; (c) 7 N $NH_3$ in MeOH (20 eq.), 90° C., 12 hours; (d) TFA/DCM (1:1), room temperature, 12 hours; (e) 4 N HCl in dioxane, dioxane, room temperature, 12 hours; (f) Acetic anhydride (1 eq), $Et_3N$ (2.2 eq.), DCM, room temperature, 12 hours; (g) $TfO_2$ (1.2 eq.), Pyridine, DCM, 0° C.-room temperature, 12 hours; (h) $NaNO_2$ (2 eq.), $Pd_2(dba)_3$ (5 mol %), BrettPhos (12 mol %), TDA (5 mol %), t-BuOH, 150° C., 24 hours; (i) 10% wt Pd on C, $N_2H_4.H_2O$ (20 eq.), MeOH, reflux, 2 hours; (j) Benzoyl chloride (1.05 eq.), $Et_3N$ (2 eq.), THF, 0° C.-room temperature, 12 hours; (k) Acetic anhydride (1.2 eq), $Et_3N$ (2 eq.), THF, room temperature, 24 hours; (l) Isopropylisocyanate (1.1 eq.), DMF, room temperature, 12 hours.
Figure 5:
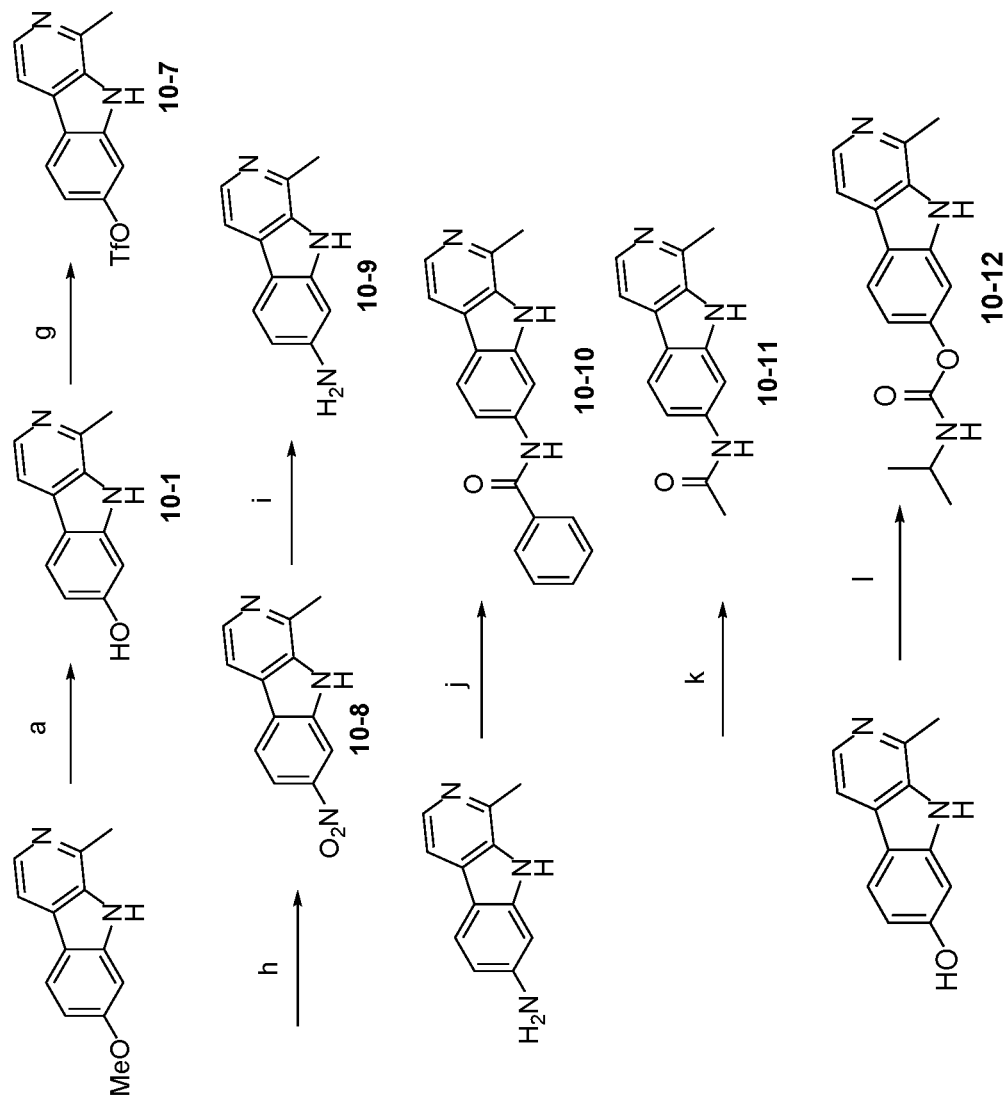

Example 8—Synthesis, SAR Analysis, and Human β-Cell Proliferation Assays of 7-Substituted Harmine Analogs 7-substituted harmine analogs were synthesized by following the reaction sequence outlined in FIG. 5. Table 4 shows that analog 10-3b had an $IC_{50}$ against DYRK1A of 91 nM, whereas analog 10-4a inhibited DYRK1A with an $IC_{50}$ of 71 nM. In contrast, analog 10-4b and 10-11 had an $IC_{50}$ against DYRK1A of 1810 nM and 389 nM, respectively. Compounds 10-2b, 10-3b, and 10-3e were assessed for their ability to induce human β-cell proliferation in vitro. Table 5 shows that these compounds showed reduced β-cell proliferation compared to harmine, at the dosages tested.

TABLE 4

DYRK1A Inhibition of Exemplary Substituted Harmine Analogs

| | | % DYRK1A Inhibition | | |
|---|---|---|---|---|
| Compound | R | 1000 nM | 300 nM | $IC_{50}$ (nM)$^a$ |
| 10-2a | MeO-C(O)-CH$_2$-* | 85 | 58 | — |
| 10-2b | MeO-C(O)-CH$_2$CH$_2$-* | — | — | 89.7 |
| 10-2c | MeO-C(O)-CH$_2$CH$_2$CH$_2$-* | 78 | 47 | — |

TABLE 4-continued

DYRK1A Inhibition of Exemplary Substituted Harmine Analogs 10-2, 10-3, 10-4, 10-5, 10-6

10-9, 10-10, 10-11

| Compound | R | % DYRK1A Inhibition | | $IC_{50}$ (nM)[a] |
|---|---|---|---|---|
| | | 1000 nM | 300 nM | |
| 10-2d | MeO-C(O)-(CH2)3-* | 67 | 35 | — |
| 10-2e | MeO-C(O)-(CH2)4-* | 81 | 56 | — |
| 10-2k | tBuO-C(O)-NH-(CH2)2-* | 61 | 35 | — |
| 10-2l | tBuO-C(O)-NH-(CH2)3-* | 50 | 24 | — |
| 10-2m | tBuO-C(O)-NH-(CH2)4-* | 58 | 31 | — |
| 10-2n | tBuO-C(O)-NH-CH2CH2-O-CH2CH2-* | 48 | 27 | — |
| 10-2o | MeO-CH2CH2-* | 48 | 23 | — |
| 10-2p | EtO-CH2CH2-* | 37 | 19 | — |
| 10-3a | H2N-C(O)-CH2-* | 30 | 10 | — |
| 10-3b | MeO-C(O)-CH2CH2-* | — | — | 91 |
| 10-3c | H2N-C(O)-(CH2)3-* | 58 | 32 | — |
| 10-3d | H2N-C(O)-(CH2)4-* | 88 | 67 | — |
| 10-3e | H2N-C(O)-(CH2)5-* | 67 | 39 | — |

TABLE 4-continued

DYRK1A Inhibition of Exemplary Substituted Harmine Analogs

Structures: 10-2, 10-3, 10-4, 10-5, 10-6 (R-O-linked harmine analog); 10-9, 10-10, 10-11 (R-linked harmine analog)

| Compound | R | % DYRK1A Inhibition 1000 nM | % DYRK1A Inhibition 300 nM | IC$_{50}$ (nM)$^a$ |
|---|---|---|---|---|
| 10-4a | HOOC-CH$_2$-* | 6 | 3 | 71 |
| 10-4b | HOOC-(CH$_2$)$_2$-* | — | — | 1810 |
| 10-4c | HOOC-(CH$_2$)$_3$-* | 19 | 6 | — |
| 10-4d | HOOC-(CH$_2$)$_4$-* | 44 | 20 | — |
| 10-4e | HOOC-(CH$_2$)$_5$-* | 74 | 43 | — |
| 10-5a | ClH$_3$N$^+$-(CH$_2$)$_2$-* | 25 | 12 | — |
| 10-5b | ClH$_3$N$^+$-(CH$_2$)$_3$-* | 28 | 8 | — |
| 10-5c | ClH$_3$N$^+$-(CH$_2$)$_4$-* | 42 | 15 | — |
| 10-5d | ClH$_3$N$^+$-CH$_2$CH$_2$-O-CH$_2$CH$_2$-* | 32 | 15 | — |
| 10-6a | CH$_3$C(O)NH-(CH$_2$)$_2$-* | 49 | 24 | — |
| 10-6b | CH$_3$C(O)NH-(CH$_2$)$_3$-* | 49 | 22 | — |
| 10-6c | CH$_3$C(O)NH-(CH$_2$)$_4$-* | 69 | 45 | — |
| 10-6d | CH$_3$C(O)NH-CH$_2$CH$_2$-O-CH$_2$CH$_2$-* | 41 | 17 | — |
| 10-9 | H$_2$N—* | 21 | 8 | — |

TABLE 4-continued

DYRK1A Inhibition of Exemplary Substituted Harmine Analogs

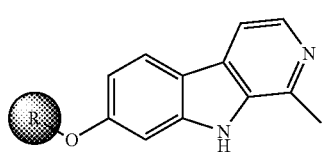  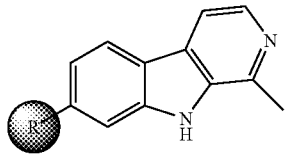

10-2, 10-3, 10-4, 10-5, 10-6        10-9, 10-10, 10-11

| Compound | R | % DYRK1A Inhibition | | $IC_{50}$ (nM)[a] |
|---|---|---|---|---|
| | | 1000 nM | 300 nM | |
| 10-10 | (acetamide structure) | 65 | 37 | — |
| 10-11 | (benzamide structure) | 77 | 48 | 389 |
| 10-12 | (isopropyl urea structure) | 69 | 42 | n.d. |
| | Harmine | — | — | 27 |

[a] = $IC_{50}$ values are determined using ten serial three fold dilutions (in duplicate)

TABLE 5

β-Cell Proliferation of Exemplary Substituted Harmine Analogs

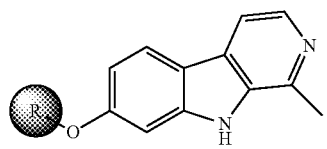

| Compound | R | Human β-Cell proliferation (Concentration μM) | $IC_{50}$ (nM) |
|---|---|---|---|
| 10-2b | (MeO-propanoate) | 0.8 (30) | 89.7 |
| 10-3b | (H2N-propanamide) | 0.4 (30) | 91 |
| 10-3e | (H2N-hexanamide) | 0.2 (10) | — |
| | Harmine | 1.5 (10) | 27 |

Example 9—Materials and Methods for Example 10

General procedure for the synthesis of 1-1. To a solution of harmine (1 mmol) in DMF (7 mL) was added NaH (2 eq.) and stirred at room temperature for 1 hour. To this solution was added alkyl bromide (1.5 eq.) at 50° C. and stirred at that temperature for 12 hours. After completion of the reaction confirmed by TLC, the reaction mixture was diluted with water, transferred to separatory funnel and extracted with ethyl acetate (50 mL×2). The organic layer was washed with water, dried over magnesium sulfate, filtered, evaporated and purified by flash column chromatography using DCM/MeOH (9/1) as eluent to yield the desired product 1-1 as white solid.

2-(7-Methoxy-1-methyl-β-carbolin-9-yl)acetic acid methyl ester (20-1a). White solid. Yield 67%. $^1$H-NMR (600 MHz, CD$_3$OD): δ 8.12 (d, J=4.8 Hz, 1H), 8.01 (d, J=8.4 Hz, 1H), 7.86 (d, J=5.4 Hz, 1H), 7.03 (d, J=1.2 Hz, 1H), 6.91 (m, 1H), 5.41 (s, 2H), 3.92 (s, 3H), 3.78 (s, 3H), 2.87 (s, 3H); MS (ESI) m/z 285.33 (M+H)+.

3-(7-Methoxy-1-methyl-β-carbolin-9-yl)propionic acid methyl ester (20-1b). White solid. Yield 81%. $^1$H-NMR (600 MHz, CD$_3$OD): δ 8.11 (d, J=5.4 Hz, 1H), 8.01 (d, J=8.4 Hz, 1H), 7.84 (d, J=4.2 Hz, 1H), 7.10 (s, 1H), 6.90 (d, J=8.4 Hz, 1H), 4.90 (t, J=7.2 Hz, 2H), 3.91 (s, 3H), 3.55 (s, 3H), 2.99 (s, 3H), 2.82 (t, J=7.2 Hz, 2H); MS (ESI) m/z 299.18 (M+H)+.

4-(7-Methoxy-1-methyl-β-carbolin-9-yl)butyric acid methyl ester (20-1c). White solid. Yield 74%. $^1$H-NMR (600 MHz, CD$_3$OD): δ 8.11 (d, J=5.4 Hz, 1H), 7.02 (d, J=8.4 Hz, 1H), 7.84 (d, J=5.4 Hz, 1H), 7.18 (s, 1H), 6.90 (m, 1H), 4.61 (t, J=7.8 Hz, 2H), 3.95 (s, 3H), 3.64 (s, 3H), 3.00 (s, 3H), 2.47 (t, J=6.6 Hz, 2H), 2.10 (m, 2H); MS (ESI) m/z 213.33 (M+H)+.

5-(7-Methoxy-1-methyl-β-carbolin-9-yl)pentanoic acid methyl ester (20-1d). White solid. Yield 79%. $^1$H-NMR (600 MHz, CD$_3$OD): δ 8.08 (d, J=5.4 Hz, 1H), 7.98 (d, J=8.4 Hz, 1H), 7.81 (d, J=5.4 Hz, 1H), 7.03 (d, J=1.8 Hz, 1H), 6.85 (m, 1H), 4.52 (t, J=8.4 Hz, 2H), 3.93 (s, 3H), 3.60 (s, 3H), 2.96 (s, 3H), 2.37 (t, J=7.2 Hz, 2H), 1.80 (m, 2H), 1.70 (m, 2H); MS (ESI) m/z 327.19 (M+H)+.

6-(7-Methoxy-1-methyl-β-carbolin-9-yl)hexanoic acid methyl ester (20-1e). White solid. Yield 82%. $^1$H-NMR (600 MHz, CD$_3$OD): δ 8.08 (d, J=5.4 Hz, 1H), 7.98 (d, J=8.4 Hz, 1H), 7.81 (d, J=5.4 Hz, 1H), 7.01 (d, J=1.8 Hz, 1H), 6.87 (m, 1H), 4.50 (t, J=7.8 Hz, 2H), 3.92 (s, 3H), 3.59 (s, 3H), 2.94 (s, 3H), 2.29 (t, J=7.2 Hz, 2H), 1.78 (m, 2H), 1.64 (m, 2H), 1.40 (m, 2H); MS (ESI) m/z 341.23 (M+H)+.

2-methyl-4-(7-Methoxy-1-methyl-β-carbolin-9-yl)butyric acid methyl ester (20-1f). White solid. Yield 72%. $^1$H-NMR (600 MHz, CD$_3$OD): δ 8.09 (d, J=4.8 Hz, 1H), 7.99 (d, J=8.4 Hz, 1H), 7.81 (d, J=5.4 Hz, 1H), 7.06 (d, J=1.8 Hz, 1H), 6.88 (m, 1H), 4.50 (m, 2H), 3.94 (s, 3H), 3.66 (s, 3H), 2.95 (s, 3H), 2.65 (m, 1H), 2.12 (m, 1H), 1.87 (m, 1H), 1.23 (d, J=7.2 Hz, 3H); MS (ESI) m/z 327.76 (M+H)+.

2,2-dimethyl-4-(7-Methoxy-1-methyl-β-carbolin-9-yl)butyric acid methyl ester (20-1g). White solid. Yield 68%. $^1$H-NMR (600 MHz, d$_6$-DMSO): δ 8.16 (d, J=4.8 Hz, 1H), 8.11 (d, J=9 Hz, 1H), 7.88 (d, J=4.8 Hz, 1H), 7.04 (s, 1H), 6.90 (d, J=9 Hz, 1H), 4.49 (t, J=8.4 Hz, 2H), 3.92 (s, 3H), 3.72 (s, 3H), 2.95 (s, 3H), 1.92 (t, J=8.4 Hz, 2H), 1.30 (s, 6H); MS (ESI) m/z 341.92 (M+H)+.

2-(7-Methoxy-1-methyl-β-carbolin-9-yl)acetic acid t-butyl ester (20-1h). White solid. Yield 100%. H-NMR (600 MHz, CD$_3$OD): δ 8.13 (d, J=5.4 Hz, 1H), 8.22 (d, J=8.4 Hz, 1H), 7.86 (d, J=4.8 Hz, 1H), 7.03 (bs, 1H), 6.92 (d, J=8.4 Hz, 1H), 5.30 (s, 2H), 3.92 (s, 3H), 2.89 (s, 3H), 1.42 (s, 9H); MS (ESI) m/z 327.44 (M+H)+.

3-(7-Methoxy-1-methyl-β-carbolin-9-yl)propionic acid t-butyl ester (20-1i). White solid. Yield 21%. $^1$H-NMR (600 MHz, d$_6$-DMSO): δ 8.17 (d, J=4.8 Hz, 1H), 8.09 (d, J=9 Hz, 1H), 7.88 (d, J=5.4 Hz, 1H), 7.23 (d, J=2.4 Hz, 1H), 6.88 (m, 1H), 4.84 (t, J=7.8 Hz, 2H), 3.90 (s, 3H), 2.95 (s, 3H), 2.71 (t, J=7.2 Hz, 2H), 1.23 (s, 9H); MS (ESI) m/z 341.54 (M+H)+.

4-(7-Methoxy-1-methyl-β-carbolin-9-yl)butyric acid t-butyl ester (20-1j). White solid. Yield 82%. $^1$H-NMR (600 MHz, d-DMSO): δ 8.16 (d, J=5.4 Hz, 1H), 8.09 (d, J=8.4 Hz, 1H), 7.88 (d, J=5.4 Hz, 1H), 7.24 (d, J=2.4 Hz, 1H), 6.88 (m, 1H), 4.55 (t, J=7.8 Hz, 2H), 3.91 (s, 3H), 2.94 (s, 3H), 2.35 (t, J=6.6 Hz, 2H), 1.94 (m, 2H), 1.38 (s, 9H); MS (ESI) m/z 355.31 (M+H)+.

5-(7-Methoxy-1-methyl-β-carbolin-9-yl)pentanoic acid t-butyl ester (20-1k). White solid. Yield 80%. $^1$H-NMR (600 MHz, CDCl$_3$): δ 8.28 (d, J=5.4 Hz, 1H), 7.98 (d, J=8.4 Hz, 1H), 7.74 (d, J=5.4 Hz, 1H), 6.89 (d, J=1.8 Hz, 1H), 6.87 (m, 1H), 4.48 (t, J=7.8 Hz, 2H), 3.96 (s, 3H), 3.02 (s, 3H), 2.28 (t, J=7.2 Hz, 2H), 1.86 (m, 2H), 1.72 (m, 2H), 1.41 (s, 9H); MS (ESI) m/z 369.45 (M+H)+.

6-(7-Methoxy-1-methyl-β-carbolin-9-yl)hexanoic acid t-butyl ester (20-1l). White solid. Yield 76%. $^1$H-NMR (600 MHz, CDCl$_3$): δ 8.28 (d, J=5.4 Hz, 1H), 7.98 (d, J=8.4 Hz, 1H), 7.74 (d, J=5.4 Hz, 1H), 6.89 (d, J=8.4 Hz, 1H), 6.84 (d, J=1.8 Hz, 1H), 4.46 (t, J=7.8 Hz, 2H), 3.95 (s, 3H), 3.01 (s, 3H), 2.21 (t, J=7.2 Hz, 2H), 1.84 (m, 2H), 1.64 (m, 2H), 1.41 (m, 11H); MS (ESI) m/z 383.81 (M+H)+.

N-(3-(7-Methoxy-1-methyl-β-carbolin-9-yl)propyl)phthalimide (20-1m). White solid. Yield 60%. $^1$H-NMR (600 MHz, CD$_3$OD): δ 8.08 (d, J=5.4 Hz, 1H), 7.95 (d, J=8.4 Hz, 1H), 7.83-7.78 (m, 5H), 7.02 (d, J=2.4 Hz, 1H), 6.85 (m, 1H), 4.64 (t, J=7.8 Hz, 2H), 3.88 (s, 3H), 3.84 (t, J=7.8 Hz, 2H), 2.92 (s, 3H), 2.24 (m, 2H); MS (ESI) m/z 400.71 (M+H)+.

N-(4-(7-Methoxy-1-methyl-β-carbolin-9-yl)butyl)phthalimide (20-1n). White solid. Yield 84%. $^1$H-NMR (600 MHz, d$_6$-DMSO): δ 8.14 (d, J=5.4 Hz, 1H), 8.06 (d, J=9 Hz, 1H), 7.86 (d, J=4.8 Hz, 1H), 7.83 (m, 4H), 7.20 (d, J=2.4 Hz, 1H), 6.84 (m, 1H), 4.57 (t, J=7.8 Hz, 2H), 3.88 (s, 3H), 3.61 (t, J=6 Hz, 2H), 2.90 (s, 3H), 1.74 (m, 4H); MS (ESI) m/z 414.23 (M+H)+.

4-(7-Methoxy-1-methyl-β-carbolin-9-yl)propionitrile (20-1o). White solid. Yield 80%. $^1$H-NMR (600 MHz, CD$_3$OD): 8.11 (d, J=5.4 Hz, 1H), 8.00 (d, J=8.4 Hz, 1H), 7.82 (d, J=5.4 Hz, 1H), 7.09 (s, 1H), 6.90 (m, 1H), 4.65 (t, J=7.8 Hz, 2H), 3.93 (s, 3H), 2.97 (s, 3H), 2.54 (t, J=7.2 Hz, 2H), 2.11 (m, 2H); MS (ESI) m/z 280.71 (M+H)+.

3-(7-Methoxy-1-methyl-β-carbolin-9-yl)propionaldehyde dimethylacetal (20-1p). White solid. Yield 100%. $^1$H-NMR (600 MHz, d$_6$-DMSO): δ 8.16 (d, J=4.2 Hz, 1H), 8.10 (d, J=9 Hz, 1H), 7.87 (d, J=5.4 Hz, 1H), 7.14 (d, J=2.4 Hz, 1H), 6.88 (m, 1H), 4.60 (t, J=7.2 Hz, 2H), 4.42 (t, J=5.4 Hz, 1H), 3.91 (s, 3H), 3.23 (s, 6H), 2.95 (s, 3H), 2.11 (m, 2H); MS (ESI) m/z 315.90 (M+H)+.

4-(7-Methoxy-1-methyl-β-carbolin-9-yl)butyraldehyde dimethylacetal (20-1q). White solid. Yield 100%. $^1$H-NMR (600 MHz, d$_6$-DMSO): δ 8.09 (d, J=5.4 Hz, 1H), 7.99 (d, J=8.4 Hz, 1H), 7.81 (d, J=5.4 Hz, 1H), 7.01 (d, J=2.4 Hz, 1H), 6.88 (m, 1H), 4.52 (t, J=7.8 Hz, 2H), 4.36 (t, J=5.4 Hz, 1H), 3.92 (s, 3H), 3.27 (s, 6H), 2.95 (s, 3H), 1.81 (m, 2H), 1.68 (m, 2H); MS (ESI) m/z 329.96 (M+H)+.

5-(7-Methoxy-1-methyl-β-carbolin-9-yl)-pent-1-yne (20-1r). White solid. Yield 63%. $^1$H-NMR (600 MHz, CDCl$_3$):

δ 8.30 (d, J=5.4 Hz, 1H), 8.02 (d, J=9 Hz, 1H), 7.90 (d, J=5.4 Hz, 1H), 7.03 (d, J=1.8 Hz, 1H), 6.98 (m, 1H), 4.67 (t, J=7.2 Hz, 2H), 3.97 (s, 3H), 3.22 (s, 3H), 2.35 (m, 2H), 2.15 (m, 1H), 2.07 (m, 2H); MS (ESI) m/z 279.52 (M+H)+.

6-(7-Methoxy-1-methyl-β-carbolin-9-yl)-hex-1-yne (20-1s). White solid. Yield 62%. $^1$H-NMR (600 MHz, d$_6$-DMSO): δ 8.16 (d, J=5.4 Hz, 1H), 8.08 (d, J=8.4 Hz, 1H), 7.87 (d, J=4.8 Hz, 1H), 7.20 (d, J=1.8 Hz, 1H), 6.87 (m, 1H), 4.56 (t, J=7.2 Hz, 2H), 3.90 (s, 3H), 2.94 (s, 3H), 2.78 (m, 1H), 2.23 (m, 2H), 1.83 (m, 2H), 1.54 (m, 2H); MS (ESI) m/z 293.36 (M+H)+.

3-(7-Methoxy-1-methyl-β-carbolin-9-yl)-propan-1-ene (20-1t). White solid. Yield 72%. $^1$H-NMR (600 MHz, d$_6$-DMSO): δ 8.66 (d, J=4.8 Hz, 1H), 8.54 (d, J=8.4 Hz, 1H), 8.29 (d, J=4.8 Hz, 1H), 7.54 (m, 1H), 7.34 (m, 1H), 6.64 (m, 1H), 5.72 (m, 2H), 5.59 (d, J=10.2 Hz, 1H), 5.19 (d, J=16.8 Hz, 1H), 4.37 (s, 3H), 3.38 (s, 3H); MS (ESI) m/z 253.23 (M+H)+.

4-(7-Methoxy-1-methyl-β-carbolin-9-yl)-but-1-ene (20-1u). White solid. Yield 81%. $^1$H-NMR (600 MHz, d$_6$-DMSO): δ 8.66 (d, J=5.4 Hz, 1H), 8.52 (d, J=8.4 Hz, 1H), 8.28 (d, J=4.8 Hz, 1H), 7.63 (m, 1H), 7.35 (m, 1H), 6.37 (m, 1H), 5.61 (d, J=16.8 Hz, 1H), 5.49 (d, J=10.8 Hz, 1H), 5.15 (t, J=7.2 Hz, 2H), 4.30 (s, 3H), 3.44 (s, 3H), 3.08 (m, 2H); MS (ESI) m/z 267.44 (M+H)+.

5-(7-Methoxy-1-methyl-β-carbolin-9-yl)-pent-1-ene (20-1v). White solid. Yield 77%. $^1$H-NMR (600 MHz, d$_6$-DMSO): δ 8.65 (d, J=5.4 Hz, 1H), 8.52 (d, J=8.4 Hz, 1H), 8.27 (d, J=4.8 Hz, 1H), 7.60 (m, 1H), 7.34 (m, 1H), 6.37 (m, 1H), 5.55 (d, J=16.8 Hz, 1H), 5.47 (d, J=9.6 Hz, 1H), 5.08 (d, J=7.2 Hz, 2H), 4.39 (s, 3H), 3.44 (s, 3H), 2.69 (m, 2H), 2.40 (m, 2H); MS (ESI) m/z 281.28 (M+H)+.

6-(7-Methoxy-1-methyl-β-carbolin-9-yl)-hex-1-ene (20-1w). White solid. Yield 82%. $^1$H-NMR (600 MHz, d$_6$-DMSO): δ 8.16 (d, J=4.8 Hz, 1H), 8.08 (d, J=8.4 Hz, 1H), 7.87 (d, J=4.8 Hz, 1H), 7.18 (d, J=1.2 Hz, 1H), 6.87 (m, 1H), 5.78 (m, 1H), 5.00 (d, J=16.8 Hz, 1H), 4.94 (d, J=10.2 Hz, 1H), 4.55 (t, J=7.8 Hz, 2H), 3.90 (s, 3H), 2.93 (s, 3H), 2.07 (d, J=7.2 Hz, 2H), 1.72 (m, 2H), 1.47 (m, 2H); MS (ESI) m/z 295.66 (M+H)+.

1-(7-Methoxy-1-methyl-β-carbolin-9-yl)-1-phenylmethane (20-1x). White solid. Yield 69%. $^1$H-NMR (600 MHz, d$_6$-DMSO): δ 8.18 (d, J=4.8 Hz, 1H), 8.15 (d, J=8.4 Hz, 1H), 7.93 (d, J=4.8 Hz, 1H), 7.28 (t, J=7.2 Hz, 2H), 7.23 (t, J=7.2 Hz, 2H), 7.19 (s, 1H), 6.91 (m, 3H), 5.89 (s, 2H), 3.82 (s, 3H), 2.73 (s, 3H); MS (ESI) m/z 303.54 (M+H)+.

2-(7-Methoxy-1-methyl-β-carbolin-9-yl)-1-phenylethane (20-1y). White solid. Yield 54%. $^1$H-NMR (600 MHz, d$_6$-DMSO): δ 8.16 (d, J=5.4 Hz, 1H), 8.08 (d, J=8.4 Hz, 1H), 7.88 (d, J=5.4 Hz, 1H), 7.24 (m, 5H), 7.08 (d, J=1.2 Hz, 1H), 6.85 (m, 1H), 4.78 (t, J=7.8 Hz, 2H), 3.87 (m, 3H), 3.06 (t, J=7.2 Hz, 2H), 2.93 (s, 3H); MS (ESI) m/z 317.82 (M+H)+.

3-(7-Methoxy-1-methyl-β-carbolin-9-yl)-1-phenylpropane (20-1z). White solid. Yield 55%. $^1$H-NMR (600 MHz, d$_6$-DMSO): δ 8.15 (d, J=4.8 Hz, 1H), 8.08 (d, J=9 Hz, 1H), 7.86 (d, J=4.8 Hz, 1H), 7.30 (m, 4H), 7.20 (m, 1H), 7.02 (s, 1H), 6.86 (m, 1H), 4.53 (t, J=7.8 Hz, 2H), 3.85 (s, 3H), 2.79 (s, 3H), 2.73 (t, J=7.2 Hz, 2H), 2.06 (m, 2H); MS (ESI) m/z 331.52 (M+H)+.

4-(7-Methoxy-1-methyl-β-carbolin-9-yl)-1-phenylbutane (20-1z'). White solid. Yield 74%. $^1$H-NMR (600 MHz, d$_6$-DMSO): δ 8.64 (d, J=4.8 Hz, 1H), 8.51 (d, J=8.4 Hz, 1H), 8.26 (d, J=4.8 Hz, 1H), 7.70 (t, J=7.2 Hz, 1H), 7.65 (d, J=7.2 Hz, 2H), 7.58 (m, 2H), 7.32 (m, 1H), 5.09 (t, J=7.2 Hz, 2H), 4.37 (s, 3H), 3.39 (s, 3H), 3.15 (t, J=7.2 Hz, 2H), 2.35 (m, 2H), 2.27 (m, 2H); MS (ESI) m/z 345.13 (M+H)+.

1-azido-3-(7-Methoxy-1-methyl-β-carbolin-9-yl)propane (20-1a'). White solid. Yield 100%. $^1$H-NMR (600 MHz, CDCl$_3$): δ 8.30 (d, J=5.4 Hz, 1H), 8.00 (d, J=8.4 Hz, 1H), 7.83 (d, J=5.4 Hz, 1H), 6.95 (s, 1H), 6.94 (m, 1H), 7.02 (s, 1H), 6.86 (m, 1H), 4.61 (t, J=7.2 Hz, 2H), 3.97 (s, 3H), 3.40 (t, J=6 Hz, 2H), 3.13 (s, 3H), 2.09 (m, 2H); MS (ESI) m/z 297.15 (M+H)+.

1-azido-4-(7-Methoxy-1-methyl-β-carbolin-9-yl)butane (20-1b'). White solid. Yield 100%. $^1$H-NMR (600 MHz, CDCl$_3$): δ 8.30 (d, J=5.4 Hz, 1H), 8.01 (d, J=9 Hz, 1H), 7.83 (d, J=5.4 Hz, 1H), 6.90 (m, 1H), 6.88 (m, 1H), 4.53 (t, J=7.8 Hz, 2H), 3.97 (s, 3H), 3.35 (t, J=6 Hz, 2H), 3.12 (s, 3H), 1.95 (m, 2H), 1.69 (m, 2H); MS (ESI) m/z 311.16 (M+H)+.

3-(7-Methoxy-1-methyl-β-carbolin-9-yl)t-butycarboxy-1-propanamide (20-1c'). White solid. Yield 78%. $^1$H-NMR (600 MHz, CDCl$_3$): δ 8.27 (d, J=5.4 Hz, 1H), 7.98 (d, J=8.4 Hz, 1H), 7.75 (d, J=4.8 Hz, 1H), 6.95 (m, 1H), 6.88 (m, 1H), 4.54 (t, J=7.8 Hz, 2H), 3.95 (s, 3H), 3.23 (m, 2H), 3.04 (s, 3H), 2.03 (m, 2H), 1.44 (s, 9H); MS (ESI) m/z 370.21 (M+H)+.

General procedure for the synthesis of 20-2. A solution of 20-1a to 20-1f (0.175 mmol) and 7 N ammonia in methanol (4 mL) in a sealed pressure vessel was stirred at 90° C. for 12 hours. After the completion of the reaction, the mixture was evaporated and purified by flash column chromatography using DCM/MeOH/Ammonia (90/9/1) as eluent to give the desired final compound 20-2 as white solid.

2-(7-Methoxy-1-methyl-β-carbolin-9-yl)acetamide (20-2a). White solid. Yield 100%. $^1$H-NMR (600 MHz, d$_6$-DMSO): δ 8.15 (d, J=5.4 Hz, 1H), 8.09 (d, J=8.4 Hz, 1H), 7.87 (d, J=4.8 Hz, 1H), 7.71 (s, 1H), 7.35 (s, 1H), 715 (d, J=1.8 Hz, 1H), 6.87 (m, 1H), 5.18 (s, 2H), 3.88 (s, 3H), 2.85 (s, 3H); MS (ESI) m/z 270.61 (M+H)+.

3-(7-Methoxy-1-methyl-β-carbolin-9-yl)propionamide (20-2b). White solid. Yield 100%. $^1$H-NMR (600 MHz, d$_6$-DMSO): δ 8.16 (d, J=4.8 Hz, 1H), 8.08 (d, J=8.4 Hz, 1H), 7.87 (d, J=5.4 Hz, 1H), 7.41 (s, 1H), 7.23 (d, J=1.8 Hz, 1H), 6.96 (s, 1H), 6.87 (m, 1H), 4.78 (t, J=7.2 Hz, 2H), 3.90 (s, 3H), 2.97 (s, 3H), 2.57 (t, J=7.8 Hz, 2H); MS (ESI) m/z 284.43 (M+H)+.

4-(7-Methoxy-1-methyl-β-carbolin-9-yl)butanamide (20-2c). White solid. Yield 99%. $^1$H-NMR (600 MHz, d$_6$-DMSO): δ 8.16 (d, J=4.8 Hz, 1H), 8.09 (d, J=8.4 Hz, 1H), 7.87 (d, J=4.8 Hz, 1H), 7.36 (s, 1H), 7.28 (d, J=1.8 Hz, 1H), 6.88 (s, 1H), 6.86 (m, 1H), 4.53 (t, J=7.8 Hz, 2H), 3.91 (s, 3H), 2.95 (s, 3H), 2.19 (t, J=7.2 Hz, 2H), 1.94 (m, 2H); MS (ESI) m/z 298.31 (M+H)+.

5-(7-Methoxy-1-methyl-β-carbolin-9-yl)pentanamide (20-2d). White solid. Yield 99%. $^1$H-NMR (600 MHz, d$_6$-DMSO): δ 8.16 (d, J=4.8 Hz, 1H), 8.09 (d, J=8.4 Hz, 1H), 7.87 (d, J=4.8 Hz, 1H), 7.26 (s, 1H), 7.19 (d, J=1.8 Hz, 1H), 6.87 (m, 1H), 6.73 (s, 1H), 4.54 (t, J=7.8 Hz, 2H), 3.90 (s, 3H), 2.94 (s, 3H), 2.10 (t, J=7.2 Hz, 2H), 1.70 (m, 2H), 1.59 (m, 2H); MS (ESI) m/z 312.26 (M+H)+.

6-(7-Methoxy-1-methyl-β-carbolin-9-yl)hexanamide (20-2e). White solid. Yield 80%. $^1$H-NMR (600 MHz, d$_6$-DMSO): δ 8.16 (d, J=5.4 Hz, 1H), 8.09 (d, J=8.4 Hz, 1H), 7.87 (d, J=4.8 Hz, 1H), 7.22 (s, 1H), 7.17 (d, J=1.8 Hz, 1H), 6.87 (m, 1H), 6.70 (s, 1H), 4.53 (t, J=7.8 Hz, 2H), 3.90 (s, 3H), 2.94 (s, 3H), 2.02 (t, J=7.2 Hz, 2H), 1.72 (m, 2H), 1.53 (m, 2H), 1.36 (m, 2H); MS (ESI) m/z 326.66 (M+H)+.

2-methyl-4-(7-Methoxy-1-methyl-β-carbolin-9-yl)butanamide (20-2f). White solid. Yield 40%. $^1$H-NMR (600 MHz, d$_6$-DMSO): δ 8.17 (d, J=4.8 Hz, 1H), 8.10 (d, J=8.4 Hz, 1H), 7.91 (bs, 1H), 7.46 (s, 1H), 7.19 (s, 1H), 6.99 (s, 1H), 6.89 (d, J=7.8 Hz, 1H), 4.52 (m, 1H), 4.40 (m, 1H), 3.91 (s, 3H), 2.98 (s, 3H), 2.46 (m, 1H), 1.96 (m, 1H), 1.72 (m, 1H), 1.11 (d, J=7.2 Hz, 3H); MS (ESI) m/z 312.21 (M+H)+.

General procedure for the synthesis of 20-3. A solution of 20-1h to 20-1l (0.18 mmol) and TFA/DCM (1:1, 4 mL) was stirred at room temperature for 24 hours. The reaction mixture was evaporated and triturated with diethyl ether to get the desired acid 1-3 as white solid.

2-(7-Methoxy-1-methyl-β-carbolin-9-yl)acetic acid (20-3a). White solid. Yield 91%. $^1$H-NMR (600 MHz, $d_6$-DMSO): 8.54 (d, J=6.6 Hz, 1H), 8.41 (d, J=6.6 Hz, 1H), 8.38 (d, J=9 Hz, 1H), 7.50 (d, J=2.4 Hz, 1H), 7.07 (m, 1H), 5.60 (s, 2H), 3.94 (s, 3H), 3.10 (s, 3H); MS (ESI) m/z 271.17 (M+H)+.

3-(7-Methoxy-1-methyl-β-carbolin-9-yl)propionic acid hydrochloride (20-3b). White solid. Yield 60%. $^1$H-NMR (600 MHz, $d_6$-DMSO): δ 8.31 (d, J=6 Hz, 1H), 8.25 (d, J=9 Hz, 2H), 7.37 (s, 1H), 6.99 (m, 1H), 4.88 (t, J=7.2 Hz, 2H), 3.95 (s, 3H), 3.10 (s, 3H), 2.82 (t, J=7.8 Hz, 2H); MS (ESI) m/z 285.67 (M+H)+.

4-(7-Methoxy-1-methyl-β-carbolin-9-yl)butyric acid hydrochloride (20-3c). White solid. Yield 100%. $^1$H-NMR (600 MHz, $d_6$-DMSO): δ 8.53 (d, J=6.6 Hz, 1H), 8.44 (d, J=6.6 Hz, 1H), 8.39 (d, J=8.4 Hz, 1H), 7.45 (s, 1H), 7.09 (d, J=8.4 Hz, 1H), 4.66 (t, J=7.8 Hz, 2H), 3.98 (s, 3H), 3.18 (s, 3H), 2.44 (t, J=6.6 Hz, 2H), 2.00 (m, 2H); MS (ESI) m/z 299.13 (M+H)+.

5-(7-Methoxy-1-methyl-β-carbolin-9-yl)pentanoic acid hydrochloride (20-3d). White solid. Yield 99%. $^1$H-NMR (600 MHz, $d_6$-DMSO): δ 8.53 (d, J=6 Hz, 1H), 8.43 (d, J=6 Hz, 1H), 8.39 (d, J=8.4 Hz, 1H), 7.40 (s, 1H), 7.08 (d, J=7.8 Hz, 1H), 4.68 (t, J=7.8 Hz, 2H), 3.97 (s, 3H), 3.16 (s, 3H), 2.30 (t, J=7.2 Hz, 2H), 1.81 (m, 2H), 1.63 (m, 2H); MS (ESI) m/z 313.38 (M+H)+.

6-(7-Methoxy-1-methyl-β-carbolin-9-yl)hexanoic acid hydrochloride (20-3e). White solid. Yield 100%. $^1$H-NMR (600 MHz, $d_6$-DMSO): δ 8.53 (d, J=6 Hz, 1H), 8.43 (d, J=6.6 Hz, 1H), 8.39 (d, J=8.4 Hz, 1H), 7.39 (s, 1H), 7.08 (d, J=9 Hz, 1H), 4.66 (t, J=7.8 Hz, 2H), 3.97 (s, 3H), 3.16 (s, 3H), 2.20 (t, J=7.2 Hz, 2H), 1.79 (m, 2H), 1.56 (m, 2H), 1.41 (m, 2H); MS (ESI) m/z 327.17 (M+H)+.

2-methyl-4-(7-Methoxy-1-methyl-β-carbolin-9-yl)butyric acid (20-4a). To a solution of 2-methyl-4-(7-Methoxy-1-methyl-β-carbolin-9-yl)butyric acid benzyl ester (216 mg, 0.53 mmol) and Pd—C(45 mg) in MeOH (3 mL) was added triethylsilane (0.84 mL, 5.3 mmol) dropwise and stirred at room temperature for 1 hour. Upon completion of reaction, catalyst was filtered over celite, the filtrate was rotary evaporated and the crude was purified by flash column chromatography using DCM/MeOH (9/1) as eluent to get the desired acid 20-4a as white solid. Yield 64%. $^1$H-NMR (600 MHz, $d_6$-DMSO): δ 8.17 (d, J=4.8 Hz, 1H), 8.11 (d, J=8.4 Hz, 1H), 7.89 (bs, 1H), 7.19 (s, 1H), 6.89 (d, J=8.4 Hz, 1H), 4.55 (t, J=4.8 Hz, 2H), 3.90 (s, 3H), 2.95 (s, 3H), 2.59 (m, 1H), 2.00 (m, 1H), 1.79 (m, 1H), 1.19 (d, J=7.2 Hz, 3H); MS (ESI) m/z 313.63 (M+H)+.

2,2-dimethyl-4-(7-Methoxy-1-methyl-β-carbolin-9-yl)butyric acid (20-4b). Similar to compound 20-4a, 2,2-dimethyl-4-(7-Methoxy-1-methyl-β-carbolin-9-yl)butyric acid (20-4b) was obtained as white solid. Yield 60%. $^1$H-NMR (600 MHz, $d_6$-DMSO): δ 8.16 (d, J=5.4 Hz, 1H), 8.10 (d, J=8.4 Hz, 1H), 7.88 (d, J=4.8 Hz, 1H), 7.11 (d, J=1.2 Hz, 1H), 6.89 (m, 1H), 4.51 (t, J=8.4 Hz, 2H), 3.90 (s, 3H), 2.96 (s, 3H), 1.90 (m, 2H), 1.27 (s, 6H); MS (ESI) m/z 327.99 (M+H)+.

General Procedure for the synthesis of 20-5. A solution of 20-1m or 20-1n (0.12 mmol) and hydrazine monohydrate (20 eq.) in methanol (4 mL) was refluxed for 4 hours. After completion of the reaction, solvent was evaporated and the crude was purified by flash column chromatography using DCM/MeOH/Et$_3$N (9:1:0.1) as eluent to get the desired product 20-5 as white solid.

3-(7-Methoxy-1-methyl-β-carbolin-9-yl)propylamine (20-5a). White solid. Yield 36%. $^1$H-NMR (600 MHz, CD$_3$OD): δ 8.11 (d, J=5.4 Hz, 1H), 8.02 (d, J=8.4 Hz, 1H), 7.84 (d, J=5.4 Hz, 1H), 7.10 (d, J=1.8 Hz, 1H), 6.88 (m, 1H), 4.61 (t, J=7.8 Hz, 2H), 3.95 (s, 3H), 3.00 (s, 3H), 2.75 (m, 2H), 1.97 (m, 2H); MS (ESI) m/z 270.30 (M+H)+.

4-(7-Methoxy-1-methyl-β-carbolin-9-yl)butylamine (20-5b). White solid. Yield 34%. $^1$H-NMR (600 MHz, $d_6$-DMSO): δ 8.13 (d, J=5.4 Hz, 1H), 8.06 (d, J=8.4 Hz, 1H), 7.84 (d, J=5.4 Hz, 1H), 7.17 (d, J=1.8 Hz, 1H), 6.84 (m, 1H), 4.52 (t, J=7.8 Hz, 2H), 3.88 (s, 3H), 2.93 (s, 3H), 2.54 (m, 2H), 1.72 (m, 2H), 1.40 (m, 2H); MS (ESI) m/z 284.27 (M+H)+.

General Procedure for the synthesis of 20-6. To a solution of 20-5 (0.21 mmol) and DIPEA (1.2 eq.) in methylene chloride (2 mL) was added acetic anhydride (1.1 eq.) at 0° C. and stirred at room temperature for 1 hour. The reaction mixture was evaporated and purified by column chromatography using DCM/MeOH (9:1) as eluent to get the desired product 20-6 as white solid.

N-acetyl-3-(7-Methoxy-1-methyl-β-carbolin-9-yl)propylamine (20-6a). White solid. Yield 47%. $^1$H-NMR (600 MHz, CDCl$_3$): β 8.20 (t, J=6 Hz, 1H), 8.06 (m, 2H), 7.40 (m, 1H), 7.06 (d, J=8.4 Hz, 1H), 6.96 (s, 1H), 4.67 (t, J=8.4 Hz, 2H), 4.01 (s, 3H), 3.52 (m, 5H), 2.16 (m, 2H), 2.08 (s, 3H); MS (ESI) m/z 312.39 (M+H)+.

N-acetyl-4-(7-Methoxy-1-methyl-β-carbolin-9-yl)butylamine (20-6b). White solid. Yield 63%. $^1$H-NMR (600 MHz, CD$_3$OD): δ 8.12 (d, J=5.4 Hz, 1H), 8.05 (d, J=9 Hz, 1H), 7.91 (d, J=5.4 Hz, 1H), 7.09 (m, 1H), 6.92 (s, 1H), 4.61 (m, 2H), 3.95 (s, 3H), 3.19 (t, J=7.2 Hz, 2H), 3.00 (s, 3H), 1.88 (s, 3H), 1.58 (m, 2H); MS (ESI) m/z 326.34 (M+H)+.

General Procedure for the synthesis of 20-7. A solution of 20-5 (0.35 mmol) and ethyl formate (0.5 eq.) in ethanol (1 mL) was heated in CEM microwave at 150° C. for 30 minute. After the completion of the reaction, solvent was evaporated and the crude reaction mixture was dissolved in THF (2 mL) and LiAlH$_4$ (3 eq.) was added in portion at room temperature. After the addition, reaction mixture was refluxed for 4 hours. Solvent was evaporated and the crude reaction mixture was purified by flash column chromatography using DCM/MeOH (9:1) as eluent to get desired product 20-7 as white solid.

N-methyl-3-(7-Methoxy-1-methyl-β-carbolin-9-yl)propylamine (20-7a). White solid. Yield 41%. $^1$H-NMR (600 MHz, CD$_3$OD): δ 8.10 (d, J=5.4 Hz, 1H), 7.98 (d, J=8.4 Hz, 1H), 7.82 (d, J=5.4 Hz, 1H), 7.06 (d, J=2.4 Hz, 1H), 6.89 (m, 1H), 4.60 (t, J=7.2 Hz, 2H), 3.94 (s, 3H), 3.04 (t, J=7.2 Hz, 2H), 2.96 (s, 3H), 2.61 (s, 3H); MS (ESI) m/z 284.53 (M+H)+.

N-methyl-4-(7-Methoxy-1-methyl-β-carbolin-9-yl)butylamine (20-7b). White solid. Yield 27%. $^1$H-NMR (600 MHz, CD$_3$OD): δ 8.07 (d, J=5.4 Hz, 1H), 7.96 (d, J=9 Hz, 1H), 7.78 (d, J=5.4 Hz, 1H), 6.98 (m, 1H), 6.86 (m, 1H), 4.46 (t, J=7.8 Hz, 2H), 3.91 (s, 3H), 2.92 (s, 3H), 2.53 (t, J=7.2 Hz, 2H), 2.31 (s, 3H), 1.78 (s, 2H), 1.54 (m, 2H); MS (ESI) m/z 298.41 (M+H)+.

General Procedure for the synthesis of 20-8. To a solution of 20-7 (0.03 mmol) and DIPEA (1.2 eq.) in methylene chloride (1 mL) was added acetic anhydride (1.1 eq.) at 0° C. and stirred at room temperature for 1 hour. The reaction mixture was evaporated and purified by column chromatography using DCM/MeOH (9:1) as eluent to get the desired product 20-8 as white solid.

N-acetyl-N-methyl-3-(7-Methoxy-1-methyl-β-carbolin-9-yl)propylamine (20-8a). White solid. Yield 41%. $^1$H-NMR (600 MHz, CDCl$_3$): β 8.27 (d, J=5.4 Hz, 1H), 7.97 (d, J=9 Hz, 1H), 7.77 (d, J=5.4 Hz, 1H), 6.91 (m, 1H), 6.86 (m, 1H), 4.51 (t, J=7.8 Hz, 2H), 3.95 (s, 3H), 3.52 (t, J=6.6 Hz, 2H), 3.05 (s, 3H), 2.97 (s, 3H), 2.09 (s, 3H), 2.02 (m, 2H); MS (ESI) m/z 326.80 (M+H)+.

N-acetyl-N-methyl-4-(7-Methoxy-1-methyl-β-carbolin-9-yl)butylamine (20-8b). White solid. Yield 38%. $^1$H-NMR (600 MHz, CDCl$_3$): δ 8.26 (d, J=5.4 Hz, 1H), 7.96 (d, J=8.4 Hz, 1H), 7.75 (d, J=4.8 Hz, 1H), 6.94 (m, 1H), 6.87 (m, 1H), 4.51 (t, J=7.8 Hz, 2H), 3.96 (s, 3H), 3.41 (t, J=7.2 Hz, 2H), 3.03 (s, 3H), 2.89 (s, 3H), 2.05 (s, 3H), 1.79 (m, 2H), 1.62 (m, 2H); MS (ESI) m/z 340.83 (M+H)+.

General Procedure for the synthesis of 20-9. To a solution of 20-5 (0.21 mmol) and formaldehyde (37% in water, 2.5 eq.) in ethanol (1 mL) was added sodium cyanoborohydride (5 eq.) and few drops of acetic acid. The reaction mixture was stirred at room temperature for 1 hour. The reaction mixture was evaporated and purified by column chromatography using DCM/MeOH (9:1) as eluent to get the desired product 20-9 as white solid.

N,N-dimethyl-3-(7-Methoxy-1-methyl-β-carbolin-9-yl)propylamine (20-9a). White solid. Yield 38%. $^1$H-NMR (600 MHz, CDCl$_3$): β 8.27 (s, 1H), 7.97 (d, J=8.4 Hz, 1H), 7.73 (s, 1H), 6.97 (m, 1H), 6.89 (d, J=8.4 Hz, 1H), 4.56 (t, J=7.8 Hz, 2H), 3.94 (s, 3H), 3.03 (s, 3H), 2.33 (t, J=6.6 Hz, 2H), 2.24 (s, 6H), 1.98 (m, 2H); MS (ESI) m/z 298.27 (M+H)+.

N,N-dimethyl-4-(7-Methoxy-1-methyl-β-carbolin-9-yl)butylamine (20-9b). White solid. Yield 100%. $^1$H-NMR (600 MHz, d-DMSO): δ 8.44 (d, J=6 Hz, 1H), 8.38 (d, J=6 Hz, 1H), 8.34 (d, J=8.4 Hz, 1H), 7.35 (m, 1H), 6.51 (m, 1H), 4.65 (t, J=7.8 Hz, 2H), 3.94 (s, 3H), 3.10 (s, 3H), 3.03 (t, J=7.8 Hz, 2H), 2.70 (s, 6H), 2.46 (s, 3H), 1.76 (m, 2H), 1.70 (m, 2H); MS (ESI) m/z 312.42 (M+H)+.

General Procedure for the synthesis of 20-10. To a solution of 20-3c or 20-4a,4b (0.24 mmol) and HATU (1.2 eq.) in DMF (2 mL) was added DIPEA (2 eq.) and the reaction was stirred at room temperature for 2 hours. Alkylamine (1 eq.) was added to the reaction mixture and was stirred at room temperature for another 12 hours. Upon completion of the reaction, reaction mixture was quenched with water (50 mL) and transferred to separatory funnel. The reaction mixture was extracted with ethyl acetate three times and subsequently, the combined organic layer was washed with brine and water. The organic layer was dried over magnesium sulfate, filtered, evaporated and purified by column chromatography using DCM/MeOH (9:1) as eluent to get the desired product 20-10 as white solid.

N-(isopropyl)-4-(7-Methoxy-1-methyl-β-carbolin-9-yl)butanamide (20-10a). White solid. Yield 31%. $^1$H-NMR (600 MHz, CD$_3$OD): δ 8.28 (d, J=6 Hz, 1H), 8.21 (m, 2H), 7.82 (d, J=6 Hz, 1H), 7.27 (d, J=2.4 Hz, 1H), 7.06 (m, 1H), 4.68 (t, J=7.8 Hz, 2H), 4.01 (s, 3H), 3.91 (m, 1H), 3.18 (s, 3H), 2.32 (t, J=6.6 Hz, 2H), 2.16 (m, 2H), 1.10 (d, J=6.6 Hz, 6H); MS (ESI) m/z 340.42 (M+H)+.

N-(t-butyl)-4-(7-Methoxy-1-methyl-β-carbolin-9-yl)butanamide (20-10b). White solid. Yield 52%. $^1$H-NMR (600 MHz, CD$_3$OD): δ 8.32 (d, J=6 Hz, 1H), 8.22 (m, 2H), 7.52 (bs, 1H), 7.30 (d, J=1.8 Hz, 1H), 7.08 (m, 1H), 4.67 (t, J=7.8 Hz, 2H), 4.02 (s, 3H), 3.19 (s, 3H), 2.31 (t, J=6.6 Hz, 2H), 2.14 (m, 2H), 1.30 (s, 9H); MS (ESI) m/z 354.37 (M+H)+.

N-(2-methoxyethyl)-4-(7-Methoxy-1-methyl-β-carbolin-9-yl)butanamide (20-10c). Yield 36%. $^1$H-NMR (600 MHz, d$_6$-DMSO): δ 8.28-8.33 (m, 2H), 7.96 (t, J=5.4 Hz, 1H), 7.38 (bs, 1H), 7.02 (d, J=9 Hz, 1H), 4.61 (t, J=7.8 Hz, 2H), 3.96 (s, 3H), 3.31 (m, 5H), 3.21 (m, 2H), 3.10 (s, 3H), 2.25 (t, J=7.2 Hz, 2H), 1.99 (m, 2H); MS (ESI) m/z 356.51 (M+H)+.

N-(butyl)-4-(7-Methoxy-1-methyl-β-carbolin-9-yl)butanamide (20-10d). White solid. Yield 44%. $^1$H-NMR (600 MHz, CD$_3$OD): δ 8.29 (d, J=6 Hz, 1H), 8.21 (m, 2H), 7.90 (bs, 1H), 7.28 (d, J=1.8 Hz, 1H), 7.06 (m, 1H), 4.69 (t, J=8.4 Hz, 2H), 4.02 (s, 3H), 3.14 (s, 3H), 3.19 (t, J=7.2 Hz, 2H), 2.39 (t, J=6.6 Hz, 2H), 2.17 (m, 2H), 1.44 (m, 2H), 1.34 (m, 2H), 0.92 (t, J=7.2 Hz, 3H); MS (ESI) m/z 354.90 (M+H)+.

N-(1-methylbutyl)-4-(7-Methoxy-1-methyl-β-carbolin-9-yl)butanamide (20-10e). White solid. Yield 46%. $^1$H-NMR (600 MHz, d$_6$-DMSO): δ 8.43 (bs, 1H), 8.39 (m, 1H), 8.35 (d, J=7.8 Hz, 1H), 7.68 (d, J=7.8 Hz, 1H), 7.43 (s, 1H), 7.06 (d, J=8.4 Hz, 1H), 4.64 (t, J=4.8 Hz, 2H), 3.97 (s, 3H), 3.76 (m, 1H), 3.14 (s, 3H), 2.22 (m, 2H), 2.08 (s, 3H), 2.00 (m, 2H), 1.25 (m, 4H), 2.75 (d, J=6.6 Hz, 3H), 2.70 (s, 6H), 0.84 (t, J=7.2 Hz, 3H); MS (ESI) m/z 368.45 (M+H)+.

N-(isopropyl)-4-(7-Methoxy-1-methyl-β-carbolin-9-yl)-α-methylbutanamide (20-10f). White solid. Yield 33%. $^1$H-NMR (600 MHz, CD$_3$OD): δ 8.14 (d, J=5.4 Hz, 1H), 8.09 (d, J=8.4 Hz, 1H), 7.99 (d, J=5.4 Hz, 1H), 7.10 (d, J=1.8 Hz, 1H), 6.96 (m, 1H), 4.61 (m, 1H), 4.47 (m, 1H), 3.99 (m, 4H), 3.05 (s, 3H), 2.48 (m, 1H), 2.14 (m, 1H), 1.86 (m, 1H), 1.14-1.18 (m, 9H); MS (ESI) m/z 354.57 (M+H)+.

N-(t-butyl)-4-(7-Methoxy-1-methyl-β-carbolin-9-yl)-α-methylbutanamide (20-10g). Yield 28%. $^1$H-NMR (600 MHz, CD$_3$OD): δ 8.11-8.16 (m, 3H), 7.60 (bs, 1H), 7.15 (d, J=2.4 Hz, 1H), 7.00 (m, 1H), 4.59 (m, 1H), 4.44 (m, 1H), 4.00 (s, 3H), 3.10 (s, 3H), 2.53 (m, 1H), 2.13 (m, 1H), 1.83 (m, 1H), 1.36 (s, 9H), 1.16 (d, J=6.6 Hz, 3H); MS (ESI) m/z 368.59 (M+H)+.

N-(2-methoxyethyl)-4-(7-Methoxy-1-methyl-β-carbolin-9-yl)-α-methylbutanamide (20-10h). White solid. Yield 41%. $^1$H-NMR (600 MHz, d$_6$-DMSO): δ 8.16 (d, J=5.4 Hz, 1H), 8.13 (d, J=8.4 Hz, 1H), 8.09 (d, J=6 Hz, 1H), 7.15 (d, J=1.8 Hz, 1H), 6.99 (m, 1H), 4.60 (m, 1H), 4.50 (m, 1H), 4.00 (m, 3H), 3.39-3.48 (m, 3H), 3.33-3.35 (m, 4H), 3.09 (s, 3H), 2.56 (m, 1H), 2.15 (m, 1H), 1.87 (m, 1H), 1.20 (d, J=7.2 Hz, 3H); MS (ESI) m/z 370.87 (M+H)+.

N-(butyl)-4-(7-Methoxy-1-methyl-β-carbolin-9-yl)-α-methylbutanamide (20-10i). White solid. Yield 42%. $^1$H-NMR (600 MHz, CD$_3$OD): δ 8.16-8.19 (m, 3H), 7.96 (bs, 1H), 7.18 (bs, 1H), 7.03 (d, J=7.8 Hz, 1H), 4.63 (m, 1H), 4.50 (m, 1H), 4.01 (s, 3H), 3.18 (m, 1H), 3.13 (s, 3H), 2.52 (m, 1H), 2.19 (m, 1H), 1.90 (m, 1H), 1.49 (m, 2H), 1.36 (m, 2H), 1.20 (d, J=6.6 Hz, 3H), 0.94 (t, J=7.2 Hz, 3H); MS (ESI) m/z 368.87 (M+H)+.

N-(1-methylbutyl)-4-(7-Methoxy-1-methyl-β-carbolin-9-yl)-α-methylbutanamide (20-10j). White solid. Yield 44%. $^1$H-NMR (600 MHz, CD$_3$D): δ 8.11 (d, J=5.4 Hz, 1H), 8.02 (d, J=8.4 Hz, 1H), 7.89 (d, J=4.8 Hz, 1H), 7.06 (s, 1H), 6.92 (d, J=8.4 Hz, 1H), 4.57 (m, 1H), 4.42 (m, 1H), 3.96 (m, 4H), 3.00 (s, 3H), 2.49 (m, 1H), 2.15 (m, 1H), 1.82 (m, 1H), 1.38-1.45 (m, 4H), 1.18 (d, J=7.2 Hz, 3H), 1.14 (t, J=7.2 Hz, 3H), 0.93 (t, J=6.6 Hz, 3H); MS (ESI) m/z 382.60 (M+H)+.

N-(2-methoxyethyl)-4-(7-Methoxy-1-methyl-β-carbolin-9-yl)-α,α-dimethylbutanamide (20-10k). White solid. Yield 31%. $^1$H-NMR (600 MHz, CD$_3$OD): δ 8.12 (d, J=5.4 Hz, 1H), 8.07 (d, J=8.4 Hz, 1H), 7.96 (d, J=4.2 Hz, 1H), 7.73 (bs, 1H), 7.13 (bs, 1H), 6.94 (d, J=8.4 Hz, 1H), 4.52 (t, J=8.4 Hz, 2H), 3.98 (s, 3H), 3.53 (m, 2H), 3.47 (m, 2H), 3.34 (s, 3H), 3.05 (s, 3H), 2.01 (m, 2H), 1.34 (s, 6H); MS (ESI) m/z 385.02 (M+H)+.

N-(1-methylbutyl)-4-(7-Methoxy-1-methyl-β-carbolin-9-yl)-α,α-dimethylbutanamide (20-101). White solid. Yield 29%. $^1$H-NMR (600 MHz, CD$_3$OD): δ 8.15 (d, J=6 Hz, 1H), 8.13 (d, J=9 Hz, 1H), 8.09 (d, J=5.4 Hz, 1H), 7.31 (d, J=9 Hz, 1H), 7.20 (bs, 1H), 6.99 (d, J=8.4 Hz, 1H), 4.57 (m, 2H), 4.06 (m, 1H), 4.00 (s, 3H), 3.11 (s, 3H), 3.05 (s, 3H), 2.04 (m, 2H), 1.56 (m, 1H), 1.46 (m, 1H), 1.38 (m, 8H), 1.18 (d, J=6.6 Hz, 3H), 0.94 (t, J=7.8 Hz, 3H); MS (ESI) m/z 396.99 (M+H)+.

N'-hydroxy-4-(7-Methoxy-1-methyl-β-carbolin-9-yl)butanimidamide (20-11). A solution of 20-10 (300 mg, 1.07 mmol), hydroxylamine hydrochloride (93 mg, 1.34 mmol) and trimethylamine (0.22 mL, 1.60 mmol) in ethanol (2 mL) was refluxed for 12 hours. Solvent was evaporated and the crude was purified by flash column chromatography using DCM/MeOH/NH$_3$ (9:1:0.5) as eluent to get the desired product 20-11 as white solid. Yield 74%. H-NMR (600 MHz, d$_6$-DMSO): δ 8.15 (d, J=4.8 Hz, 1H), 8.09 (d, J=8.4 Hz, 1H), 7.88 (d, J=5.4 Hz, 1H), 7.20 (d, J=1.2 Hz, 1H), 6.87 (m, 1H), 5.50 (bs, 2H), 4.54 (t, J=7.8 Hz, 2H), 3.91 (s, 3H), 3.76 (m, 1H), 2.94 (s, 3H), 2.10 (t, J=7.2 Hz, 2H), 1.95 (m, 2H); MS (ESI) m/z 313.46 (M+H)+.

3-(3-(7-Methoxy-1-methyl-β-carbolin-9-yl)propyl)-5-trichloromethyl-1,2,4-oxadiazole (20-12). To a solution of 20-11 (150 mg, 0.48 mmol) and pyridine (0.154 mL, 1.92 mmol) in toluene was added trichloroacetyl chloride (0.06 mL, 0.57 mmol) at 0° C. and stirred for another hour at the same temperature. The reaction mixture was then, heated to 85° C. for 12 hours. After the completion of the reaction, solvent was evaporated and the crude was purified by flash column chromatography using DCM/MeOH (9:1) as eluent to get the desired product 20-12 as white solid. Yield 8%. H-NMR (600 MHz, CDCl$_3$): δ 8.31 (d, J=4.8 Hz, 1H), 8.01 (d, J=8.4 Hz, 1H), 7.86 (d, J=4.8 Hz, 1H), 6.98 (m, 2H), 4.66 (t, J=7.8 Hz, 2H), 3.97 (s, 3H), 3.15 (s, 3H), 2.97 (t, J=7.2 Hz, 2H), 2.38 (m, 2H); MS (ESI) m/z 439.27 (M+H)+.

3-(3-(7-Methoxy-1-methyl-β-carbolin-9-yl)propyl)-5-amino-1,2,4-oxadiazole (20-13). A solution of 20-12 (18 mg, 0.04 mmol) and 7 N ammonia in methanol (2 mL) was stirred at room temperature for 12 hours. After the completion of the reaction, solvent was evaporated and the crude was purified by flash column chromatography using DCM/MeOH/NH3 (9:1:1) as eluent to get the desired product 20-13 as white solid. Yield 46%. H-NMR (600 MHz, d$_6$-DMSO): δ 8.16 (d, J=4.8 Hz, 1H), 8.09 (d, J=8.4 Hz, 1H), 7.88 (d, J=4.8 Hz, 1H), 7.72 (bs, 2H), 7.23 (d, J=1.8 Hz, 1H), 6.87 (m, 1H), 4.62 (t, J=7.8 Hz, 2H), 3.90 (s, 3H), 2.90 (s, 3H), 2.57 (t, J=7.2 Hz, 2H), 2.06 (m, 2H); MS (ESI) m/z 338.43 (M+H)+.

1-(3-(3-(7-Methoxy-1-methyl-β-carbolin-9-yl))propyl-1-aminocyclopropane (20-14). To a solution of 20-1o (146 mg. 0.52 mmol) and titanium (IV) isopropoxide (0.168 mL, 0.57 mmol) in THF (5 mL) was added ethylmagnesium bromide (1M in THF, 1.04 mL, 1.04 mmol) at room temperature dropwise and stirred for 1 hour. After that BF3.OEt2 (0.128 mL, 1.04 mmol) was added to the reaction and stirred for additional 30 minutes. The reaction was quenched by addition of water (10 mL) and saturated aqueous solution of sodium bicarbonate (15 mL). The solution was transferred to separatory funnel and extracted with ethyl acetate (3 times, 20 mL). Organic layers were collected, dried over magnesium sulfate, filtered, evaporated and purified by flash column chromatography using DCM/MeOH (9:1) as eluent to get the desired product 20-14 as white solid. Yield 5%. $^1$H-NMR (600 MHz, CD$_3$OD): δ 8.17 (d, J=5.4 Hz, 1H), 8.12 (d, J=8.4 Hz, 1H), 8.07 (d, J=5.4 Hz, 1H), 7.17 (d, J=1.2 Hz, 1H), 6.87 (m, 1H), 4.66 (t, J=7.2 Hz, 2H), 3.98 (s, 3H), 3.09 (s, 3H), 2.01 (m, 2H), 1.80 (m, 2H), 0.88 (m, 2H), 0.80 (m, 2H); MS (ESI) m/z 310.55 (M+H)+.

General procedure for the synthesis of 20-15. A solution of 20-1p or 20-1q (5.44 mmol) in AcOH/1,4-dioxane/water (4:2:1, 14 mL) was heated to 110° C. for 4 hours. The reaction was cooled down and neutralized with saturated solution of sodium bicarbonate. The reaction mixture was transferred to separatory funnel and extracted with ethyl acetate (3 times, 50 mL). Organic layers were collected, dried over magnesium sulfate, filtered and evaporated to get the final compound 20-15 as white solid.

3-(7-Methoxy-1-methyl-β-carbolin-9-yl)propanal (20-15a). Yield 95%. $^1$H-NMR (600 MHz, CD$_3$OD): δ 8.11 (d, J=5.4 Hz, 1H), 8.03 (d, J=8.4 Hz, 1H), 7.87 (d, J=5.4 Hz, 1H), 7.12 (d, J=1.8 Hz, 1H), 6.87 (m, 1H), 4.70 (t, J=7.8 Hz, 2H), 3.95 (s, 3H), 3.02 (s, 3H), 2.06 (m, 2H); MS (ESI) m/z 269.20 (M+H)+.

4-(7-Methoxy-1-methyl-β-carbolin-9-yl)butanal (20-15b). Yield 92%. $^1$H-NMR (600 MHz, CD$_3$OD): δ 8.09 (d, J=5.4 Hz, 1H), 8.00 (d, J=9 Hz, 1H), 7.84 (d, J=5.4 Hz, 1H), 7.05 (d, J=1.8 Hz, 1H), 6.87 (m, 1H), 4.54 (t, J=7.8 Hz, 2H), 3.93 (s, 3H), 2.97 (s, 3H), 1.88 (m, 2H), 1.67 (m, 2H); MS (ESI) m/z 283.50 (M+H)+.

General procedure for the synthesis of 20-16. Ammonium hydroxide (1.59 mL) was added to a mixture of potassium cyanide (109 mg, 1.67 mmol) and ammonium chloride (89 mg, 1.67 mmol) at 0° C. and the solution was stirred at room temperature for 30 minutes. To the reaction mixture was added solution of 20-15 (150 mg, 0.56 mmol) and MeOH (2 mL) and stirred at 80° C. for 12 hours. After the completion of the reaction, solvent was evaporated and the crude was purified by flash column chromatography using DCM/MeOH/NH3 (9:1:1) as eluent to get the desired product 20-16 as white solid.

3-(7-Methoxy-1-methyl-β-carbolin-9-yl)-1-cyanopropylmine (20-16a). Yield 31%. $^1$H-NMR (600 MHz, d$_6$-DMSO): δ 8.17 (d, J=5.4 Hz, 1H), 8.10 (d, J=8.4 Hz, 1H), 7.88 (d, J=4.8 Hz, 1H), 7.24 (d, J=2.4 Hz, 1H), 6.87 (m, 1H), 4.73 (m, 1H), 4.64 (m, 1H), 3.91 (s, 3H), 3.82 (m, 1H), 2.97 (s, 3H), 2.12 (m, 1H), 2.04 (m, 1H); MS (ESI) m/z 295.28 (M+H)+.

4-(7-Methoxy-1-methyl-β-carbolin-9-yl)-1-cyanobutylamine (20-16b). Yield 61%. $^1$H-NMR (600 MHz, d$_6$-DMSO): δ 8.17 (d, J=4.8 Hz, 1H), 8.09 (d, J=8.4 Hz, 1H), 7.88 (d, J=5.4 Hz, 1H), 7.23 (bs, 1H), 6.88 (m, 1H), 4.59 (t, J=7.8 Hz, 2H), 3.90 (s, 3H), 3.77 (m, 1H), 2.95 (s, 3H), 1.85 (m, 2H), 1.75 (m, 2H); MS (ESI) m/z 309.36 (M+H)+.

General procedure for the synthesis of 20-17. To a solution of 20-16 (15 mg, 0.05 mmol) and MeOH (0.5 mL) was added 1 N NaOH solution (0.104 mL), followed by 35% hydrogen peroxide (0.02 mL) and stirred at room temperature for 1 hour. After the completion of the reaction, solvent was evaporated and the crude was purified by flash column chromatography using DCM/MeOH/NH3 (9:1:1) as eluent to get the desired product 20-17 as white solid.

3-(7-Methoxy-1-methyl-β-carbolin-9-yl)-1-(carboxylamide)propylmine(20-17a). Yield 60%. $^1$H-NMR (600 MHz, CD$_3$OD): δ 8.11 (d, J=5.4 Hz, 1H), 8.03 (d, J=8.4 Hz, 1H), 7.86 (d, J=5.4 Hz, 1H), 7.15 (d, J=2.4 Hz, 1H), 6.89 (m, 1H), 4.68 (t, J=7.8 Hz, 2H), 3.95 (s, 3H), 3.54 (m, 1H), 3.01 (s, 3H), 2.17 (m, 1H), 2.04 (m, 1H); MS (ESI) m/z 313.42 (M+H)+.

4-(7-Methoxy-1-methyl-β-carbolin-9-yl)-1-(carboxylamide)butylamine (20-17b). Yield 61%. $^1$H-NMR (600 MHz, CD$_3$OD): δ 8.10 (d, J=5.4 Hz, 1H), 8.02 (d, J=8.4 Hz, 1H), 7.84 (d, J=5.4 Hz, 1H), 7.09 (d, J=2.4 Hz, 1H), 6.88 (m, 1H), 4.59 (t, J=7.8 Hz, 2H), 3.94 (s, 3H), 3.41 (m, 1H), 2.99 (s, 3H), 1.91 (m, 2H), 1.78 (m, 1H), 1.68 (m, 1H); MS (ESI) m/z 327.18 (M+H)+.

4-(7-Methoxy-1-methyl-β-carbolin-9-yl)-1-trifluoromethylbutanol (20-18). To a solution of 20-15b (384 mg, 1.36 mmol) and TMSCF$_3$ (0.5 M in THF, 1.77 mmol) in THF (2 mL) was added TBAF (1 M in THF, 0.013 mL, 0.013 mmol) at 0° C. and the solution was stirred for 30 minutes at that temperature and for 12 hours at room temperature. The reaction was cooled down to 0° C. and was added water (0.134 mL, 7.48 mmol) and TBAF (1 M in THF, 0.136 mL, 0.136 mmol) and stirred at room temperature for 4 hours. After the completion of the reaction, solvent was evaporated and the crude was purified by flash column chromatography using ethyl acetate as eluent to get the desired product 20-18 as white solid. Yield 75%. $^1$H-NMR (600 MHz, $d_6$-DMSO): δ 8.11 (d, J=5.4 Hz, 1H), 8.03 (d, J=7.8 Hz, 1H), 7.85 (d, J=5.4 Hz, 1H), 7.09 (bs, 1H), 6.90 (d, J=9 Hz, 1H), 3.94 (m, 4H), 2.99 (s, 3H), 1.94-2.04 (m, 2H), 1.79 (m, 1H), 1.66 (m, 1H); MS (ESI) m/z 353.79 (M+H)+.

4-(7-Methoxy-1-methyl-β-carbolin-9-yl)-1-trifluoromethylbutylamine (20-21). To a solution of 20-18 (78 mg, 0.22 mmol) and pyridine (0.035 mL, 0.44 mmol) in dichloromethane (1.5 mL) at −40° C. was added solution of trofluoromethanesulfonic anhydride (0.044 mL, 0.265 mmol) in dichloromethane (0.2 mL) dropwise. The solution was stirred and allowed to warm to room temperature overnight. The reaction was quenched by addition of water (10 mL) and extracted with ethyl acetate (3 times, 20 mL). Organic layers were collected, dried over magnesium sulfate, filtered, and evaporated to afford the compound 20-19 as white solid which was taken to next step without purification. A solution of 20-19 (115 mg, 0.23 mmol) and sodium azide (30 mg, 0.47 mmol) in DMSO (2 mL) was heated to 40° C. for 5 hours. The reaction was quenched by addition of water (10 mL) and extracted with ethyl acetate 3 times, 20 mL) Organic layers were collected, dried over magnesium sulfate, filtered, and evaporated to afford the compound 20-20 as white solid which was taken to next step without purification. A solution of 20-20 (60 mg, 0.16 mmol), ammonium formate (50 mg, 0.80 mmol) and 10 mol % Pd/C in methanol (2 mL) was refluxed for 3 hours. The catalyst was filtered over celite and solvent was evaporated. The crude reaction mixture was purified by flash column chromatography using DCM/MeOH (9:1:1) as eluent to get the desired product 20-21 as white solid. Yield 51%. $^1$H-NMR (600 MHz, d-DMSO): δ 8.16 (d, J=5.4 Hz, 1H), 8.09 (d, J=9 Hz, 1H), 7.88 (d, J=5.4 Hz, 1H), 7.26 (d, J=1.2 Hz, 1H), 6.87 (d, J=8.4 Hz, 1H), 4.57 (m, 2H), 3.90 (m, 3H), 3.24 (m, 1H), 2.96 (s, 3H), 1.94 (m, 2H), 1.82 (m, 1H), 1.73 (m, 1H), 1.46 (m, 1H); MS (ESI) m/z 352.42 (M+H)+.

Ethyl 4-(7-Methoxy-1-methyl-β-carbolin-9-yl)butanecarboximidate hydrochloride (20-22). To a solution of 1-10 (100 mg, 0.35 mmol) in ethanol (0.3 mL) was bubbled hydrochloric acid gas for 1 hour and the reaction was stirred at room temperature for 12 hours. Upon completion of the reaction monitored by LCMS, solvent was evaporated to get the final compound 20-22 as white solid. Yield 100%. $^1$H-NMR (600 MHz, $d_6$-DMSO): δ 8.38 (d, J=5.4 Hz, 1H), 8.27 (d, J=8.4 Hz, 1H), 8.23 (m, 1H), 7.29 (s, 1H), 7.09 (d, J=9 Hz, 1H), 4.60 (m, 2H), 3.92 (s, 3H), 3.88 (m, 2H), 3.11 (s, 3H), 2.43 (m, 2H), 2.02 (m, 2H), 1.06 (t, J=7.2 Hz, 3H); MS (ESI) m/z 327.39 (M+H)+.

General procedure for the synthesis of 20-23. To a solution of 3-(7-Methoxy-1-methyl-β-carbolin-9-yl)propanal or 2-(7-Methoxy-1-methyl-β-carbolin-9-yl)ethanal (1.12 mmol) and $K_2CO_3$ (3 eq.) in MeOH/THF (1:1, 3 mL) was added dimethyl (1-diazo-2-oxopropyl)phosphonate (10% in acetonitrile, 2 eq.) and stirred at room temperature for 24 hours. After the completion of the reaction, solvent was evaporated and the crude was purified by flash column chromatography using DCM/MeOH (9:1) as eluent to get the desired product 20-23 as white solid.

3-(7-Methoxy-1-methyl-β-carbolin-9-yl)-propan-1-yne (20-23a). Yield 71%. $^1$H-NMR (600 MHz, CDCl$_3$): δ 8.20 (d, J=5.4 Hz, 1H), 8.10 (d, J=8.4 Hz, 1H), 7.88 (d, J=5.4 Hz, 1H), 7.33 (d, J=2.4 Hz, 1H), 6.91 (m, 1H), 5.45 (s, 2H), 3.91 (s, 3H), 3.37 (t, J=2.4 Hz, 1H), 3.04 (s, 3H); MS (ESI) m/z 251.94 (M+H)+.

4-(7-Methoxy-1-methyl-β-carbolin-9-yl)-but-1-yne (20-23b). Yield 67%. $^1$H-NMR (600 MHz, CDCl$_3$): δ 8.30 (d, J=4.8 Hz, 1H), 7.98 (d, J=9 Hz, 1H), 7.73 (d, J=4.8 Hz, 1H), 7.91 (m, 2H), 4.70 (t, J=7.2 Hz, 2H), 3.95 (s, 3H), 3.05 (s, 3H), 2.70 (m, 2H), 2.05 (t, J=3 Hz, 1H); MS (ESI) m/z 265.86 (M+H)+.

General procedure for the synthesis of 20-24. To a solution of 3-(7-Methoxy-1-methyl-β-carbolin-9-yl)-propan-1yne or 4-(7-Methoxy-1-methyl-β-carbolin-9-yl)-pentan-1-yne (0.44 mmol) and 1-azido-2-methoxyethane (10 eq.) in t-butanol/water (1:1, 4 mL) was added sodium ascorbate (0.1 eq.) and copper sulfate pentahydrate (0.01 eq.) sequentially and stirred at room temperature for 24 hours. After the completion of the reaction, solvent was evaporated and the crude was purified by flash column chromatography using DCM/MeOH (9:1) as eluent to get the desired product 20-24 as white solid.

4-(2-(7-Methoxy-1-methyl-β-carbolin-9-yl)ethyl)-1-(2-methoxyethyl)-1,2,3-triazole (20-24a). Yield 73%. $^1$H-NMR (600 MHz, CDCl$_3$): δ 8.30 (d, J=5.4 Hz, 1H), 7.93 (d, J=8.4 Hz, 1H), 7.73 (d, J=5.4 Hz, 1H), 7.97 (s, 1H), 6.84 (m, 1H), 6.69 (d, J=1.8 Hz, 1H), 4.86 (t, J=7.2 Hz, 2H), 4.34 (t, J=5.4 Hz, 2H), 3.89 (s, 3H), 3.53 (t, J=5.4 Hz, 2H), 3.22 (m, 5H), 3.01 (s, 3H); MS (ESI) m/z 367.14 (M+H)+.

4-(3-(7-Methoxy-1-methyl-β-carbolin-9-yl)propyl)-1-(2-methoxyethyl)-1,2,3-triazole (20-24b). Yield 64%. $^1$H-NMR (600 MHz, CDCl$_3$): δ 7.96 (d, J=8.4 Hz, 1H), 7.76 (bs, 1H), 7.40 (s, 1H), 6.93 (d, J=1.8 Hz, 1H), 6.88 (m, 1H), 4.61 (t, J=7.8 Hz, 2H), 4.49 (t, J=4.8 Hz, 2H), 3.94 (s, 3H), 3.73 (t, J=4.8 Hz, 2H), 3.34 (s, 3H), 2.94 (s, 3H), 2.82 (t, J=7.2 Hz, 2H), 2.26 (m, 2H); MS (ESI) m/z 381.07 (M+H)+.

General procedure for the synthesis of 20-25. To a solution of 3-(7-Methoxy-1-methyl-β-carbolin-9-yl)-propylazide or 4-(7-Methoxy-1-methyl-β-carbolin-9-yl)-pentylazide (0.31 mmol) and methyl propargyl ether (1.05 eq.) in t-butanol/water (1:1, 4 mL) was added sodium ascorbate (0.1 eq.) and copper sulfate pentahydrate (0.01 eq.) sequentially and stirred at room temperature for 24 hours. After the completion of the reaction, solvent was evaporated and the crude was purified by flash column chromatography using DCM/MeOH (9:1) as eluent to get the desired product 20-25 as white solid.

1-(3-(7-Methoxy-1-methyl-β-carbolin-9-yl)propyl)-4-(methoxymethyl)-1,2,3-triazole (20-25a). Yield 72%. %. $^1$H-NMR (600 MHz, CDCl$_3$): δ 8.30 (d, J=5.4 Hz, 1H), 7.97 (d, J=8.4 Hz, 1H), 7.74 (d, J=5.4 Hz, 1H), 7.50 (s, 1H), 6.89 (m, 1H), 6.81 (d, J=1.8 Hz, 1H), 4.61 (m, 4H), 4.40 (t, J=6 Hz, 2H), 3.93 (s, 3H), 3.43 (s, 3H), 2.92 (s, 3H), 2.47 (m, 2H), 3.01 (s, 3H); MS (ESI) m/z 366.96 (M+H)+.

1-(4-(7-Methoxy-1-methyl-β-carbolin-9-yl)butyl)-1-(methoxymethyl)-1,2,3-triazole (20-25b). Yield 63%. $^1$H-NMR (600 MHz, CDCl$_3$): δ 8.30 (d, J=5.4 Hz, 1H), 7.97 (d, J=8.4 Hz, 1H), 7.74 (d, J=5.4 Hz, 1H), 7.41 (s, 1H), 6.89 (m, 1H), 6.84 (d, J=1.8 Hz, 1H), 4.55 (s, 2H), 4.51 (t, J=7.8 Hz, 2H), 3.96 (s, 3H), 3.39 (s, 3H), 2.97 (s, 3H), 2.00 (m, 2H), 1.86 (m, 2H); MS (ESI) m/z 381.04 (M+H)+.

General procedure for the synthesis of 20-26. To a solution of 20-1r-20-1s or 20-23 (0.179 mmol) in THF (0.2 mL) was added BuLi (2.5 M in hexanes, 1.05 eq.) at −20° C. and stirred for 30 min followed by addition of zinc chloride (0.7 M in THF, 1.1 eq.) while maintaining −20° C. temperature. After stirring for 5 min, trichoroacetyl isocyanate (1.1 eq.) was added to the reaction and was allowed to warm to room temperature over 2 hours. Subsequently, potassium carbonate (1.5 eq.) and MeOH (2 mL) was sequentially and the reaction was stirred for 12 hours at room temperature. After the completion of the reaction, solvent was evaporated and the crude was purified by flash column chromatography using DCM/MeOH (9:1) as eluent to get the desired product 20-25 as white solid.

4-(7-Methoxy-1-methyl-β-carbolin-9-yl)-but-1-ynamide (20-26a). Yield 75%. $^1$H-NMR (600 MHz, d$_6$-DMSO): δ 8.31 (s, 1H), 8.20 (d, J=4.8 Hz, 1H), 8.10 (d, J=8.4 Hz, 1H), 7.97 (s, 1H), 7.89 (d, J=6.6 Hz, 1H), 7.55 (s, 1H), 7.36 (d, J=1.8 Hz, 1H), 6.92 (m, 1H), 5.65 (s, 2H), 3.92 (s, 3H), 3.04 (s, 3H); MS (ESI) m/z 294.26 (M+H)+.

5-(7-Methoxy-1-methyl-β-carbolin-9-yl)-pent-1-ynamide (20-26b). Yield 70%. $^1$H-NMR (600 MHz, d$_6$-DMSO): δ 8.31 (s, 1H), 8.18 (d, J=5.4 Hz, 1H), 8.09 (d, J=8.4 Hz, 1H), 7.88 (d, J=5.4 Hz, 1H), 7.72 (s, 1H), 7.43 (s, 1H), 7.28 (d, J=1.8 Hz, 1H), 6.88 (m, 1H), 4.80 (t, J=7.2 Hz, 2H), 3.92 (s, 3H), 2.98 (s, 3H), 2.88 (t, J=7.2 Hz, 2H); MS (ESI) m/z 308.22 (M+H)+.

6-(7-Methoxy-1-methyl-β-carbolin-9-yl)-hex-1-ynamide (20-26c). Yield 28%. $^1$H-NMR (600 MHz, d$_6$-DMSO): δ 8.18 (d, J=5.4 Hz, 1H), 8.09 (d, J=8.4 Hz, 1H), 7.89 (m, 2H), 7.46 (s, 1H), 7.23 (d, J=2.4 Hz, 1H), 6.88 (m, 1H), 4.65 (t, J=7.2 Hz, 2H), 3.91 (s, 3H), 2.97 (s, 3H), 2.45 (t, J=6.6 Hz, 2H), 1.96 (m, 2H); MS (ESI) m/z 322.67 (M+H)+.

General procedure for the synthesis of 20-27. To a solution of 10-1a/b (2.32 mmol) in THF (25 m) was added LiAlH$_4$ (1.5 eq.) at 0° C. in portions. After the addition, the reaction was refluxed for 6 hours. Reaction was quenched with water and stirred at room temperature for 1 hour. The precipitate was filtered and the filterate was transferred to separatory funnel and extracted with ethyl acetate (50 mL×3). Organic layers were collected, dried over magnesium sulfate, filtered, evaporated and the crude was purified flash column chromatography using DCM/MeOH (9:1) as eluent to get desired product 20-27 as white solid.

2-(7-Methoxy-1-methyl-β-carbolin-9-yl)ethanol (20-27a). Yield 100%. $^1$H-NMR (600 MHz, CD$_3$OD): δ 8.10 (d, J=5.4 Hz, 1H), 8.00 (d, J=8.4 Hz, 1H), 7.84 (d, J=5.4 Hz, 1H), 7.09 (d, J=1.2 Hz, 1H), 6.89 (m, 1H), 4.69 (t, J=6 Hz, 2H), 3.92 (m, 5H), 3.01 (s, 3H); MS (ESI) m/z 257.42 (M+H)+.

3-(7-Methoxy-1-methyl-β-carbolin-9-yl)propanol (20-27b). Yield 100%. $^1$H-NMR (600 MHz, CD$_3$OD): δ 8.10 (d, J=5.4 Hz, 1H), 8.00 (d, J=9 Hz, 1H), 7.83 (d, J=4.8 Hz, 1H), 7.12 (s, 1H), 6.88 (m, 1H), 4.67 (t, J=7.2 Hz, 2H), 3.93 (s, 3H), 3.63 (t, J=6 Hz, 2H), 3.00 (s, 3H), 2.01 (m, 2H); MS (ESI) m/z 271.69 (M+H)+.

DYRK1A Binding Assays. Compounds were tested for DYRK1A binding activity at a commercial kinase profiling services, Life Technologies which uses the FRET-based LanthaScreen® Eu Kinase Binding Assay. Compounds were screened for DYRK1A activity at concentrations of 1000 nM and 300 nM in duplicates. The IC$_{50}$ was determined by 10 point LanthaScreen® Eu Kinase Binding Assay in duplicates.

B-Cell Proliferation Assay. Human pancreatic islets were obtained from the NIH/NIDDK-supported Integrated Islet Distribution Program (IIDP). Islets were first dispersed with Accutase (Sigma, St. Louis, MO) onto coverslips as described earlier (Wang et al., 2015, which is hereby incorporated by reference in its entirety). After 2 hours, dispersed human islet cells were treated with compound in RPMI1640 complete medium for 96 hours. Then the cells were fixed and stained for insulin and Ki67 staining (Wang et al., 2015, which is hereby incorporated by reference in its entirety). Total insulin positive cells and double Ki67 and insulin positive cells were imaged and counted. At least 1000 cells were counted.

Figure 6:
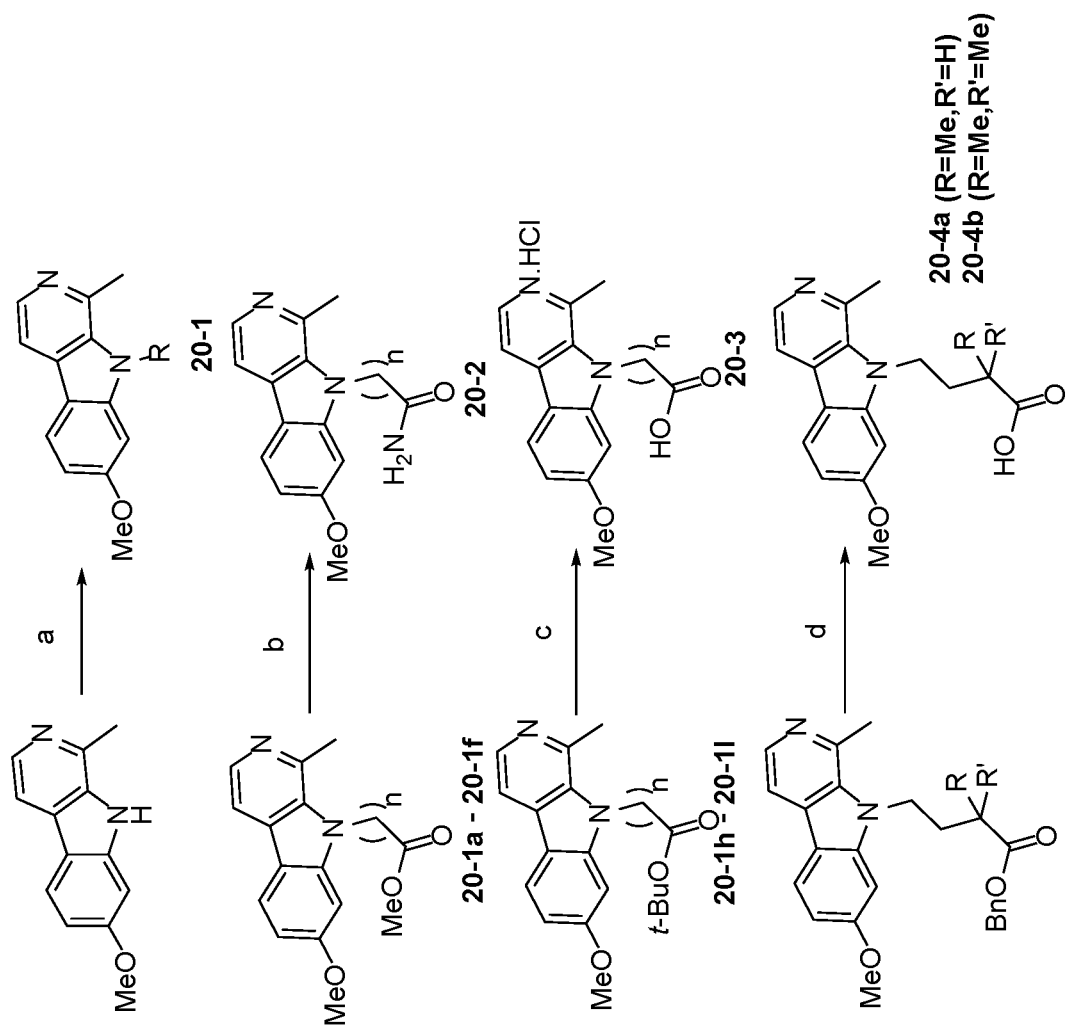
FIG. 6 is a schematic illustration showing the synthesis of 7-substituted harmine analog compounds. Reagents and conditions: (a) NaH (2 eq.), RBr (2 eq.), DMF, 50° C., 12 hours; (b) 7 N $NH_3$ in MeOH (20 eq.), 90° C., 12 hours; (c) TFA/DCM (1:1), room temperature, 12 hours; (d) $Et_3SiH$ (8 eq.), Pd—C, MeOH, reflux; (e) hydrazine monohydrate (20 eq.), MeOH, reflux, 3 hours; (f) Acetic anhydride (1 eq), $Et_3N$ (2.2 eq.), DCM, room temperature, 12 hours; (g) (i) ethylformate (0.5 eq.), EtOH, Microwave, 150° C., 30 minutes; (ii) $LiAlH_4$ (3 eq.), THF, reflux, 4 hours; (h) formaldeyde (2.5 eq.), $NaCNBH_3$ (5 eq.), EtOH, room temperature, 2 hours; (i) HATU (1.1 eq.), DIPEA (2 eq.), $RNH_2$ (1 eq.), DMF, room temperature, 12 hours; (j) $NH_2OH.HCl$ (1.5 eq.), $Et_3N$ (1.5 eq.), EtOH, reflux, 12 hours; (k) $CCl_3COCl$ (1.2 eq.), Pyridine (4 eq.), Toluene, 85° C., 24 hours; (l) 7 N $NH_3$ in MeOH, room temperature, 12 hours; (m) (i) EtMgBr (2 eq.), $Ti(OiPr)_4$ (1.1 eq.), THF, room temperature, 1 hour; (ii) $BF_3.Et_2O$ (2 eq.), room temperature, 1 hour; (n) AcOH:THF:$H_2O$ (16:4:4 mL), reflux, 3 hours; (o) (i) TMSCN (1.2 eq.), $ZnI_2$ (0.05 eq.), THF, reflux, 12 hours; (ii) 7 N $NH_3$ in MeOH, room temperature, 12 hours; (p) 1 N NaOH, H$_2$O$_2$ (35%), MeOH, room temperature, 1 hour; (q) (i) TMSCF$_3$ (1.2 eq.), TBAF (0.01 eq.), THF, 0° C., room temperature, 12 hours; (ii) TBAF (0.1 eq.), water (5.5 eq.), 0° C., room temperature, 2 hours; (r) Tf$_2$O (1.1 eq.), pyridine (2 eq.), DCM, −40° C.-room temperature, 12 hours; (s) Sodium azide (2 eq.), DMSO, 40° C., 4 hours; (t) Pd—C(20 mol %), ammonium formate (5 eq.), MeOH, reflux, 3 hours; (u) HCl gas, EtOH, room temperature, 12 hours; (v) 2-oxopropyl diazodimethyl phosphonate (2 eq.), MeOH/THF (1:1), K$_2$CO$_3$ (3 eq.), room temperature, 24 hours; (w) MeOCH$_2$CH$_2$N$_3$ (1.05 eq.), CuSO$_4$.5H$_2$O (0.01 eq.), Sodium ascorbate (0.1 eq.), t BuOH/water, room temperature, 12 hours; (x) methyl propargyl ether (1 eq.), CuSO$_4$.5H$_2$O (0.1 eq.), Sodium ascorbate (0.1 eq.), t-BuOH/water, room temperature, 12 hours; (y) n-BuLi (1.2 eq.), ZnCl$_2$ (1.1 eq.), trichloroacetyl isocyanate (1.1 eq.), K$_2$CO$_3$ (1.5 eq.), MeOH, THF, −20° C.-rt, 2 hours; (z) LiAlH$_4$ (1.5 eq.), THF, reflux, 6 hours.
Figure 6:
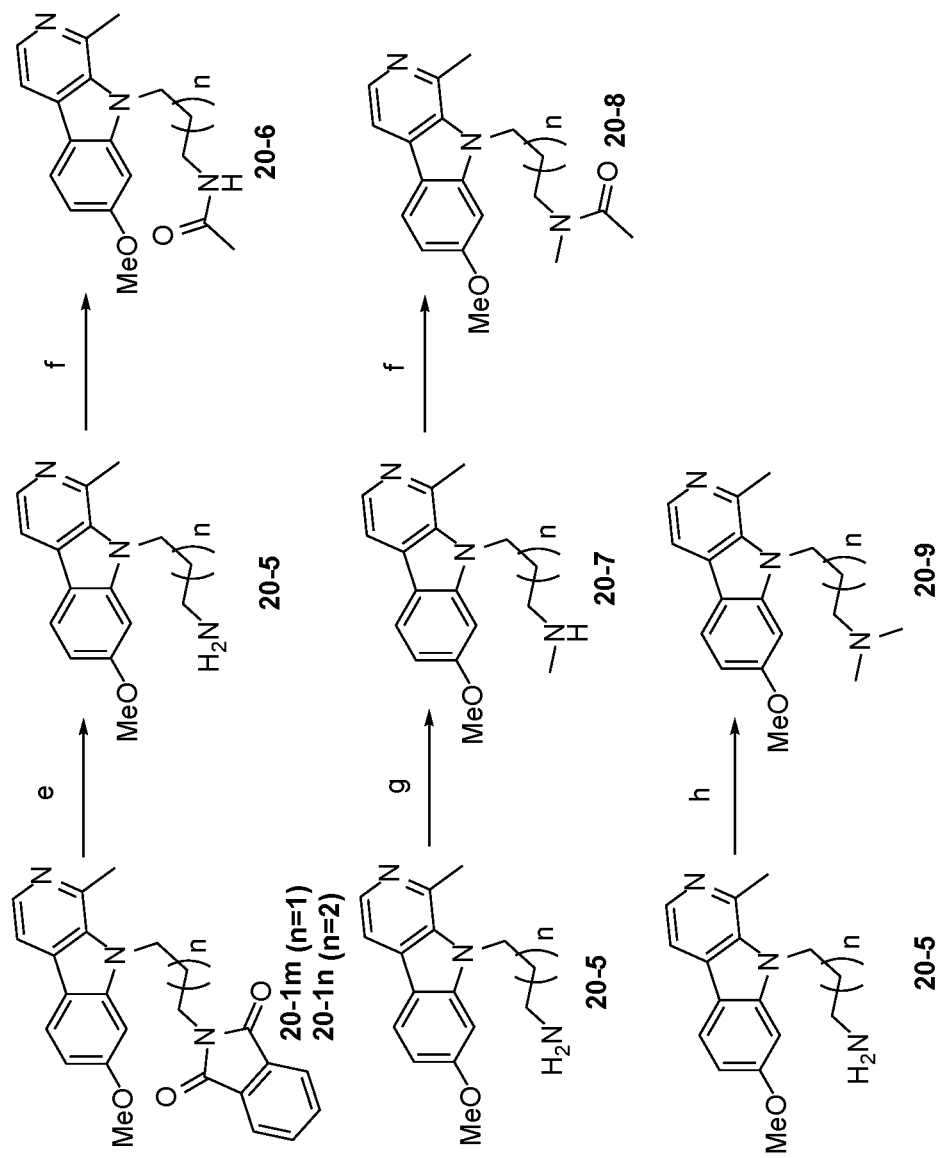
Figure 6:
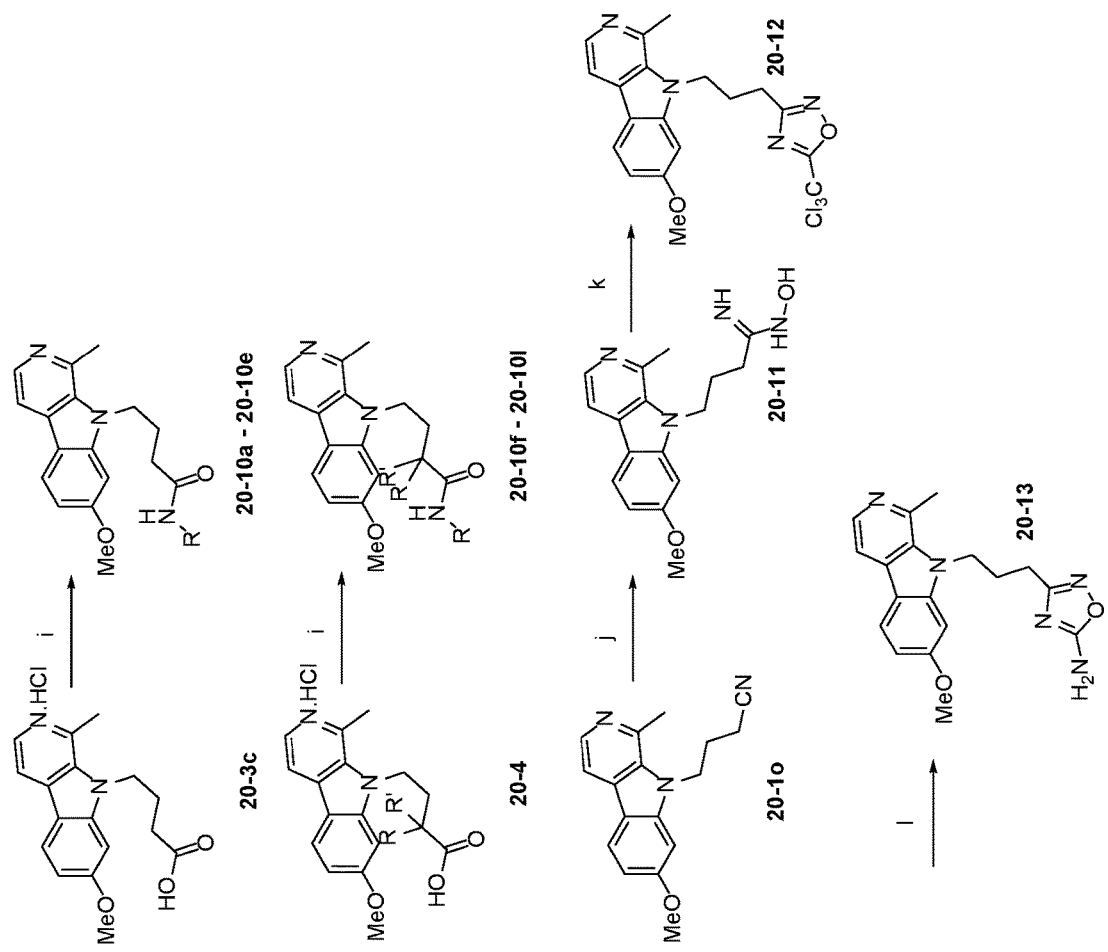
Figure 6:
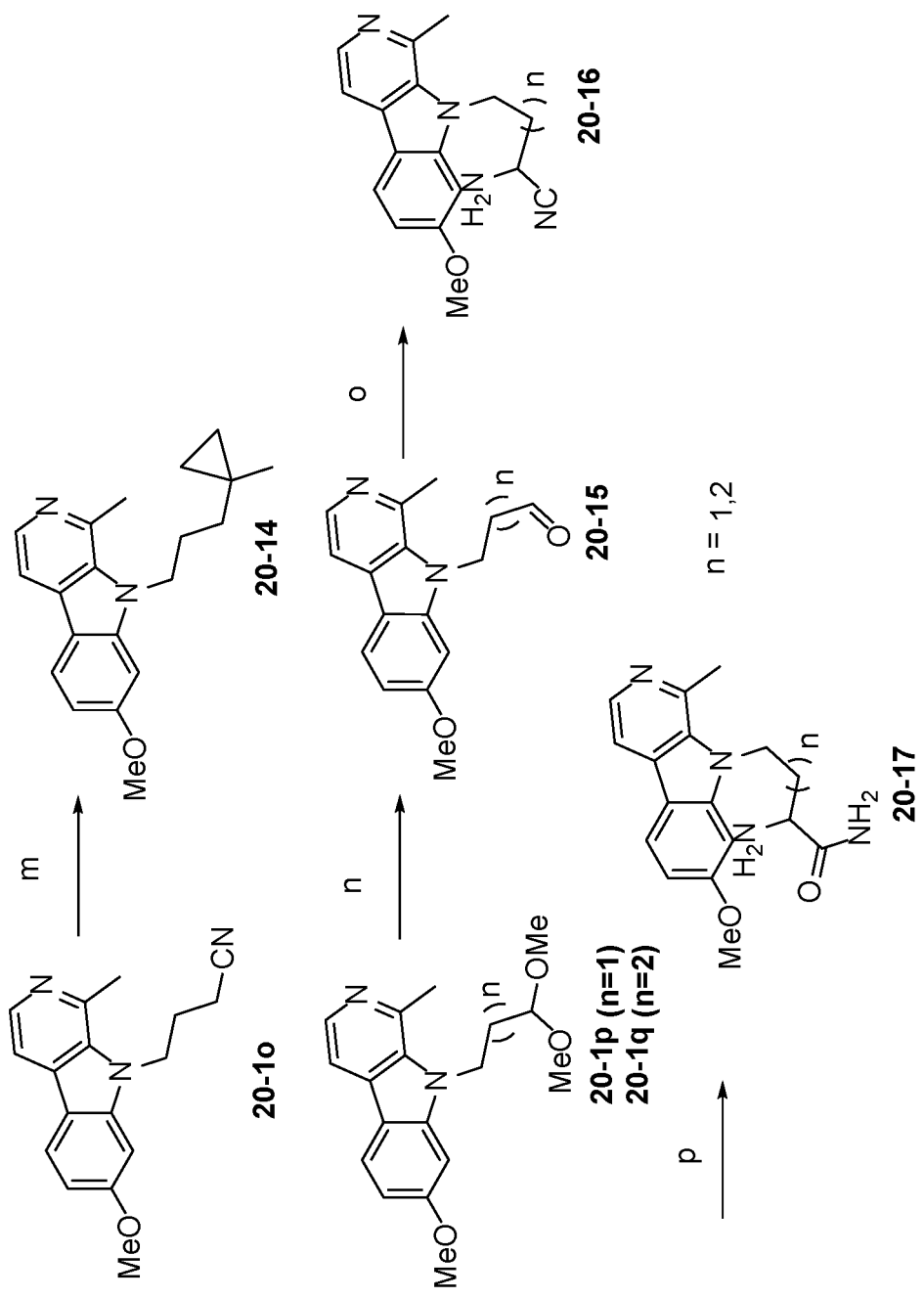
Figure 6:
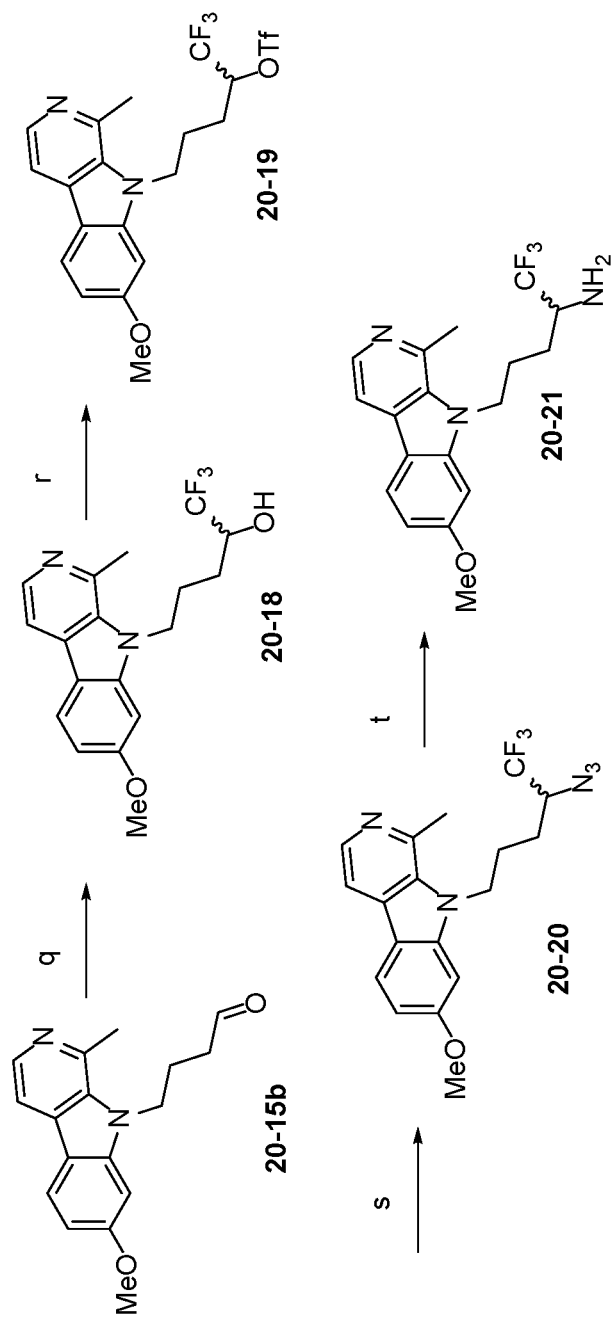
Figure 6:
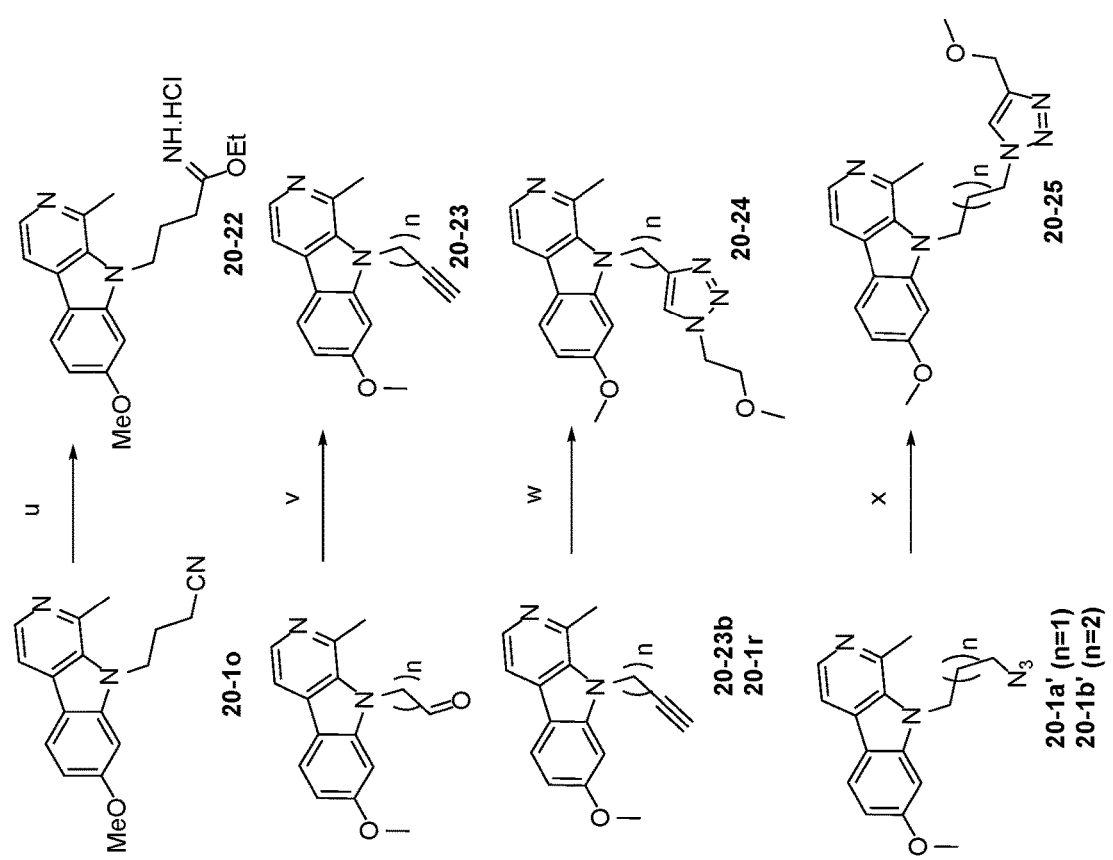
Figure 6:
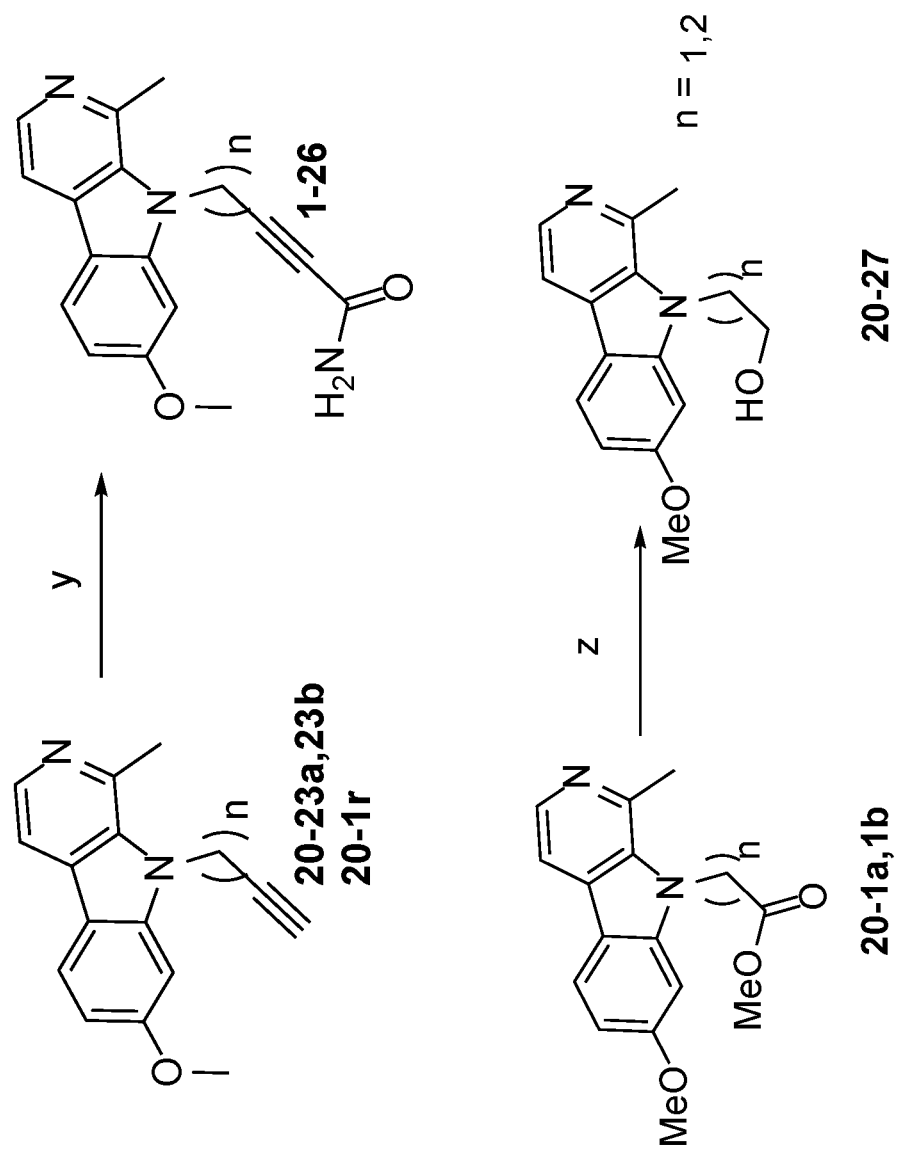

Example 10—SAR Analysis and Human β-Cell Proliferation Assays of 9-Substituted Harmine Analogs 9-substituted harmine analogs were synthesized as described in FIG. 6. Table 6 shows that various 9-substituted harmine analogs have an IC$_{50}$ against DYRK1A comparable to that of harmine. More specifically, compounds 20-1c and 20-2c have an IC$_{50}$ of 26.8 nM and 25 nM, respectively (Table 6). Tables 7 and 8 shows the ability of various additional 9-substituted harmine analogs to inhibit DYRK1A. Table 9 shows that these compounds differentially modulate β-cell proliferation. In particular, compound 20-13 at a concentration of 5 μM from Table 6 induced Human β-Cell proliferation to a greater extent that harmine at a concentration of 10 μM.

TABLE 6

DYRK1A Inhibition of Exemplary Substituted Harmine Analogs

| Compound | R | % DYRK1A Inhibition 1000 nM | 300 nM | IC$_{50}$ (nM)$^a$ |
|---|---|---|---|---|
| 20-1a | MeO-C(O)-CH$_2$-* | 94 | 82 | — |
| 20-1b | MeO-C(O)-CH$_2$CH$_2$-* | 94 | 82 | — |
| 20-1c | MeO-C(O)-CH$_2$CH$_2$CH$_2$-* | 97 | 89 | 26.8 |

TABLE 6-continued

DYRK1A Inhibition of Exemplary Substituted Harmine Analogs

| Compound | R | % DYRK1A Inhibition 1000 nM | 300 nM | IC$_{50}$ (nM)[a] |
|---|---|---|---|---|
| 20-1d | MeO-C(O)-(CH$_2$)$_3$-* | 91 | 75 | — |
| 20-1e | MeO-C(O)-(CH$_2$)$_5$-* | 91 | 75 | — |
| 20-1f | MeO-C(O)-CH(CH$_3$)-CH$_2$-* | 99 | 96 | — |
| 20-1g | MeO-C(O)-C(CH$_3$)$_2$-CH$_2$-* | 99 | 96 | — |
| 20-3a | HO-C(O)-CH$_2$-* | 23 | 11 | — |
| 20-3b | HO-C(O)-(CH$_2$)$_2$-* | — | — | 1020 |
| 20-3c | HO-C(O)-(CH$_2$)$_3$-* | — | — | 950 |
| 20-3d | HO-C(O)-(CH$_2$)$_4$-* | 47 | 23 | — |
| 20-3e | HO-C(O)-(CH$_2$)$_5$-* | 56 | 28 | — |
| 20-4a | HO-C(O)-CH(CH$_3$)-CH$_2$-* | 68 | 42 | — |
| 20-4b | HO-C(O)-C(CH$_3$)$_2$-CH$_2$-* | 70 | 43 | — |

TABLE 6-continued
DYRK1A Inhibition of Exemplary Substituted Harmine Analogs
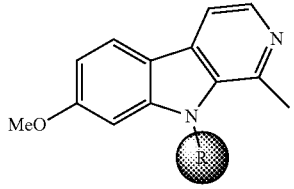
| Compound | R | % DYRK1A Inhibition 1000 nM | 300 nM | IC$_{50}$ (nM)[a] |
|---|---|---|---|---|
| 20-2a | 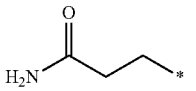 | 52 | 26 | — |
| 20-2b | 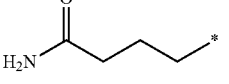 | — | — | 139 |
| 20-2c | 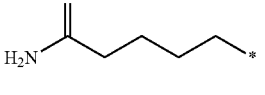 | — | — | 25 |
| 20-2d | 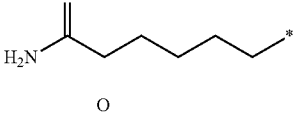 | 93 | 77 | 83.5 |
| 20-2e | 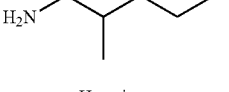 | 86 | 65 | — |
| 20-2f | 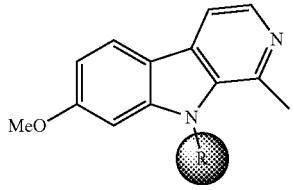 | 99 | 96 | 13.9 |
| Harmine | | — | — | 27 |
[a] = IC$_{50}$ values are determined using ten serial three fold dilutions (in duplicate)
TABLE 7
DYRK1A Inhibition of Additional Exemplary Harmine Analogs
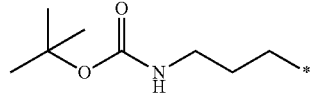 [SMILES: *CCCNC(=O)OC(C)(C)C]
| Compound | R | % DYRK1A Inhibition 1000 nM | 300 nM | IC$_{50}$ (nM)[a] |
|---|---|---|---|---|
| 20-5a | H$_2$N~~~* | 86 | 64 | 152 |
| 20-1c' | (Boc-NH-propyl) | 97 | 88 | 39 |

TABLE 7-continued

DYRK1A Inhibition of Additional Exemplary Harmine Analogs

| Compound | R | % DYRK1A Inhibition 1000 nM | 300 nM | IC$_{50}$ (nM)$^a$ |
|---|---|---|---|---|
| 20-7a | MeHN-(CH$_2$)$_3$-* | 69 | 41 | — |
| 20-9a | Me$_2$N-(CH$_2$)$_3$-* | 26 | 10 | — |
| 20-6a | AcNH-(CH$_2$)$_3$-* | 84 | 61 | — |
| 20-8a | Ac(Me)N-(CH$_2$)$_3$-* | 81 | 56 | — |
| 20-5b | H$_2$N-(CH$_2$)$_4$-* | 64 | 35 | — |
| 20-7b | MeHN-(CH$_2$)$_4$-* | 60 | 32 | — |
| 20-9b | Me$_2$N-(CH$_2$)$_4$-* | 93 | 78 | 6240 |
| 20-6b | AcNH-(CH$_2$)$_4$-* | 90 | 74 | 168 |
| 20-8b | Ac(Me)N-(CH$_2$)$_4$-* | — | — | 215 |
| 20-10a | iPrNHC(O)-(CH$_2$)$_3$-* | 71 | 46 | 307 |
| 20-10b | tBuNHC(O)-(CH$_2$)$_3$-* | 85 | 64 | 120 |
| 20-10c | MeOCH$_2$CH$_2$NHC(O)-(CH$_2$)$_3$-* | 73 | 45 | 253 |

TABLE 7-continued

DYRK1A Inhibition of Additional Exemplary Harmine Analogs

| Compound | R | % DYRK1A Inhibition 1000 nM | 300 nM | IC$_{50}$ (nM)$^a$ |
|---|---|---|---|---|
| 20-10d | [n-butyl-NH-C(O)-propyl-*] | 76 | 38 | — |
| 20-10e | [sec-butyl-NH-C(O)-propyl-*] | 74 | 42 | — |
| 20-10f | [iPr-NH-C(O)-CH(CH$_3$)-CH$_2$-*] | 75 | 43 | 303 |
| 20-10g | [tBu-NH-C(O)-CH(CH$_3$)-CH$_2$-*] | 87 | 69 | 135 |
| 20-10h | [MeO-CH$_2$CH$_2$-NH-C(O)-CH(CH$_3$)-CH$_2$-*] | 79 | 51 | 250 |
| 20-10i | [n-butyl-NH-C(O)-CH(CH$_3$)-CH$_2$-*] | 53 | 25 | — |
| 20-10j | [sec-butyl-NH-C(O)-CH(CH$_3$)-CH$_2$-*] | 69 | 33 | — |
| 20-10k | [MeO-CH$_2$CH$_2$-NH-C(O)-C(CH$_3$)$_2$-CH$_2$-*] | 87 | 62 | 150 |
| 20-10l | [sec-butyl-NH-C(O)-C(CH$_3$)$_2$-CH$_2$-*] | 96 | 83 | 77 |
| 20-13 | [5-amino-1,2,4-oxadiazol-3-yl-propyl-*] | 99 | 92 | 21 |

TABLE 7-continued

DYRK1A Inhibition of Additional Exemplary Harmine Analogs

| Compound | R | % DYRK1A Inhibition 1000 nM | 300 nM | IC$_{50}$ (nM)$^a$ |
|---|---|---|---|---|
| 2014 | cyclopropyl-NH$_2$ propyl* | 80 | 60 | 269 |
| 20-16a | NC-CH(NH$_2$)-CH$_2$CH$_2$* | 97 | 88 | — |
| 20-16b | NC-CH(NH$_2$)-(CH$_2$)$_3$* | 96 | 86 | 34 |
| 20-17a | H$_2$NOC-CH(NH$_2$)-CH$_2$CH$_2$* | 98 | 93 | — |
| 20-17b | H$_2$NOC-CH(NH$_2$)-(CH$_2$)$_3$* | 90 | 72 | 100 |
| 20-18 | F$_3$C-CH(OH)-(CH$_2$)$_3$* | 98 | 92 | 21 |
| 20-21 | F$_3$C-CH(NH$_2$)-(CH$_2$)$_3$* | 91 | 74 | 97 |
| 20-22 | EtO-C(=NH$_2^+$Cl$^-$)-CH$_2$CH$_2$CH$_2$* | 91 | 79 | 75 |
| 20-24a | MeO-CH$_2$CH$_2$-triazole-CH$_2$CH$_2$* | 52 | 26 | 1110 |
| 20-24b | MeO-CH$_2$CH$_2$-triazole-(CH$_2$)$_3$* | 78 | 42 | 437 |
| 20-25a | MeO-CH$_2$-triazole-(CH$_2$)$_3$* | 81 | 58 | 251 |
| 20-25b | MeO-CH$_2$-triazole-(CH$_2$)$_3$* | 78 | 53 | 294 |
| Harmine | | — | — | 27 |

$^a$ = IC$_{50}$ values are determined using ten serial three fold dilutions (in duplicate)

TABLE 8

DYRK1A Inhibition of Additional Exemplary Substituted Harmine Analogs

| Compound | R | % DYRK1A Inhibition 1000 nM | 300 nM | IC$_{50}$ (nM)$^a$ |
|---|---|---|---|---|
| 20-23a | propargyl (CH₂C≡CH) | 100 | 98 | 8 |
| 20-23b | but-3-ynyl | 97 | 89 | 33 |
| 20-1r | pent-4-ynyl | 98 | 95 | 14 |
| 20-1s | hex-5-ynyl | 99 | 97 | 11 |
| 20-1t | allyl | 97 | 90 | 42 |
| 20-1u | but-3-enyl | 99 | 96 | 21 |
| 20-1v | pent-4-enyl | 98 | 95 | 16 |
| 20-1w | hex-5-enyl | 99 | 97 | 14 |
| 20-1x | benzyl | — | — | 275 |
| 20-1y | phenethyl | 98 | 93 | 31 |
| 20-1z | 3-phenylpropyl | 99 | 97 | 16 |
| 20-1z' | 4-phenylbutyl | 94 | 84 | 73 |
| 20-26a | 4-amido-but-2-ynyl | 90 | 75 | 136 |
| 20-23b | 5-amido-pent-3-ynyl | 78 | 50 | 437 |

TABLE 8-continued

DYRK1A Inhibition of Additional Exemplary Substituted Harmine Analogs

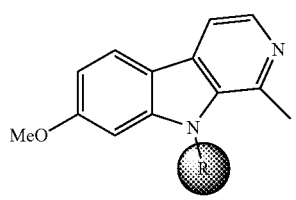

| Compound | R | % DYRK1A Inhibition 1000 nM | 300 nM | IC$_{50}$ (nM)[a] |
|---|---|---|---|---|
| 20-26c | H$_2$N-C(O)-C≡C-CH$_2$CH$_2$-* | 92 | 78 | 117 |
| 20-27a | HO-CH$_2$-* | 90 | 76 | 109 |
| 20-27b | HO-CH$_2$CH$_2$CH$_2$-* | 94 | 82 | 60 |
| 20-15b | OHC-CH$_2$CH$_2$CH$_2$-* | 98 | 95 | — |
| 20-10 | NC-CH$_2$CH$_2$CH$_2$-* | 94 | 86 | — |
| Harmine | | — | — | 27 |

[a] = IC$_{50}$ values are determined using ten serial three fold dilutions (in duplicate)

TABLE 9

β-Cell Proliferation of Exemplary Substituted Harmine Analogs

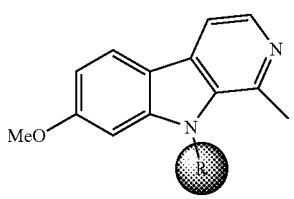

| Compound | R | Human β-Cell proliferation (Concentration μM) | IC$_{50}$ (nM) |
|---|---|---|---|
| 20-1c | MeO-C(O)-CH$_2$CH$_2$-* | 0.5 (10) | 27 |
| 20-2c | H$_2$N-C(O)-CH$_2$CH$_2$-* | 2 (5) | 28 |
| 20-2d | MeO-C(O)-CH$_2$CH$_2$CH$_2$-* | 1.2 (10) | 83 |
| 20-13 | H$_2$N-(oxadiazole)-CH$_2$CH$_2$CH$_2$-* | 1.3 (10) | 21 |

TABLE 9-continued

β-Cell Proliferation of Exemplary Substituted Harmine Analogs

| Compound | R | Human β-Cell proliferation (Concentration μM) | IC$_{50}$ (nM) |
|---|---|---|---|
| 20-2f | H$_2$N-C(O)-CH(CH$_3$)-CH$_2$-CH$_2$-* | 1.6 (5) | 13.9 |
| 20-2f | MeO-C(O)-CH(CH$_3$)-CH$_2$-CH$_2$-* | 1.4 (5) | — |
| 20-1g | MeO-C(O)-C(CH$_3$)$_2$-CH$_2$-CH$_2$-* | 1.5 (10) | — |
| 20-17b | H$_2$NOC-CH(NH$_2$)-CH$_2$-CH$_2$-CH$_2$-* | 0.2 (5) | 100 |
| 20-18 | F$_3$C-CH(OH)-CH$_2$-CH$_2$-CH$_2$-* | 0.6 (10) | 21 |
| 20-21 | F$_3$C-CH(NH$_2$)-CH$_2$-CH$_2$-CH$_2$-* | 0.5 (10) | 97 |
| 20-1o | NC-CH$_2$-CH$_2$-CH$_2$-* | 1 (10) | — |
| 20-15b | OHC-CH$_2$-CH$_2$-CH$_2$-* | 0.6 (5) | — |
| 20-22 | EtO-C(=NH$_2^+$Cl$^-$)-CH$_2$-CH$_2$-CH$_2$-* | 0.8 (10) | 75 |
| 20-23a | HC≡C-CH$_2$-* | 3 (10) | 8 |
| 20-23b | HC≡C-CH$_2$-CH$_2$-* | 1 (10) | 33 |
| 20-1r | HC≡C-CH$_2$-CH$_2$-CH$_2$-* | 1.2 (10) | 14 |
| | Harmine | 1.5 (10) | 27 |

Example 11-Kinome Scan Profile

To understand kinase selectivity on a subset of compounds, kinome profiling of compounds 2-23a, 20-13, 20-2c, and 2-8 was carried out on 468 kinases at 10 M concentration (Table 10, activities 20 indicated below).

TABLE 10

Kinome Scan of Compounds 2-23a, 20-13, 20-2c, and 2-8[a]

| Target | 20-23a | 20-13 | 20-2c | 2-8 |
|---|---|---|---|---|
| ADCK4 | 9.3[b] | 100 | 100 | 84 |
| CAMK2A | 13[c] | 72 | 57 | 53 |
| CAMK2B | 3[b] | 69 | 39 | 42 |
| CDK11 | 40 | 81 | 75 | 4.8[b] |
| CDK7 | 0.8[b] | 51 | 17[c] | 0.65[b] |
| CDK8 | 26 | 100 | 62 | 0[b] |
| CDKL5 | 22 | 21 | 49 | 6.1[b] |
| CIT | 26 | 66 | 45 | 8.1[b] |
| CLK1 | 1.9[b] | 4.1[b] | 1.6[b] | 7.2[b] |
| CLK2 | 0.9[b] | 4.2[b] | 3.2[b] | 1.8[b] |
| CLK3 | 19[c] | 54 | 42 | 36 |
| CLK4 | 1.1[b] | 1.7[b] | 18[c] | 5[b] |
| CSNK1A1 | 13[c] | 33 | 46 | 7.8[b] |
| CSNK1D | 38 | 65 | 60 | 8[b] |
| CSNK1E | 26 | 61 | 47 | 1[b] |
| CSNK1G2 | 56 | 91 | 83 | 18[c] |
| CSNK2A1 | 46 | 49 | 31 | 8.3[b] |
| CSNK2A2 | 54 | 50 | 52 | 2.3[b] |
| DAPK1 | 89 | 91 | 92 | 8.8[b] |
| DAPK2 | 70 | 92 | 86 | 2.8[b] |
| DAPK3 | 75 | 91 | 90 | 1.4[b] |
| DRAK2 | 100 | 100 | 100 | 11 |
| DYRK1A | 0[b] | 0[b] | 0b | 0[b] |
| DYRK1B | 1.1[b] | 1[b] | 8.5[b] | 0.35[b] |
| DYRK2 | 5.2[b] | 9.1[b] | 10[b] | 4.1[b] |
| EGFR(G719C)[d] | 92 | 93 | 93 | 98 |
| EGFR(L858R, T790M)[d] | 100 | 9.2[b] | 100 | 79 |
| FLT3 | 65 | 86 | 98 | 100 |
| FLT3(D835V)[d] | 2.5[b] | 2.6[b] | 9.2[b] | 42 |
| FLT3(ITD)[d] | 61 | 72 | 57 | 87 |
| FLT3(ITD, D835V)[d] | 11[c] | 11[c] | 38 | 37 |
| FLT3(K663Q)[d] | 93 | 98 | 81 | 100 |
| FLT3(N841I)[d] | 41 | 78 | 63 | 74 |
| FLT3-autoinhibited | 100 | 85 | 100 | 100 |
| HASPIN | 1.7[b] | 0.35[b] | 5.2[b] | 0.75[b] |
| HIPK1 | 12 | 9.5[b] | 27 | 2.7[b] |
| HIPK2 | 71[b] | 2.3[b] | 10[b] | 13[b] |
| HIPK3 | 4.5[b] | 6.2[b] | 14c | 2.1[b] |
| IRAK1 | 42 | 58 | 74 | 18[c] |
| IRAK3 | 34 | 62 | 20[c] | 70 |
| IRAK4 | 6.4[b] | 90 | 100 | 70 |
| JAK3 (JH1DOMAIN-CATALYTIC) | 100 | 87 | 100 | 96 |
| KIT | 83 | 100 | 95 | 98 |
| KIT(L576P)[d] | 74 | 100 | 99 | 94 |
| KIT(V559D)[d] | 90 | 100 | 99 | 82 |
| KIT(V559D, V654A)[d] | 100 | 98 | 100 | 100 |
| LRRK2(G2019S)[d] | 100 | 5.1[b] | 100 | 98 |
| MEK2 | 96 | 0[b] | 97 | 100 |
| PDGFRA | 100 | 83 | 90 | 100 |
| PDGFRB | 77 | 100 | 96 | 97 |

TABLE 10-continued

Kinome Scan of Compounds 2-23a, 20-13, 20-2c, and 2-8[a]

| Target | 20-23a | 20-13 | 20-2c | 2-8 |
|---|---|---|---|---|
| PIK3C2G | 38 | 1.2[b] | 30 | 36 |
| PIK3CA(I800L)[d] | 73 | 10[c] | 58 | 63 |
| PIK3CG | 42 | 3.3[b] | 13[c] | 67 |
| PIK4CB | 0[b] | 9.9[b] | 6.8[b] | 19c |
| PIKFYVE | 60 | 3.2[b] | 94 | 88 |
| PIM1 | 26 | 28 | 34 | 19[c] |
| PIM2 | 19[c] | 38 | 37 | 4.7[b] |
| PIM3 | 32 | 39 | 54 | 15 |
| PIP5K2C | 41 | 13[c] | 42 | 5[b] |
| ROCK1 | 9.2[b] | 24 | 33 | 33 |
| ROCK2 | 16 | 86 | 50 | 88 |
| RPS6KA4(Kin. Dom. 2-C-terminal) | 55 | 85 | 100 | 1[b] |
| SGK | 63 | 90 | 92 | 31 |
| TAOK3 | 93 | 77 | 100 | 70 |
| TGFBR2 | 98 | 100 | 93 | 17[c] |
| TYK2(JH1domain-catalytic) | 91 | 17[c] | 83 | 64 |
| VPS34 | 89 | 42 | 75 | 28 |

[a]Compounds were screened 10 μM against 468 kinases, and results for primary screen binding interactions are reported as '% DMSO Ctrl,' where lower values indicate stronger affinity.
[b]≤10.
[c]11 ≤ 20.
[d]mutant Example 12—CNS Off-Target Activity of Harmine and Compound 20-2c Since, harmine is known to exhibit hallucinogenic properties by acting as a central nervous system stimulant, due to its affinity for the serotonin, tryptamine and other related receptors, compound 20-2c and harmine were screened against a panel of CNS off-targets known for harmine (and closely related targets) at 10 μM (Eurofins CEREP Screen) (Table 11). Compound 20-2c was more selective than harmine, showing no binding activity to any receptors except for monoamine oxidase A at the screening dose. Thus, analogs with potent DYRK1A inhibitory activity, improved β-cell proliferation ability, and safer off-target profile, can be identified by systematic modification of harmine.

TABLE 11

CNS Off-Target Activity of Harmine analogs[a]

| Target | % Inhibition[a] 20-2c | Harmine |
|---|---|---|
| Monoamine Oxidase MAO-A | 96[b] | 95[b] |
| Adrenergic α2A | 26 | 59[b] |
| Adrenergic α2B | 4 | 32 |
| Adrenergic α2C | 37 | 45[b] |
| Serotonin (5-Hydroxytryptamine) 5-HT2A | 15 | 23 |
| Serotonin (5-Hydroxytryptamine) 5-HT2C | 7 | 75[b] |

TABLE 11-continued

| Serotonin (5-Hydroxytryptamine) 5-HT6 | 1 | 37 |
| Serotonin (5-Hydroxytryptamine) 5-HT7 | 7 | 30 |
| Transporter, Norepinephrine (NET) | 19 | 86[b] |

[a]Eurofins CEREP Screen at Several CNS Drug Targets; higher number indicates great affinity for the target. Compounds were screened at 10 μM
[b]≥45% inhibition Example 13—Materials and Methods for Example 14

7-deuteromethoxy-1-methyl-9H-pyrido[3,4-b]-indole (20-28). A solution of harmalol (600 mg, 3.03 mmol) and cesium carbonate (1.18 g, 3.63 mmol) in DMF (10 mL) was stirred at room temperature for 1 hour. To this solution was added $d_3$-methyliodide (0.224 mL, 3.63 mmol) and stirred at room temperature for 12 hours. After completion of the reaction confirmed by TLC, the reaction mixture was diluted with water, transferred to separatory funnel and extracted with ethyl acetate (50 mL×2). The organic layer was washed with water, dried over magnesium sulfate, filtered, evaporated, and purified by flash column chromatography using DCM/MeOH (9:1) as eluent to yield the desired product 20-28 as white solid. Yield 45% $^1$H-NMR (600 MHz, $CD_3OD$): δ 8.36 (d, J=6 Hz, 1H), 8.25 (d, J=8.4 Hz, 1H), 7.17 (s, 1H), 7.09 (d, J=9 Hz, 1H), 3.04 (s, 3H); MS (ESI) m/z 216.32 (M+H)+.

4-(7-deuteromethoxy-1-methyl-β-carbolin-9-yl)butyronitrile (20-29). To a solution of 20-28 (177 mg, 0.82 mmol) in DMF (3 mL) was added NaH (66 mg, 1.64 mmol) and stirred at room temperature for 1 hour. To this solution was added 4-bromobutyronitrile (0.163 mL, 1.64 mmol) at 50° C. and stirred at that temperature for 12 hours. After completion of the reaction confirmed by TLC, the reaction mixture was diluted with water, transferred to separatory funnel, and extracted with ethyl acetate (50 mL×2). The organic layer was washed with water, dried over magnesium sulfate, filtered, evaporated, and purified by flash column chromatography using DCM/MeOH (9:1) as eluent to yield the desired product 20-29 as white solid. $^1$H-NMR (600 MHz, $d_6$-DMSO): δ 8.21 (d, J=5.4 Hz, 1H), 8.14 (d, J=8.4 Hz, 1H), 7.95 (d, J=5.4 Hz, 1H), 7.24 (d, J=2.4 Hz, 1H), 6.91 (m, 1H), 4.63 (t, J=7.8 Hz, 2H), 2.98 (s, 3H), 2.66 (t, J=7.2 Hz, 2H), 2.06 (t, J=7.8 Hz, 2H); MS (ESI) m/z 283.24 (M+H)+. The same Procedure was used for the synthesis of 20-33, 20-36a to 20-36d and 20-39.

4-(7-deuteromethoxy-1-methyl-β-carbolin-9-yl)butanamide (20-30). To a solution of 20-29 (60 mg, 0.21 mmol) in DMSO (0.5 mL) was added 50% hydrogen peroxide solution (0.024 mL) at 0° C. followed by potassium carbonate (5 mg, 0.03 mmol). The reaction mixture was allowed to warm up to room temperature and stirred overnight. Upon the completion of reaction, the reaction mixture was vacuum dried and purified using flash chromatography with mixture of DCM/MeOH (9:1) as eluent to get the final product as white solid. Yield 81%. $^1$H-NMR (600 MHz, $d_6$-DMSO): δ 8.16 (m, 1H), 8.08 (d, J=7.8 Hz, 1H), 7.87 (s, 1H), 7.35 (m, 1H), 7.27 (s, 1H), 6.87 (m, 2H), 4.54 (t, J=7.8 Hz, 2H), 2.95 (s, 3H), 2.19 (t, J=7.2 Hz, 2H), 1.94 (m, 2H); MS (ESI) m/z 301.42 (M+H)+. The same procedure was used for the synthesis of 20-40.

N'-hydroxy-4-(7-deuteromethoxy-1-methyl-β-carbolin-9-yl)butanimidamide (20-31). A solution of 20-29 (142 mg, 0.50 mmol), hydroxylamine hydrochloride (139 mg, 2.01 mmol), and trimethylamine (0.28 mL, 2.01 mmol) in ethanol (2 mL) was refluxed for 12 hours. Solvent was evaporated and the crude was purified by flash column chromatography using DCM/MeOH (9:1) as eluent to get the desired product 20-31 as white solid. Yield 74%. $^1$H-NMR (600 MHz, $d_6$-DMSO): δ 8.26 (d, J=6 Hz, 1H), 8.22 (d, J=9.6 Hz, 1H), 8.15 (m, 1H), 7.27 (s, 1H), 6.96 (m, 1H), 4.60 (t, J=7.8 Hz, 2H), 3.04 (s, 3H), 2.23 (m, 2H), 2.02 (m, 2H); MS (ESI) m/z 316.46 (M+H)+. The same procedure was used for the synthesis of 20-37a to 20-37d.

3-(3-(7-deuteromethoxy-1-methyl-β-carbolin-9-yl)propyl)-5-amino-1,2,4-oxadiazole (20-32). To a solution of 20-11 (150 mg, 0.48 mmol) and pyridine (0.154 mL, 1.92 mmol) in toluene was added trichloroacetyl chloride (0.06 mL, 0.57 mmol) at 0° C. and stirred for another hour at the same temperature. The reaction mixture was then heated to 85° C. for 12 hours. After the completion of the reaction, solvent was evaporated and 7 N ammonia in methanol (2 mL) was added to the crude and stirred at room temperature for 12 hours. After the completion of the reaction, solvent was evaporated and the crude was purified by flash column chromatography using DCM/MeOH(9:1) as eluent to get the desired product 20-32 as white solid. Yield 46%. $^1$H-NMR (600 MHz, $d_6$-DMSO): δ 8.16 (d, J=4.8 Hz, 1H), 8.09 (d, J=8.4 Hz, 1H), 7.88 (d, J=5.4 Hz, 1H), 7.72 (bs, 2H), 7.23 (d, J=1.8 Hz, 1H), 6.87 (m, 1H), 4.62 (t, J=7.8 Hz, 2H), 2.90 (s, 3H), 2.57 (t, J=7.2 Hz, 2H), 2.08 (m, 2H); MS (ESI) m/z 341.72 (M+H)+. The same procedure was used for the synthesis of 20-38a to 20-38d.

3-(7-deuteromethoxy-1-methyl-β-carbolin-9-yl)-propan-1-yne (20-33). White solid. Yield 51%. $^1$H-NMR (600 MHz, d-DMSO): δ 8.19 (d, J=4.8 Hz, 1H), 8.10 (d, J=8.4 Hz, 1H), 7.88 (d, J=5.4 Hz, 1H), 7.33 (d, J=2.4 Hz, 1H), 6.89 (m, 1H), 5.78 (d, J=6.6 Hz, 1H), 5.45 (d, J=2.4 Hz, 2H), 3.04 (s, 3H); MS (ESI) m/z 354.72 (M+H)+.

7-trifluoromethoxy-1-methyl-9H-pyrido[3,4-b]-indole (20-35). To the mixture of 6-trifluoromethoxy tryptamine (200 mg, 0.81 mmol) and acetaldehyde (40% in water, 0.058 mL, 0.81 mmol) in 1.5 mL of dichloromethane, 0.08 mL of trifluoroacetic acid was added drops wise at 0° C. Then, reaction mixture was stirred at room temperature for 12 hours. After completion of reaction as monitored by LCMS, the reaction mixture was evaporated to get 20-34 as a white solid which was taken to next step without purification. A mixture of 20-34, lithium carbonate (60 mg, 0.81 mmol) and Pd on carbon (10 mg, 0.008 mmol) in ethanol (2.5 mL) was heated in CEM microwave reactor at 150° C. for 10 minutes. Catalyst was filtered over celite, concentrated under reduced pressure, and purified by flash column chromatography using DCM/MeOH (9:1) as eluent to afford 20-35 as brown solid. Yield 25%. $^1$H-NMR (600 MHz, $d_6$-DMSO): δ 11.82 (s, 1H), 8.34 (d, J=8.4 Hz, 1H), 8.25 (d, J=5.4 Hz, 1H), 7.98 (d, J=4.8 Hz, 1H), 7.50 (s, 1H), 7.21 (d, J=7.8 Hz, 1H), 2.76 (s, 3H); MS (ESI) m/z 367.72 (M+H)+.

2-(7-methoxy-1-methyl-β-carbolin-9-yl)acetonitrile (20-36a). White solid. Yield 61%. $^1$H-NMR (600 MHz, $d_6$-DMSO): δ 8.25 (d, J=4.8 Hz, 1H), 8.13 (d, J=8.4 Hz, 1H), 7.92 (d, J=4.8 Hz, 1H), 7.47 (s, 1H), 6.96 (m, 1H), 5.89 (s, 2H), 3.92 (s, 3H), 3.02 (s, 3H); MS (ESI) m/z 252.61 (M+H)+.

3-(7-methoxy-1-methyl-β-carbolin-9-yl)propionitrile (20-36b). White solid. Yield 57%. $^1$H-NMR (600 MHz, $d_6$-DMSO): δ 8.19 (d, J=4.8 Hz, 1H), 8.10 (d, J=8.4 Hz, 1H), 7.89 (d, J=4.8 Hz, 1H), 7.36 (d, J=1.8 Hz, 1H), 6.90 (m, 1H), 4.92 (t, J=6.6 Hz, 2H), 3.91 (s, 3H), 3.09 (t, J=6.6 Hz, 2H), 2.98 (s, 3H); MS (ESI) m/z 266.45 (M+H)+.

5-(7-methoxy-1-methyl-β-carbolin-9-yl)pentanenitrile (20-36c). White solid. Yield 34%. $^1$H-NMR (600 MHz, $d_6$-DMSO): δ 8.17 (d, J=4.8 Hz, 1H), 8.10 (d, J=8.4 Hz, 1H), 7.88 (d, J=4.8 Hz, 1H), 7.23 (d, J=1.8 Hz, 1H), 6.88 (m, 1H), 4.59 (t, J=7.2 Hz, 2H), 3.91 (s, 3H), 2.94 (s, 3H), 2.57 (t, J=7.2 Hz, 2H), 1.81 (m, 2H), 1.65 (m, 2H); MS (ESI) m/z 294.23 (M+H)+.

6-(7-methoxy-1-methyl-β-carbolin-9-yl)hexanenitrile (20-36d). White solid. Yield 42%. $^1$H-NMR (600 MHz, $d_6$-DMSO): δ 8.16 (d, J=5.4 Hz, 1H), 8.09 (d, J=8.4 Hz, 1H), 7.87 (d, J=5.4 Hz, 1H), 7.20 (d, J=1.8 Hz, 1H), 6.885 (m, 1H), 4.55 (t, J=7.8 Hz, 2H), 3.91 (s, 3H), 2.94 (s, 3H), 1.73 (m, 2H), 1.60 (m, 2H), 1.48 (m, 2H); MS (ESI) m/z 308.33 (M+H)+.

N'-hydroxy-2-(7-methoxy-1-methyl-β-carbolin-9-yl)acetanimidamide (20-37a). White solid. Yield 54%. $^1$H-NMR (600 MHz, $d_6$-DMSO): δ 9.99 (bs, 2H), 8.48 (d, J=4.8 Hz, 1H), 8.36 (m, 2H), 7.88 (d, J=5.4 Hz, 1H), 7.43 (d, J=1.8 Hz, 1H), 7.06 (m, 1H), 1.86 (s, 2H), 3.95 (s, 3H), 3.16 (s, 3H); MS (ESI) m/z 285.71 (M+H)+.

N'-hydroxy-3-(7-methoxy-1-methyl-β-carbolin-9-yl)propionanimidamide (20-37b). White solid. Yield 69%. MS (ESI) m/z 299.53 (M+H)+.

N'-hydroxy-5-(7-methoxy-1-methyl-β-carbolin-9-yl)pentanimidamide (20-37c). White solid. Yield 44%. $^1$H-NMR (600 MHz, $d_6$-DMSO): δ 8.17 (m, 1H), 8.10 (d, J=8.4 Hz, 1H), 7.90 (m, 1H), 7.18 (s, 1H), 6.88 (d, J=8.4 Hz, 1H), 5.50 (bs, 2H), 4.55 (t, J=7.2 Hz, 2H), 3.91 (s, 3H), 2.95 (s, 3H), 2.05 (m, 2H), 1.71 (m, 2H), 1.62 (m, 2H); MS (ESI) m/z 327.88 (M+H)+.

N'-hydroxy-6-(7-methoxy-1-methyl-β-carbolin-9-yl)hexananimidamide (20-37d). White solid. Yield 74%. $^1$H-NMR (600 MHz, $d_6$-DMSO): δ 8.24 (d, J=5.4 Hz, 1H), 8.18 (d, J=8.4 Hz, 1H), 8.10 (s, 1H), 7.26 (s, 1H), 6.94 (m, 1H), 4.58 (t, J=7.8 Hz, 2H), 3.93 (s, 3H), 3.03 (s, 3H), 2.18 (t, J=7.2 Hz, 2H), 1.76 (m, 2H), 1.61 (m, 2H), 1.40 (m, 2H); MS (ESI) m/z 341.22 (M+H)+.

1-(1-(7-methoxy-1-methyl-β-carbolin-9-yl)methyl)-5-amino-1,2,4-oxadiazole (20-38a). White solid. Yield 35%. $^1$H-NMR (600 MHz, $d_6$-DMSO): δ 8.17 (d, J=5.4 Hz, 1H), 8.09 (d, J=8.4 Hz, 1H), 7.88 (d, J=4.8 Hz, 1H), 7.85 (bs, 2H), 7.28 (s, 1H), 6.89 (m, 1H), 5.72 (s, 2H), 3.87 (s, 3H), 2.95 (s, 3H); MS (ESI) m/z 310.33 (M+H)+.

3-(3-(7-methoxy-1-methyl-β-carbolin-9-yl)ethyl)-5-amino-1,2,4-oxadiazole (20-38b). White Solid. Yield 46%. MS (ESI) m/z 324.55 (M+H)+.

5-(5-(7-methoxy-1-methyl-β-carbolin-9-yl)butyl)-5-amino-1,2,4-oxadiazole (20-38c). White solid. Yield 72%. $^1$H-NMR (600 MHz, $d_6$-DMSO): δ 8.26 (m, 1H), 8.21 (d, J=6.6 Hz, 1H), 8.15 (m, 1H), 7.63 (bs, 2H), 7.28 (s, 1H), 6.95 (m, 1H), 4.61 (t, J=7.8 Hz, 2H), 3.94 (s, 3H), 3.03 (s, 3H), 1.80 (m, 2H), 1.71 (m, 2H); MS (ESI) m/z 352.27 (M+H)+.

6-(6-(7-methoxy-1-methyl-β-carbolin-9-yl)pentyl)-5-amino-1,2,4-oxadiazole (20-38d). White solid. Yield 46%. $^1$H-NMR (600 MHz, $d_6$-DMSO): δ 8.16 (d, J=4.8 Hz, 1H), 8.09 (d, J=8.4 Hz, 1H), 7.88 (d, J=4.8 Hz, 1H), 7.62 (bs, 2H), 7.17 (s, 1H), 6.86 (m, 1H), 4.54 (t, J=7.8 Hz, 2H), 3.90 (s, 3H), 2.93 (s, 3H), 2.42 (m, 2H), 1.74 (m, 2H), 1.65 (tm, 2H), 1.42 (m, 2H); MS (ESI) m/z 366.82 (M+H)+.

2,2-dimethyl-4-(7-Methoxy-1-methyl-β-carbolin-9-yl)butyronitrile (20-39). Yellow solid. Yield 71%. $^1$H-NMR (600 MHz, $CD_3OD$): δ 8.12 (d, J=5.4 Hz, 1H), 8.03 (d, J=8.4 Hz, 1H), 7.85 (d, J=5.4 Hz, 1H), 7.01 (s, 1H), 6.91 (d, J=8.4 Hz, 1H), 4.67 (t, J=8.4 Hz, 2H), 3.94 (s, 3H), 3.00 (s, 3H), 2.03 (m, 2H), 1.49 (s, 6H); MS (ESI) m/z 308.23 (M+H)+.

2,2-dimethyl-4-(7-Methoxy-1-methyl-β-carbolin-9-yl)butanamide (20-40). Yellow solid. Yield 81%. $^1$H-NMR (600 MHz, $d_6$-DMSO): δ 8.29 (d, J=6 Hz, 1H), 8.25 (d, J=8.4 Hz, 1H), 7.21 (bs, 1H), 7.35 (s, 1H), 7.28 (d, J=1.8 Hz, 1H), 7.15 (s, 1H), 6.99 (m, 1H), 4.51 (m, 2H), 3.95 (s, 3H), 3.08 (s, 3H), 1.91 (d, J=7.2 Hz, 1H), 1.24 (s, 6H); MS (ESI) m/z 326.71 (M+H)+.

Figure 7:
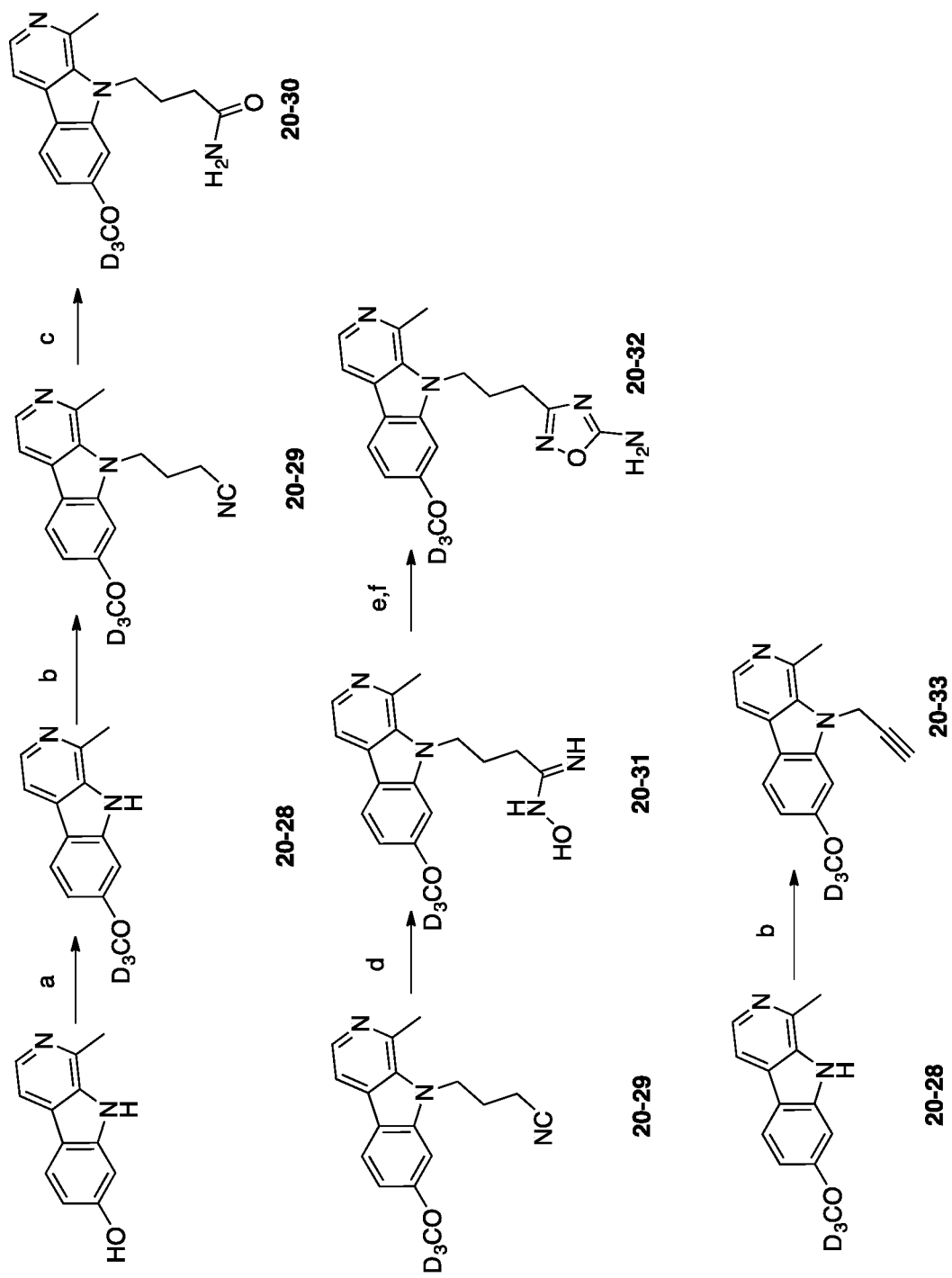
FIG. 7 is a schematic illustration showing the synthesis of 7-deuteromethoxy harmine analogs. Reagents and conditions: (a) Cs$_2$CO$_3$ (1.1 eq.), CD$_3$I (1.1 eq.), DMF, room temperature, 12 hours; (b) NaH (2 eq.), 4-bromoalkylnitrile or propargyl bromide (2 eq.), DMF, 50° C., 12 hours; (c) H$_2$O$_2$ (60% in water), K$_2$CO$_3$ (0.15 eq.), DMSO, room temperature, 12 hours; (d) NH$_2$OH.HCl (1.5 eq.), Et$_3$N (1.5 eq.), EtOH, reflux, 12 hours; (e) CCl$_3$COCl (1.2 eq.), Toluene, 85° C., 24 hours; (f) 7 N NH$_3$ in MeOH, room temperature, 12 hours; (g) acetaldehyde (1eq.), TFA, DCM, room temperature, 12 hours; (h) 10% Palladium on carbon, Li$_2$CO$_3$ (2 eq.), µW, 150° C., 10 minutes.
Figure 7:
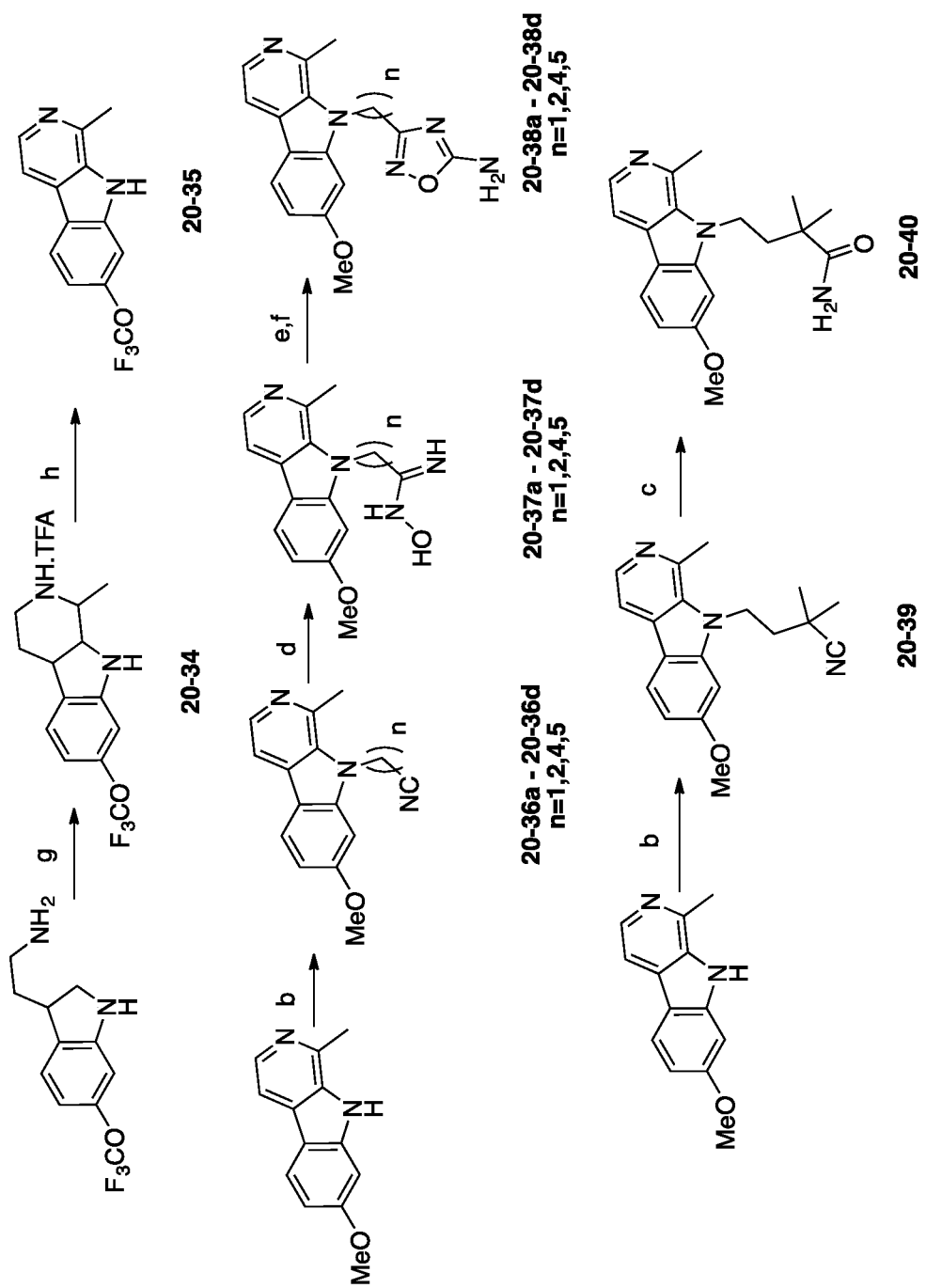

Example 14—DYRK1A Inhibition of 7-Deuteromethoxy Harmine Analogs 7-deuteromethoxy harmine analogs were synthesized by following the reaction sequence outlined in FIG. 7. Table 12 shows that analog 20-33 showed the best activity with $IC_{50}$ of 8 nM. Analogs 20-28, 20-30, and 20-32 had an $IC_{50}$ against DYRK1A of 39 nM, 37 nM, and 35 nM, respectively.

TABLE 12

DYRK1A Inhibition of Novel Harmine Analogs

| Compound | $R^1$ | $R^2$ | % DYRK1A Inhibition 1000 nM | $IC_{50}$ (nM)$^a$ |
|---|---|---|---|---|
| 20-28 | $D_3CO$—* | H—* | — | 39 |
| 20-30 | $D_3CO$—* | 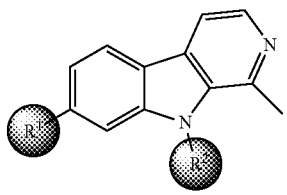 | — | 37 |

TABLE 12-continued

DYRK1A Inhibition of Novel Harmine Analogs

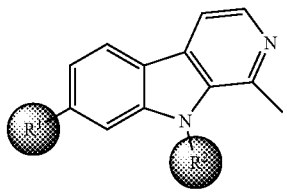

| Compound | R[1] | R[2] | % DYRK1A Inhibition 1000 nM | IC$_{50}$ (nM)[a] |
|---|---|---|---|---|
| 20-32 | D$_3$CO—* | H$_2$N-oxadiazole-(CH$_2$)$_3$—* | — | 35 |
| 20-33 | D$_3$CO—* | HC≡C-CH$_2$—* | — | 8 |
| 20-35 | F$_3$CO—* | H—* | 31 | — |
| 20-38a | H$_3$CO—* | H$_2$N-oxadiazole-CH$_2$—* | — | 138 |
| 20-38b | H$_3$CO—* | H$_2$N-oxadiazole-(CH$_2$)$_2$—* | — | 66 |
| 20-38c | H$_3$CO—* | H$_2$N-oxadiazole-(CH$_2$)$_4$—* | — | 103 |
| 20-38d | H$_3$CO—* | H$_2$N-oxadiazole-(CH$_2$)$_5$—* | — | 178 |
| 20-40 | H$_3$CO—* | H$_2$N-C(=O)-C(CH$_3$)$_2$-CH$_2$CH$_2$—* | — | 20 |
| Harmine | | | — | 27 |

[a] = IC$_{50}$ values are determined using ten serial three fold dilutions (in duplicate)

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (I) having the following structure:

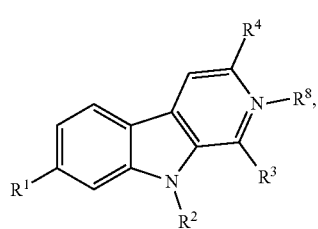

(I)

or a stereoisomer, pharmaceutically acceptable salt, oxide, or solvate thereof, wherein
- $R^1$ is a branched or unbranched $C_{1-6}$ alkoxy optionally substituted with Y, —$NHR^5$, —$C(O)NHCH(CH_3)_2$, or —$O(CH_2)_2OR^6$, wherein the alkoxy is optionally halogenated or deuterated;
- $R^2$ is H or branched or unbranched $C_{1-6}$ alkyl, $C_{2-6}$ alkenyl, or $C_{2-6}$ alkynyl, wherein the branched or unbranched $C_{1-6}$ alkyl, $C_{2-6}$ alkenyl, or $C_{2-6}$ alkynyl is optionally substituted with Z;
- $R^3$ is $C_{1-6}$ alkyl, halogen, branched or unbranched $C_{1-6}$ hydroxyalkyl, —$C(O)CH_3$, —OH, or heterocyclyl optionally substituted with $R^7$;
- $R^4$ is H, —OH, branched or unbranched $C_{1-6}$ hydroxyalkyl, or —$C(O)CH_3$;
- $R^5$ is H, —$C(O)CH_3$, or —$C(O)Ar$;
- $R^6$ is branched or unbranched $C_{1-6}$ alkyl, —$(CH_2)_2NHBoc$, —$(CH_2)_2NH(O)CH_3$, or —$(CH_2)_2NH_3Cl$;
- $R^7$ is —ArX or —$CH_2ArX$;
- $R^8$ is optional, and when present is O;
- X is H or halogen;
- Y is —$CO_2CH_3$, —NHBoc, —$C(O)NH_2$, —$CO_2H$, —$NH_3Cl$, —$NHC(O)CH_3$; and
- Z is —$CO_2CH_3$, —$CO_2H$, —$C(O)NH_2$, or an amino-substituted heteroaryl selected from the group consisting of furan, thiophene, pyrrole, oxazole, thiazole, imidazole, pyrazole, isoxazole, isothiazole, 1,2,3-oxadiazole, 1,2,4-oxadiazole, 1,2,3-thiadiazole, 1,2,3-triazole, 1,2,4-triazole, tetrazole, and 1,2,3,4-oxatriazole;

with the following provisos:
when $R^1$ is —$OCH_3$, $R^3$ is —$CH_3$, and $R^4$ is H, $R^2$ cannot be —$(CH_2)_2CO_2CH_3$, —$(CH_2)_2CO_2H$, or —$(CH_2)_2C(O)NH_2$;
when $R^1$ is —$OCH_3$, $R^2$ is H, and $R^4$ is H, $R^3$ cannot be —$CH_2OH$ or Cl; and
when $R^1$ is —$OCH_3$, $R^2$ is H, $R^3$ is —$CH_3$, $R^4$ cannot be H.

2. The compound according to claim 1, wherein
$R^1$ is —$OCH_3$;
$R^2$ is branched or unbranched $C_{1-6}$ alkyl substituted with —$CO_2CH_3$;
$R^3$ is methyl; and
$R^4$ is H.

3. The compound according to claim 1, wherein
$R^1$ is —$OCH_3$;
$R^2$ is branched or unbranched $C_{1-6}$ alkyl substituted with —$CO_2H$;
$R^3$ is methyl; and
$R^4$ is H.

4. The compound according to claim 1, wherein
$R^1$ is —$OCH_3$;
$R^2$ is branched or unbranched $C_{1-6}$ alkyl substituted with —$C(O)NH_2$;
$R^3$ is methyl; and
$R^4$ is H.

5. The compound according to claim 1, wherein
$R^1$ is —$OCH_3$;
$R^2$ is branched or unbranched $C_{1-6}$ alkyl substituted with a substituted heteroaryl;
$R^3$ is methyl; and
$R^4$ is H.

6. The compound according to claim 1, wherein
$R^2$ is H;
$R^3$ is methyl; and
$R^4$ is H.

7. The compound according to claim 6, wherein $R^1$ is independently selected from —$NH_2$; —$O(CH_2)_2OR^6$; —$OCD_3$; —$OCF_3$; and $C_{1-6}$ alkoxy substituted with —$CO_2CH_3$, —NHBoc, —$C(O)NH_2$, —$CO_2H$, —$NH_3Cl$, or —$NHC(O)CH_3$.

8. The compound according to claim 1, wherein
$R^1$ is —$OCH_3$;
$R^2$ is H; and
$R^4$ is H.

9. The compound according to claim 8, wherein $R^3$ is halogen.

10. The compound according to claim 8, wherein $R^3$ is selected from the group consisting of

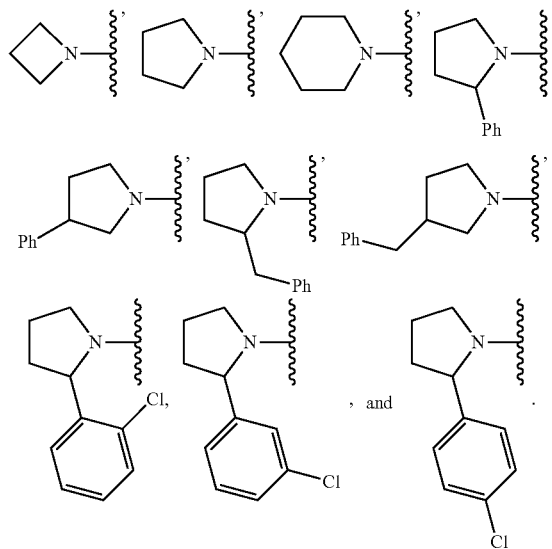

11. The compound according to claim 1, wherein
$R^1$ is —$OCD_3$;
$R^3$ is methyl; and
$R^4$ is H.

12. The compound according to claim 11, wherein R² is selected from the group consisting of
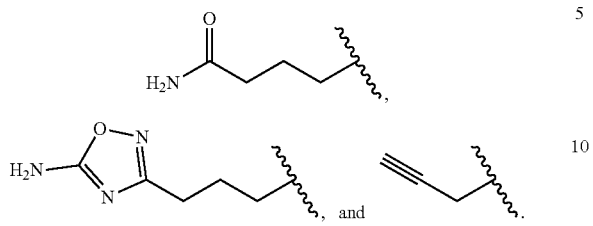
13. The compound according to claim 1, wherein the compound is selected from the group consisting of:
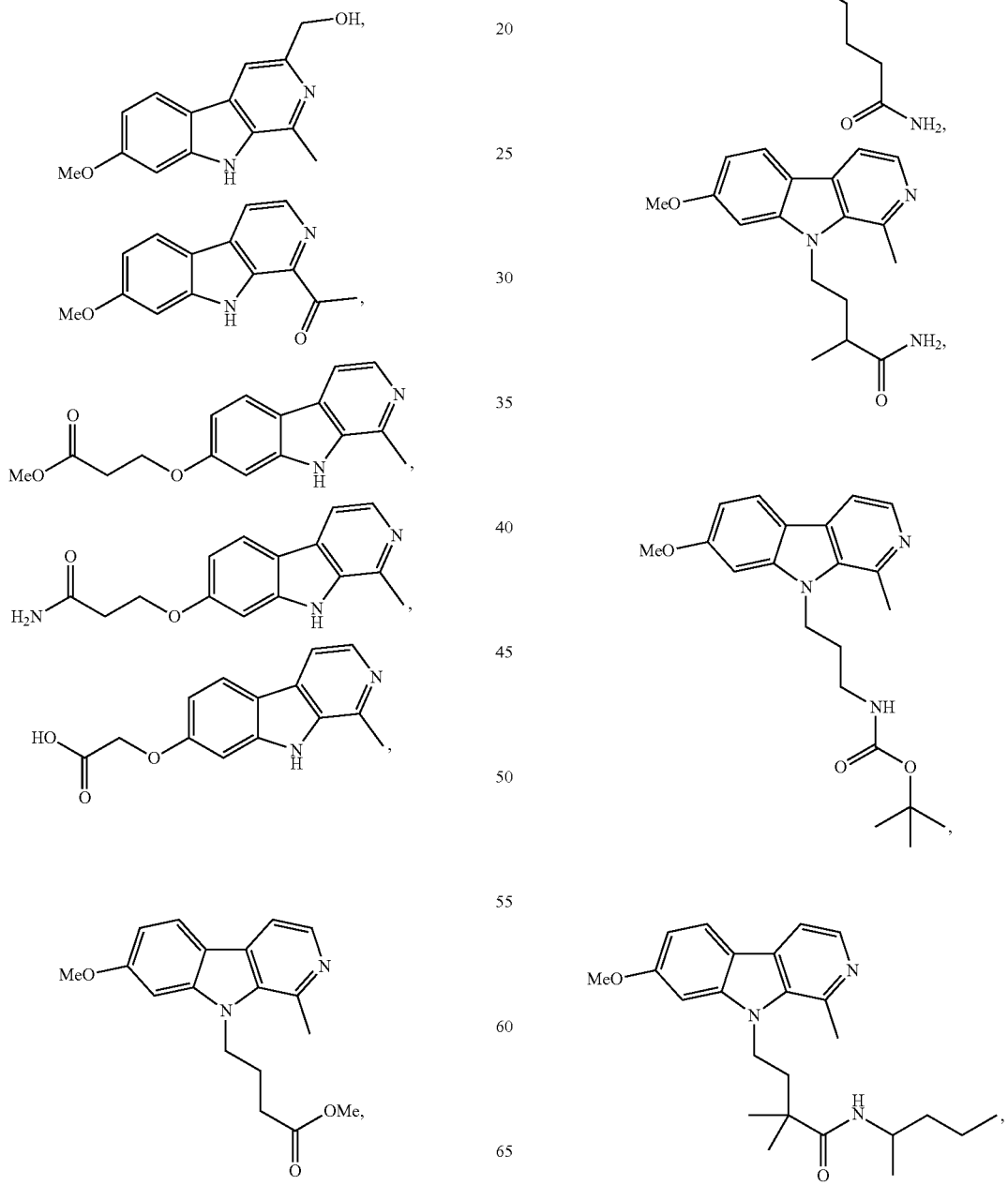
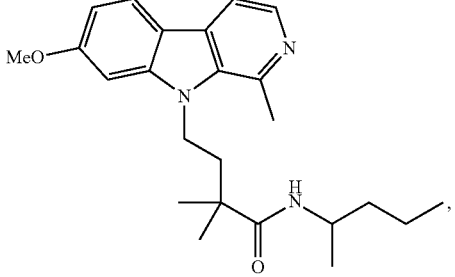

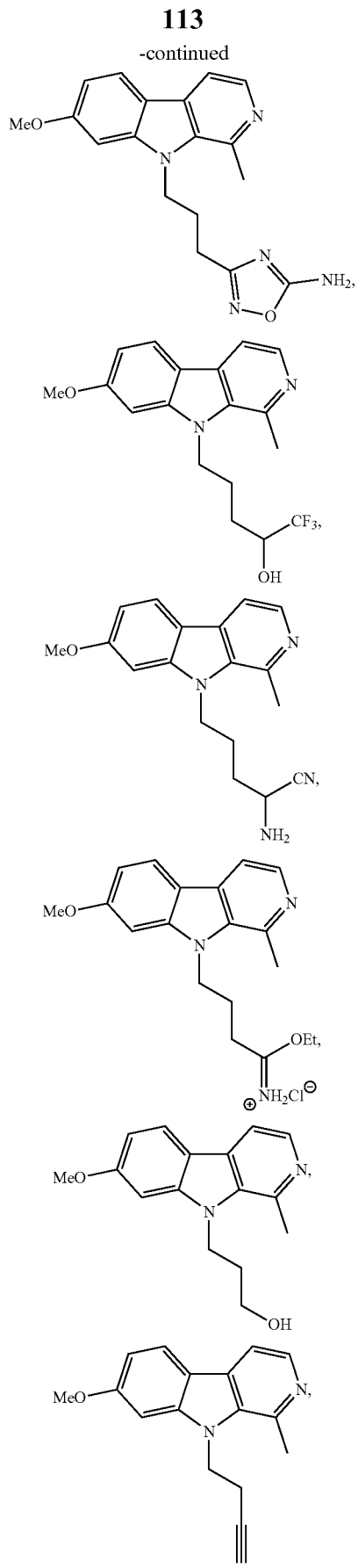

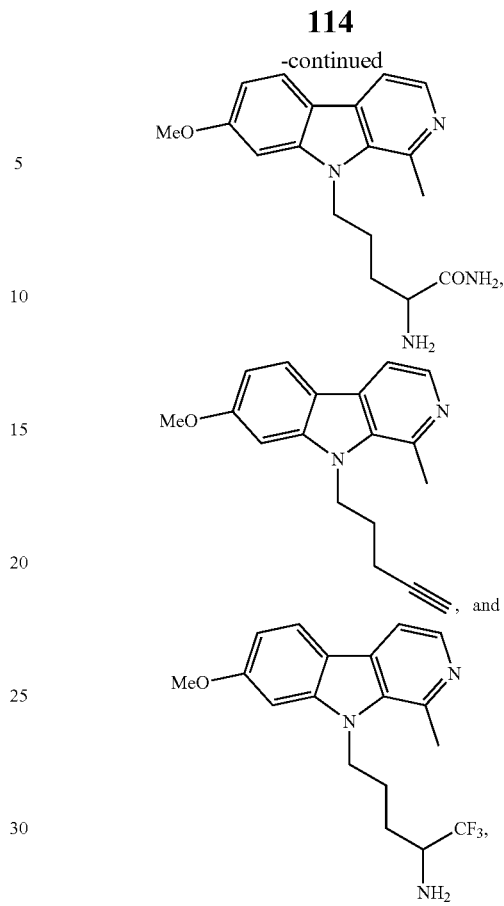

14. A method of inhibiting activity of dual-specificity tyrosine phosphorylation-regulated kinase 1A (DYRK1A) in a cell, said method comprising:
contacting the cell with a compound according to claim 1 under conditions effective to inhibit activity of DYRK1A in the cell.

15. A method of increasing cell proliferation in a population of pancreatic beta cells, said method comprising:
contacting a population of pancreatic beta cells with a compound according to claim 1 under conditions effective to increase cell proliferation in the population of pancreatic beta cells.

16. A composition comprising:
a compound according to claim 1 and
a carrier.

17. The composition according to claim 16 further comprising:
a transforming growth factor beta (TGFβ) superfamily signaling pathway inhibitor, a glucagon-like peptide-1 receptor (GLP1R) agonist, and/or a Dipeptidyl Peptidase IV (DPP4) inhibitor.

18. The composition according to claim 16, wherein the carrier is a pharmaceutically-acceptable carrier.

19. A method of treating a subject for a condition associated with insufficient insulin secretion, said method comprising:
administering to a subject in need of treatment for a condition associated with an insufficient level of insulin secretion a compound according to claim 1 under conditions effective to treat the subject for the condition.

20. A method of treating a subject for a neurological disorder, said method comprising:

administering to a subject in need of treatment for a neurological disorder a compound of claim 1 under conditions effective to treat the subject for the condition.

\* \* \* \* \*